United States Patent
Brady et al.

(10) Patent No.: US 10,582,939 B2
(45) Date of Patent: Mar. 10, 2020

(54) CLOT CAPTURE SYSTEMS AND ASSOCIATED METHODS

(71) Applicant: Neuravi Limited, Galway (IE)

(72) Inventors: Eamon Brady, County Galway (IE); David Vale, County Galway (IE); Michael Gilvarry, County Galway (IE); Mahmood Razavi, Irvine, CA (US); John O'Shaughnessy, County Galway (IE)

(73) Assignee: Neuravi Limited, Galway (IE)

( * ) Notice: Subject to any disclaimer, the term of this patent is extended or adjusted under 35 U.S.C. 154(b) by 0 days.

(21) Appl. No.: 15/204,537

(22) Filed: Jul. 7, 2016

(65) Prior Publication Data
US 2016/0317168 A1    Nov. 3, 2016

Related U.S. Application Data

(63) Continuation of application No. 13/662,299, filed on Oct. 26, 2012, now Pat. No. 9,402,707, which is a
(Continued)

(51) Int. Cl.
*A61B 17/221*    (2006.01)
*A61F 2/01*    (2006.01)

(52) U.S. Cl.
CPC .............. *A61B 17/221* (2013.01); *A61F 2/01* (2013.01); *A61F 2/013* (2013.01);
(Continued)

(58) Field of Classification Search
CPC  A61B 17/221; A61B 2017/2212; A61F 2/013
See application file for complete search history.

(56) References Cited

U.S. PATENT DOCUMENTS

| 4,793,348 A | 12/1988 | Palmaz |
| 4,873,978 A | 10/1989 | Ginburg |

(Continued)

FOREIGN PATENT DOCUMENTS

| DE | 202009001951 U1 | 4/2010 |
| DE | 102009056450 | 6/2011 |

(Continued)

OTHER PUBLICATIONS

US 6,348,062 B1, 02/2002, Khosravi (withdrawn)
(Continued)

*Primary Examiner* — Diane D Yabut
(74) *Attorney, Agent, or Firm* — Troutman Sanders LLP

(57) ABSTRACT

A clot capture system for disengaging a clot from a vessel wall and removing the clot from the vessel. The system may include a clot capture device for placement on a distal side of a clot. The clot capture device may have a retracted delivery configuration and an expanded deployed configuration. The clot removal device may have a proximal support frame, and a distal fiber net. The support frame may have a retracted delivery configuration and an expanded deployed configuration. The proximal support frame in the expanded configuration may define a proximal inlet mouth for engaging a clot and a net for confining the clot. An elongate member may facilitate capture and/or withdrawal of a clot from a vessel.

19 Claims, 126 Drawing Sheets

Related U.S. Application Data continuation-in-part of application No. 12/737,527, filed as application No. PCT/IE2009/000051 on Jul. 22, 2009, now Pat. No. 8,777,976, and a continuation-in-part of application No. PCT/IE2011/000026, filed on Apr. 28, 2011.

(60) Provisional application No. 61/202,612, filed on Mar. 18, 2009, provisional application No. 61/129,823, filed on Jul. 22, 2008, provisional application No. 61/282,950, filed on Apr. 28, 2010.

(52) U.S. Cl.
CPC . *A61B 2017/2212* (2013.01); *A61F 2230/001* (2013.01); *A61F 2230/005* (2013.01); *A61F 2230/0006* (2013.01); *A61F 2230/0008* (2013.01); *A61F 2230/0058* (2013.01)

(56) References Cited

U.S. PATENT DOCUMENTS

| | | |
|---|---|---|
| 5,011,488 A | 4/1991 | Ginsburg |
| 5,092,839 A | 3/1992 | Kipperman |
| 5,102,415 A | 4/1992 | Guenther et al. |
| 5,122,136 A | 6/1992 | Guglielmi et al. |
| 5,171,233 A | 12/1992 | Amplatz |
| 5,234,437 A | 8/1993 | Sepetka |
| 5,387,219 A | 2/1995 | Rappe |
| 5,387,226 A | 2/1995 | Miraki |
| 5,449,372 A | 9/1995 | Schmaltz |
| 5,538,512 A | 7/1996 | Zenzon et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mills |
| 5,645,558 A | 7/1997 | Horton |
| 5,658,296 A | 8/1997 | Bates |
| 5,695,519 A | 12/1997 | Summers et al. |
| 5,709,704 A | 1/1998 | Nott et al. |
| 5,713,853 A | 2/1998 | Clark |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Daniel et al. |
| 5,827,304 A | 10/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,947,995 A | 9/1999 | Samuels |
| 6,063,113 A | 5/2000 | Kavteladze et al. |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul et al. |
| 6,238,412 B1 | 5/2001 | Dubrul et al. |
| 6,245,087 B1 | 6/2001 | Addis |
| 6,251,122 B1 | 6/2001 | Tsukemik |
| 6,254,571 B1 | 7/2001 | Hart |
| 6,264,663 B1 | 7/2001 | Cano |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates |
| 6,350,271 B1 | 2/2002 | Kurz et al. |
| 6,361,545 B1 | 3/2002 | Macoviak et al. |
| 6,375,668 B1 | 4/2002 | Gifford et al. |
| 6,383,205 B1 | 5/2002 | Samson et al. |
| 6,383,206 B1 | 5/2002 | Gillick |
| 6,402,771 B1 | 6/2002 | Palmer |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Denardo |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,530,935 B2 | 3/2003 | Wensel |
| 6,530,939 B1 | 3/2003 | Hopkins |
| 6,540,768 B1 | 4/2003 | Miller, III |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 * | 8/2003 | Mazzocchi ...... A61B 17/12022 606/200 |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothius et al. |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |

(56) References Cited

U.S. PATENT DOCUMENTS

| | | |
|---|---|---|
| 7,058,456 B2 | 6/2006 | Pierce |
| 7,063,707 B2 | 6/2006 | Bose |
| 7,175,655 B1 | 2/2007 | Molaei |
| 7,179,273 B1 | 2/2007 | Palmer et al. |
| 7,220,271 B2 | 5/2007 | Clubb |
| 7,226,464 B2 | 6/2007 | Garner et al. |
| 7,229,472 B2 | 6/2007 | DePalma et al. |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Clubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin, Jr. et al. |
| 7,618,434 B2 | 11/2009 | Santra |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,819,893 B2 | 10/2010 | Brady et al. |
| 7,828,815 B2 | 11/2010 | Mazzocchi |
| 7,828,816 B2 | 11/2010 | Mazzocchi et al. |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne et al. |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu |
| 8,361,095 B2 | 1/2013 | Osborne |
| 8,366,663 B2 | 2/2013 | Fiorella et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Martin et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Imamura et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |

(56) References Cited

U.S. PATENT DOCUMENTS

| | | |
|---|---|---|
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 2001/0001315 A1 | 5/2001 | Bates |
| 2001/0016755 A1 | 8/2001 | Addis |
| 2001/0051810 A1 | 12/2001 | Dubrul |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter et al. |
| 2002/0052620 A1 | 5/2002 | Barbut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0040772 A1 | 2/2003 | Hyodoh et al. |
| 2003/0050663 A1 | 3/2003 | Khachin |
| 2003/0125798 A1 | 7/2003 | Martin |
| 2003/0130682 A1 | 7/2003 | Broome et al. |
| 2003/0144687 A1 | 7/2003 | Brady et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | White |
| 2003/0171769 A1 | 9/2003 | Barbut |
| 2003/0176884 A1 | 9/2003 | Berrada et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0236533 A1 | 12/2003 | Wilson |
| 2004/0064179 A1* | 4/2004 | Linder .................. A61F 2/013 623/1.11 |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung et al. |
| 2004/0153118 A1 | 8/2004 | Clubb et al. |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0125024 A1 | 6/2005 | Sepetka |
| 2005/0171566 A1 | 8/2005 | Kanamaru |
| 2005/0216030 A1 | 9/2005 | Sepetka |
| 2005/0216050 A1 | 9/2005 | Sepetka |
| 2005/0228417 A1 | 10/2005 | Teitelbaum et al. |
| 2005/0267491 A1 | 12/2005 | Kellet et al. |
| 2005/0288686 A1 | 12/2005 | Sepetka |
| 2006/0009799 A1 | 1/2006 | Kleshinski et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1* | 7/2006 | Freudenthal .......... A61B 17/221 606/114 |
| 2006/0161187 A1 | 7/2006 | Levine et al. |
| 2006/0195137 A1 | 8/2006 | Sepetka et al. |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0156170 A1 | 7/2007 | Hancock |
| 2007/0165170 A1 | 7/2007 | Fukuda |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0225749 A1 | 9/2007 | Martin et al. |
| 2007/0244505 A1 | 10/2007 | Gilson et al. |
| 2007/0270902 A1 | 11/2007 | Slazas et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0312681 A1 | 12/2008 | Ansel |
| 2009/0024157 A1 | 1/2009 | Anukhin |
| 2009/0069828 A1* | 3/2009 | Martin ................ A61B 17/221 606/159 |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0292297 A1 | 11/2009 | Ferrere |
| 2009/0292307 A1 | 11/2009 | Razack |
| 2009/0299393 A1* | 12/2009 | Martin ................ A61B 17/221 606/159 |
| 2009/0306702 A1 | 12/2009 | Miloslavski |
| 2010/0004607 A1 | 1/2010 | Wilson et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |

(56) References Cited

U.S. PATENT DOCUMENTS

| | | |
|---|---|---|
| 2010/0211094 A1 | 8/2010 | Sargent, Jr. |
| 2010/0268264 A1* | 10/2010 | Bonnette ............... A61B 17/221 606/200 |
| 2010/0268265 A1* | 10/2010 | Krolik .................. A61B 17/221 606/200 |
| 2010/0318178 A1 | 12/2010 | Rapaport et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0054504 A1 | 5/2011 | Wolf et al. |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0276120 A1 | 11/2011 | Gilson et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0089216 A1 | 4/2012 | Rapaport et al. |
| 2012/0101510 A1 | 4/2012 | Lenker et al. |
| 2012/0143237 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0296362 A1 | 11/2012 | Cam et al. |
| 2012/0316600 A1 | 12/2012 | Ferrera et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0046359 A1 | 2/2014 | Bowman et al. |
| 2014/0121672 A1 | 5/2014 | Folk |
| 2014/0128905 A1 | 5/2014 | Molaei |
| 2014/0180377 A1 | 6/2014 | Bose et al. |
| 2014/0194919 A1 | 7/2014 | Losordo et al. |
| 2014/0200608 A1 | 7/2014 | Brady et al. |
| 2014/0236220 A1 | 8/2014 | Inoue |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0112376 A1 | 4/2015 | Molaei et al. |
| 2015/0133990 A1 | 5/2015 | Davidson |
| 2015/0164523 A1 | 6/2015 | Brady et al. |
| 2015/0250497 A1 | 9/2015 | Marks et al. |
| 2015/0257775 A1 | 9/2015 | Gilvarry et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Seifert et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |

(56) References Cited

U.S. PATENT DOCUMENTS

| | | |
|---|---|---|
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |

FOREIGN PATENT DOCUMENTS

| | | |
|---|---|---|
| DE | 102010010849 | 9/2011 |
| DE | 102010014778 | 10/2011 |
| DE | 102010024085 | 12/2011 |
| DE | 102011014586 B3 | 9/2012 |
| EP | 2301450 B1 | 3/2011 |
| EP | 2628455 A1 | 8/2013 |
| JP | 0919438 A1 | 1/1997 |
| WO | WO 94/24926 | 11/1994 |
| WO | WO 97/027808 | 8/1997 |
| WO | WO 97/038631 A | 10/1997 |
| WO | WO 99/20335 | 4/1999 |
| WO | WO 99/56801 | 11/1999 |
| WO | WO 99/60933 | 12/1999 |
| WO | WO 01/21077 | 3/2001 |
| WO | WO 02/02162 | 1/2002 |
| WO | WO 02/11627 | 2/2002 |
| WO | WO 02/43616 | 6/2002 |
| WO | WO 02/070061 | 9/2002 |
| WO | WO 02/094111 | 11/2002 |
| WO | WO 03/002006 | 1/2003 |
| WO | WO 03/030751 | 4/2003 |
| WO | WO 03/051448 | 6/2003 |
| WO | WO 2004/028571 A2 | 4/2004 |
| WO | WO 2005/000130 A1 | 1/2005 |
| WO | WO 2005/027779 A2 | 3/2005 |
| WO | WO 2006/021407 | 3/2006 |
| WO | WO 2006/031410 | 3/2006 |
| WO | WO 2006/107641 | 10/2006 |
| WO | WO 2006/135823 A2 | 12/2006 |
| WO | WO 2007/054307 | 5/2007 |
| WO | WO 2007/068424 | 6/2007 |
| WO | WO 2004/056275 A1 | 7/2007 |
| WO | WO 2008/034615 | 3/2008 |
| WO | WO 2008/051431 A1 | 5/2008 |
| WO | WO 2008/131116 | 10/2008 |
| WO | WO 2009/031338 A1 | 3/2009 |
| WO | WO 2009/076482 | 6/2009 |
| WO | WO 2009/086482 | 7/2009 |
| WO | WO 2009/105710 A1 | 8/2009 |
| WO | WO 2010/010545 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A9 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/134625 A1 | 9/2015 |
| WO | WO 2015/161365 A1 | 10/2015 |
| WO | WO 2015/179324 A2 | 11/2015 |
| WO | WO 2015/189354 A1 | 12/2015 |
| WO | WO 2016/010995 A1 | 1/2016 |

OTHER PUBLICATIONS

Office Action in U.S. Appl. No. 14/318,300, dated Nov. 19, 2014 (8 pages).

Office Action in U.S. Appl. No. 14/318,300, dated Apr. 8, 2015 (8 pages).

International Search Report of PCT/IE2012/000011, dated Oct. 10, 2012 (3 pages).

Written Opinion and International Search Report, dated Jul. 27, 2011, from international Application No. PCT/IE2011/000026 (8 pages).

International Search Report of PCT/IE2011/000057, dated Feb. 3, 2012 (5 pages).

Notice of Allowance in U.S. Appl. No. 12/737,527, dated Jun. 2, 2014 (11 pages).

Office Action in U.S. Appl. No. 12/737,527, dated Jun. 11, 2013 (10 pages).

\* cited by examiner

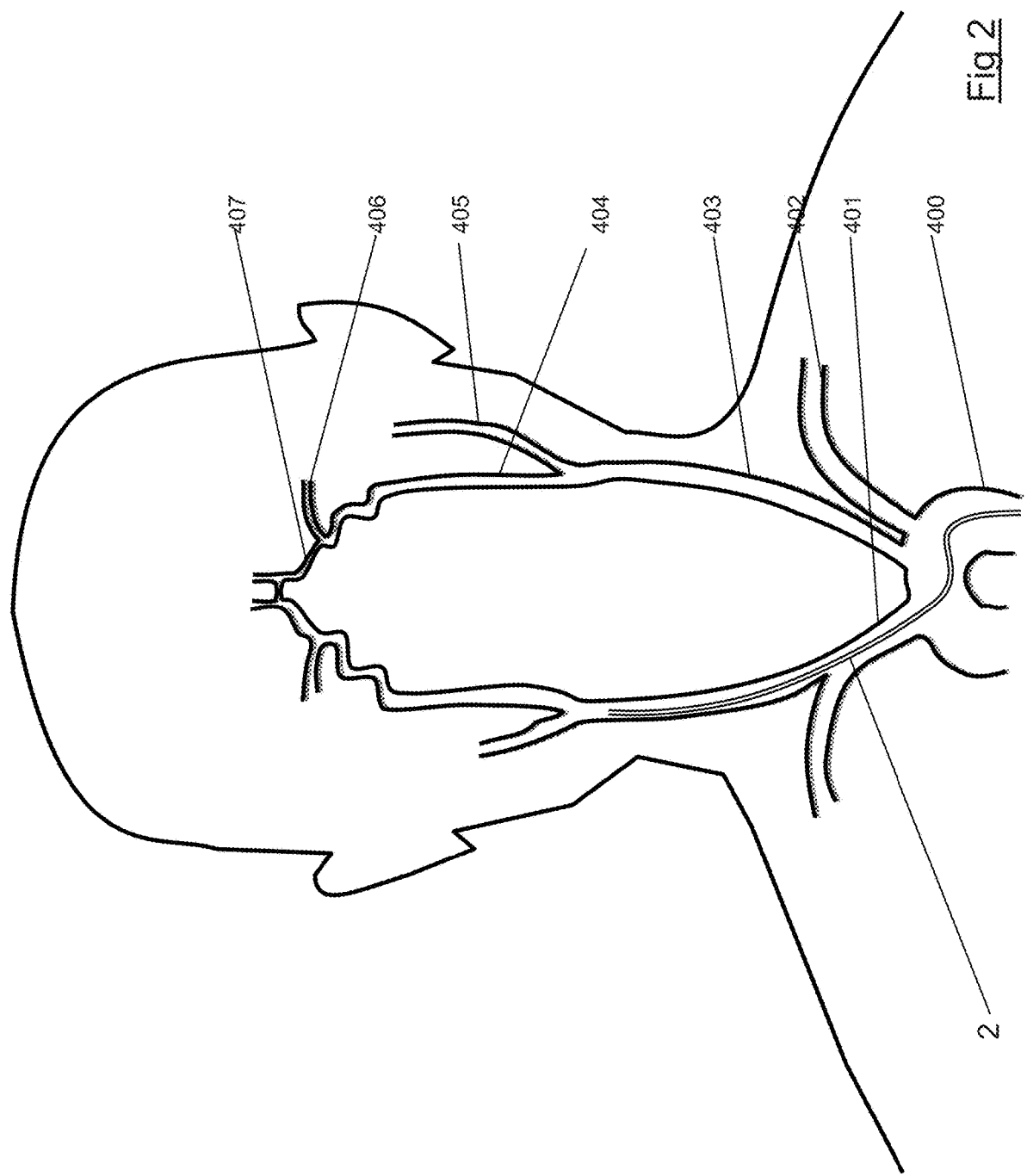

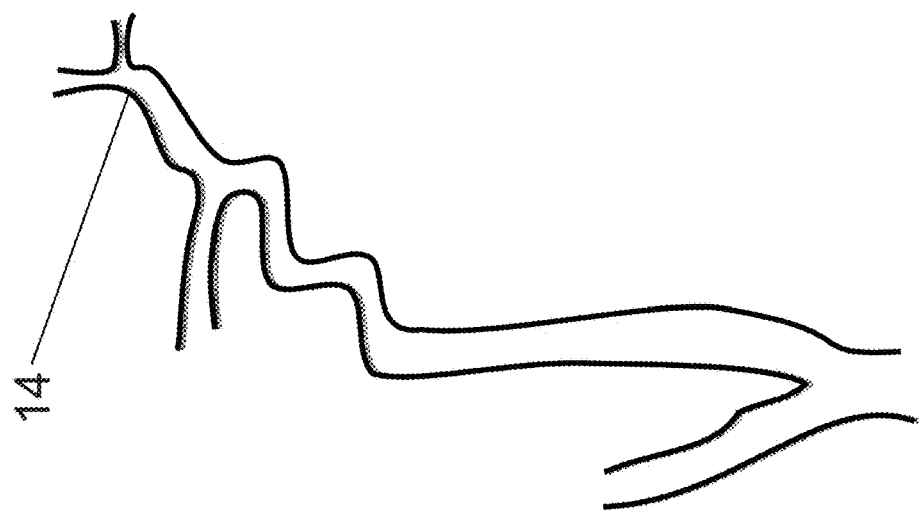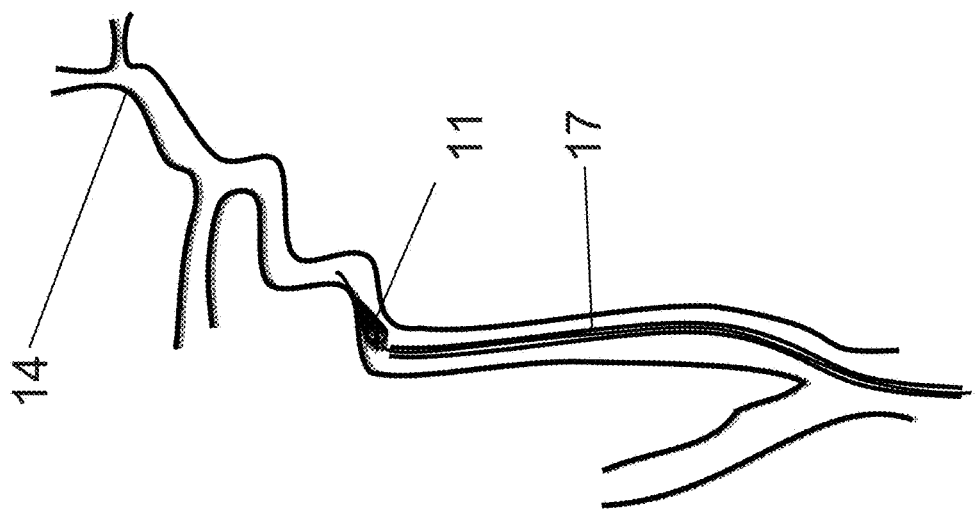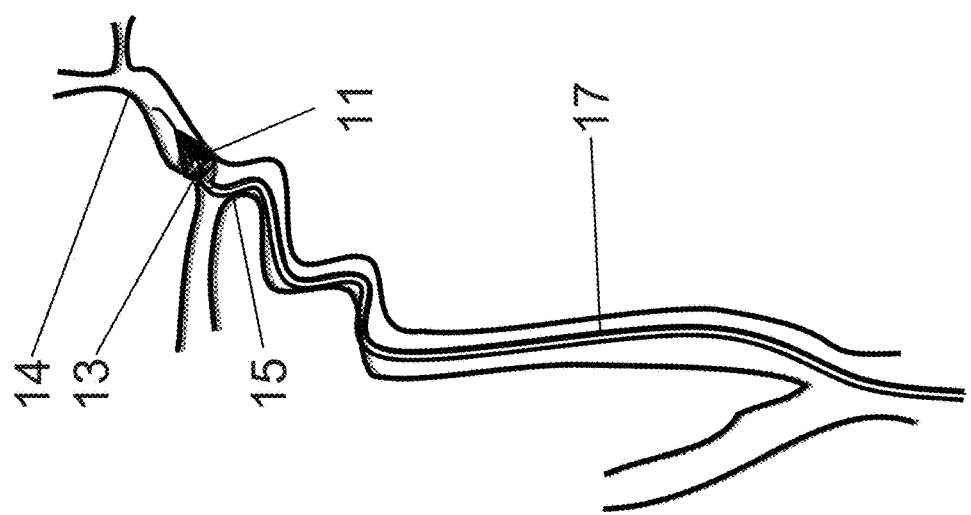

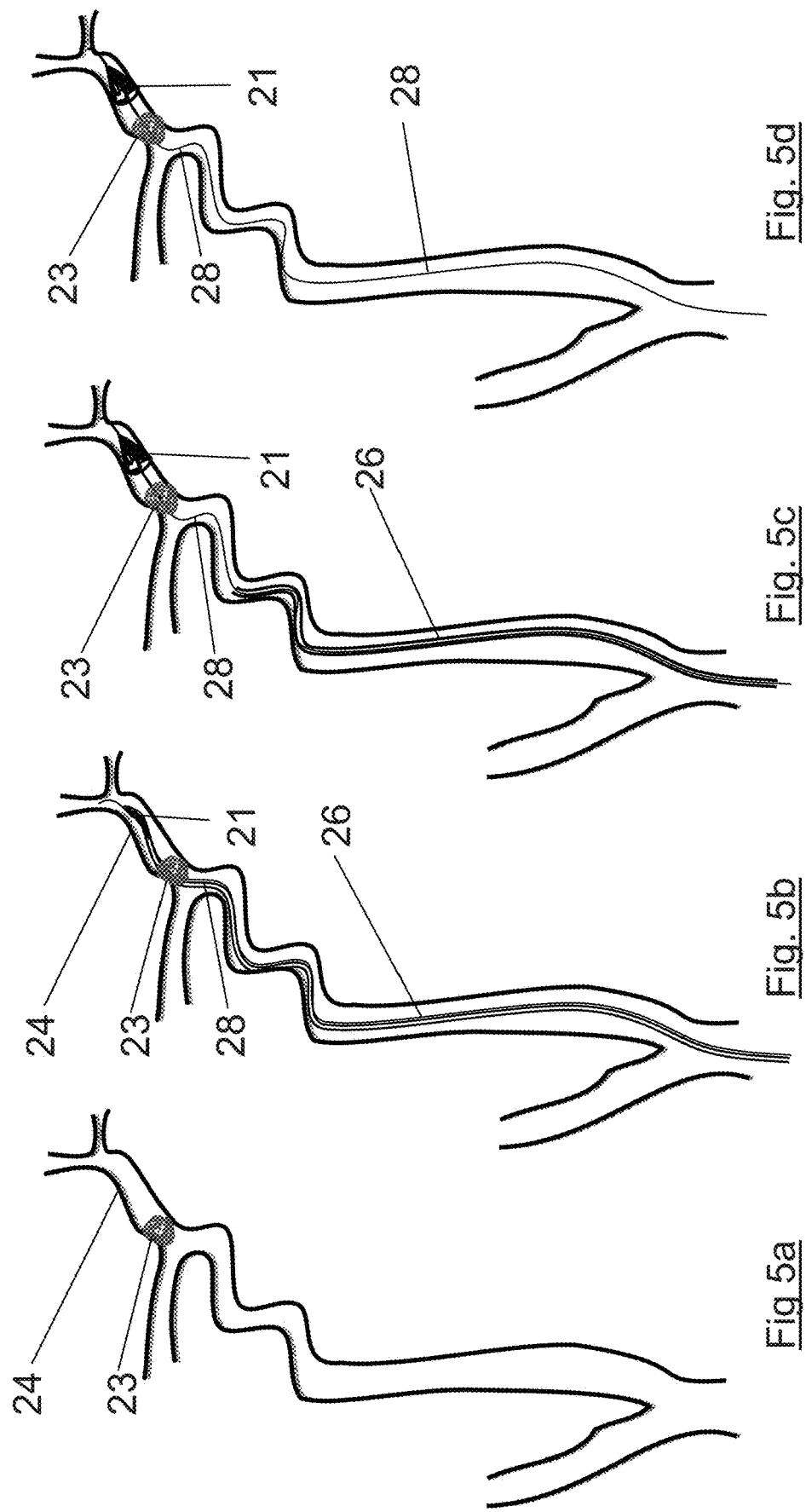

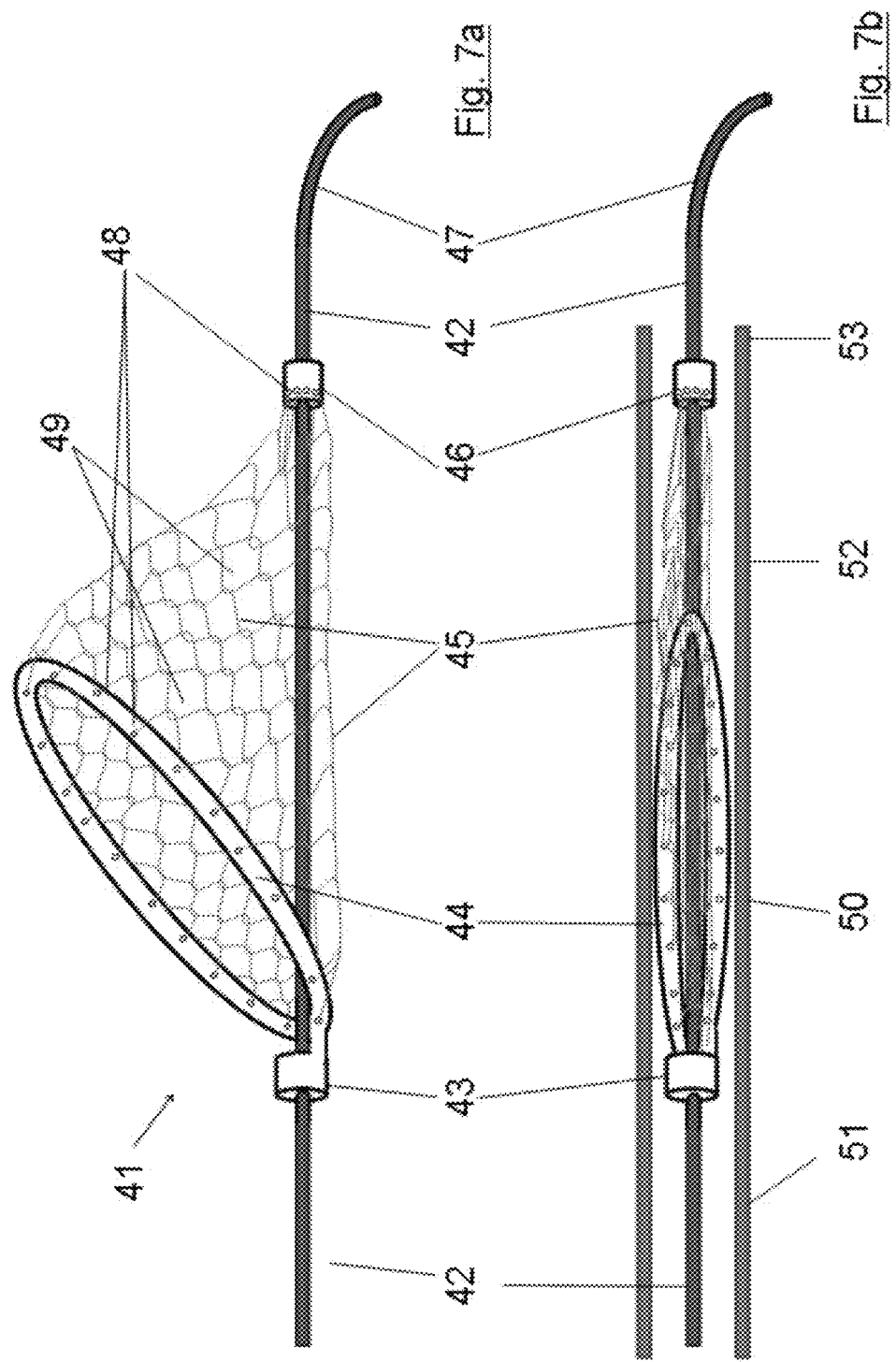

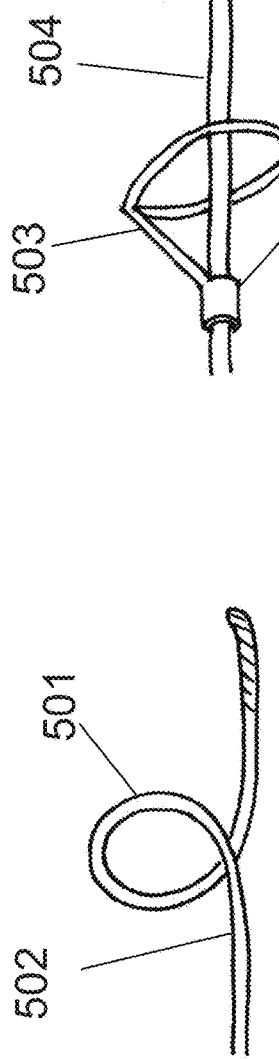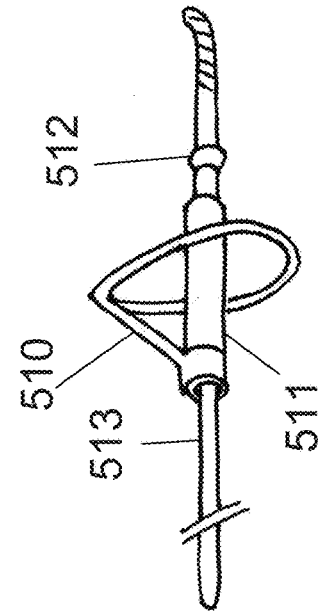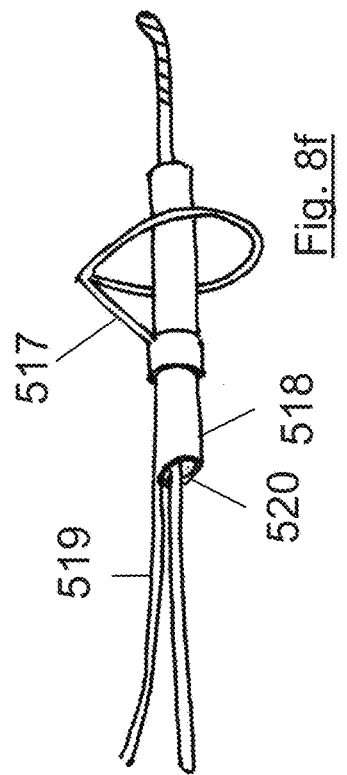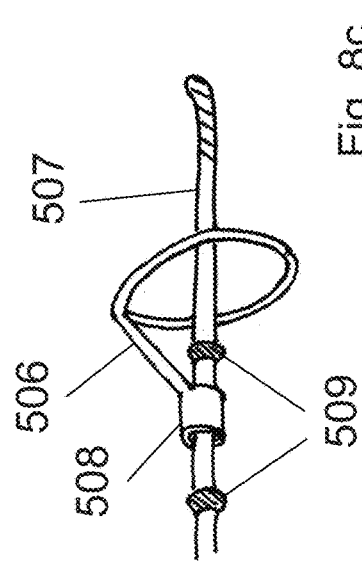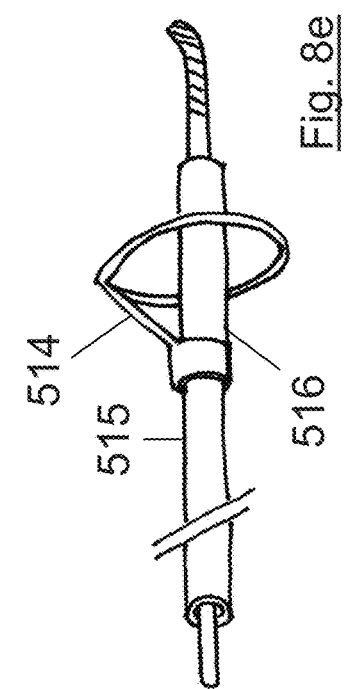

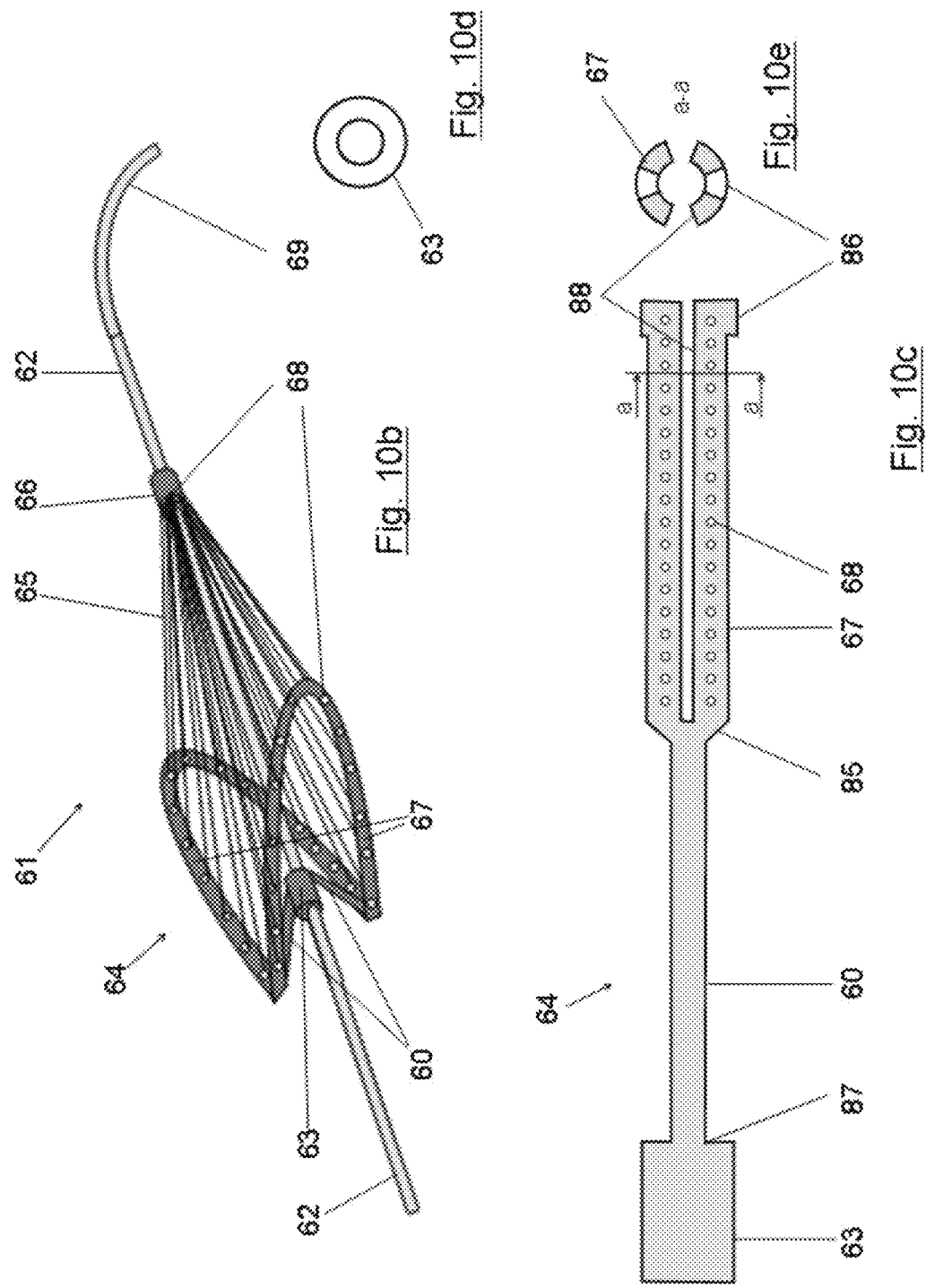

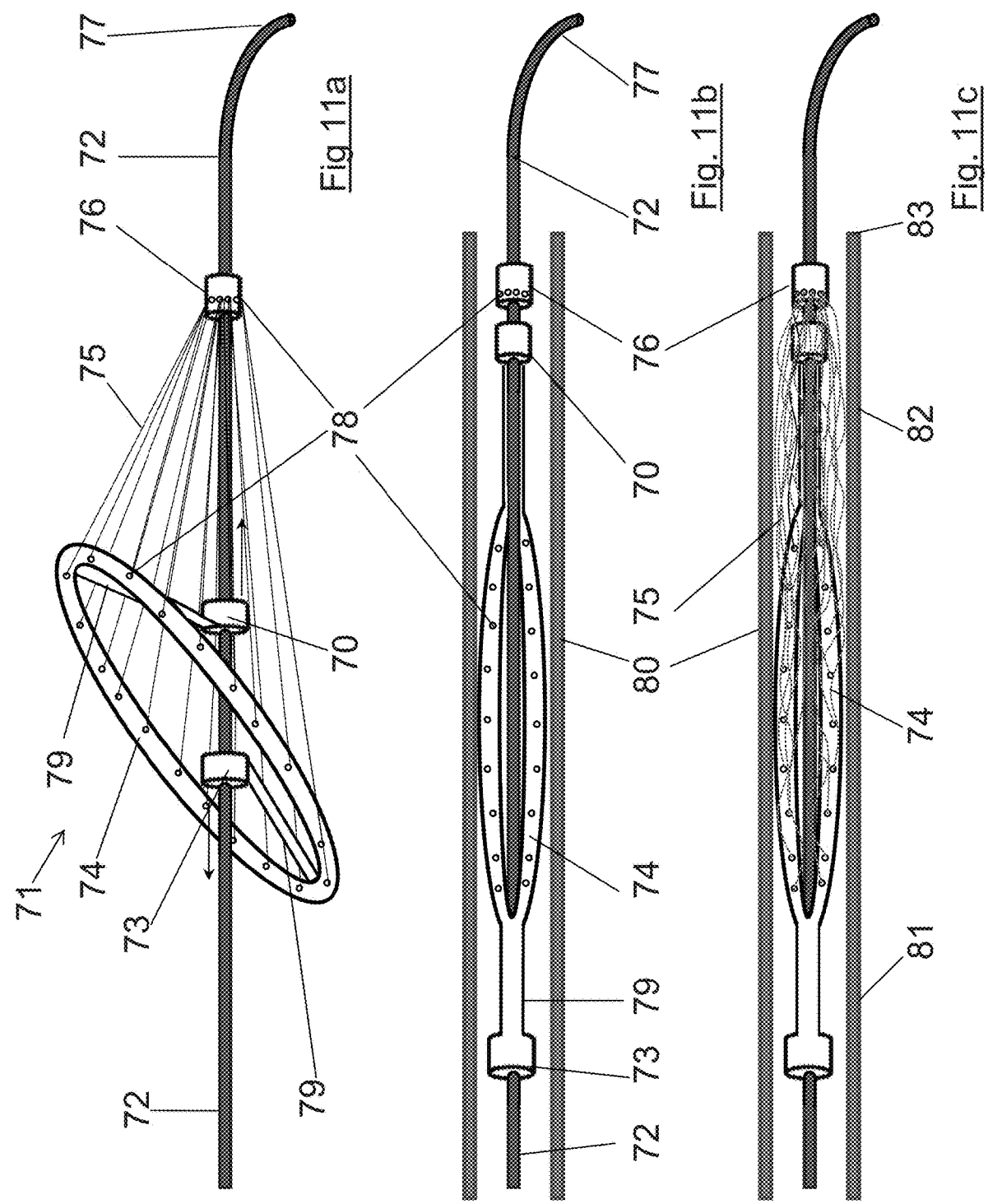

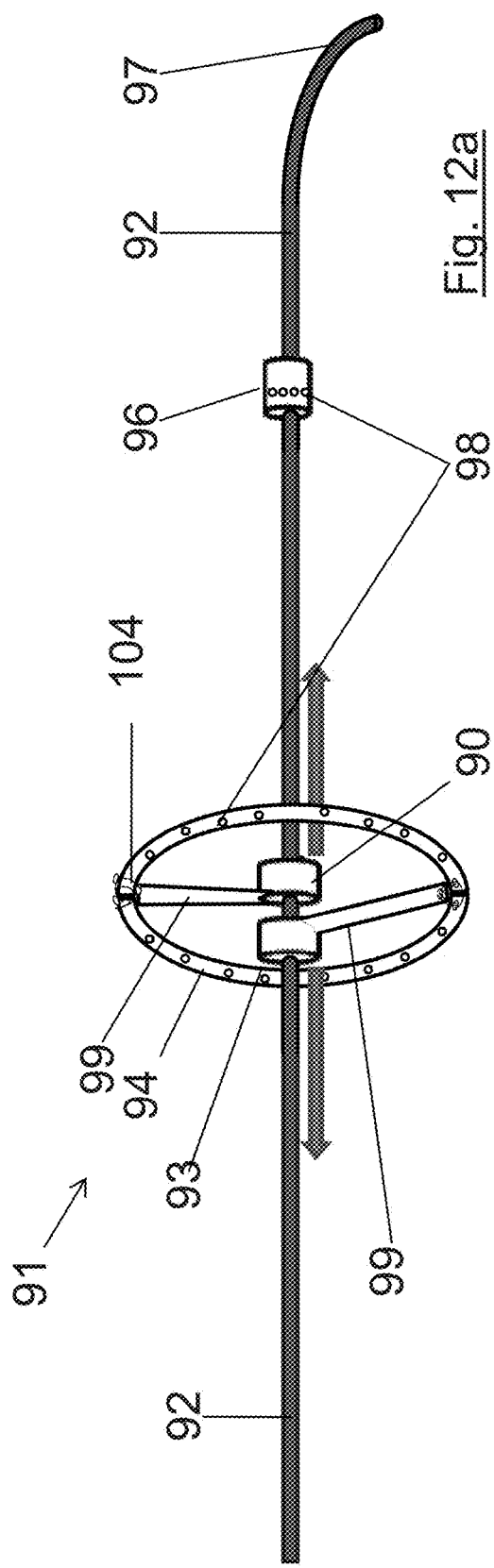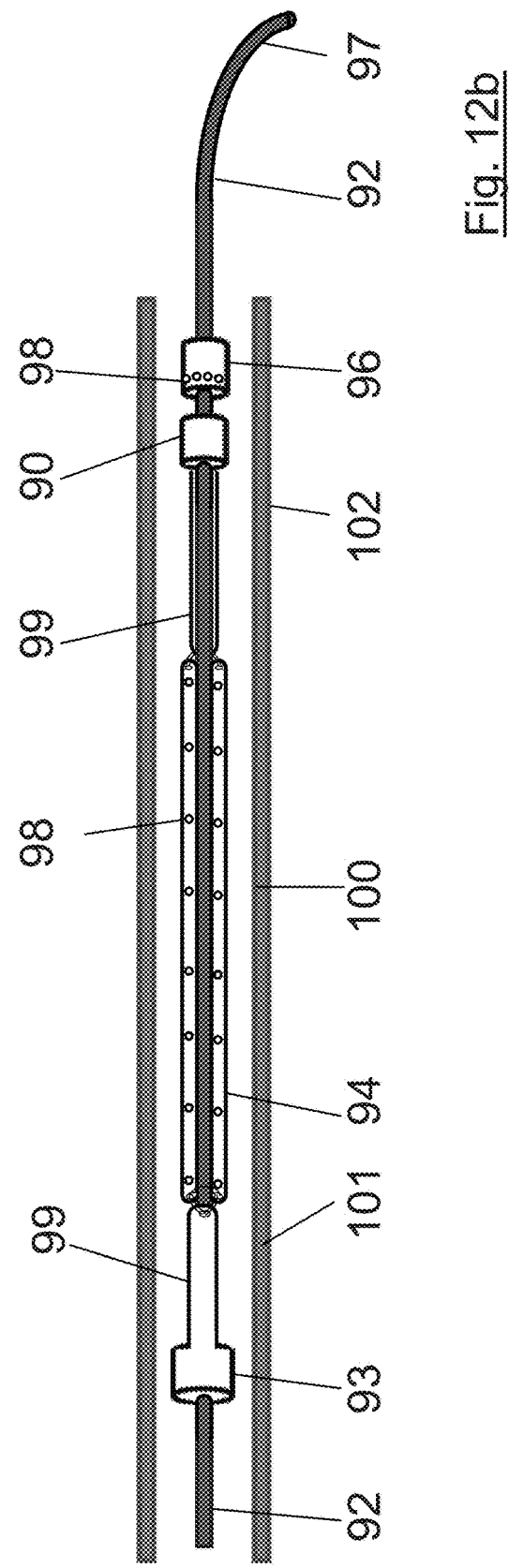

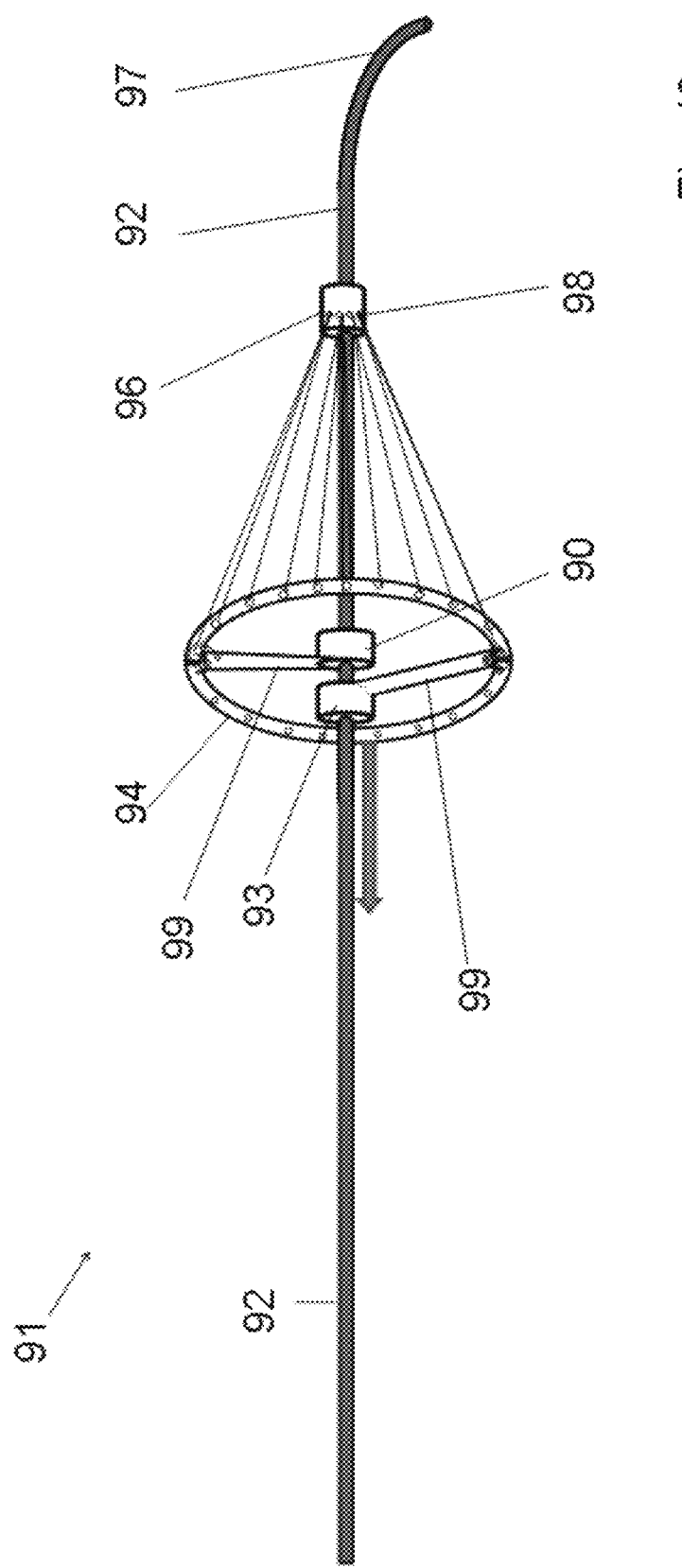

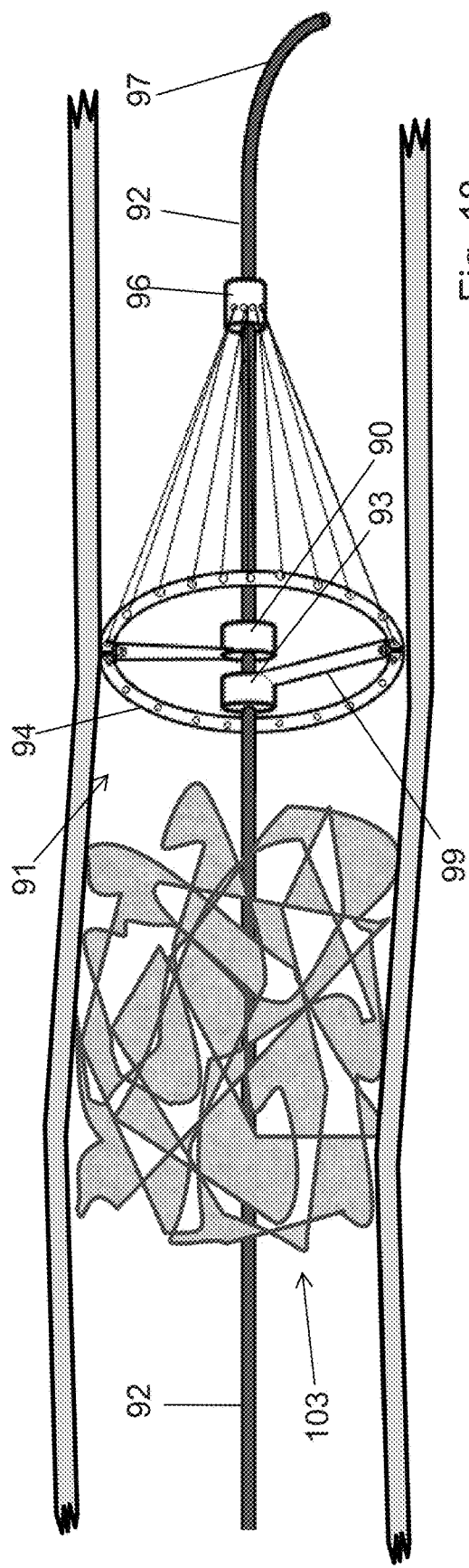
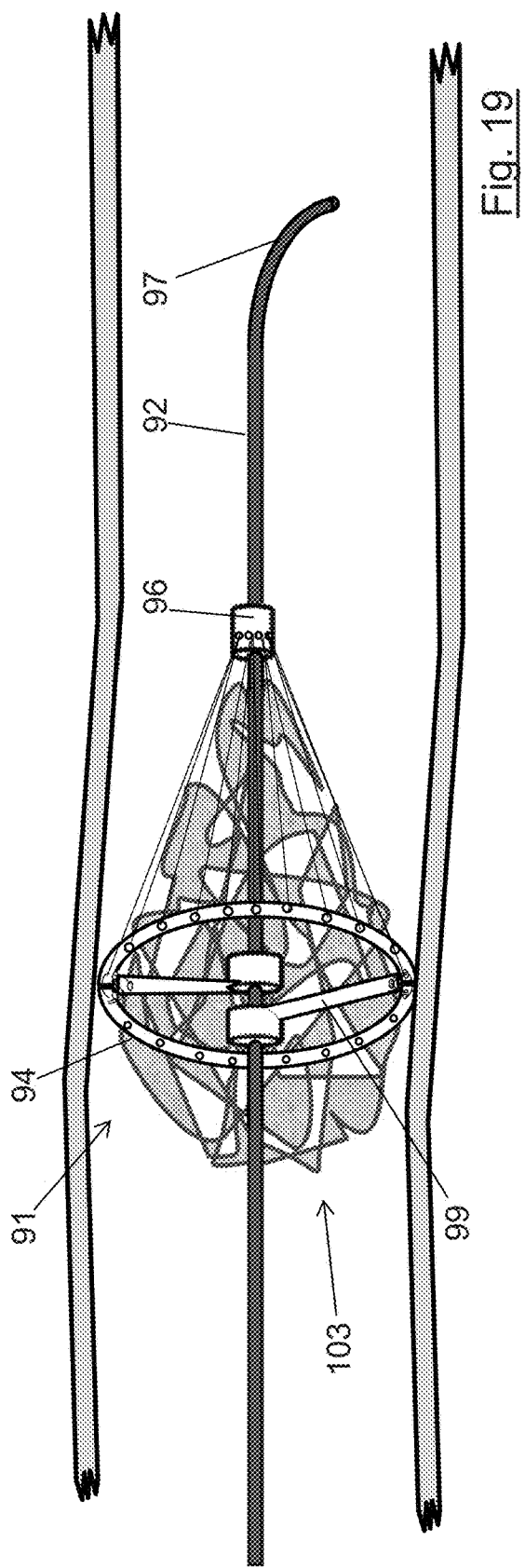

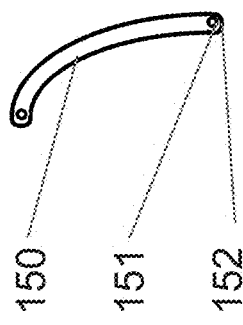
Fig. 20c
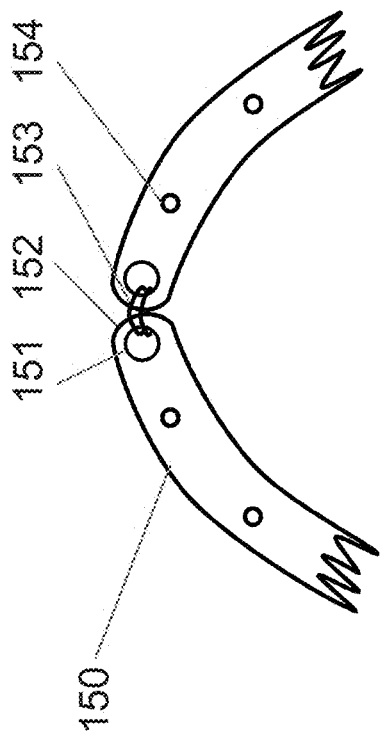
Fig. 20d
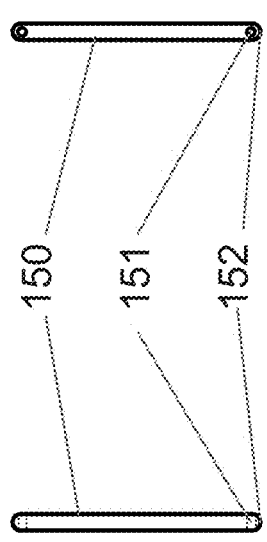
Fig. 20b
Fig. 20a
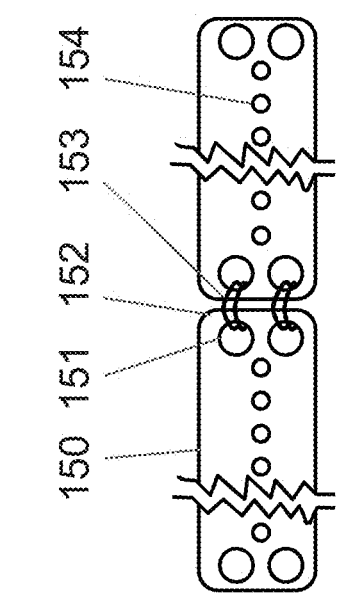
Fig. 20e

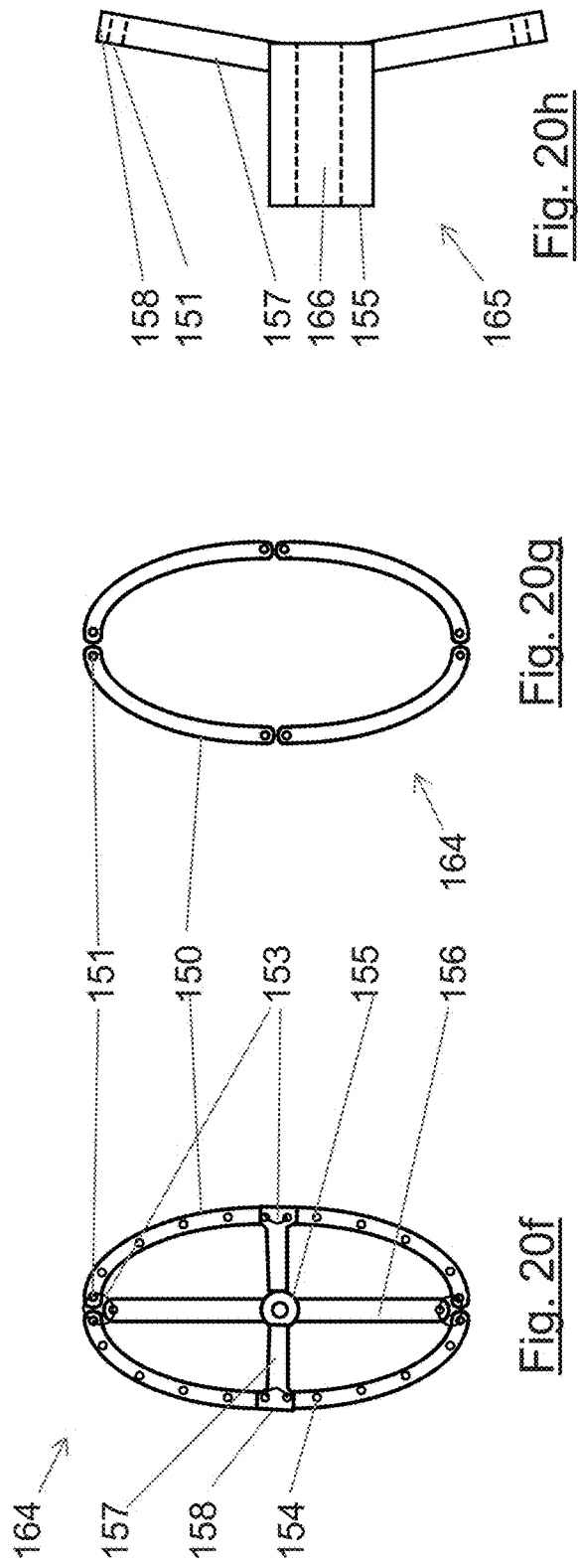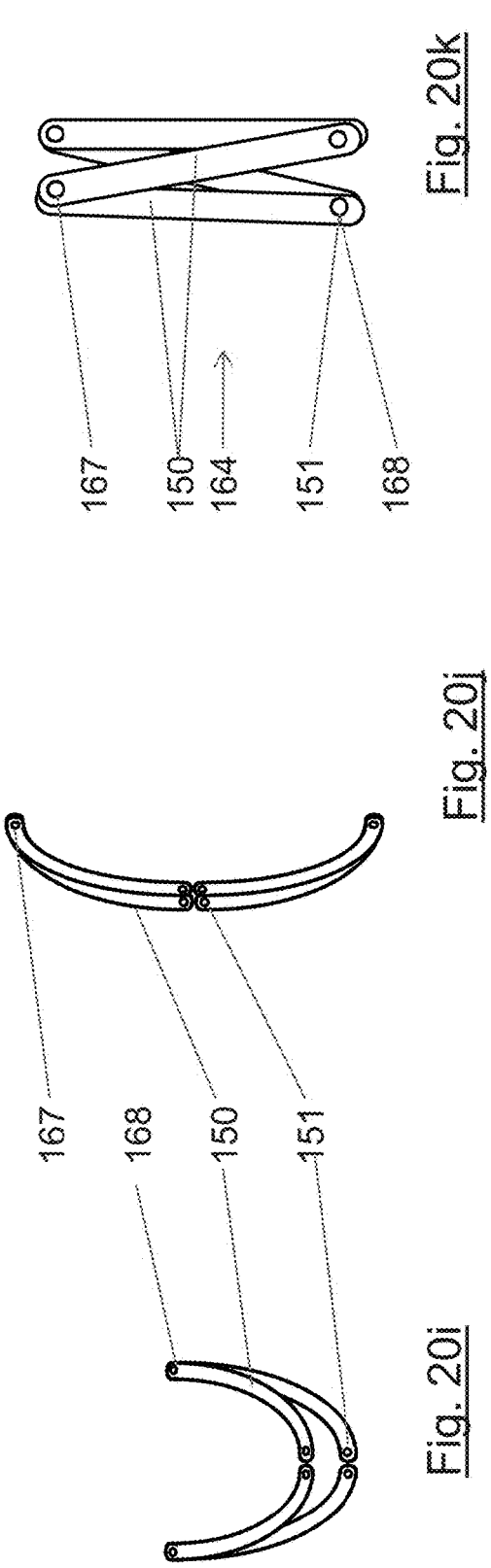

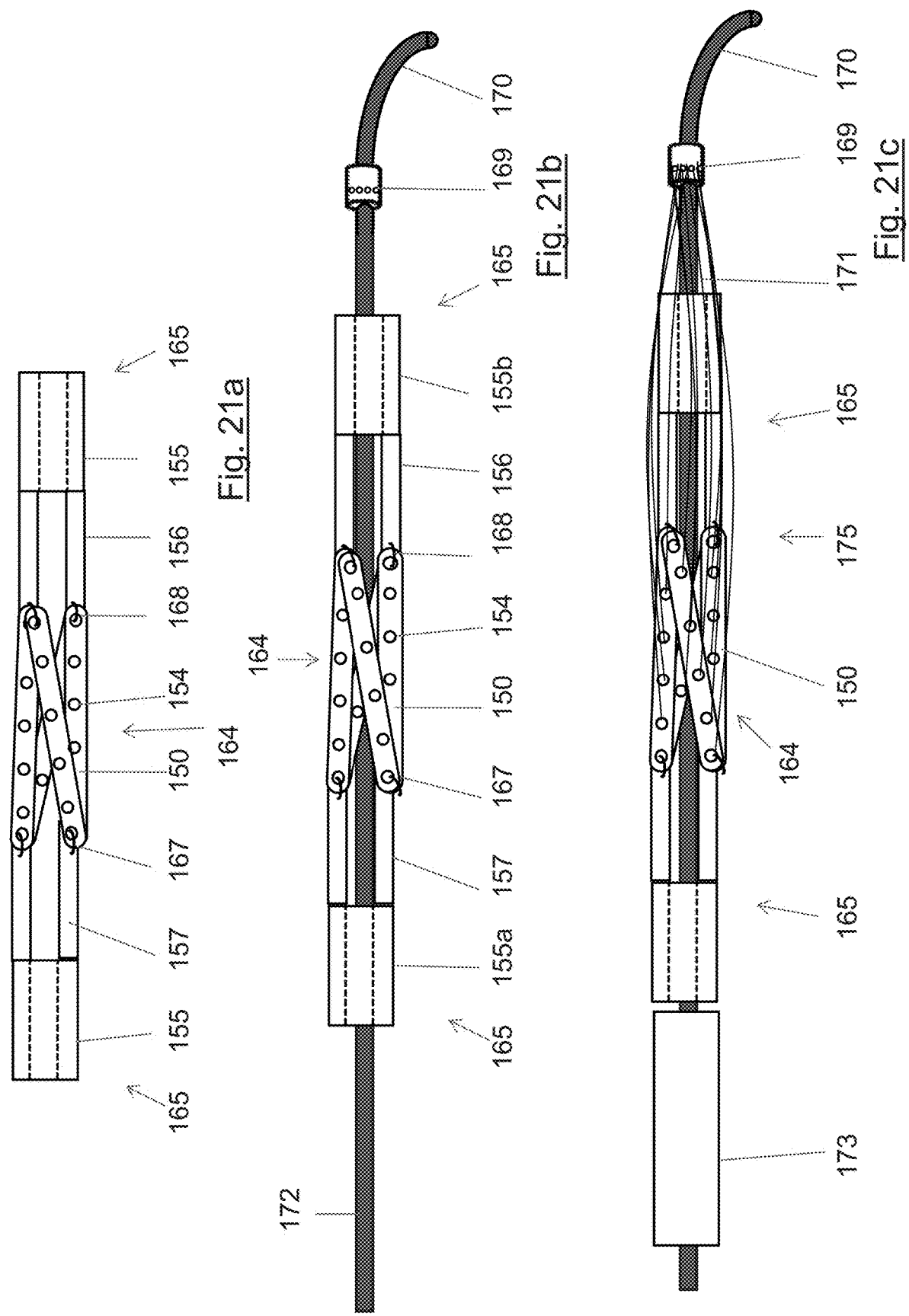

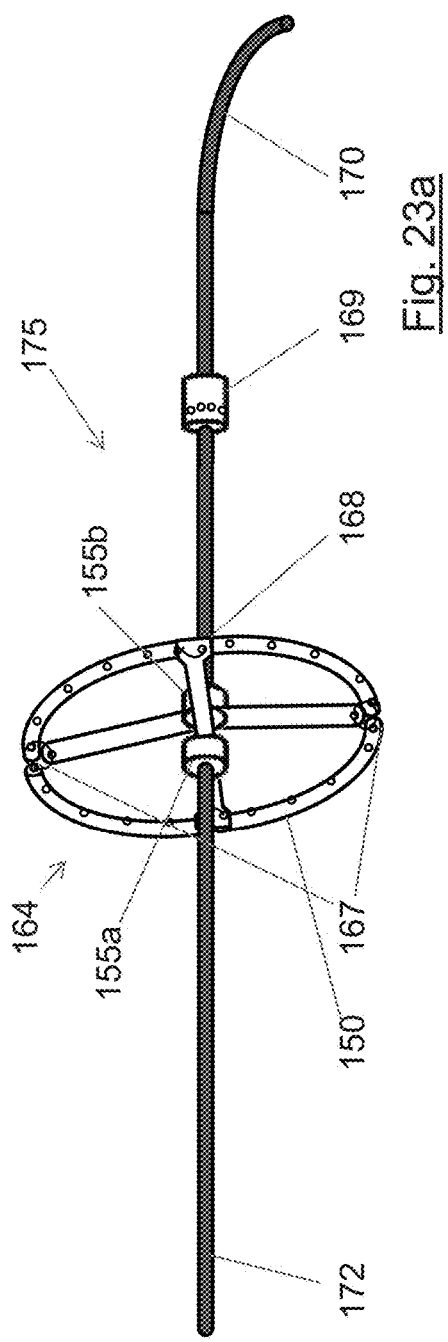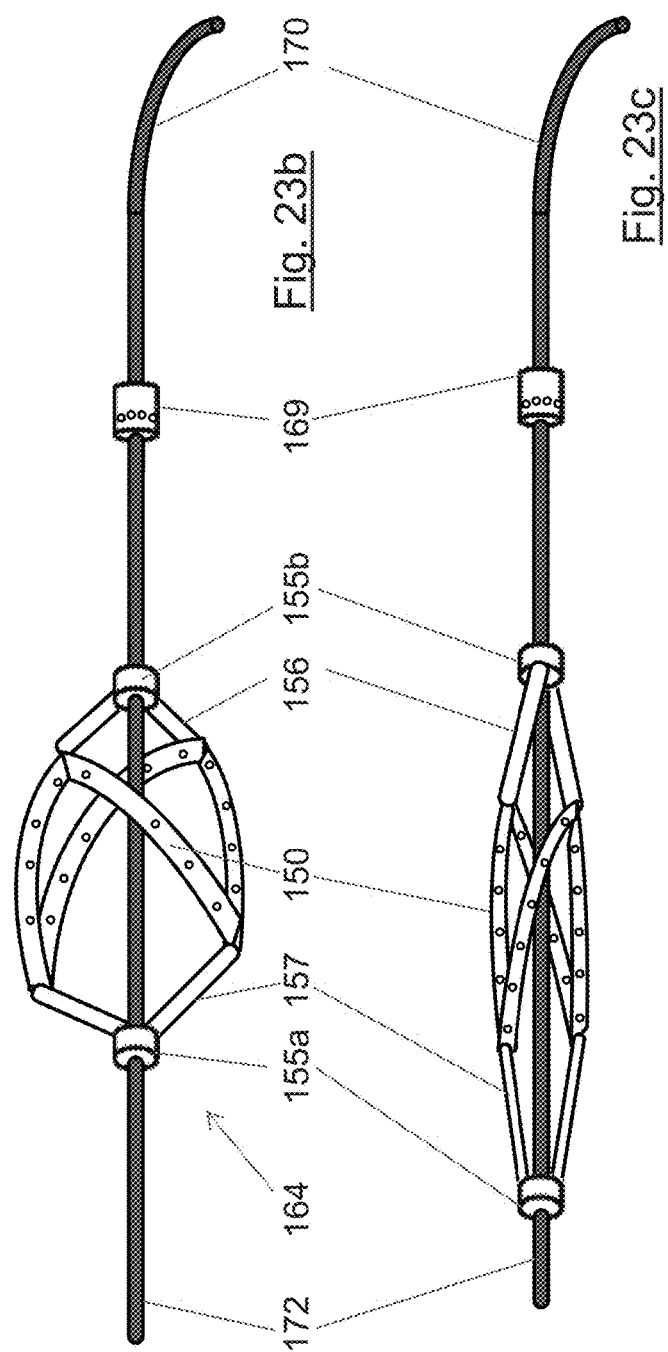

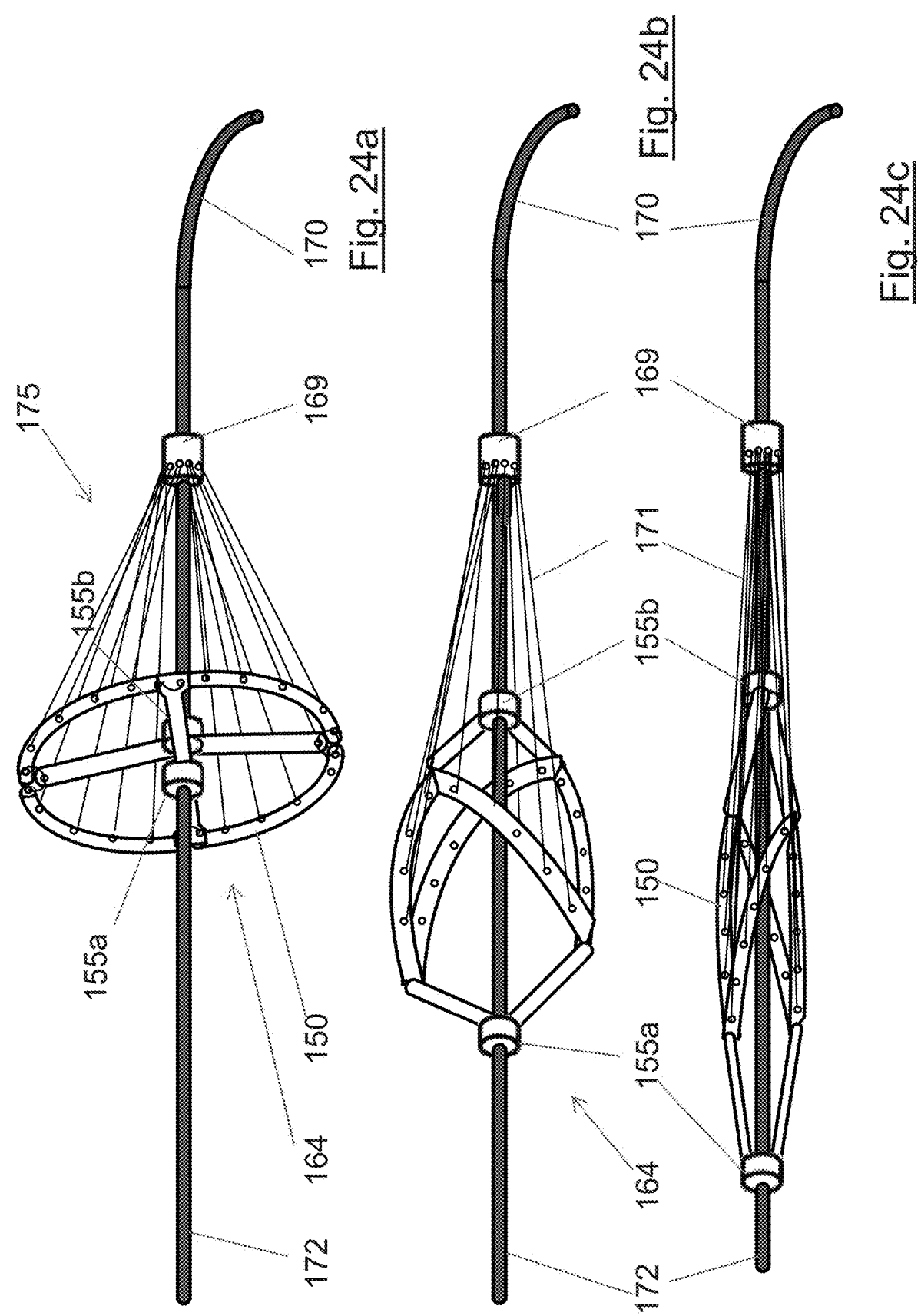

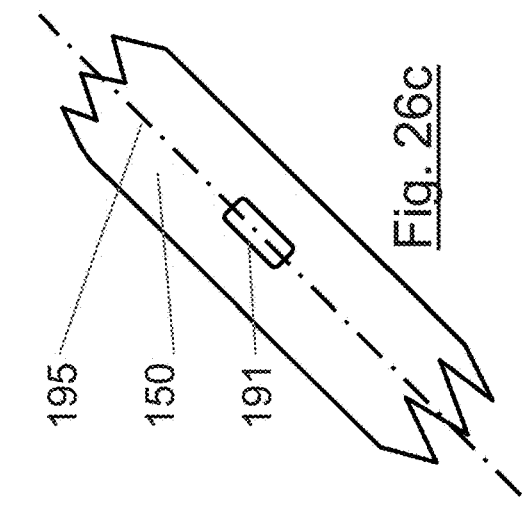
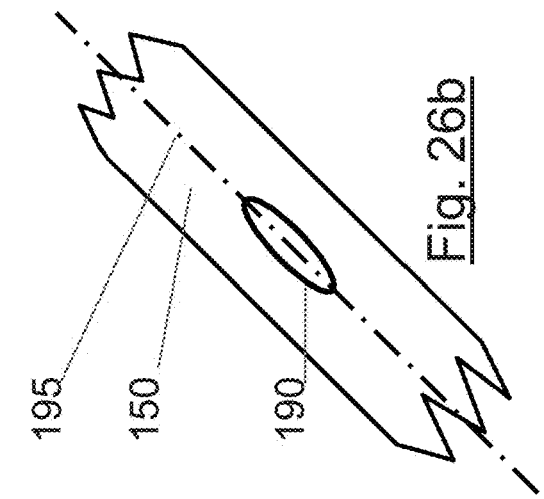
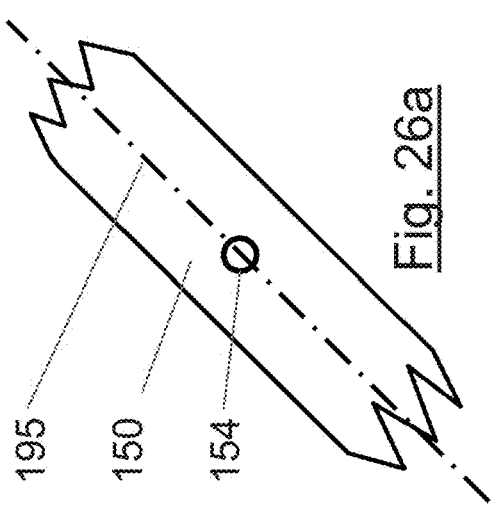
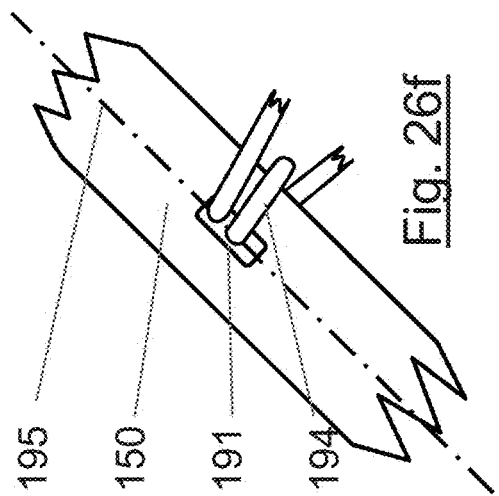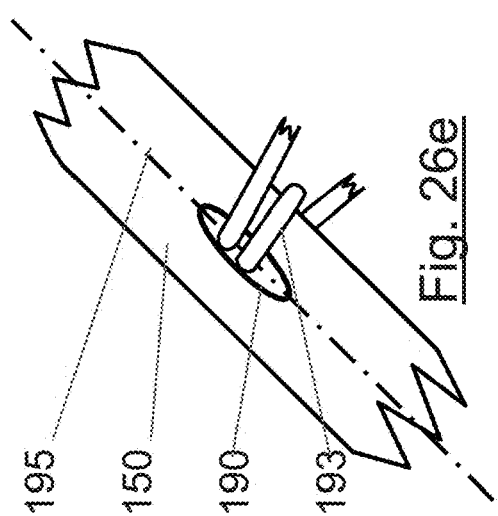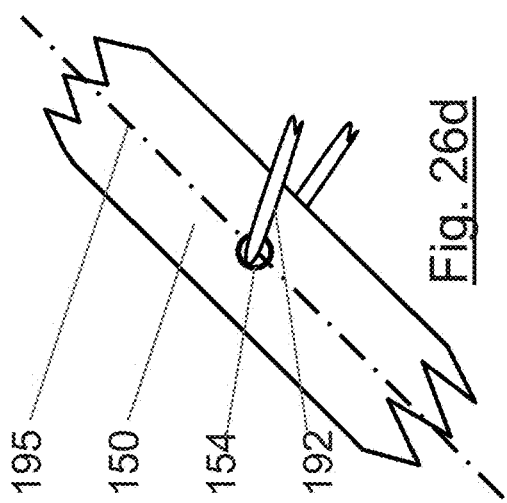

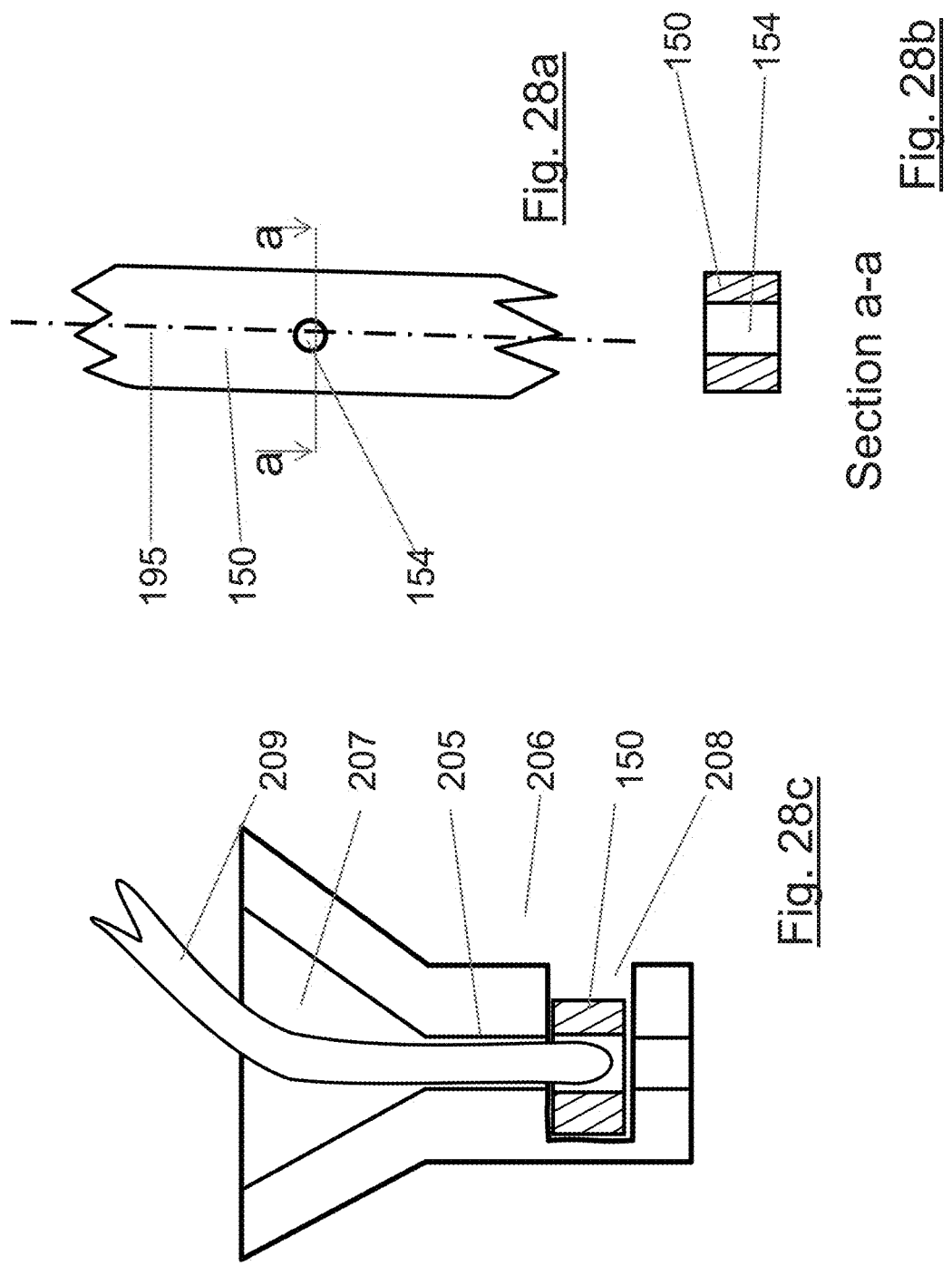

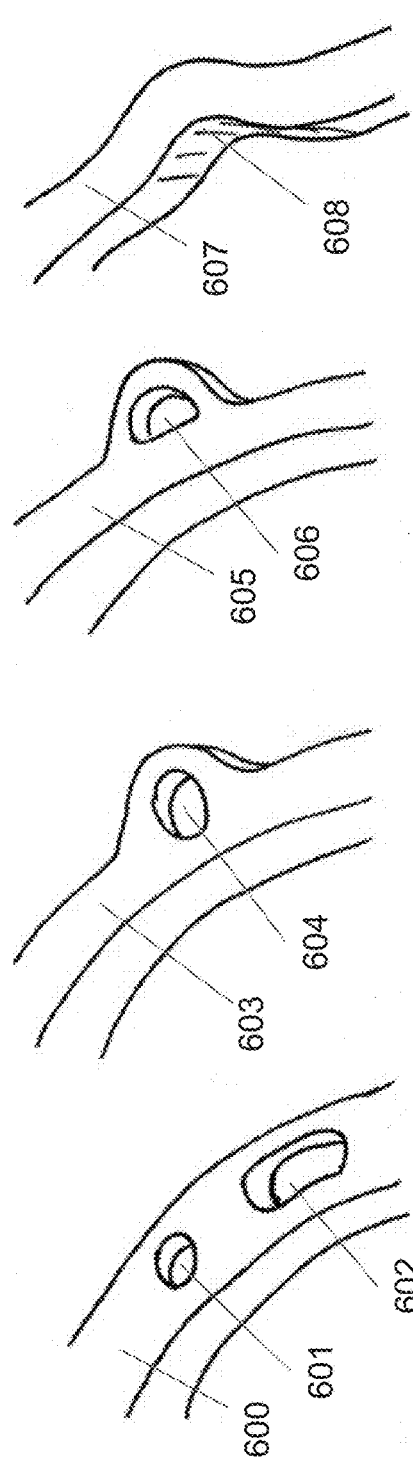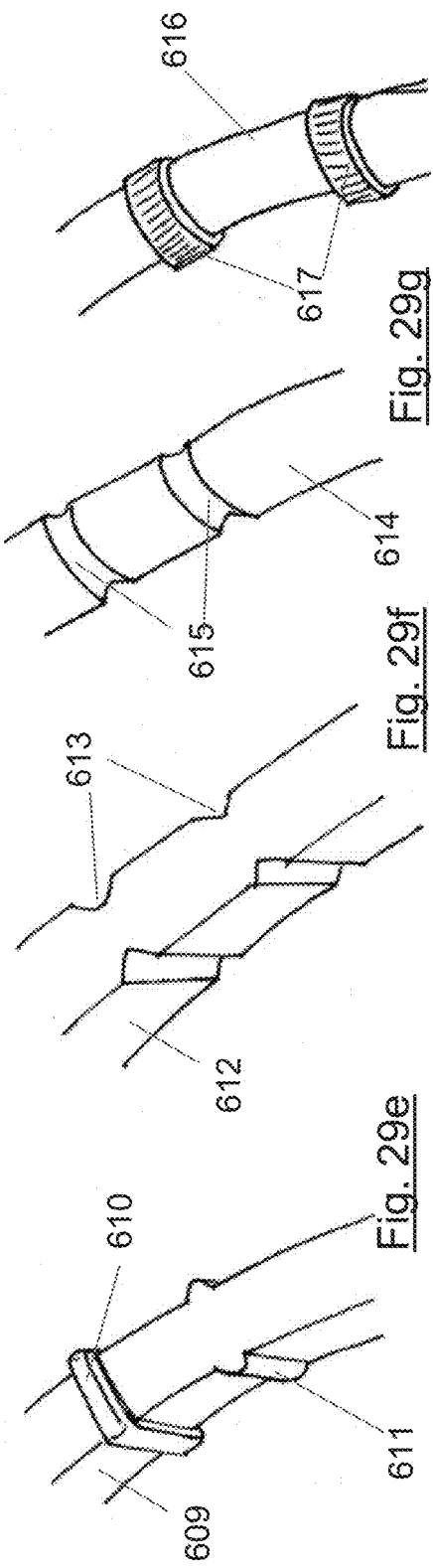

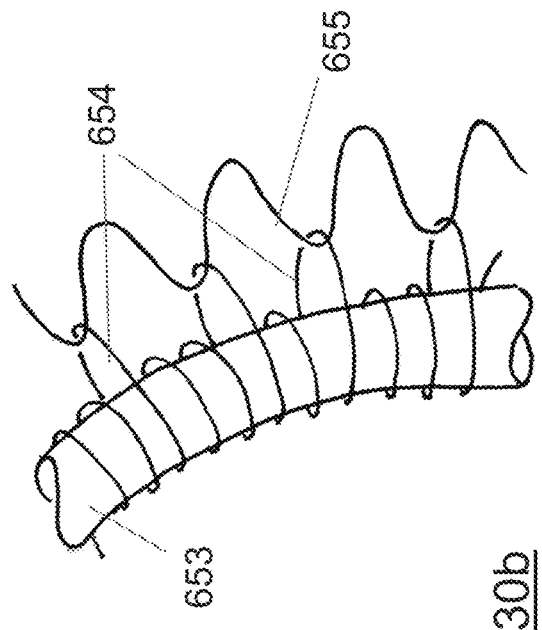
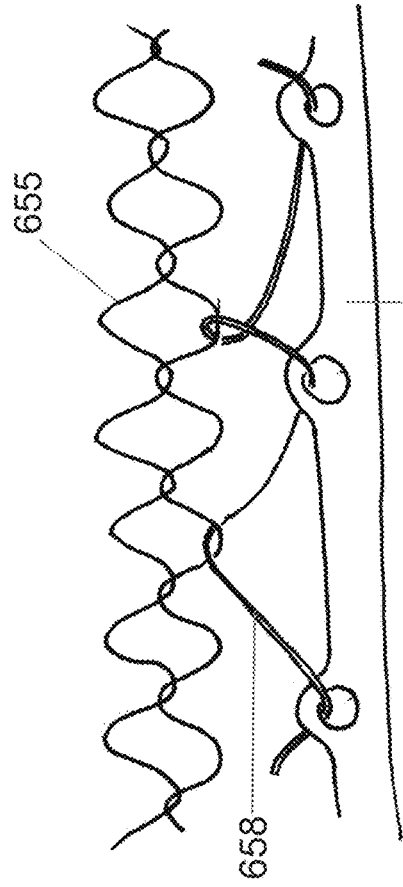
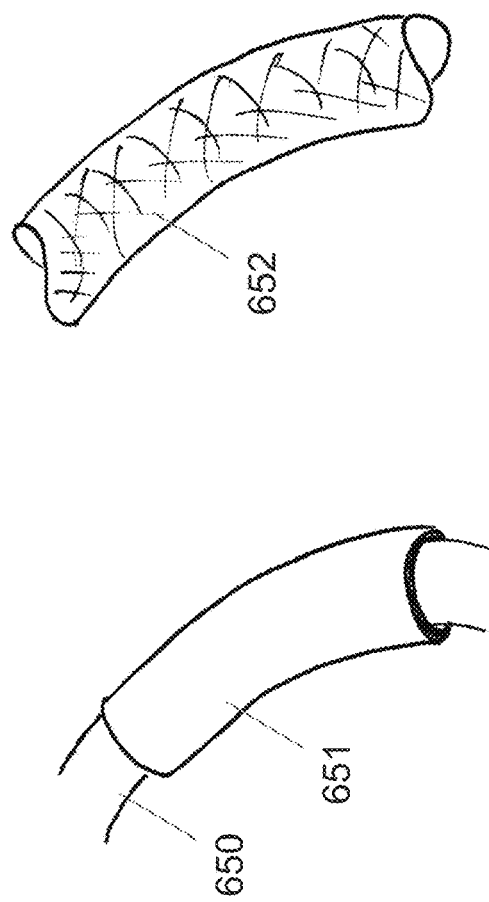
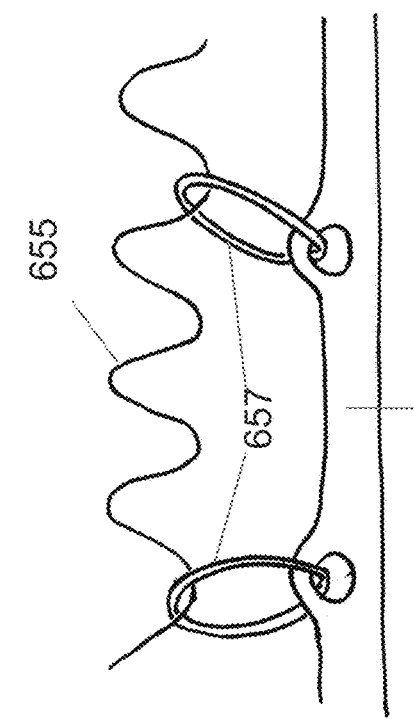

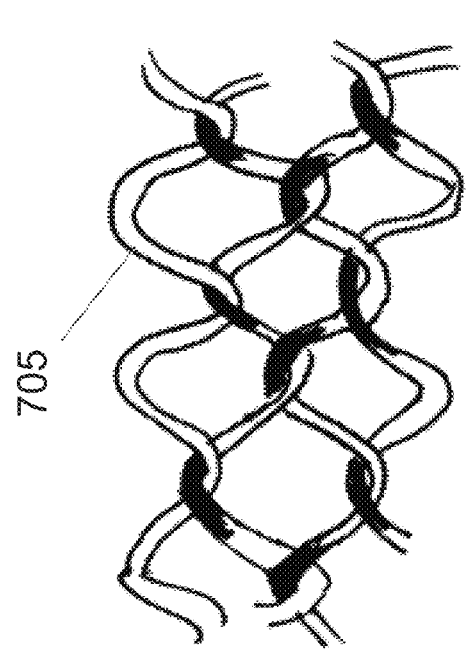
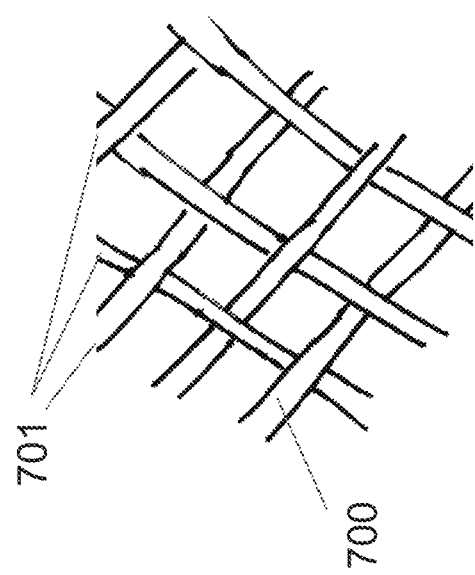
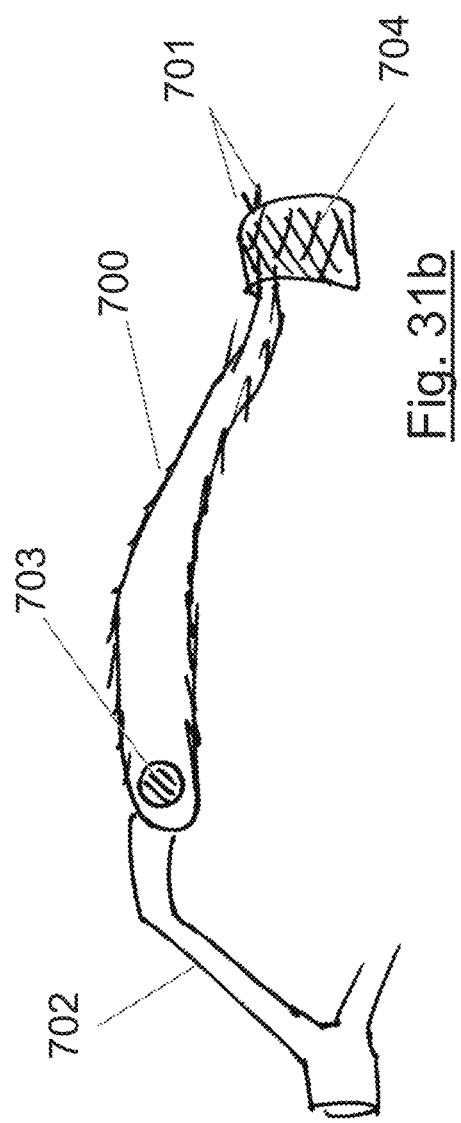

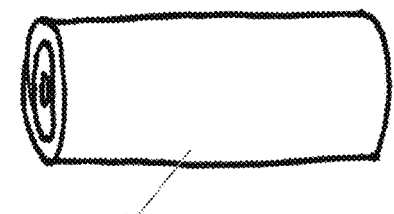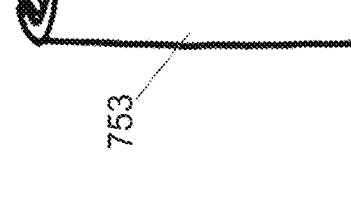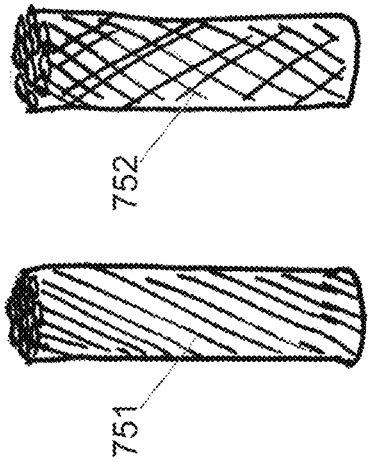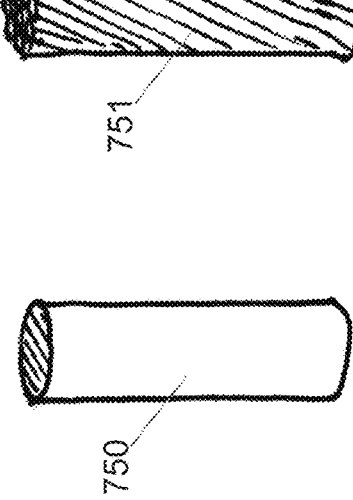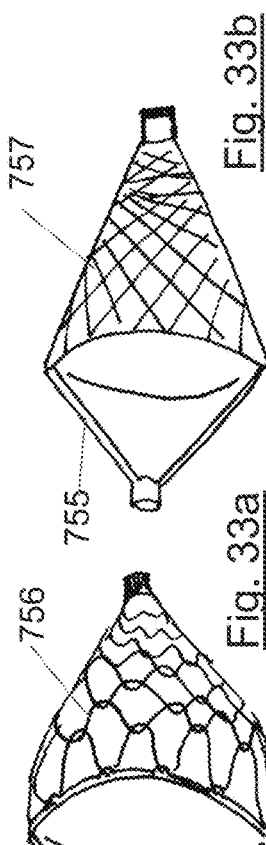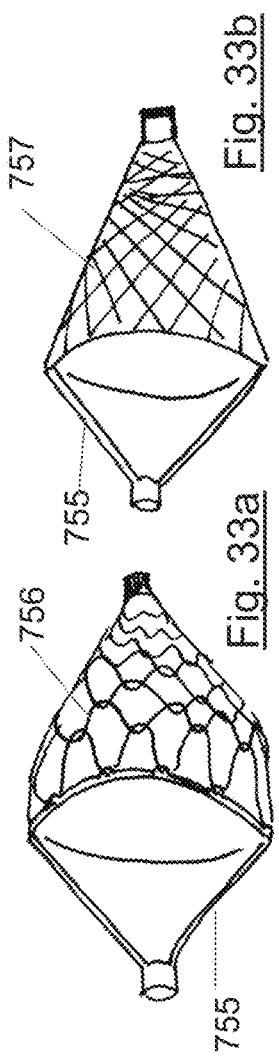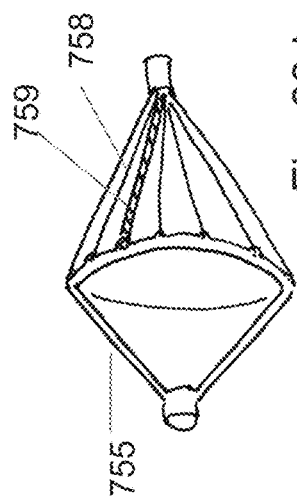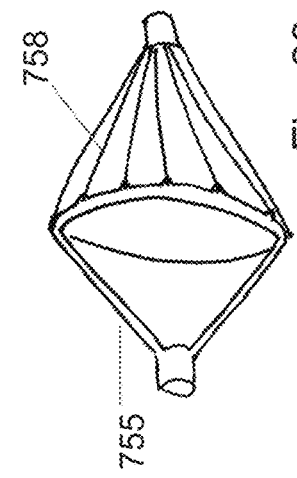

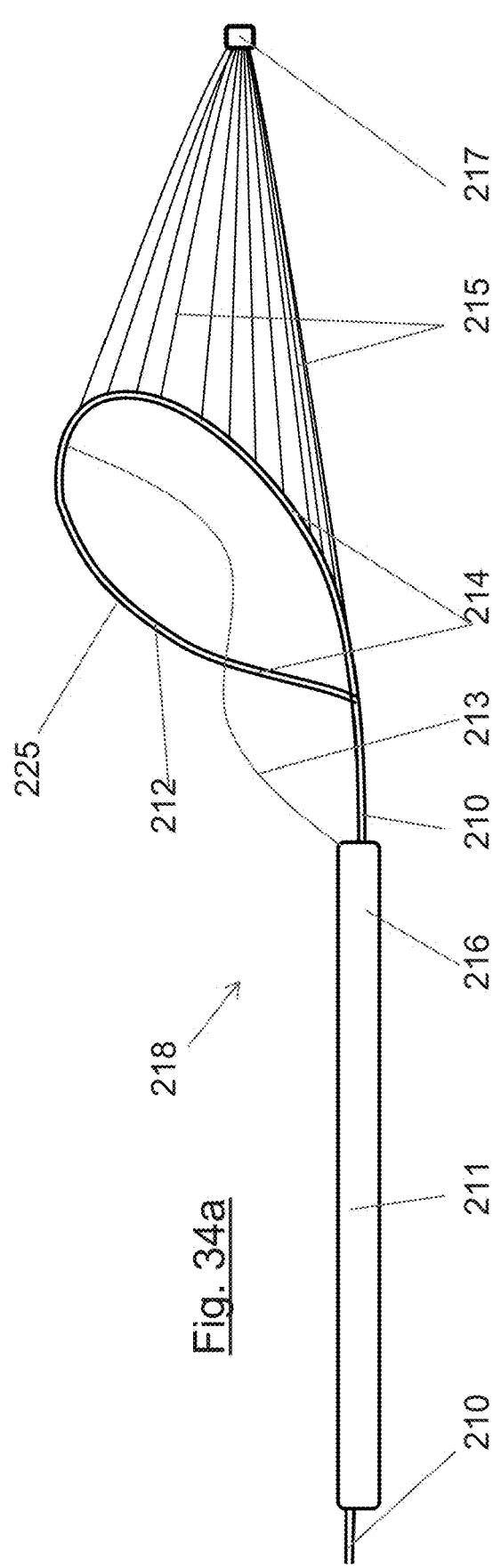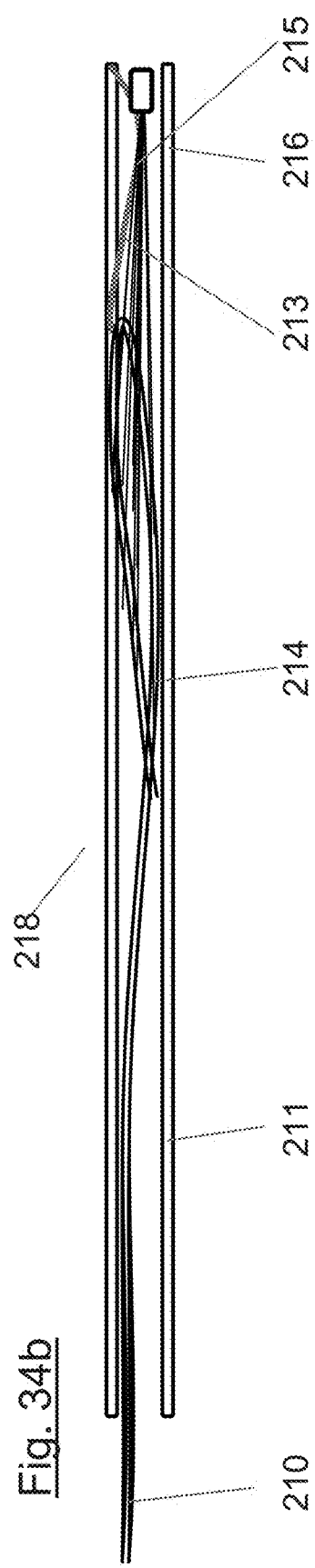

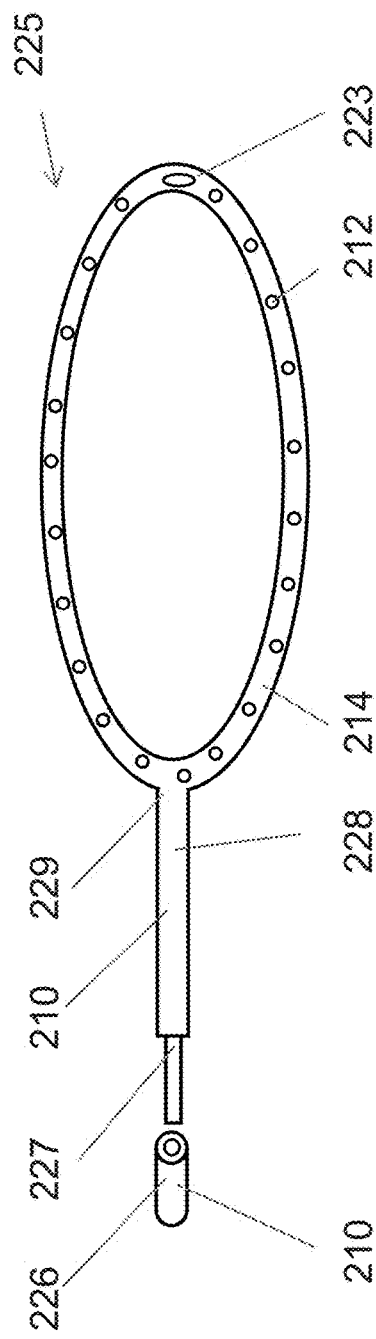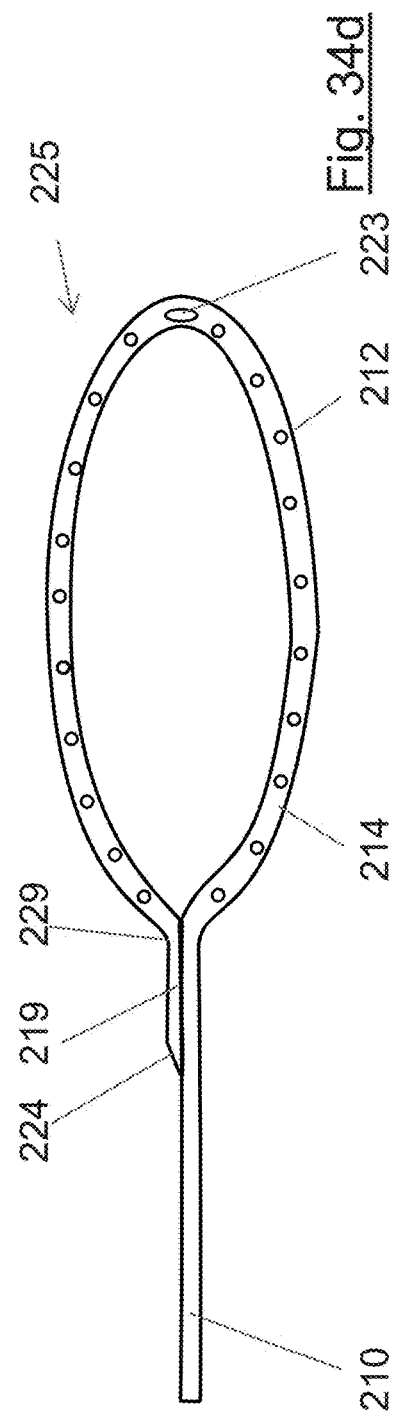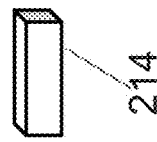

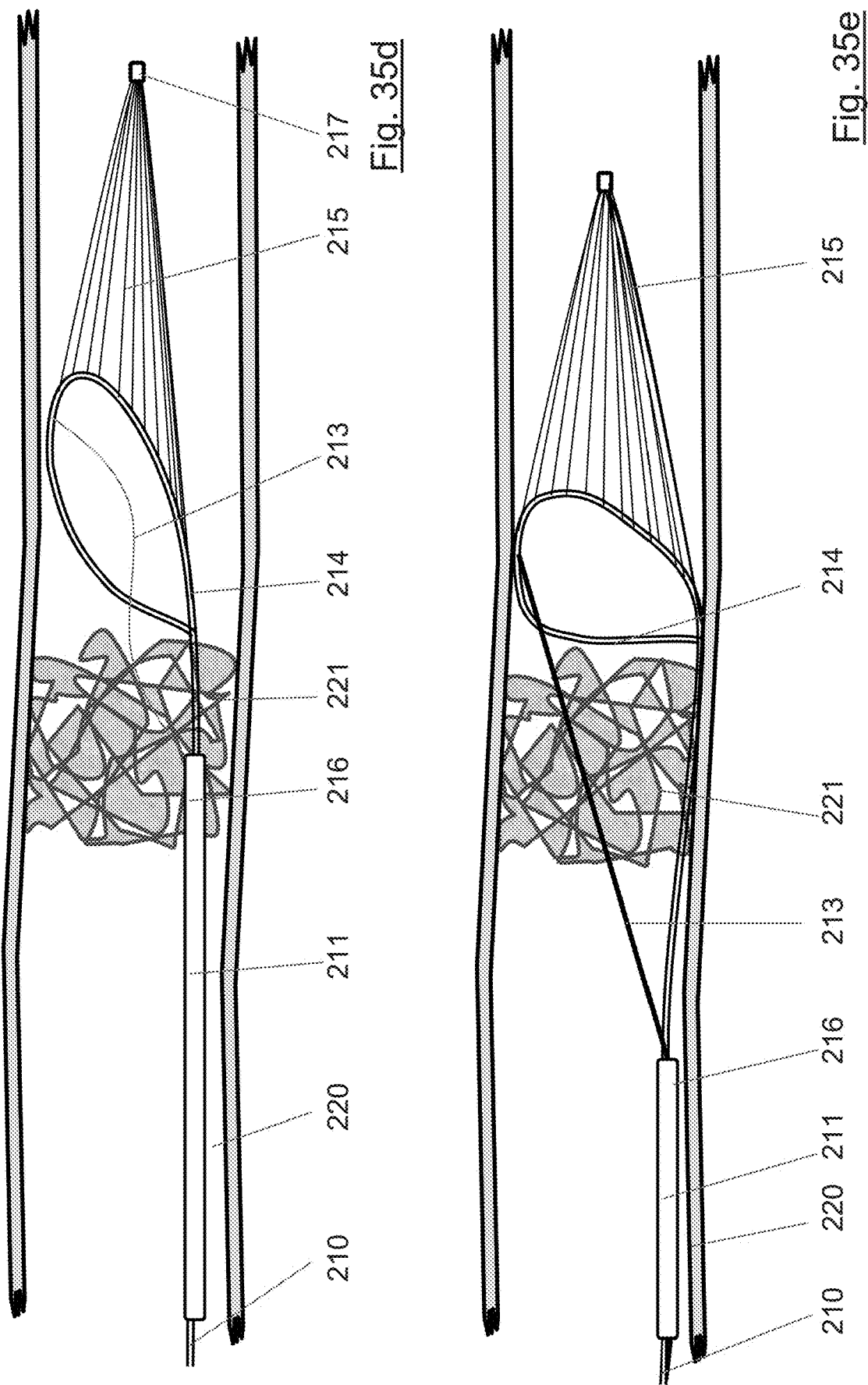

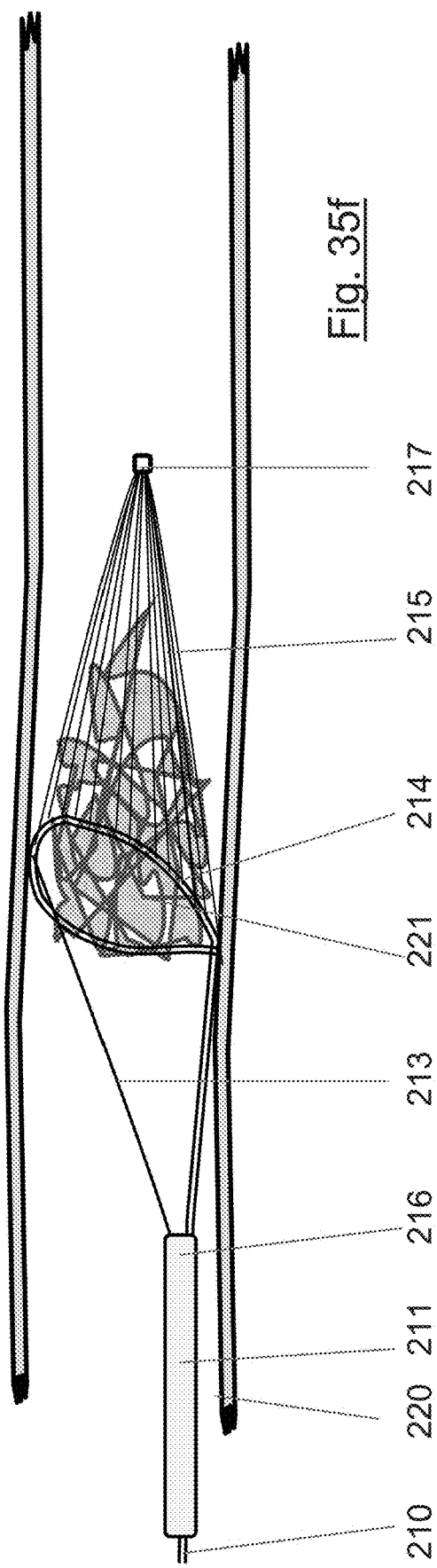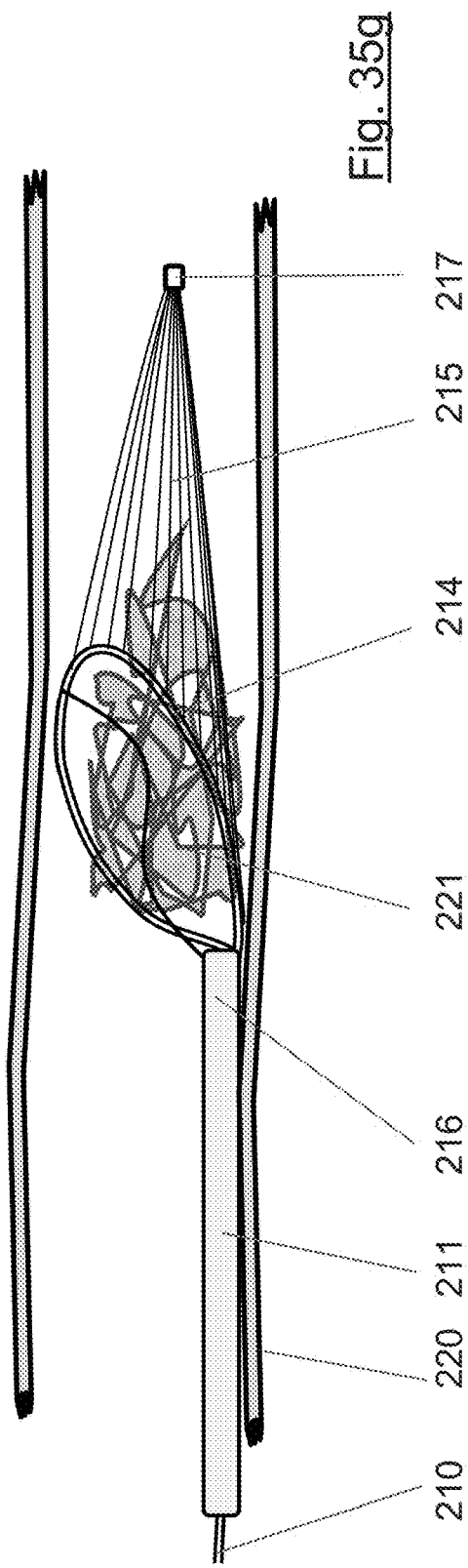

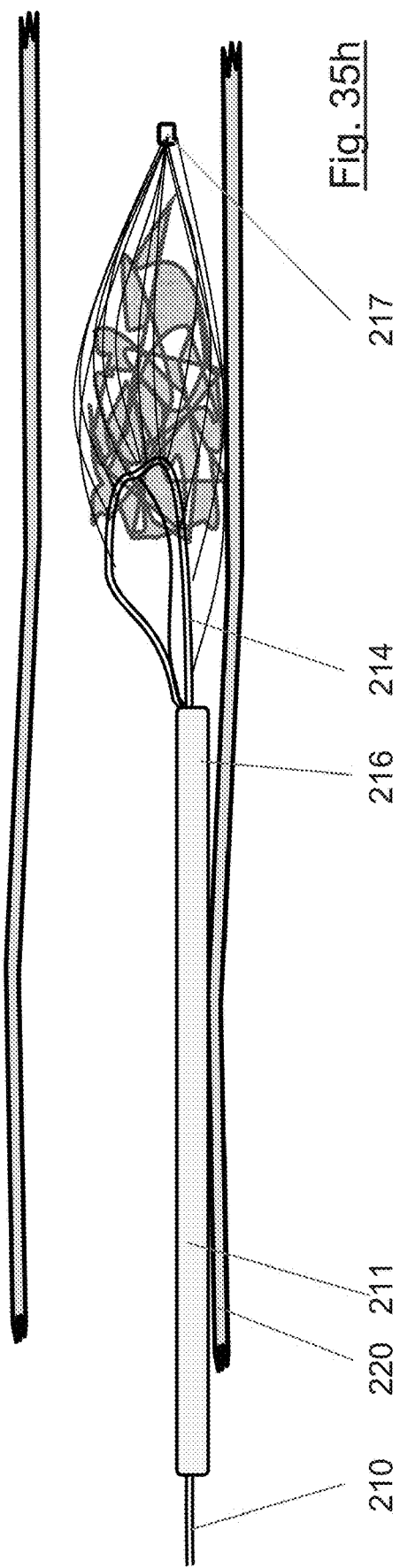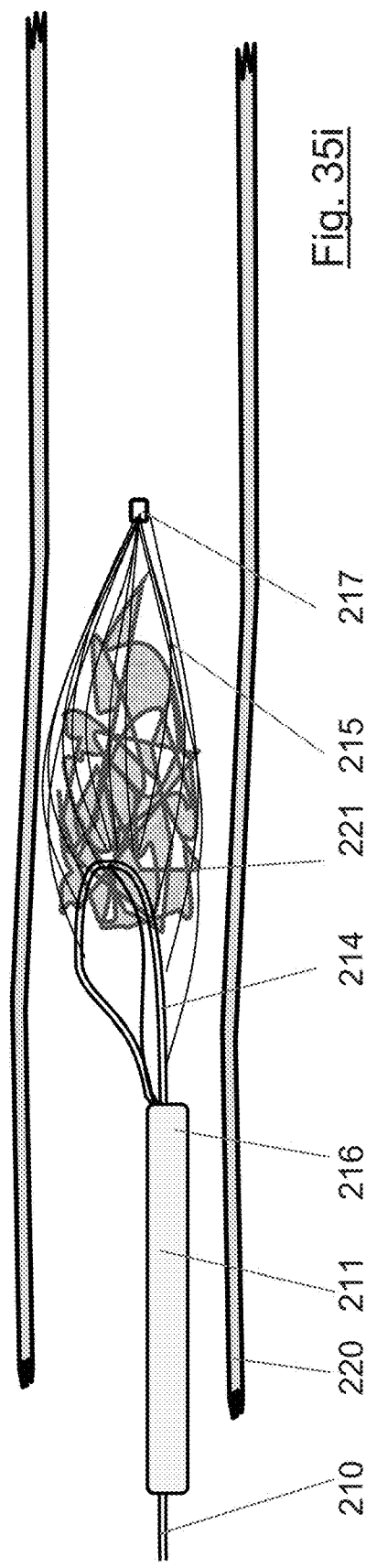

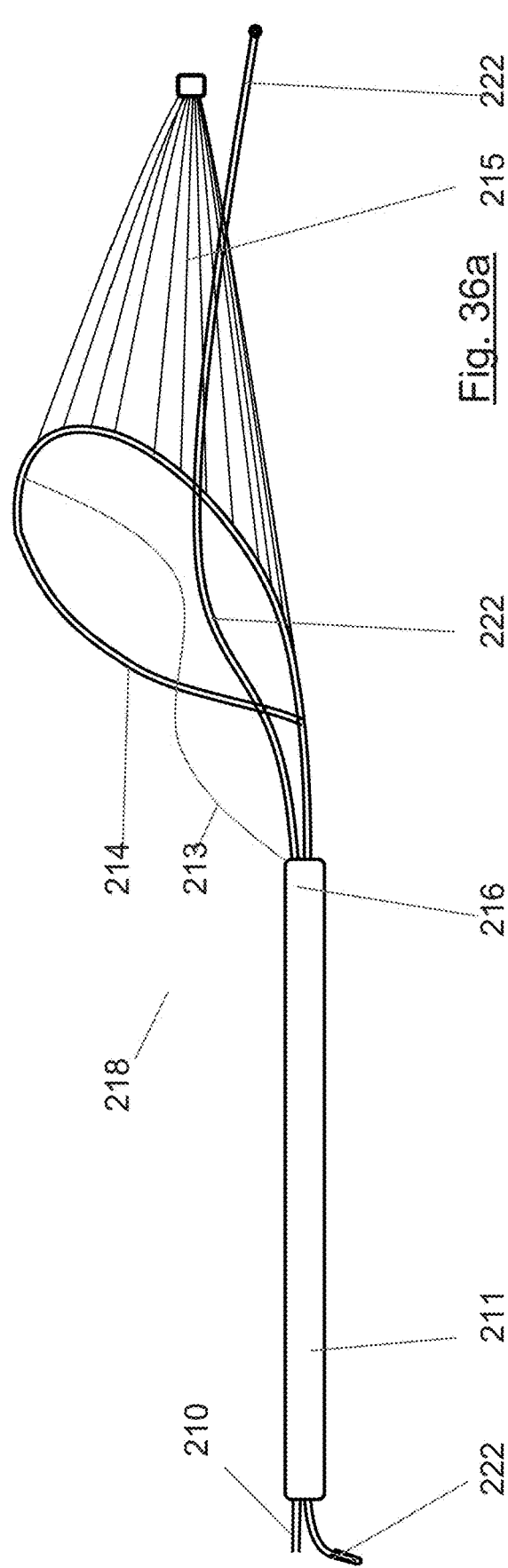
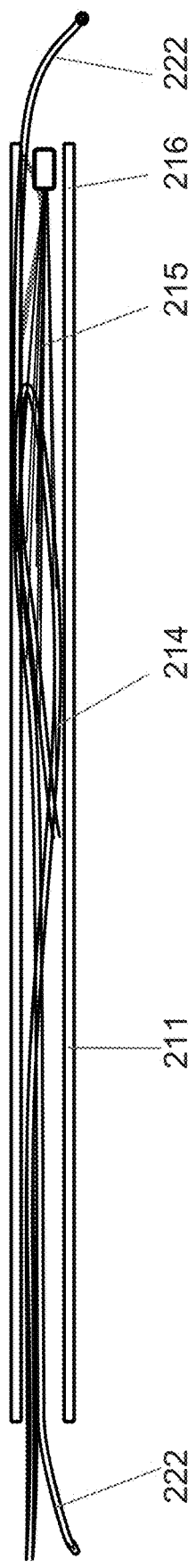
Fig. 36a
Fig. 36b

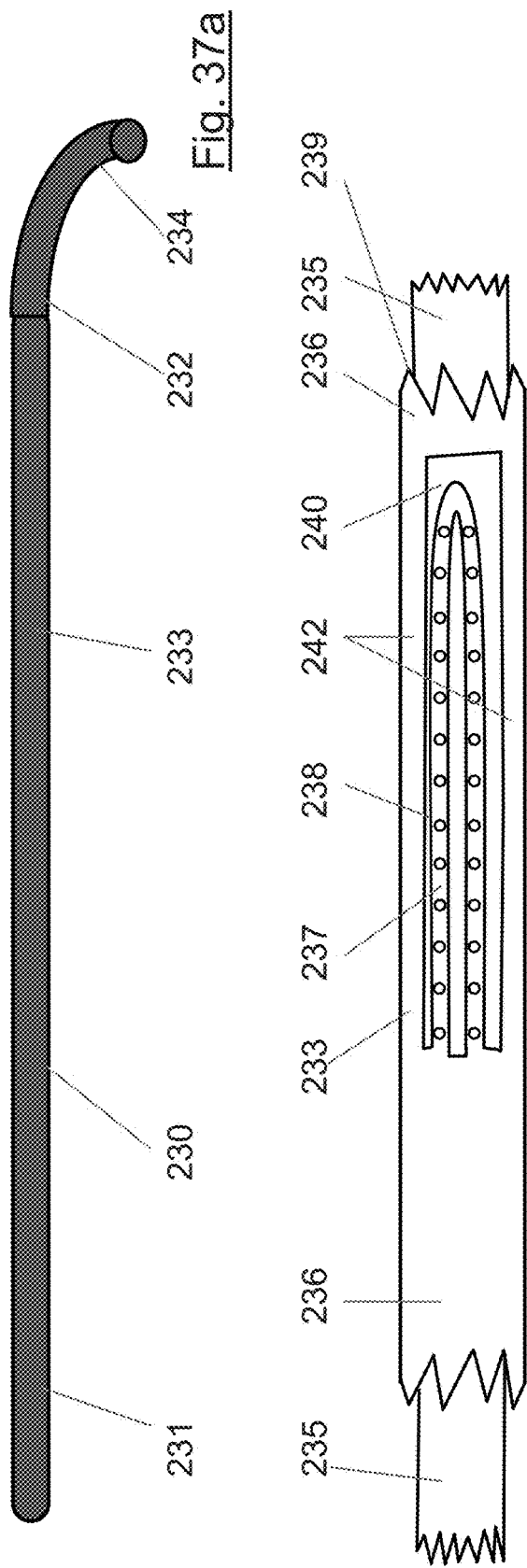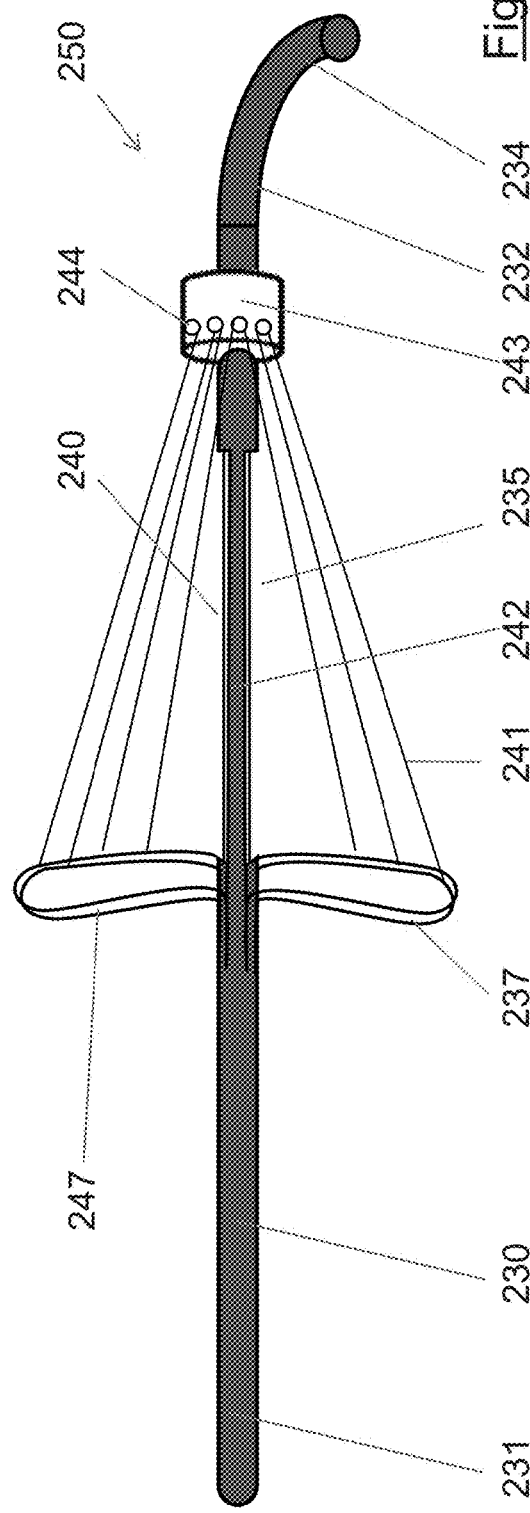

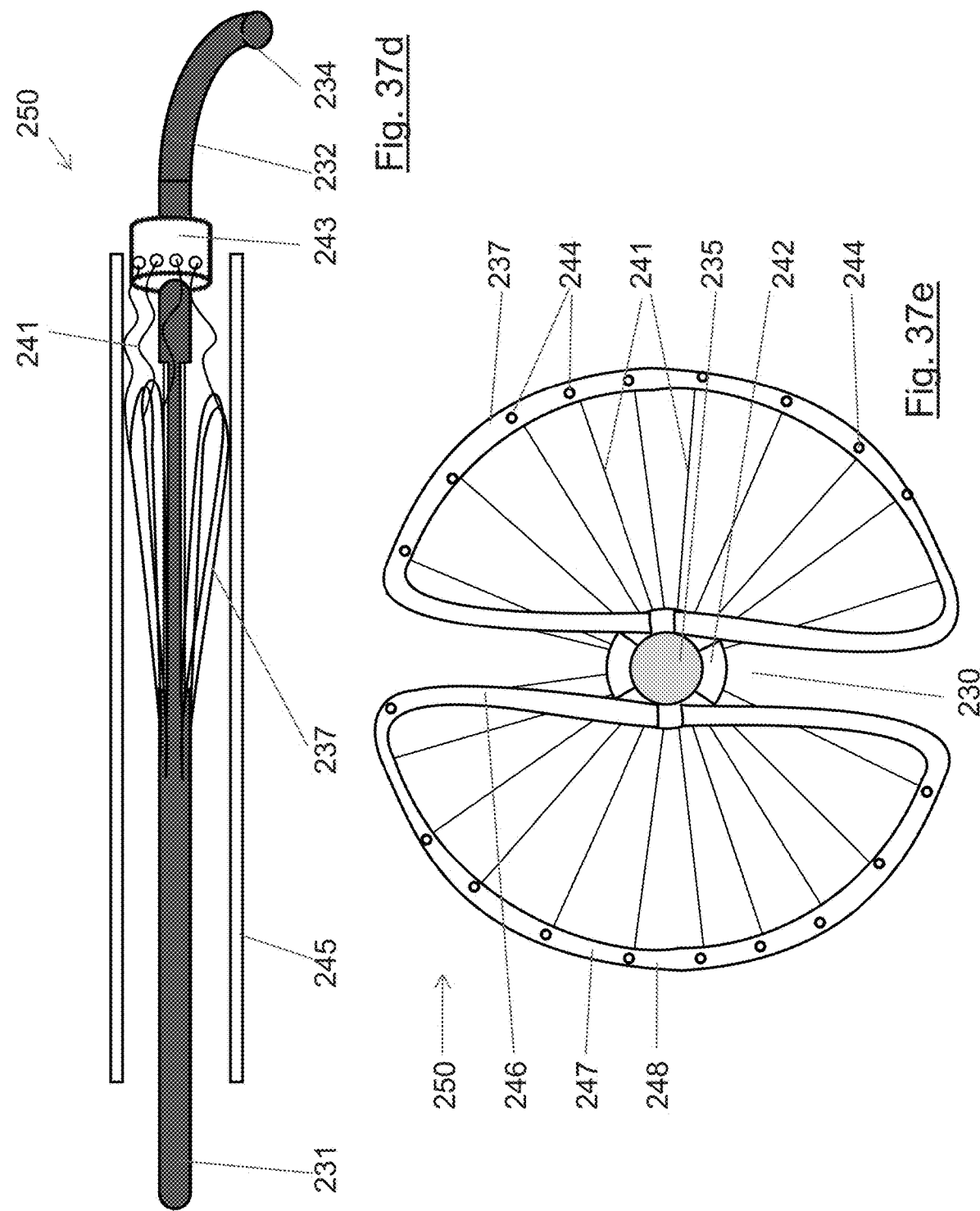

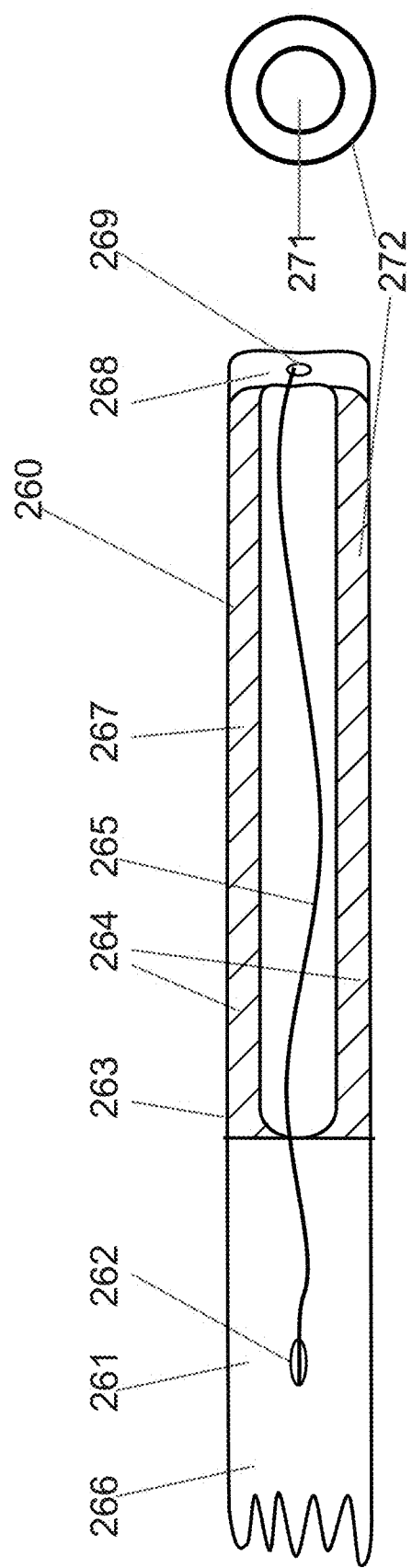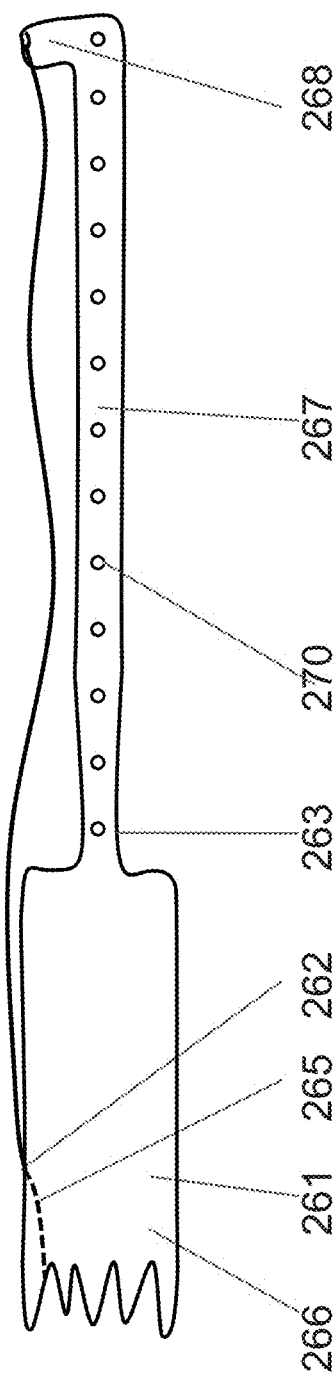

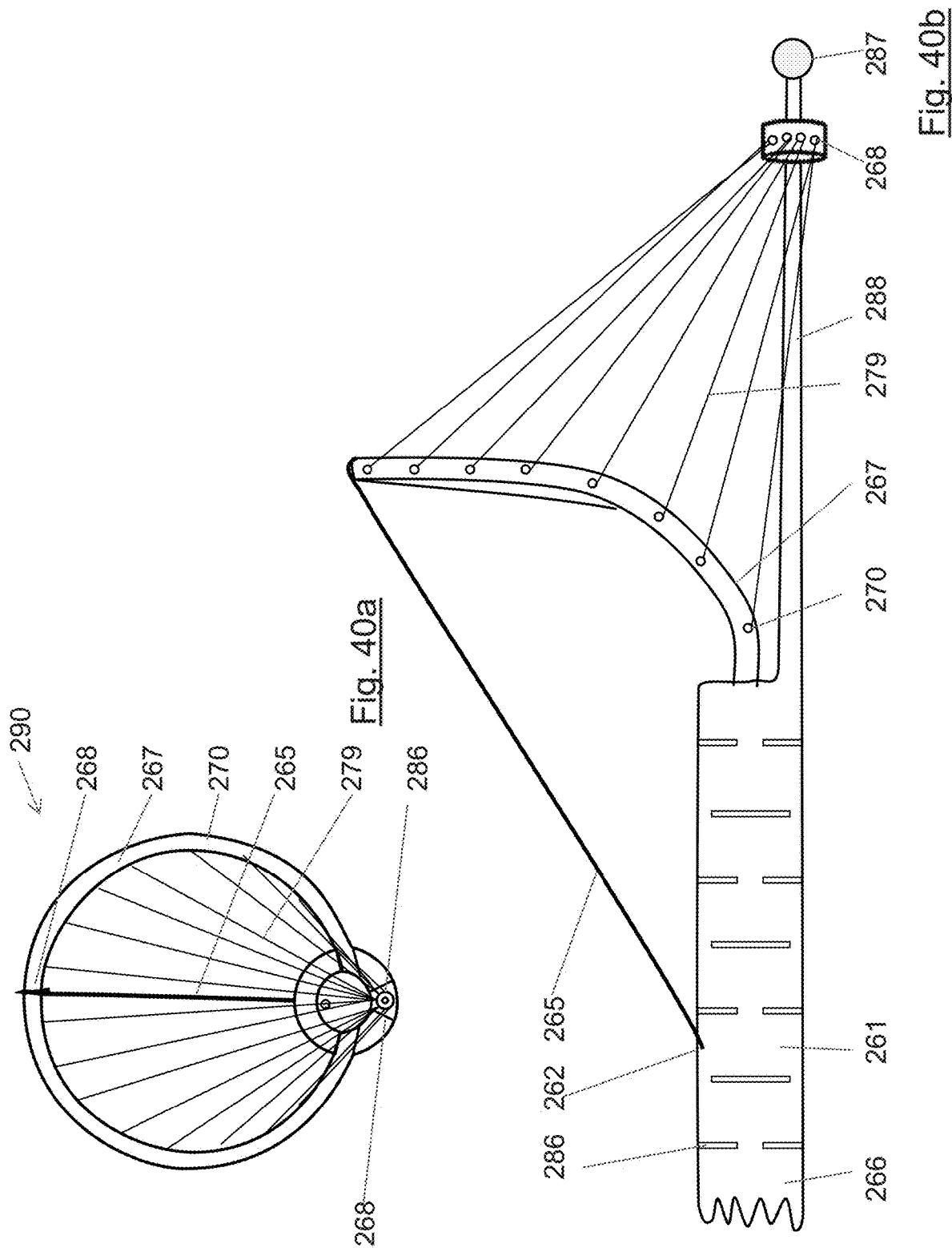

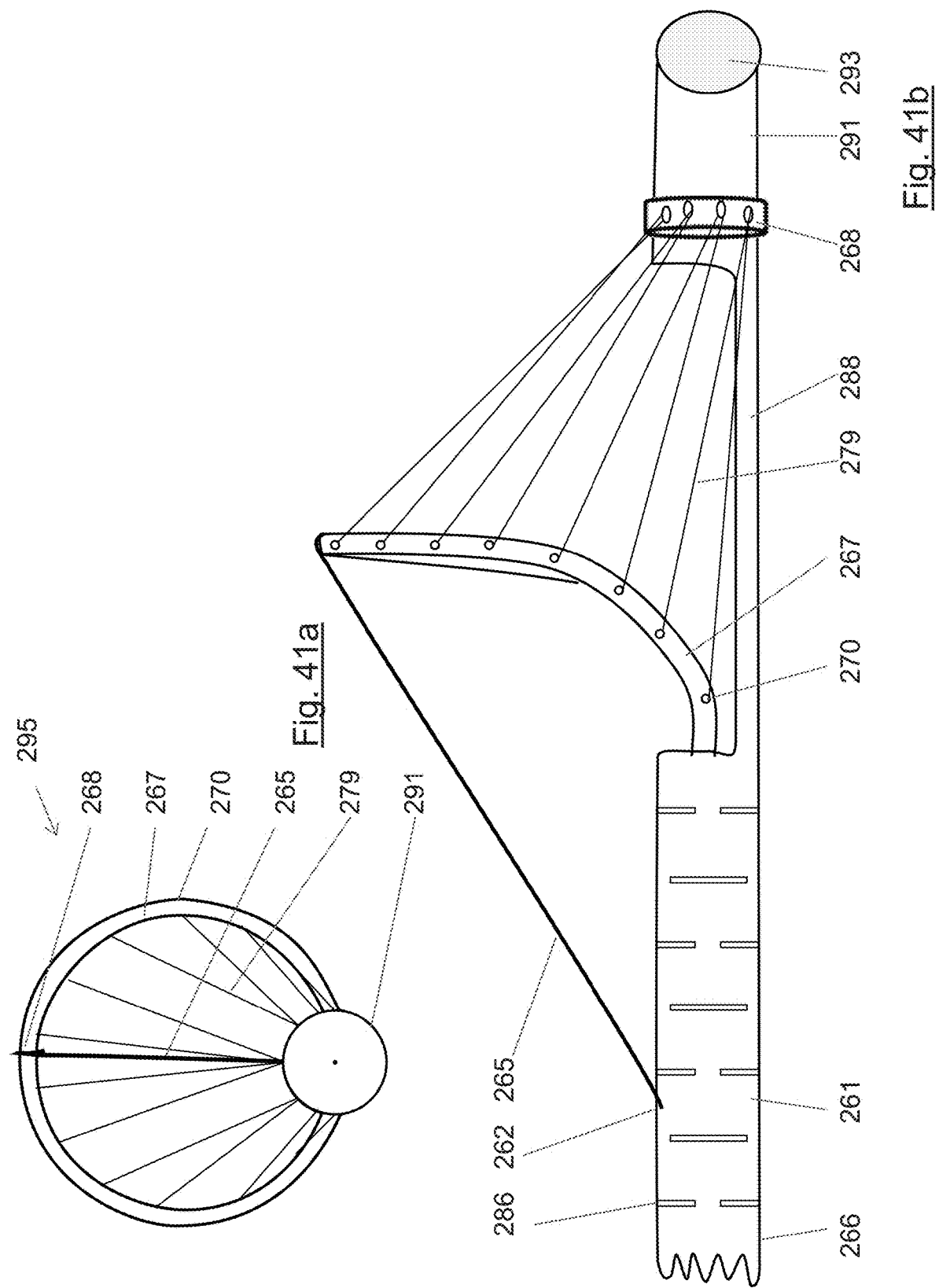

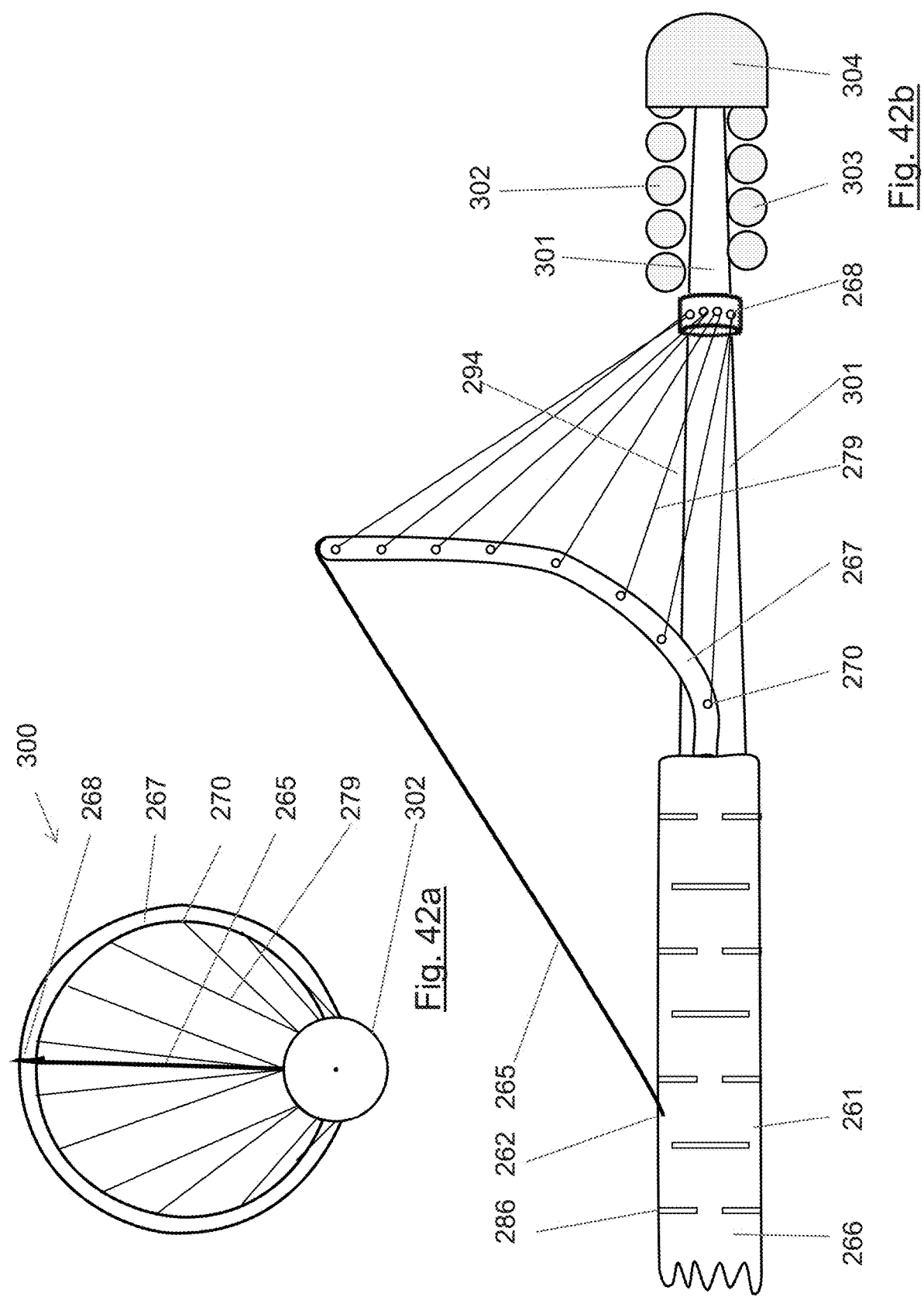

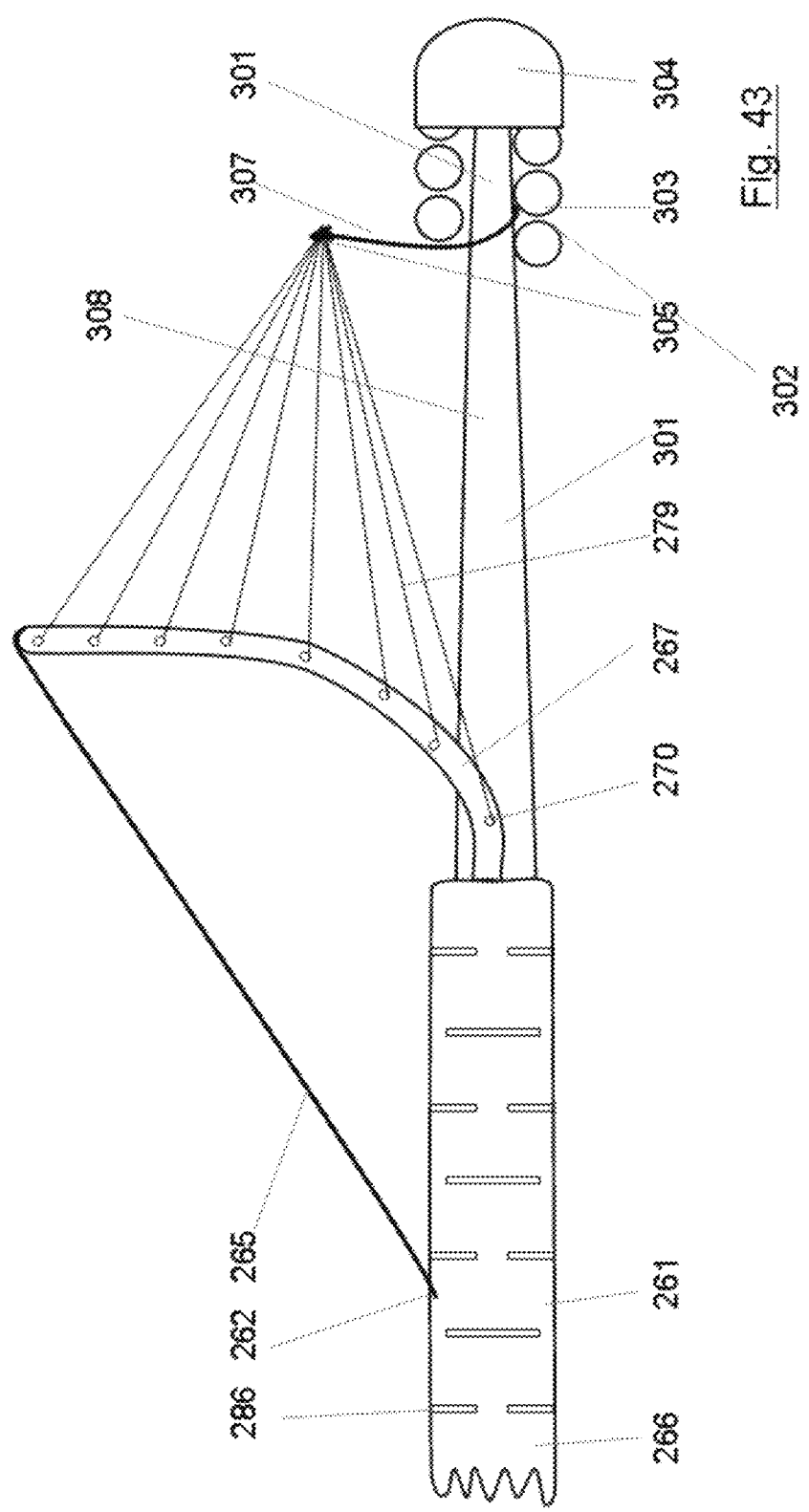

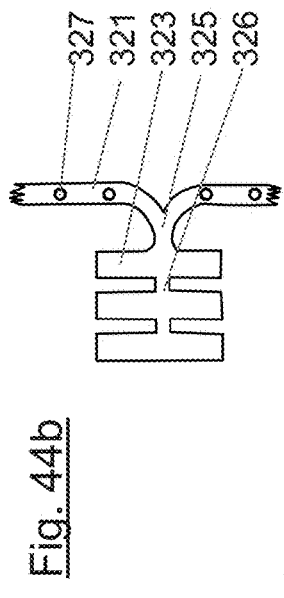
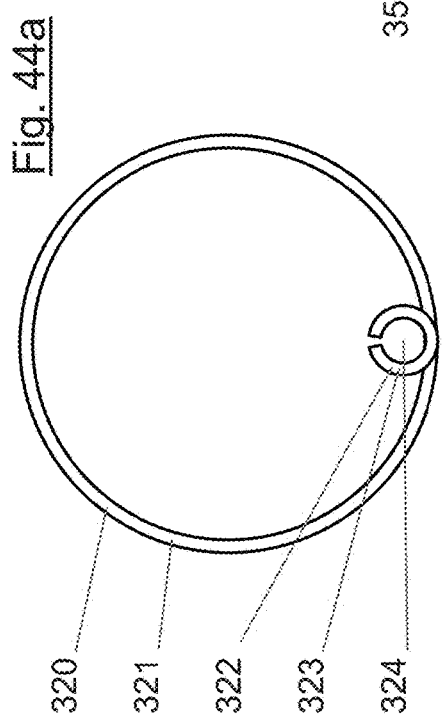
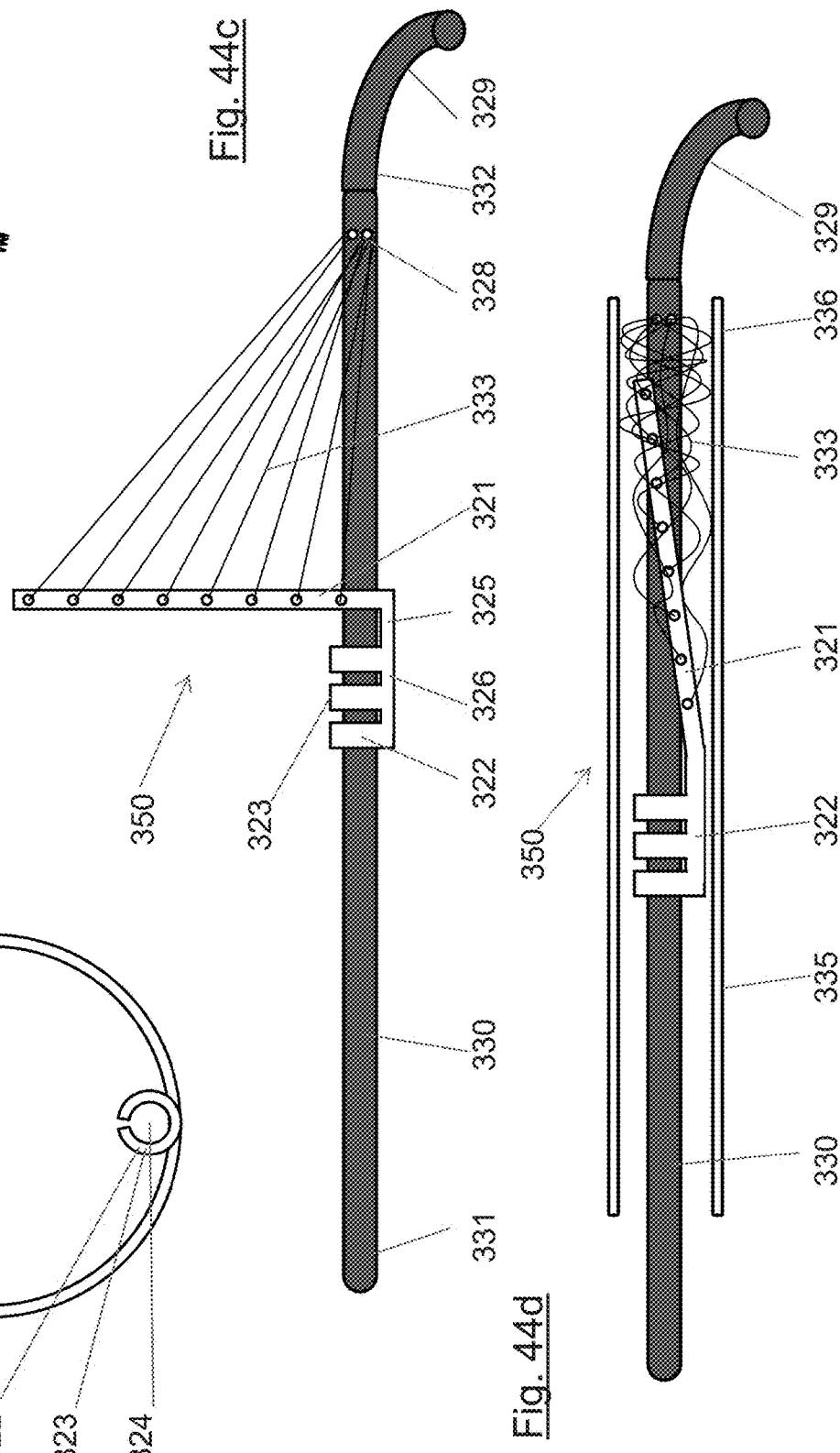

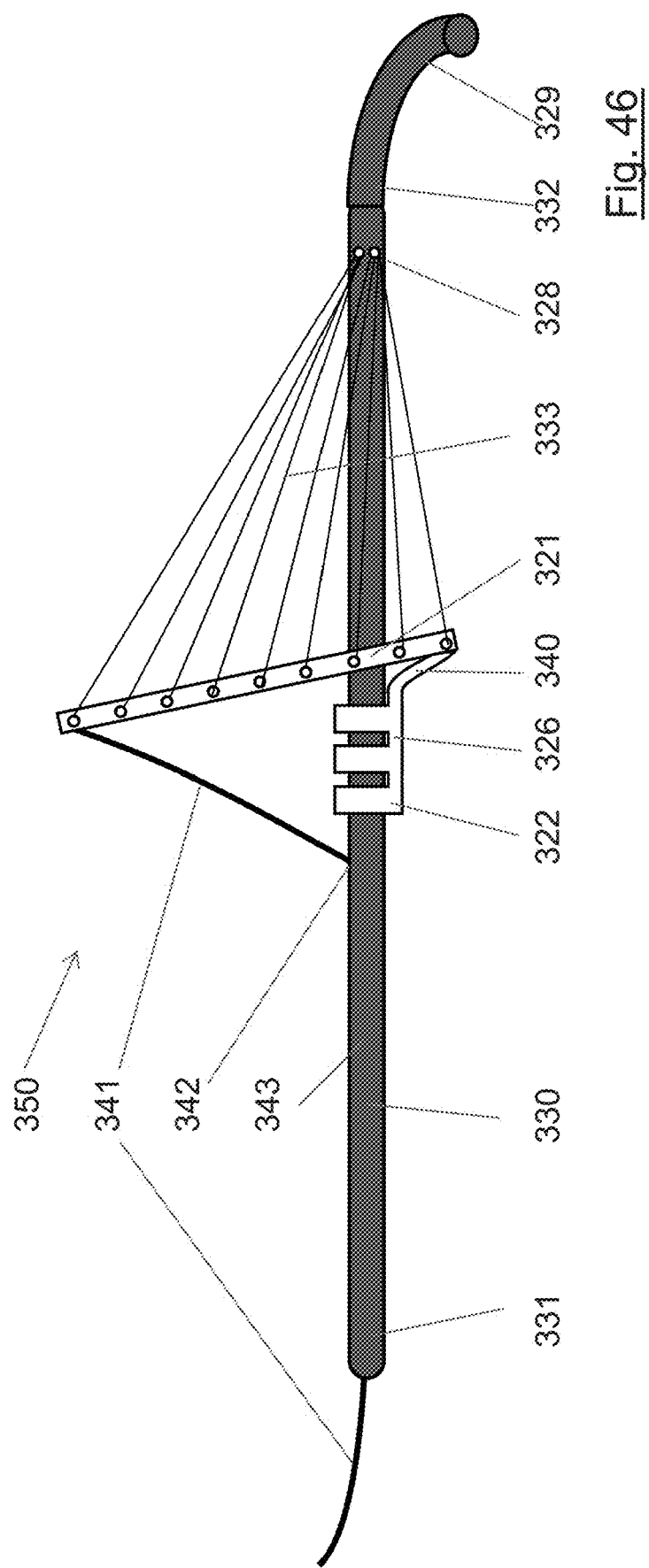

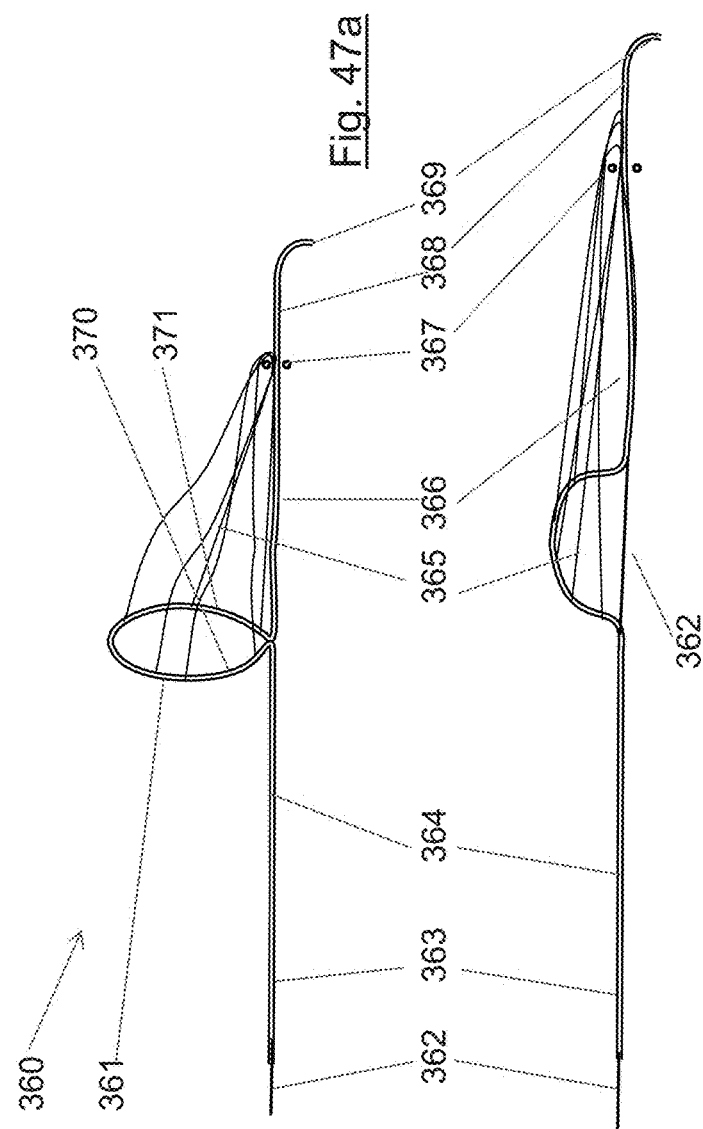
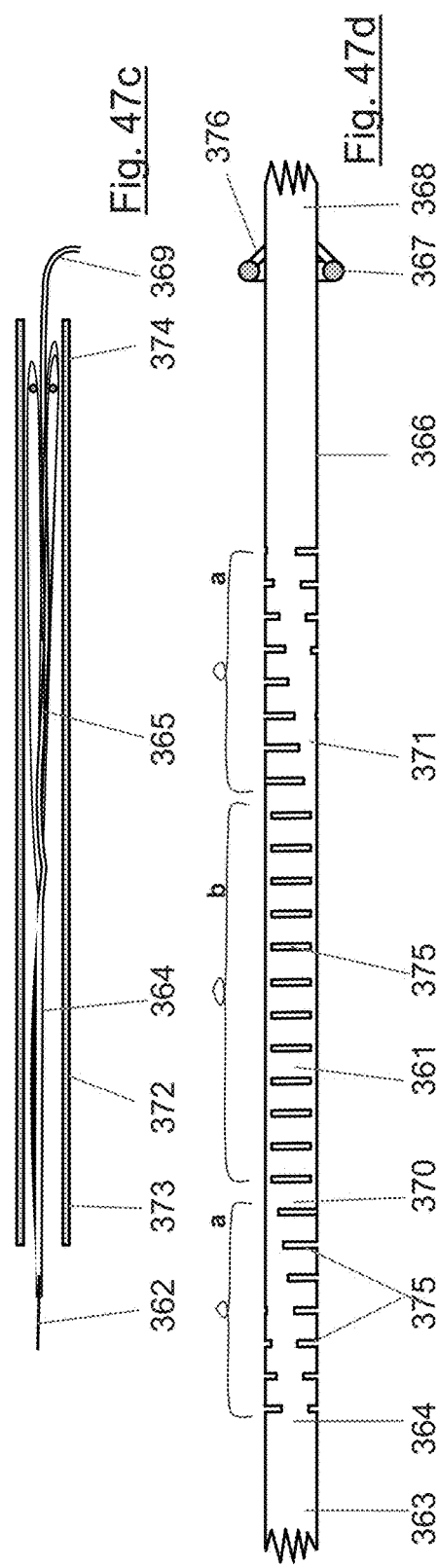

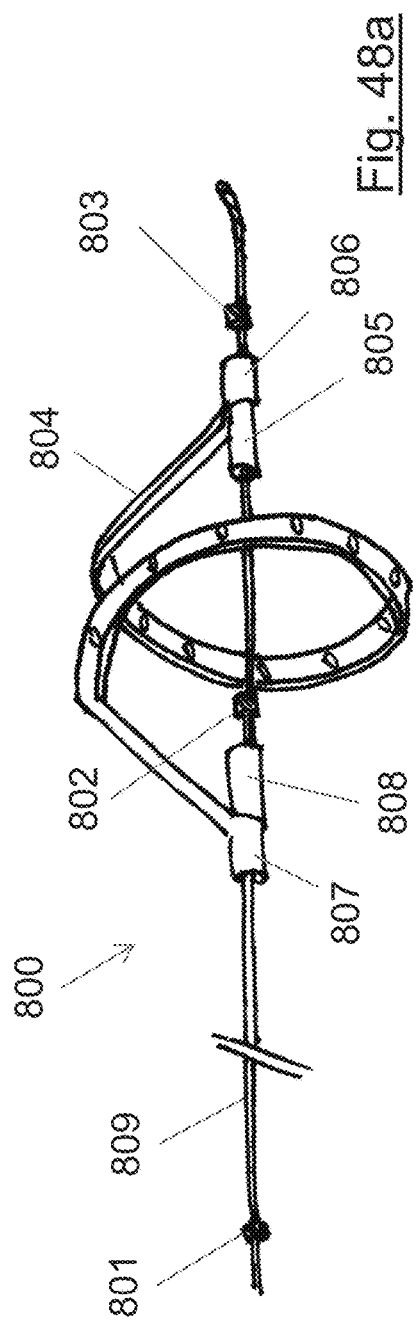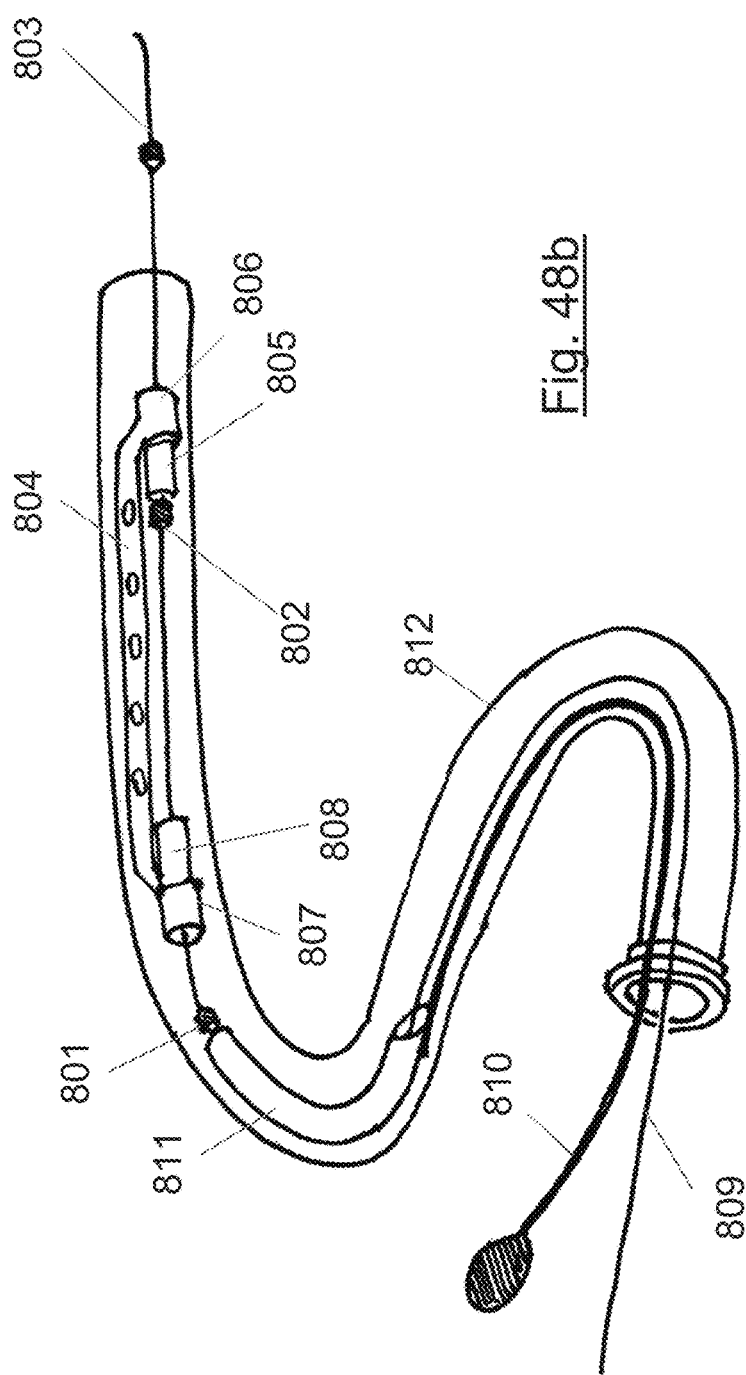

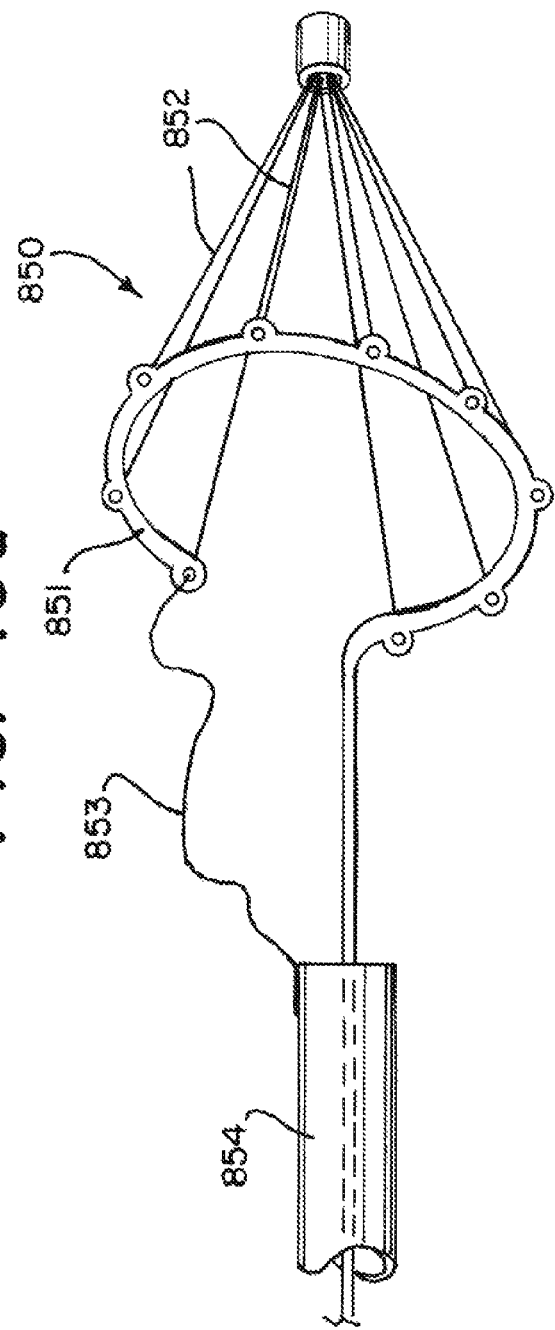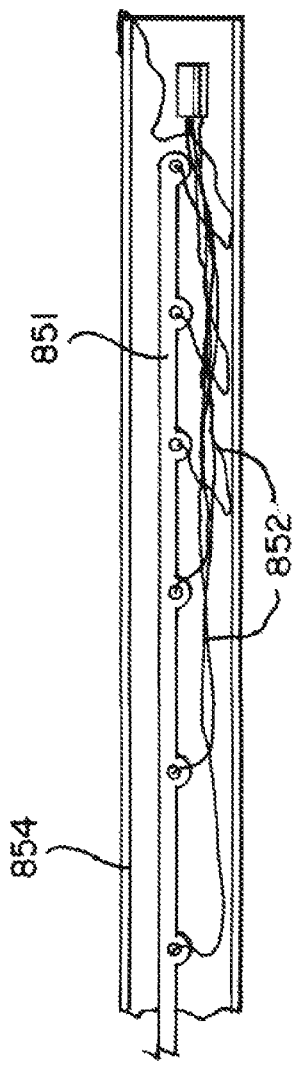

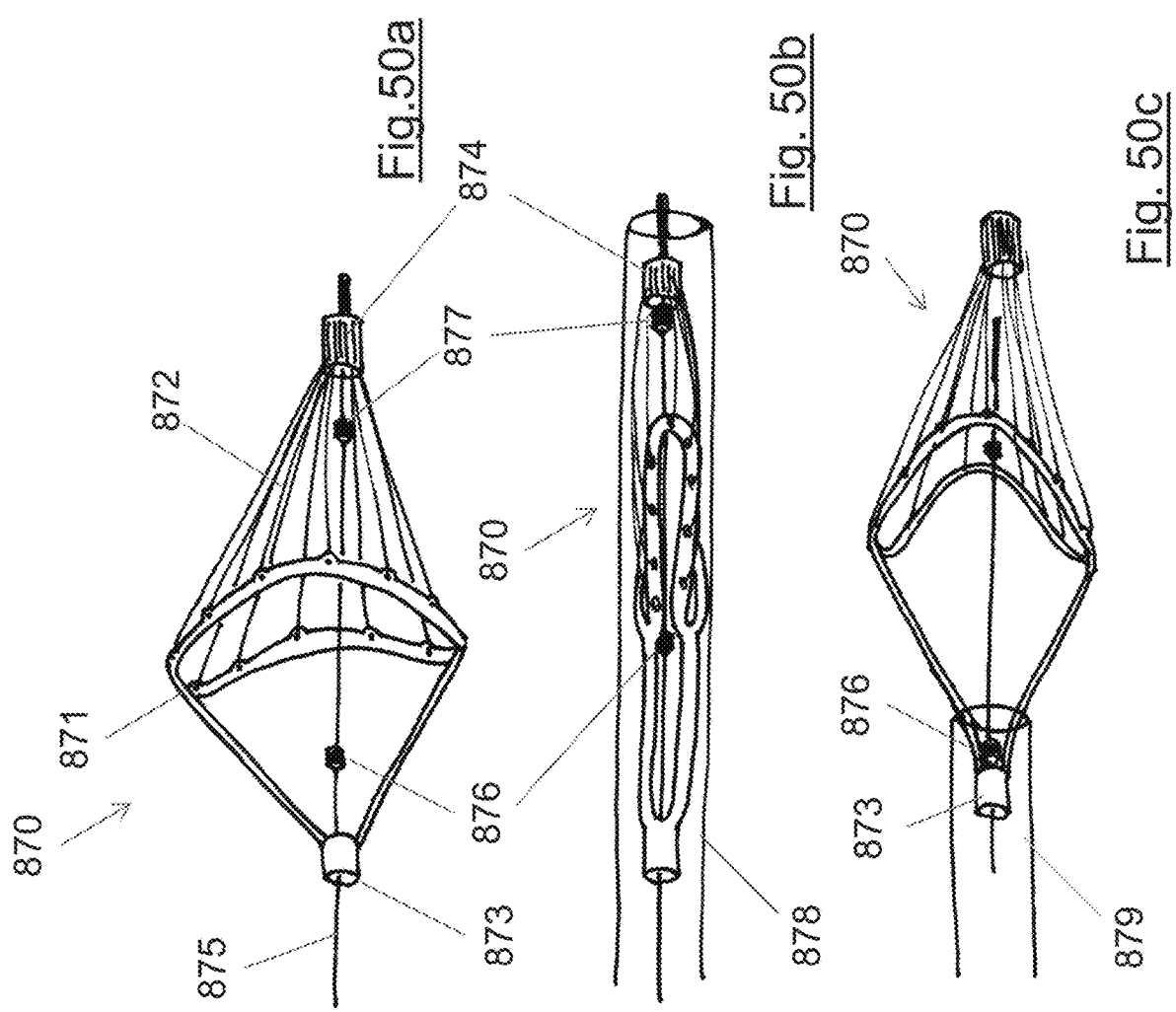

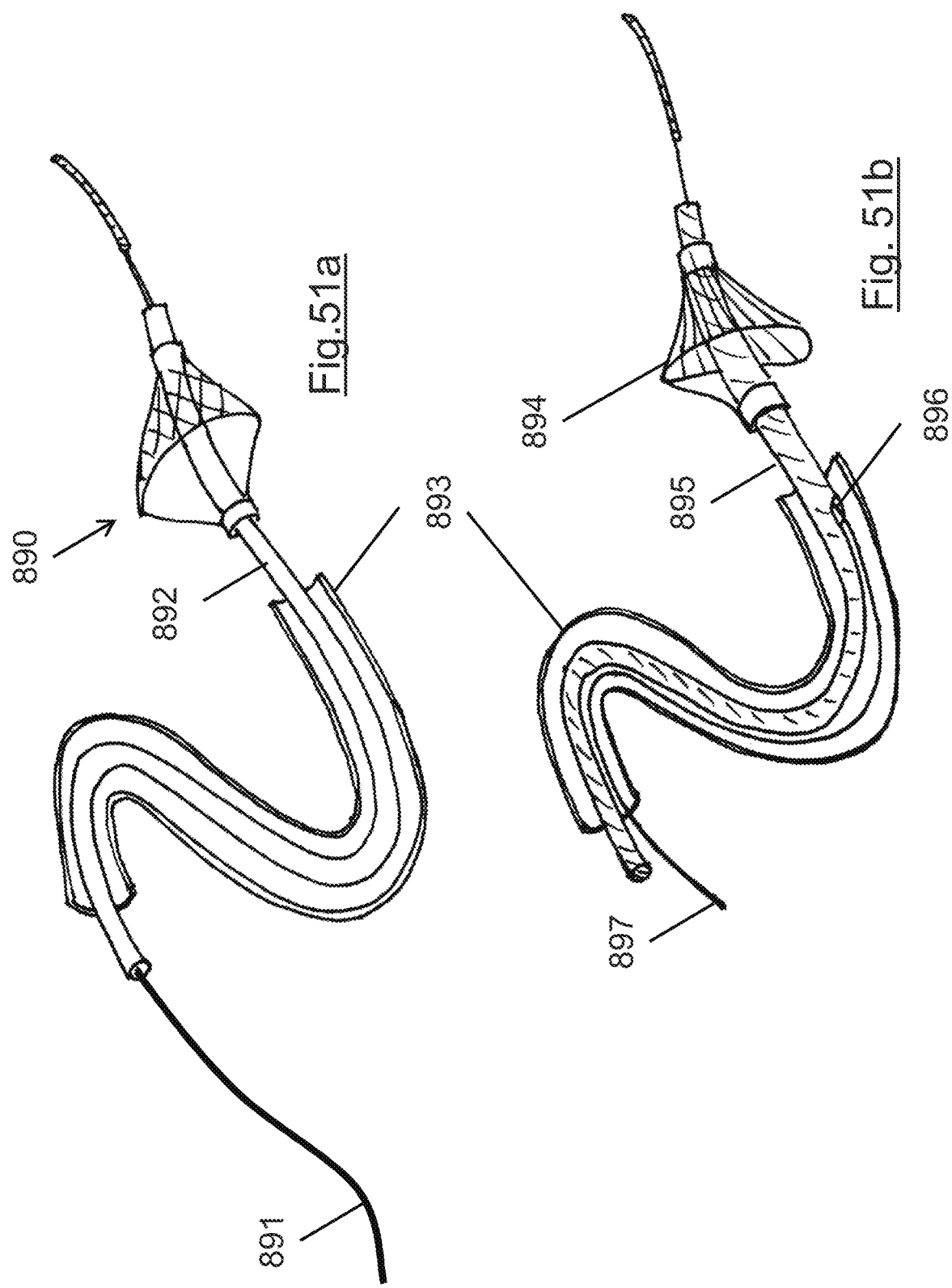

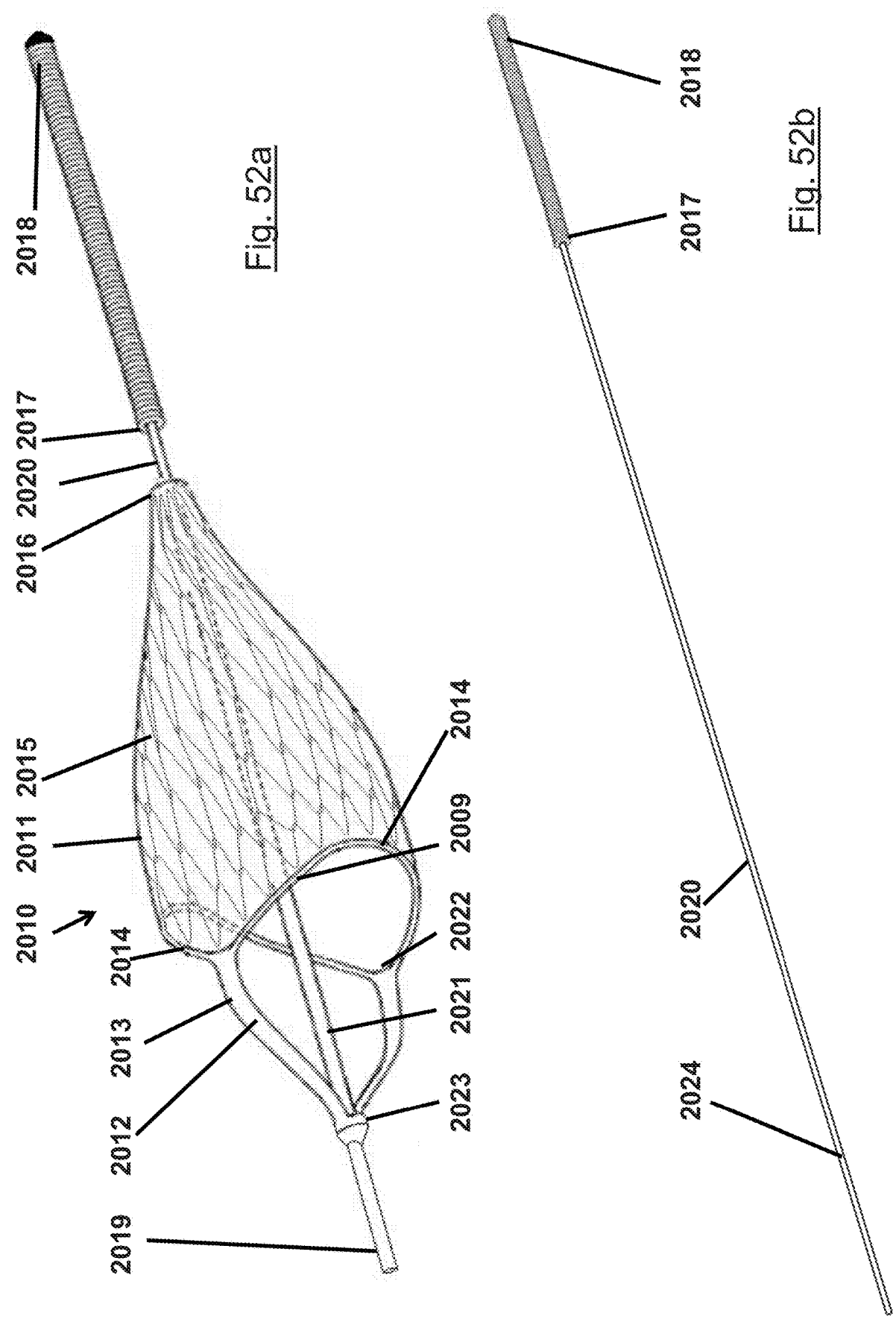

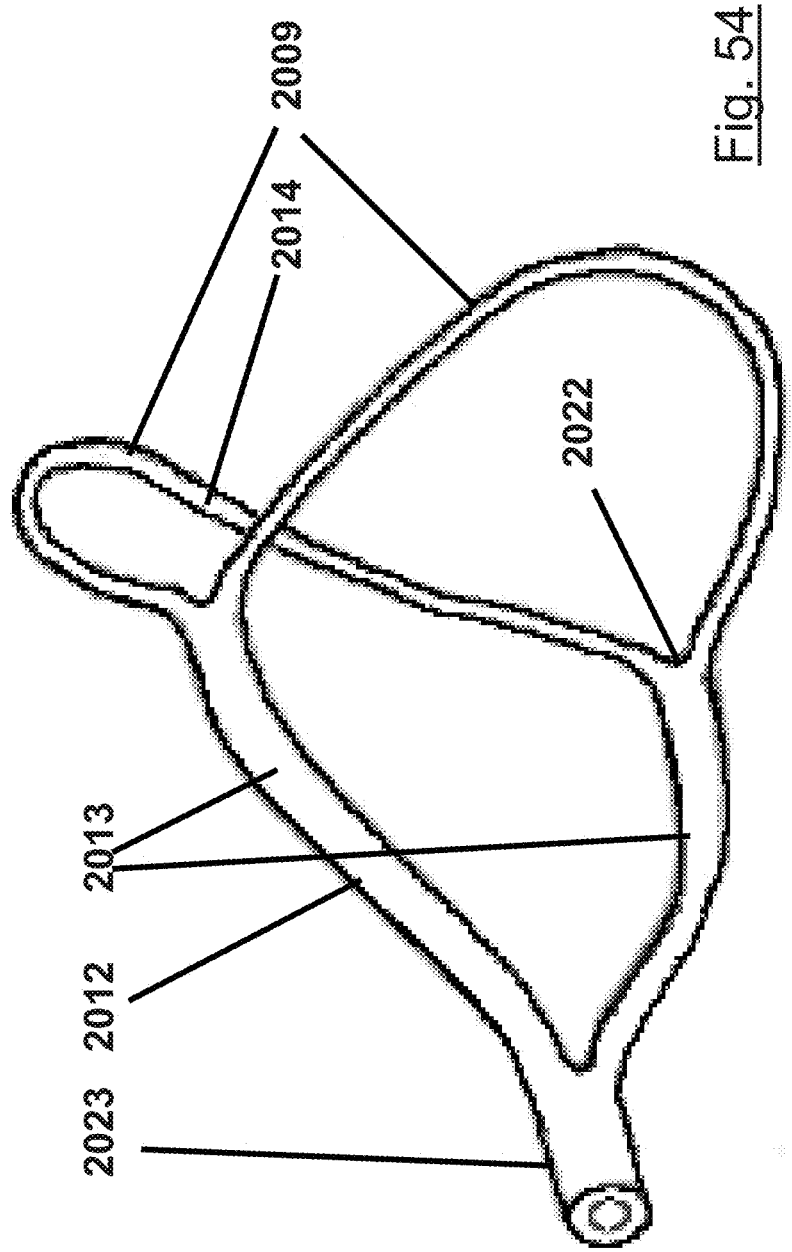

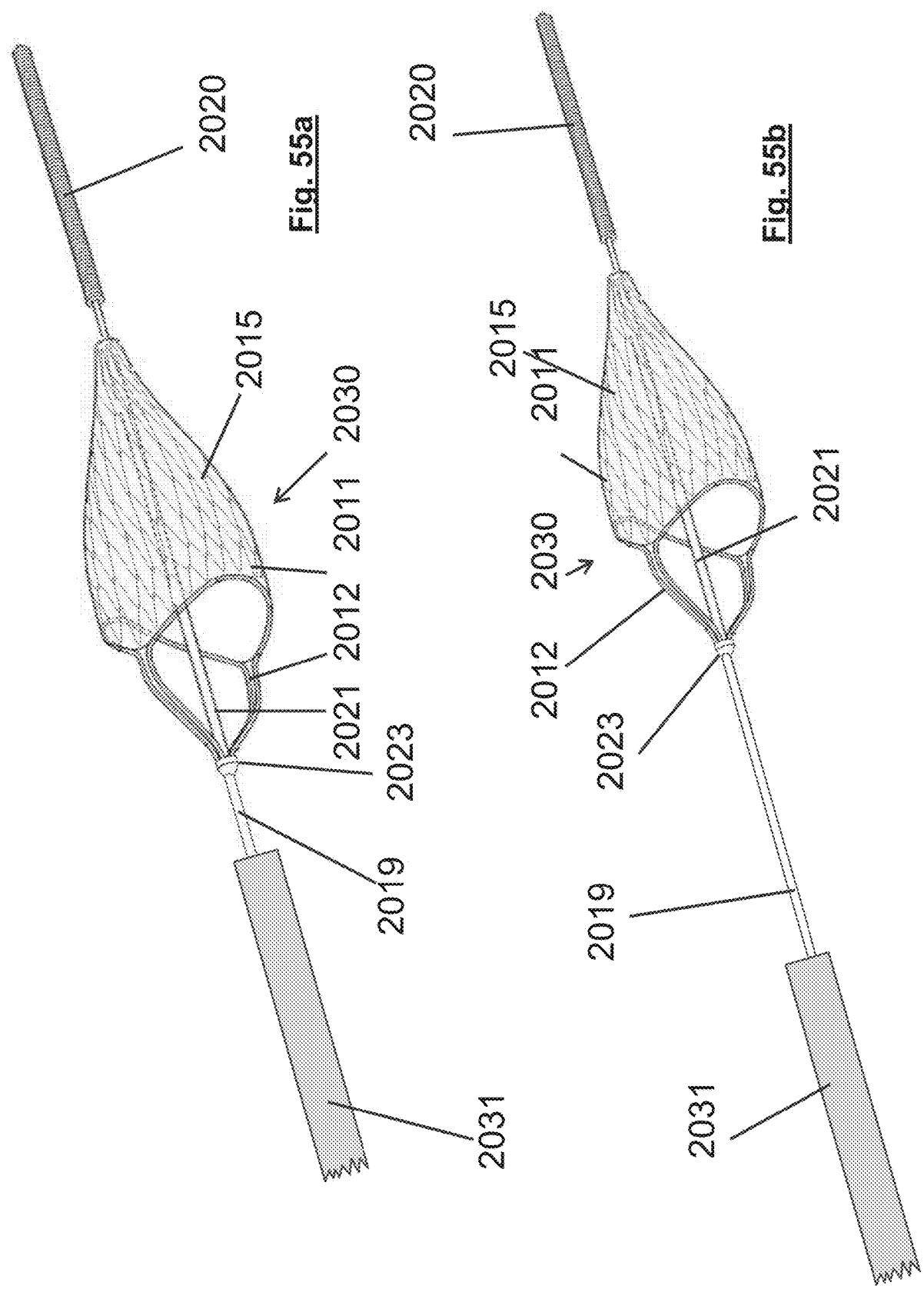

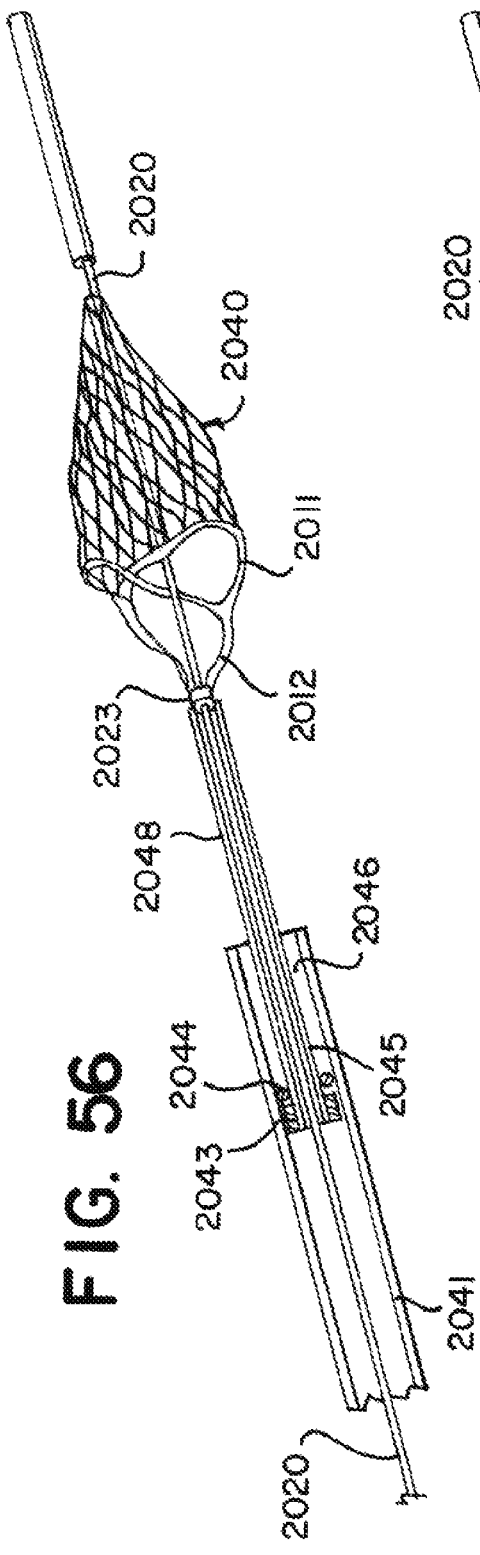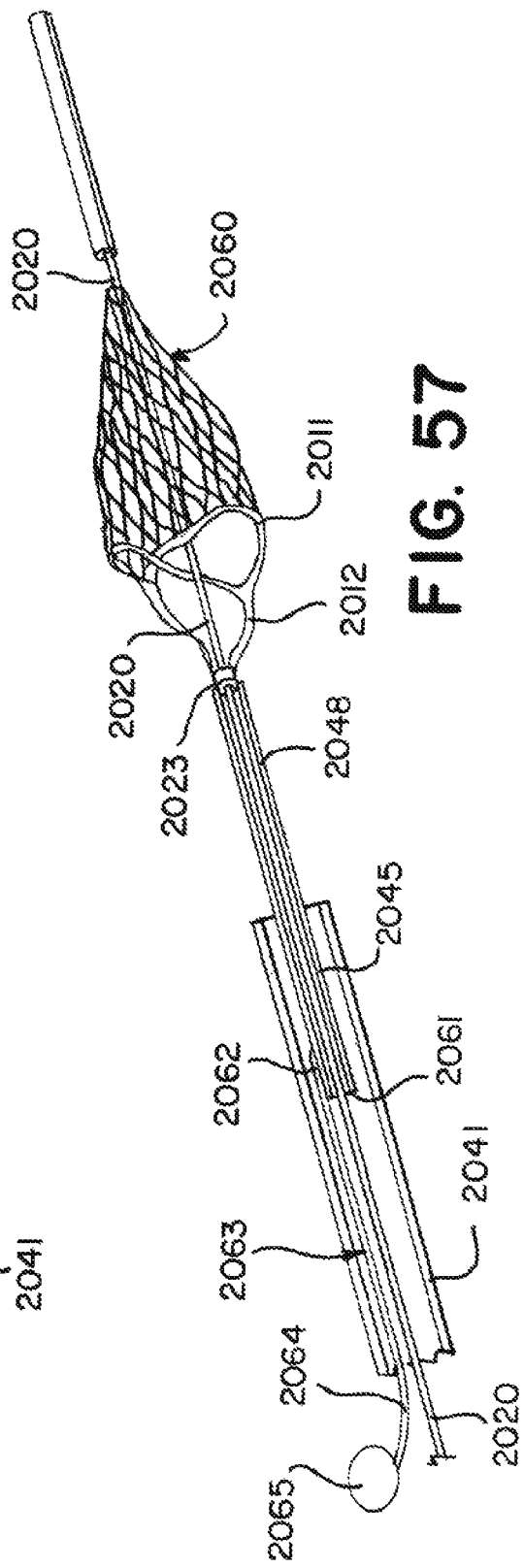

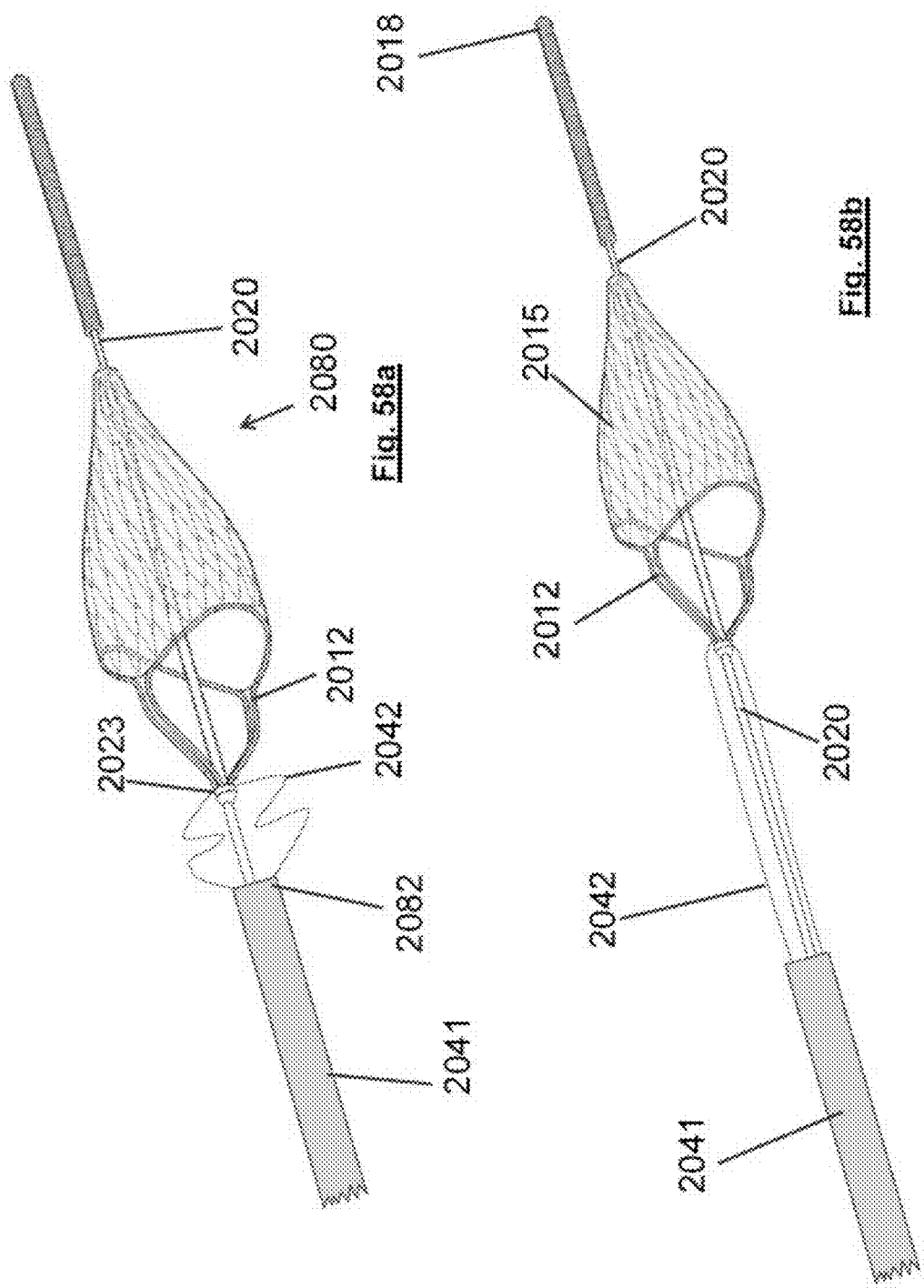

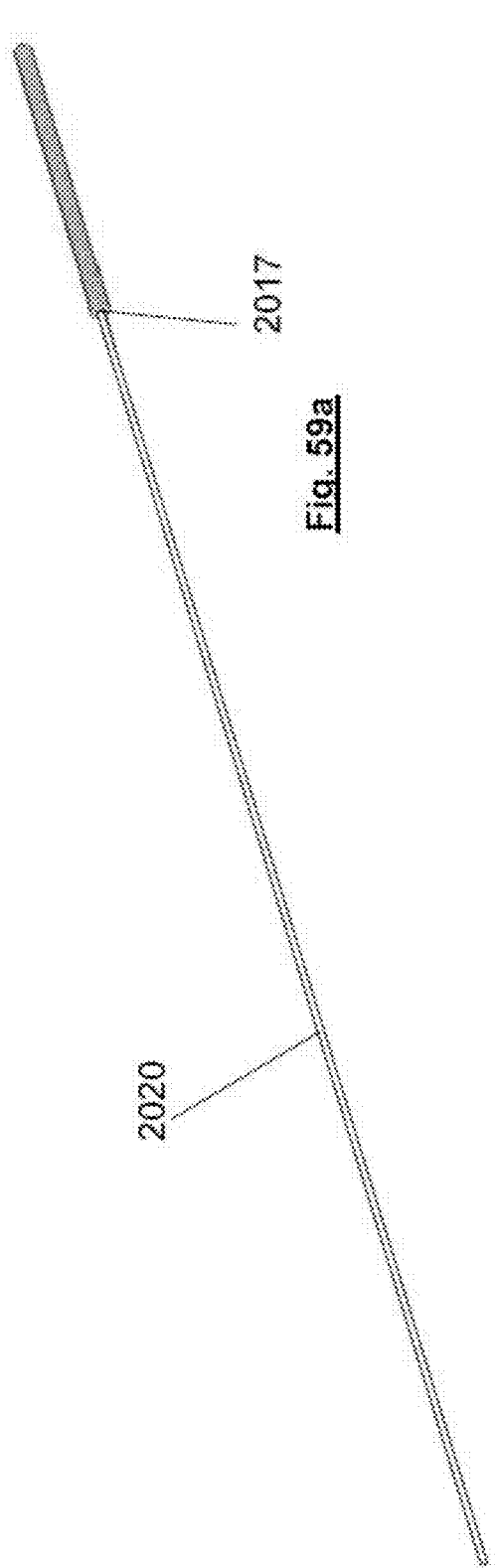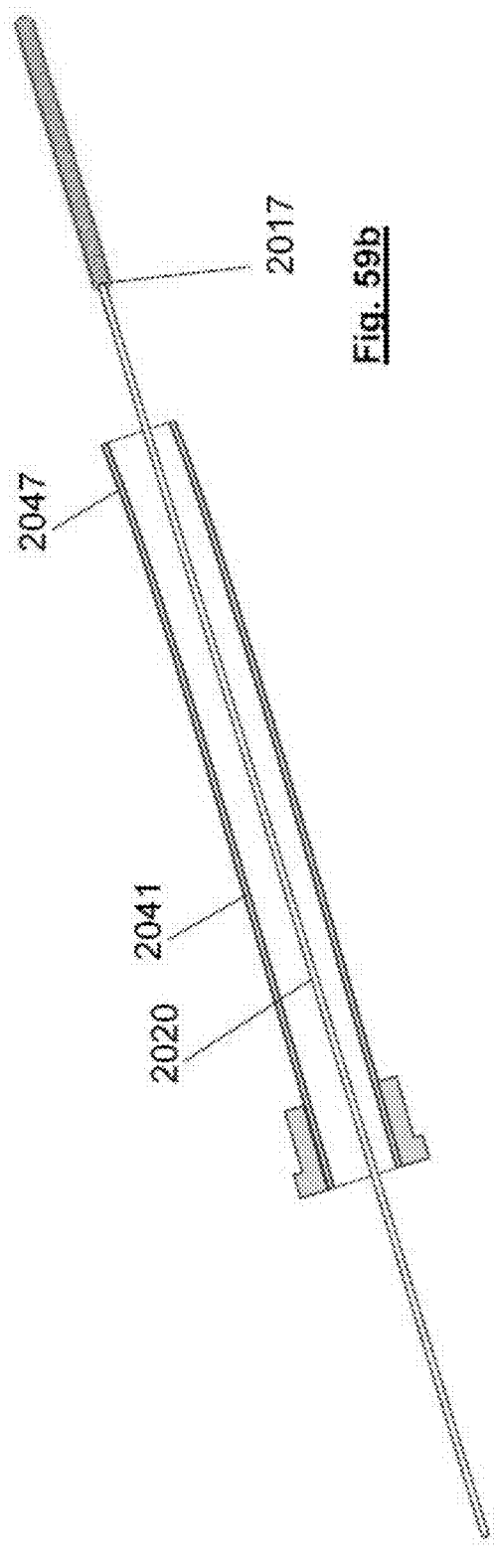

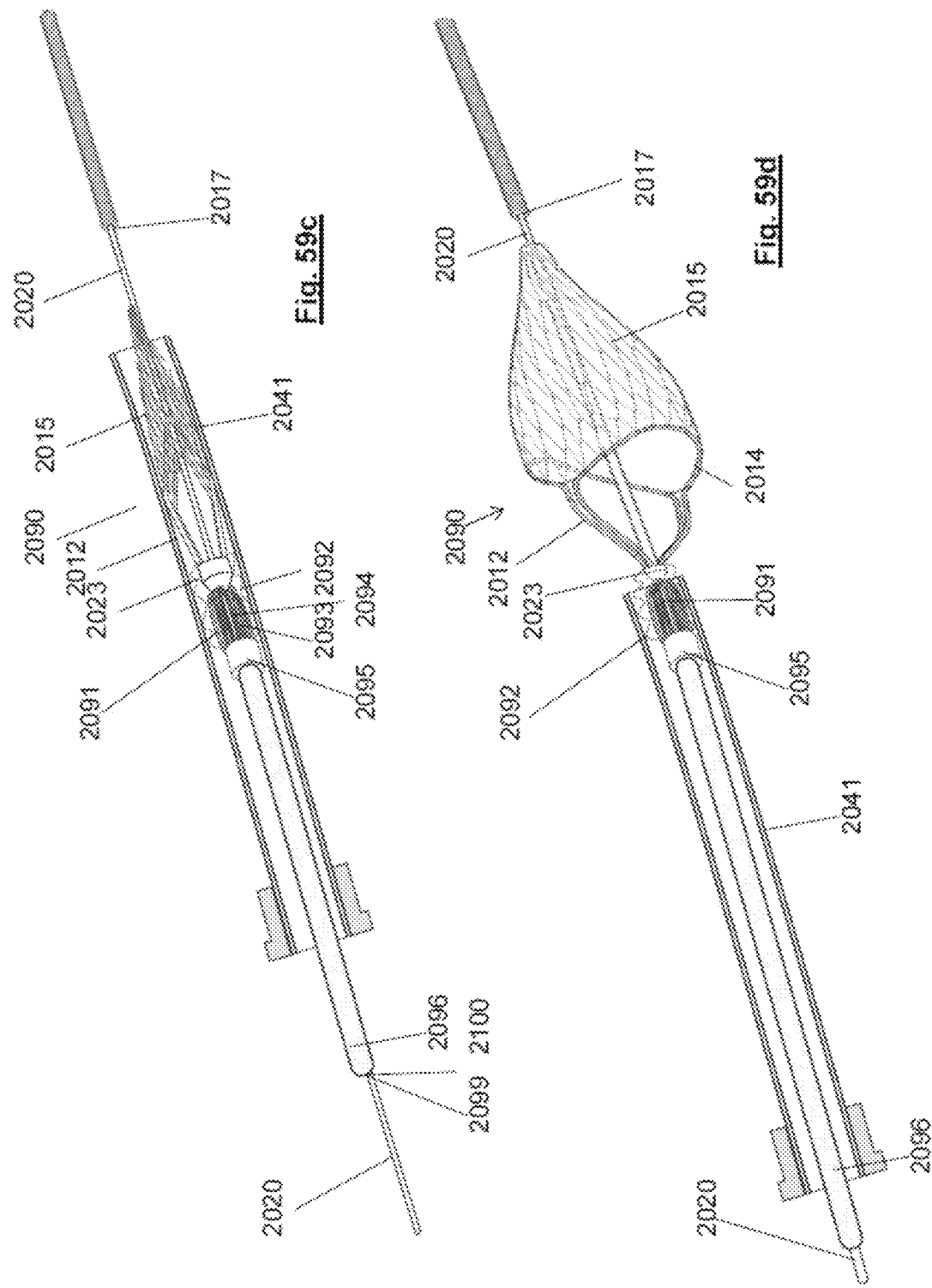

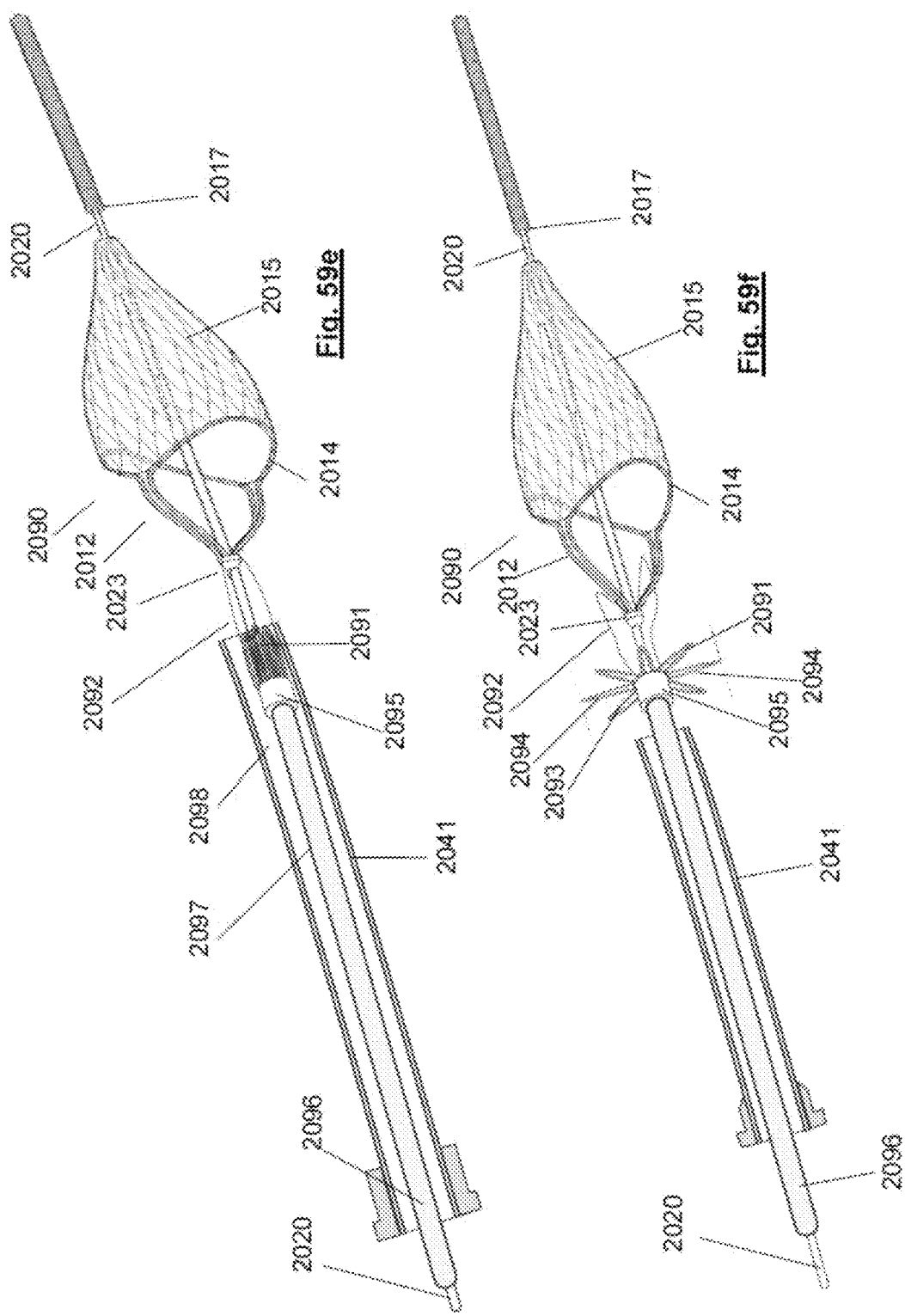

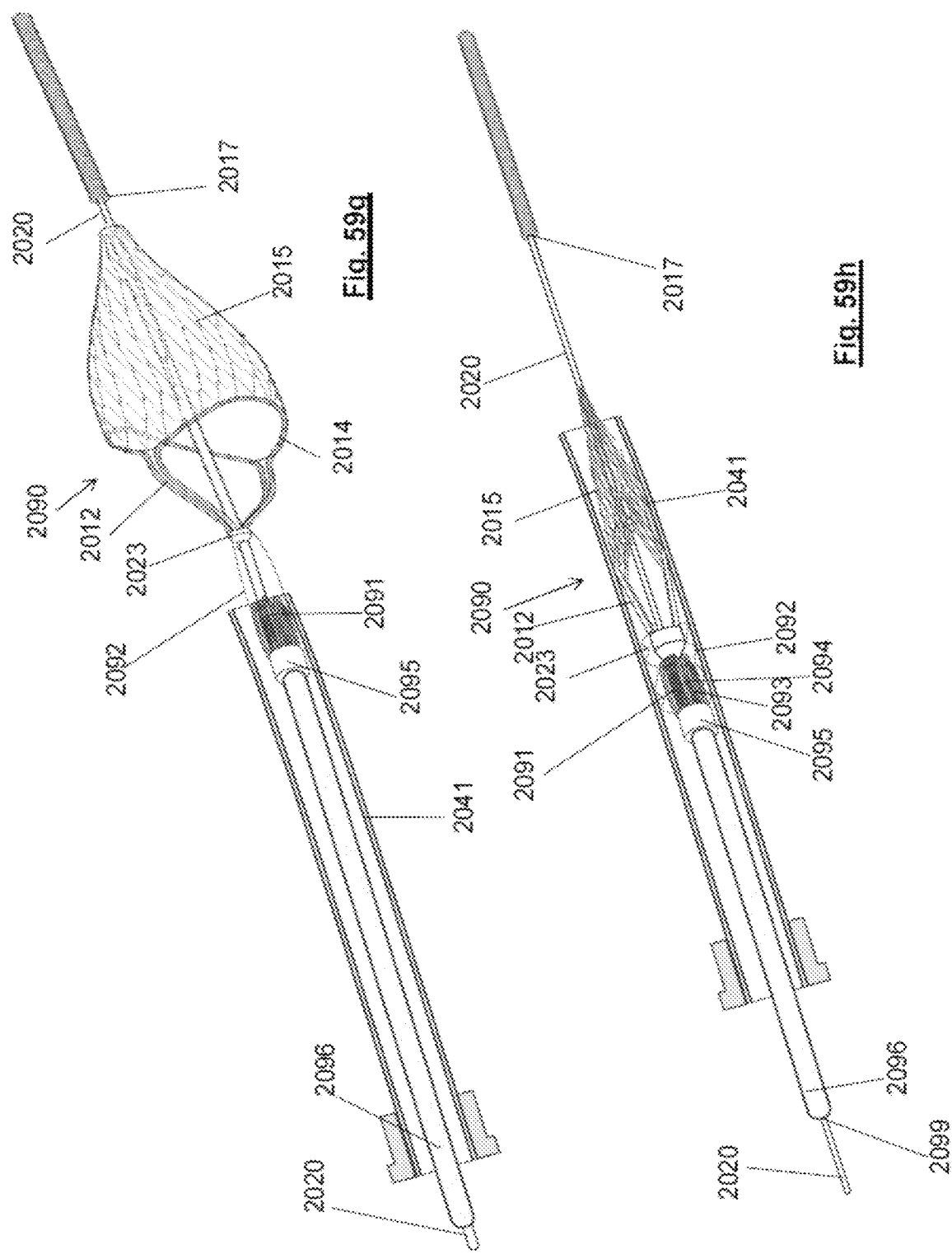

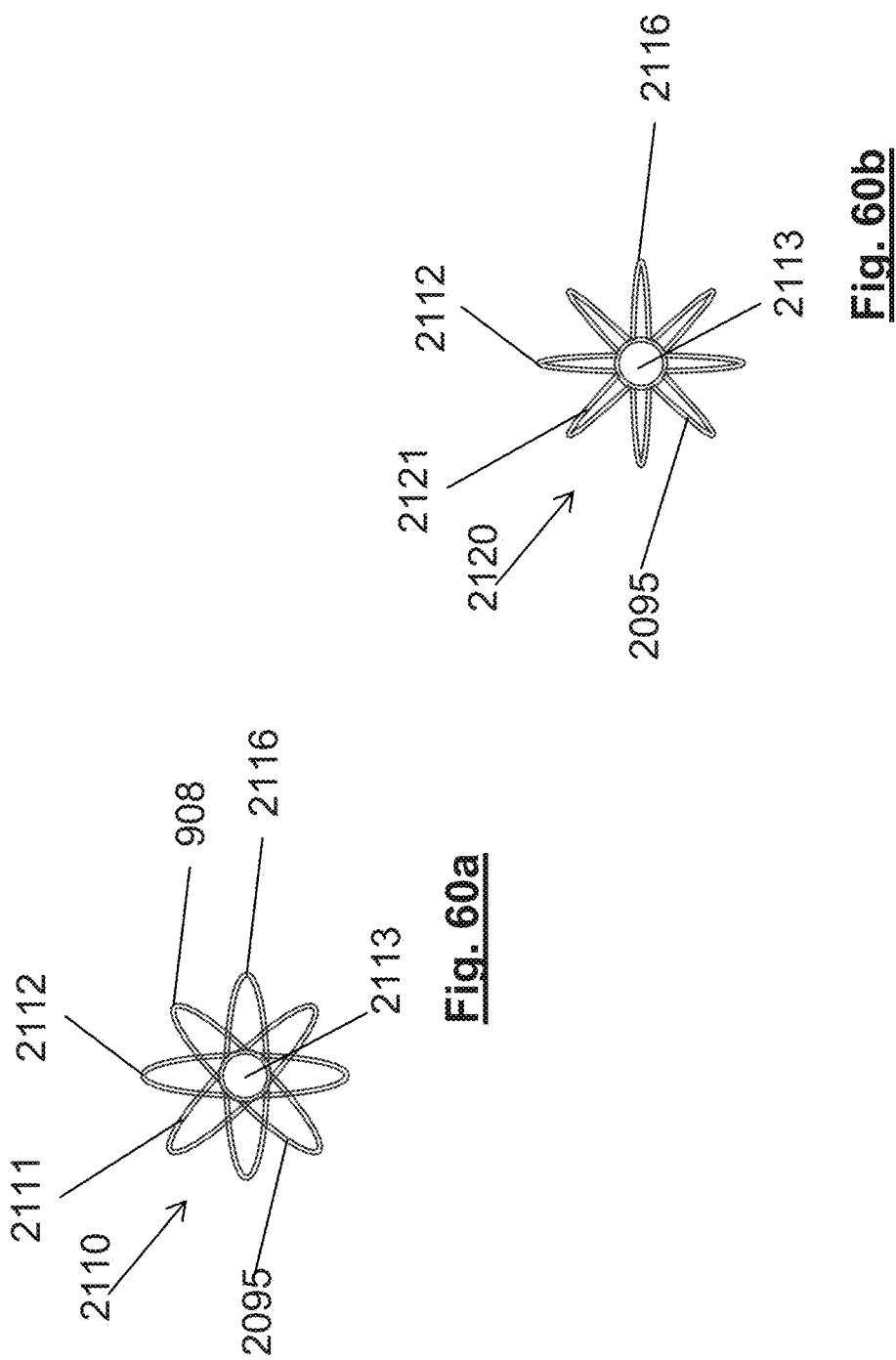

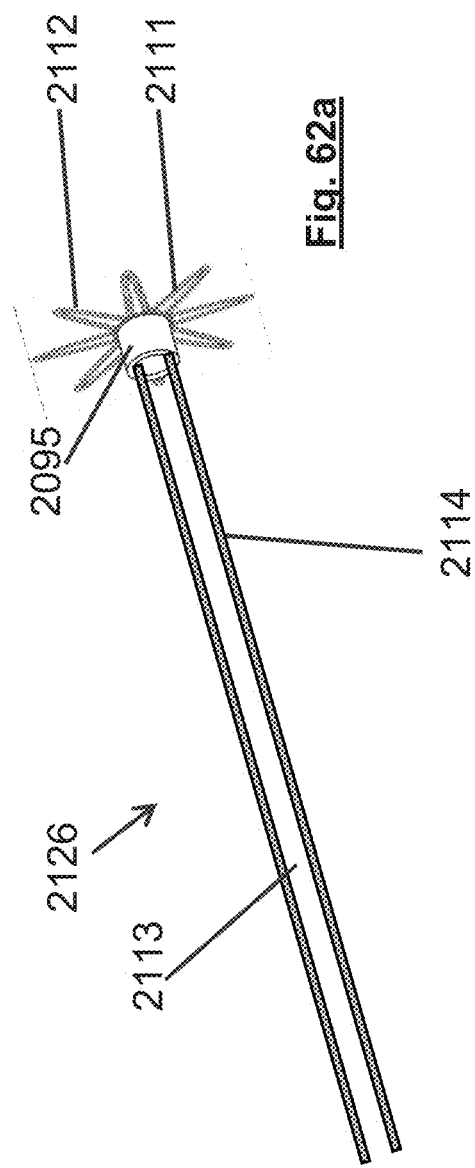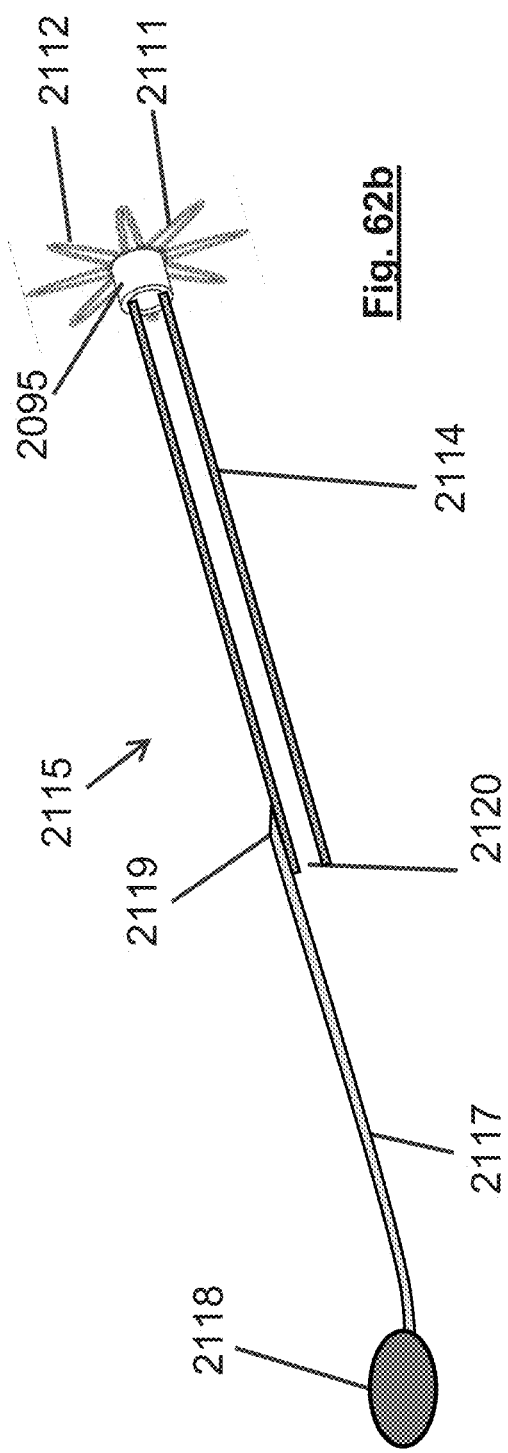

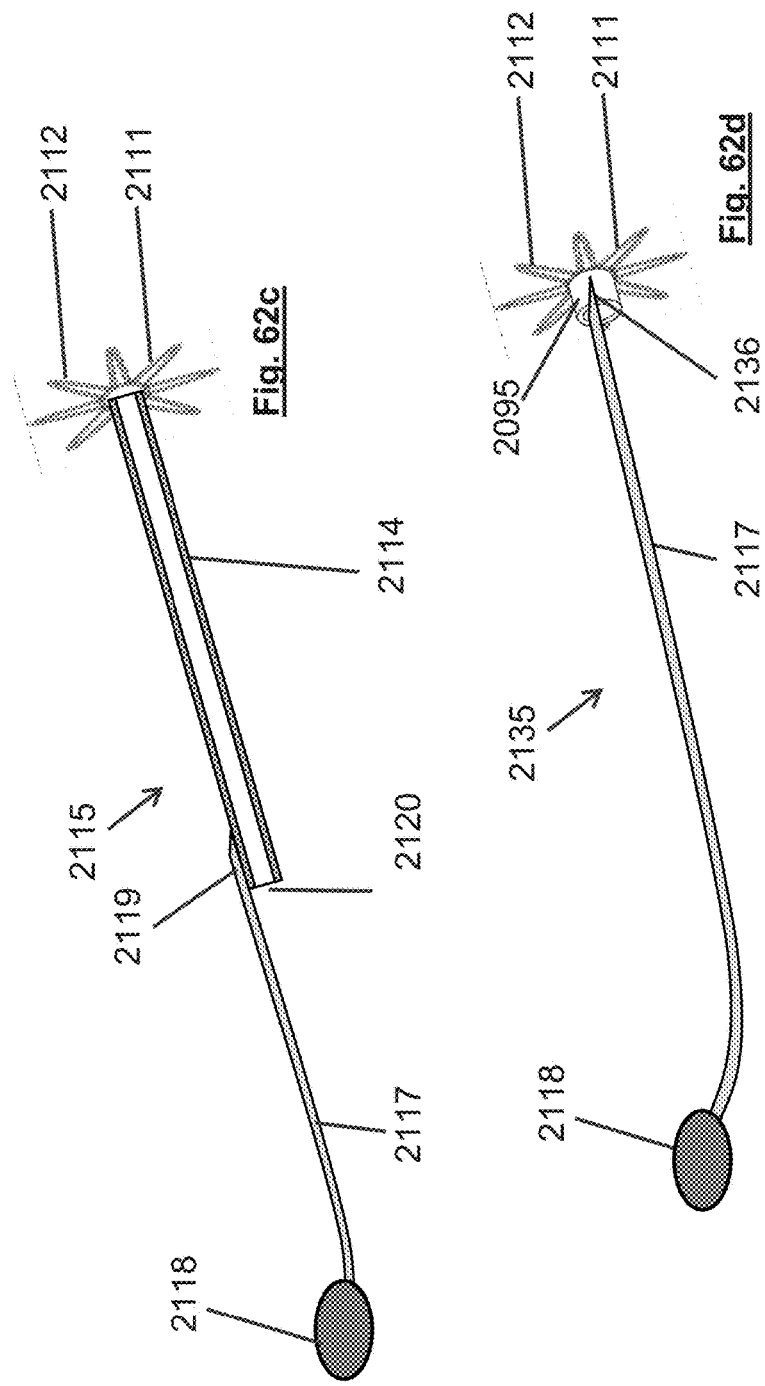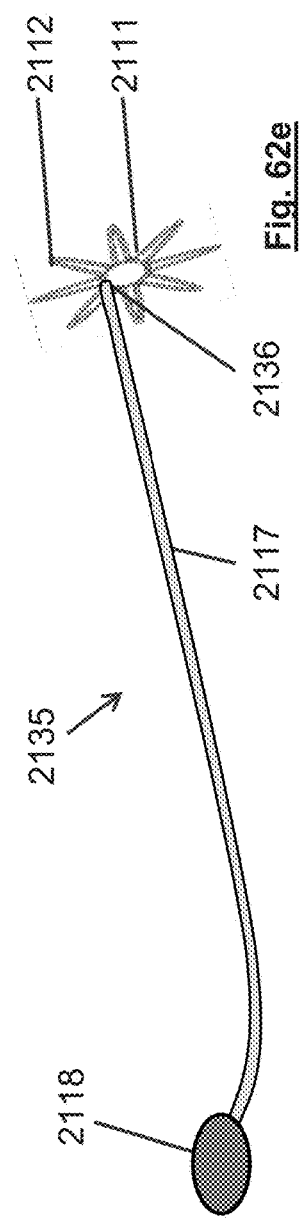

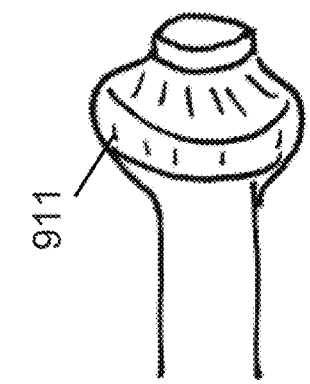
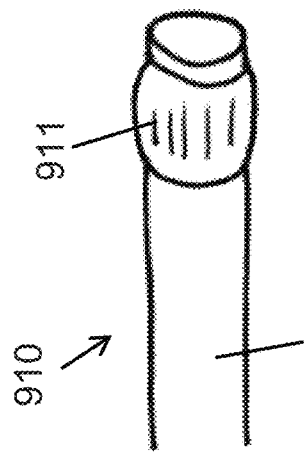
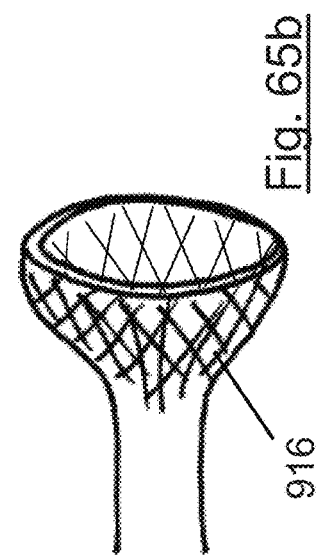
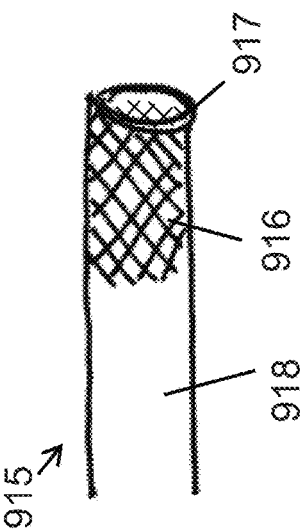
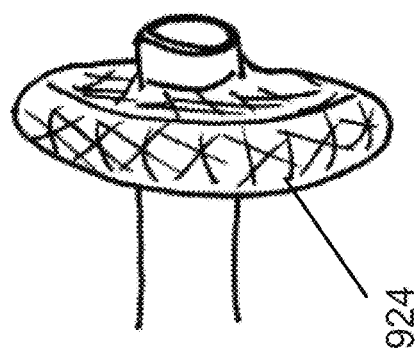
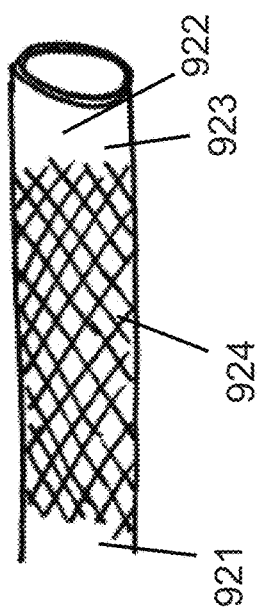

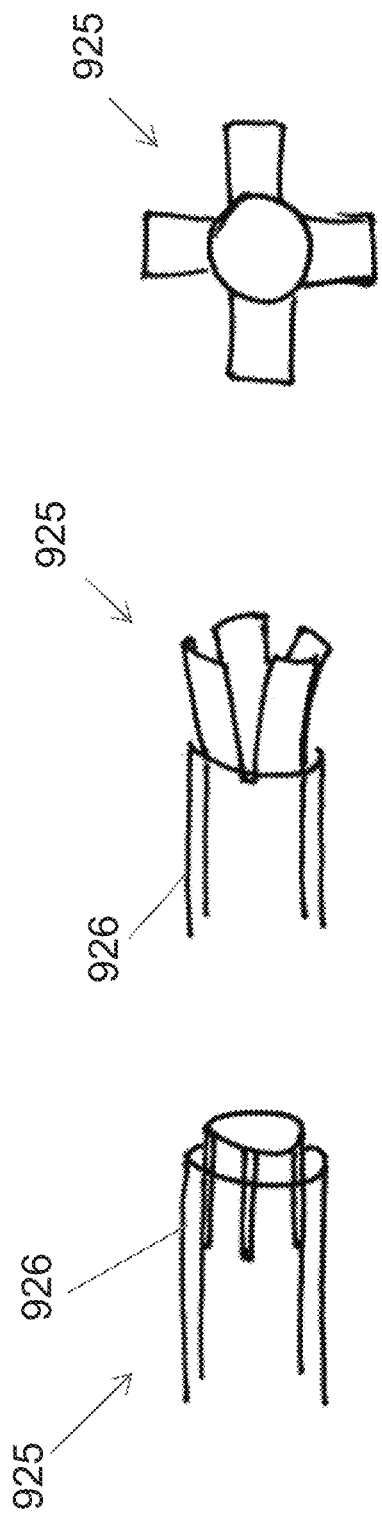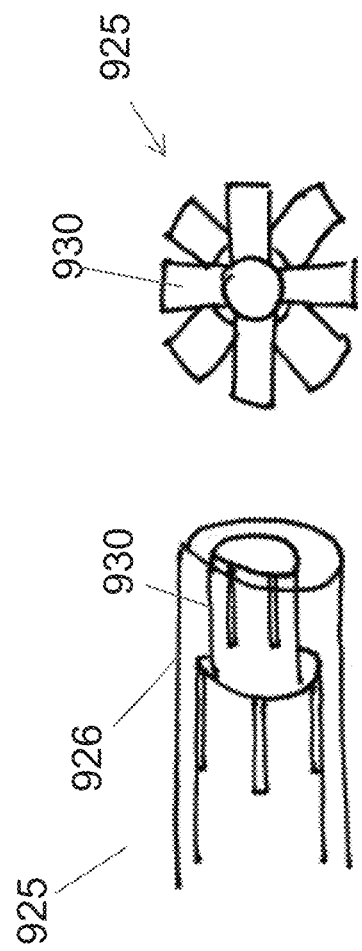

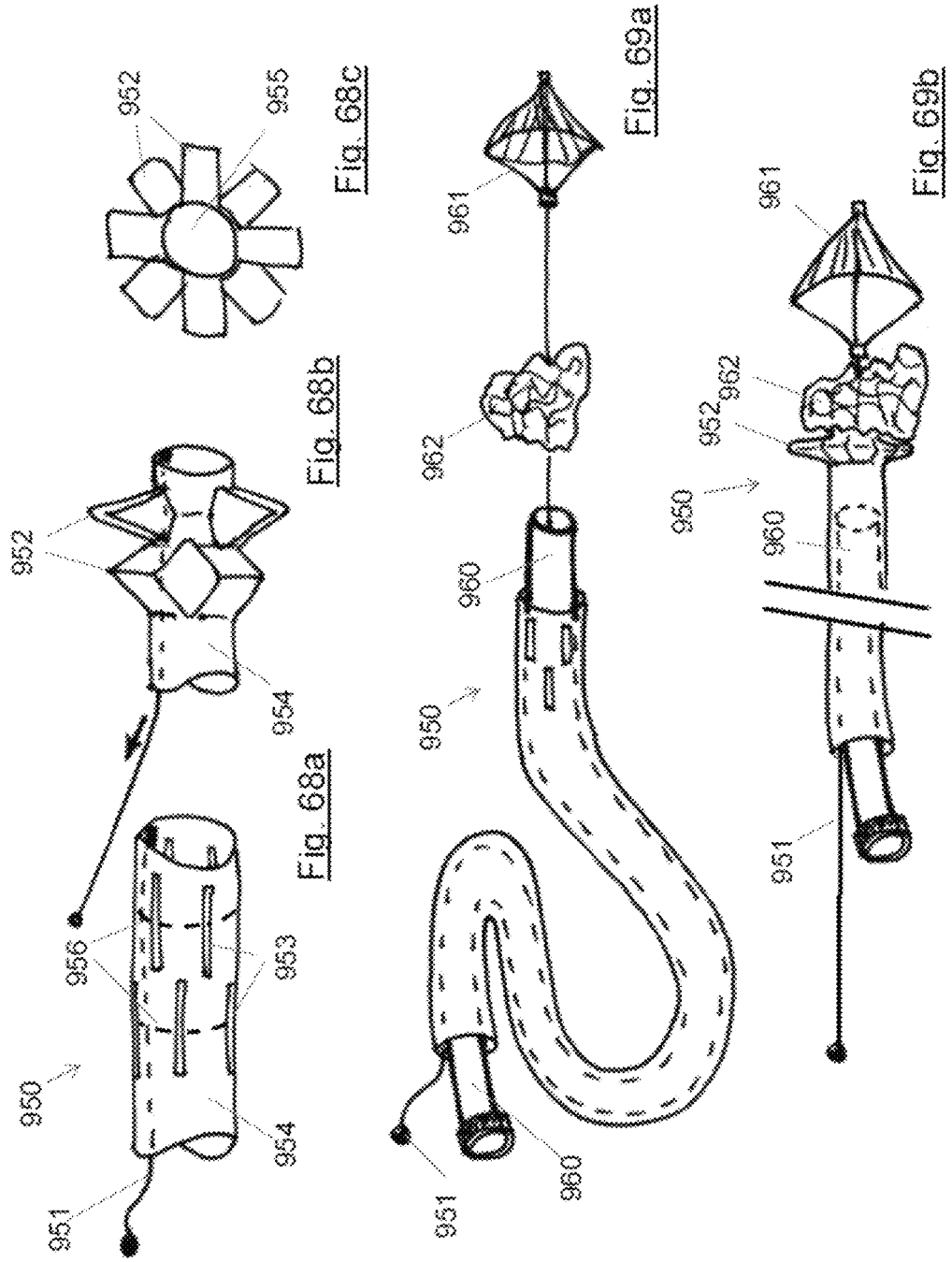

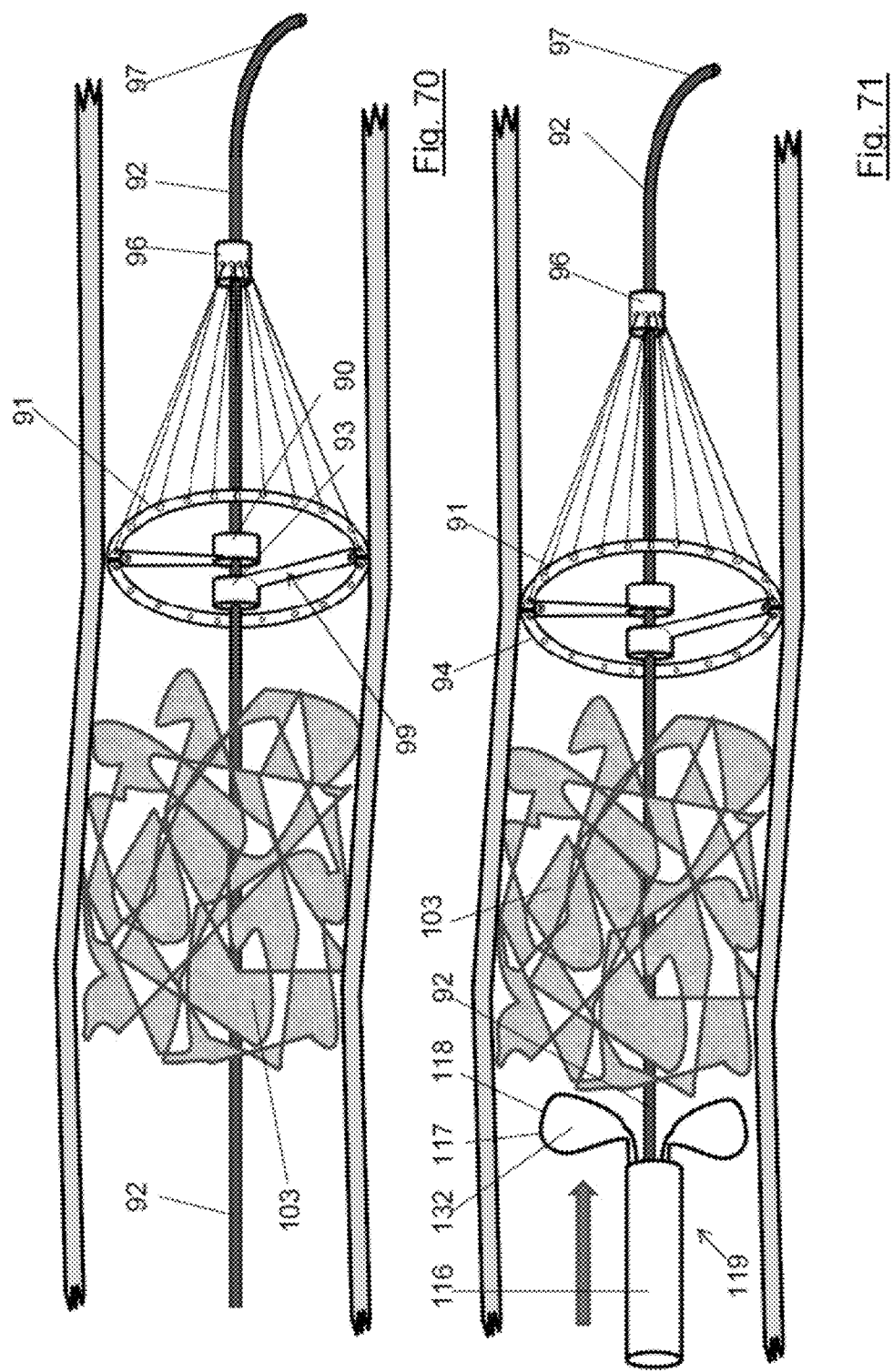

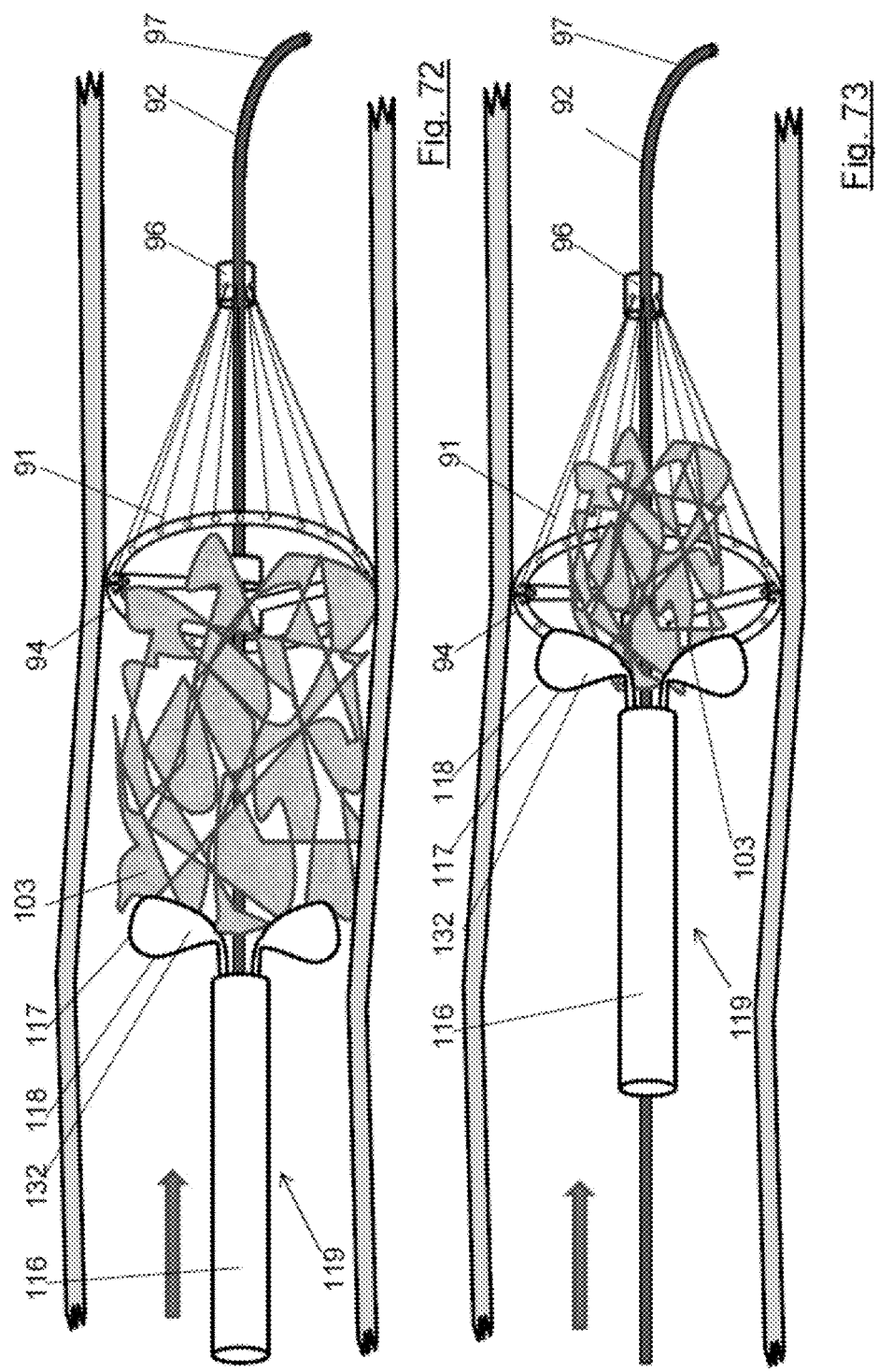

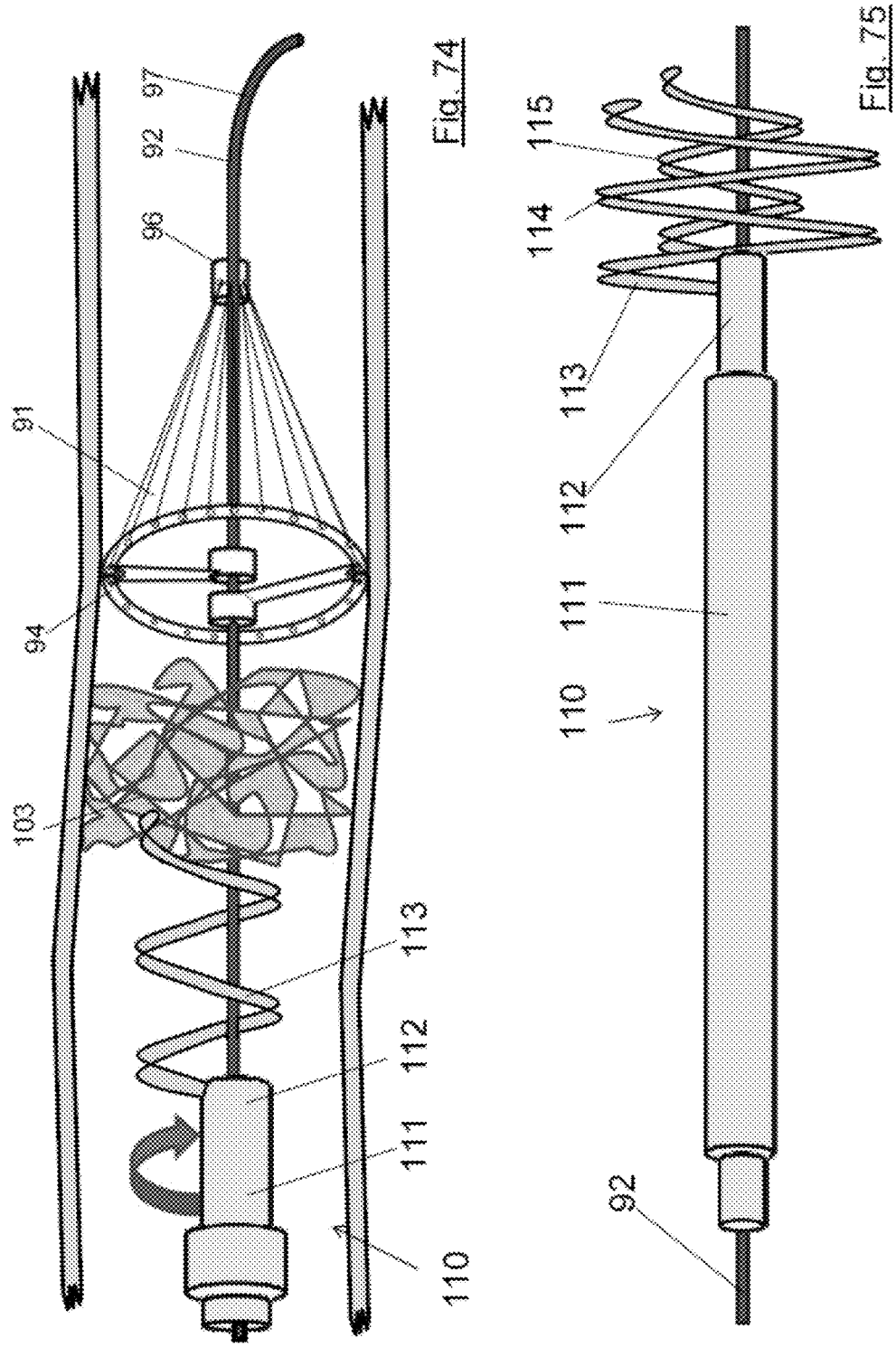

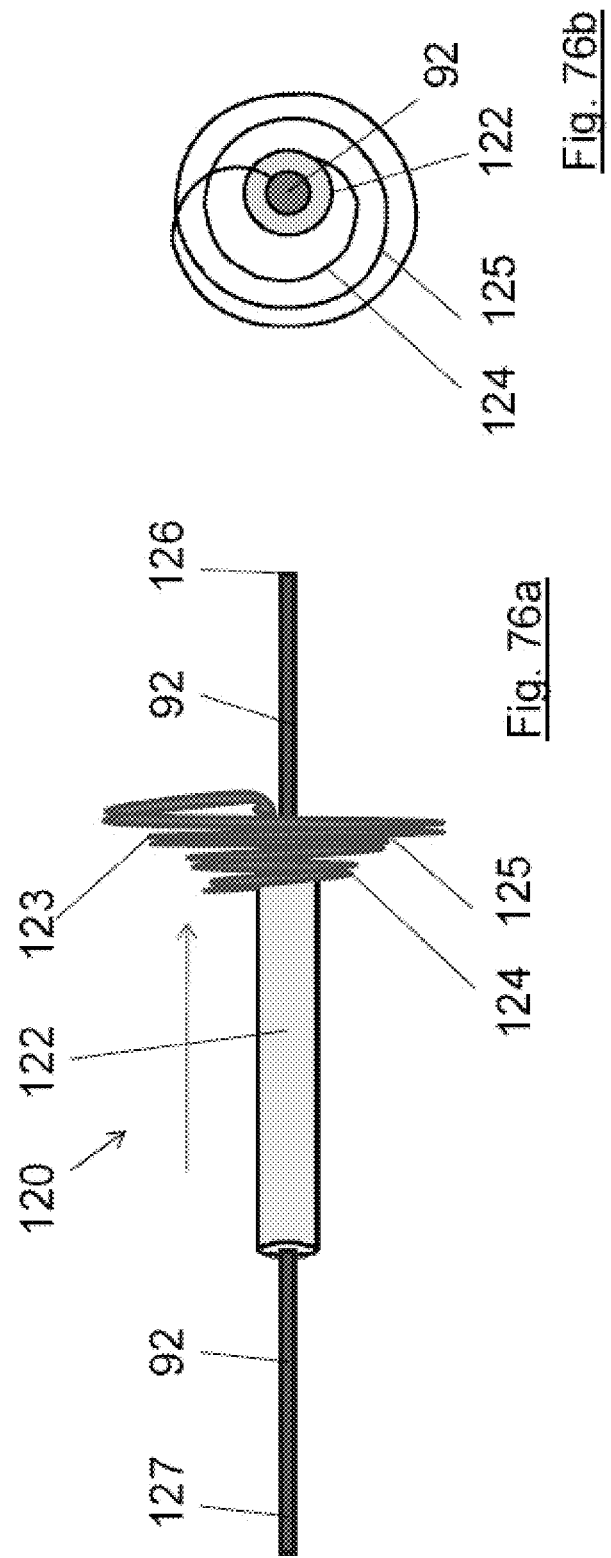

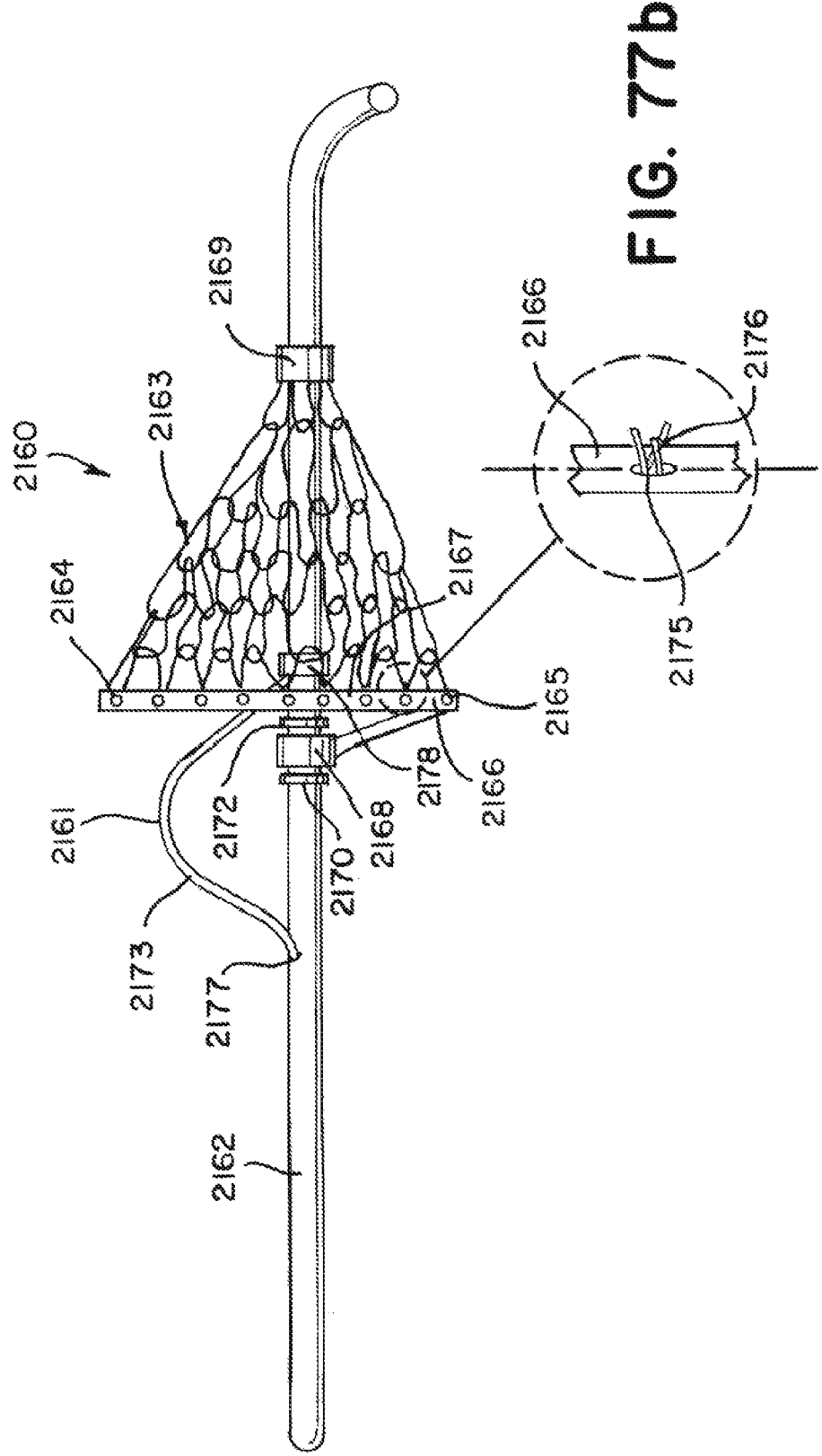

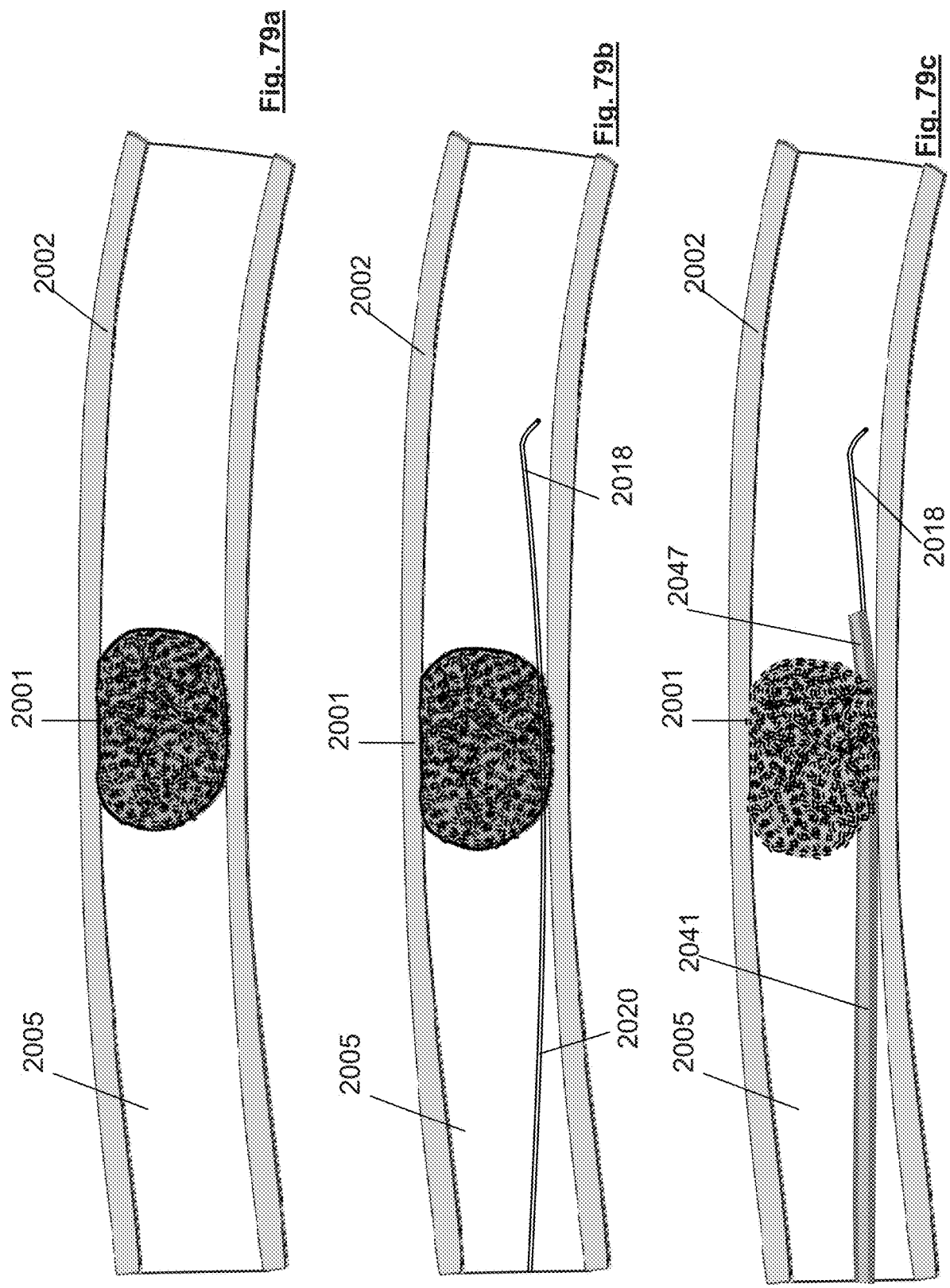

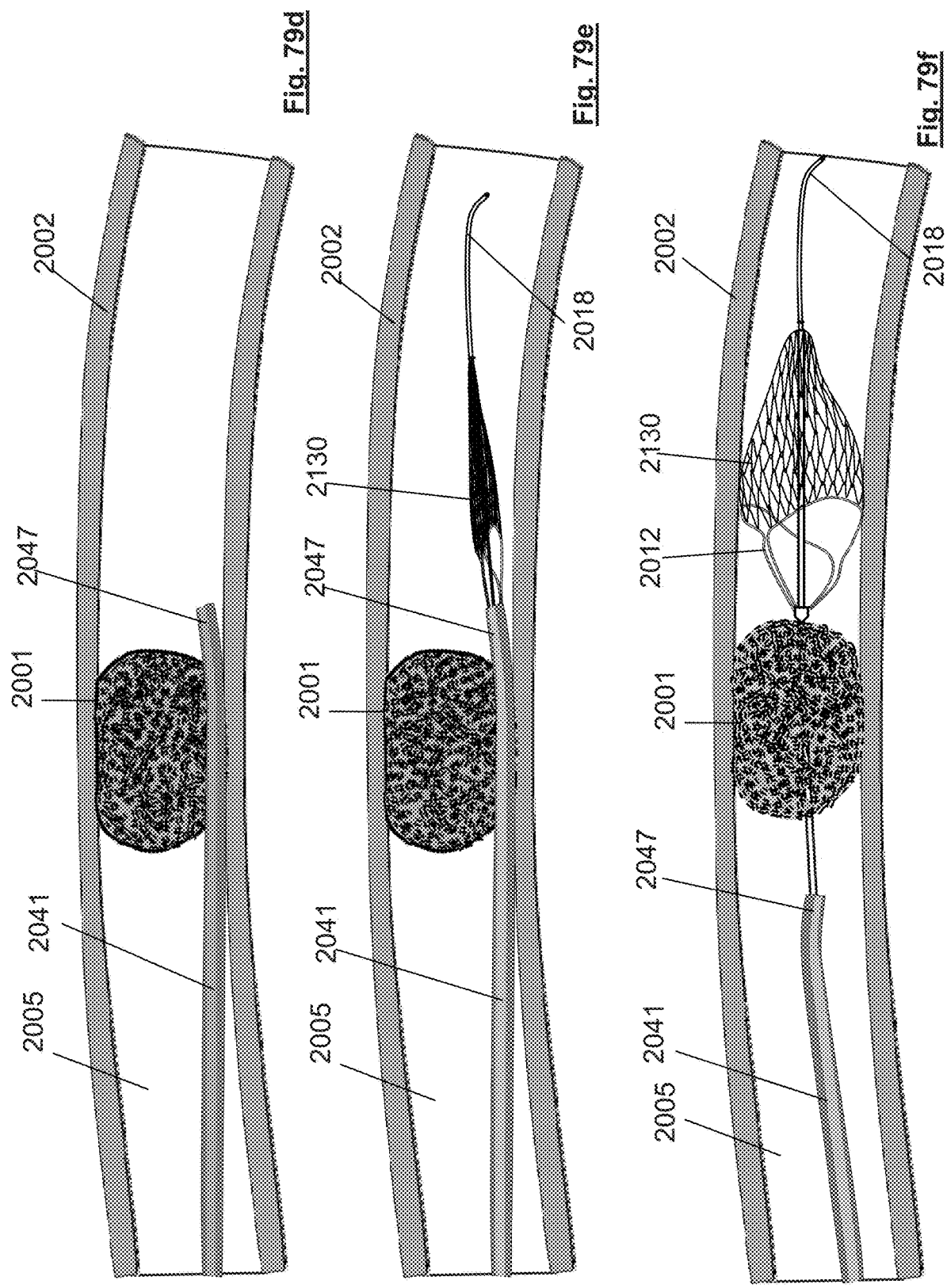

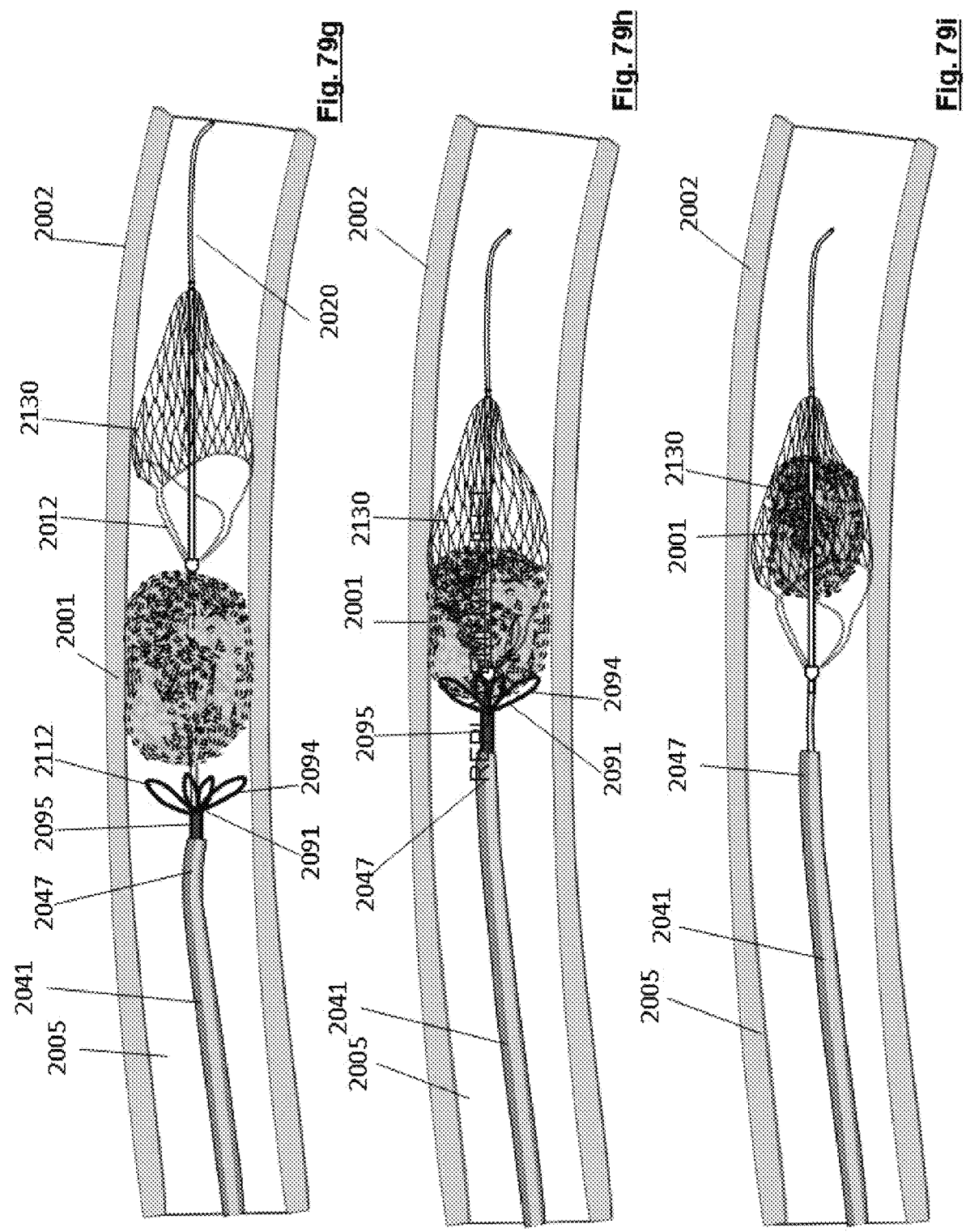

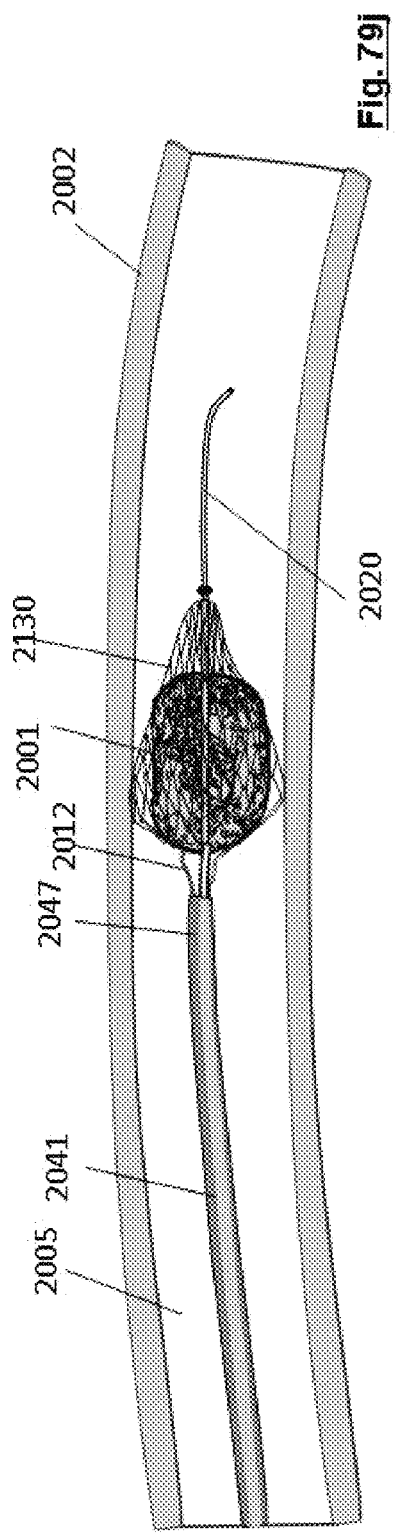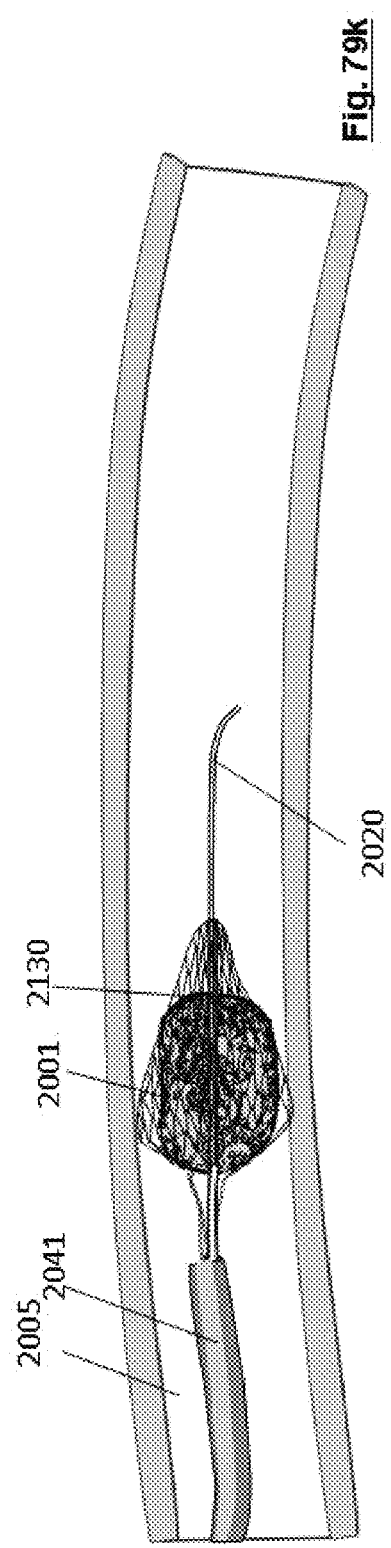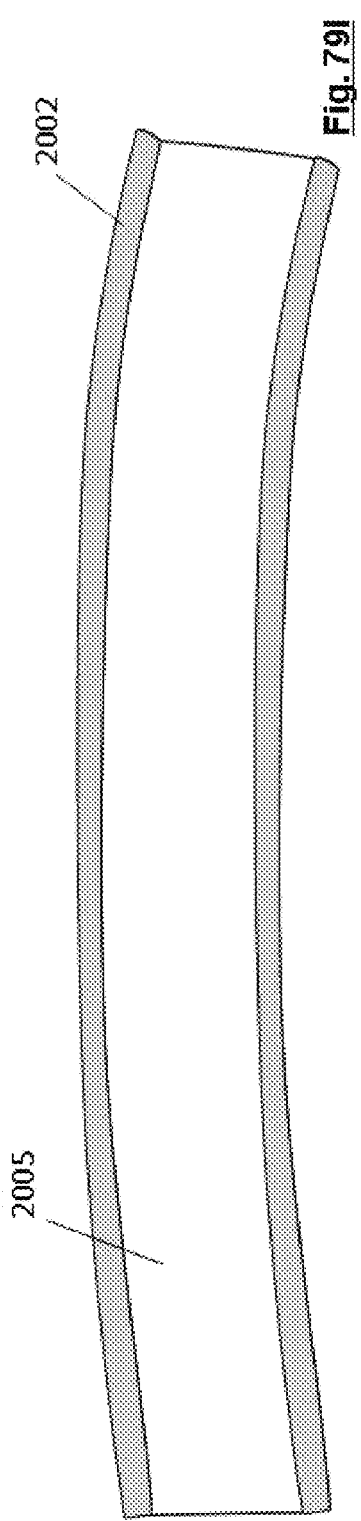

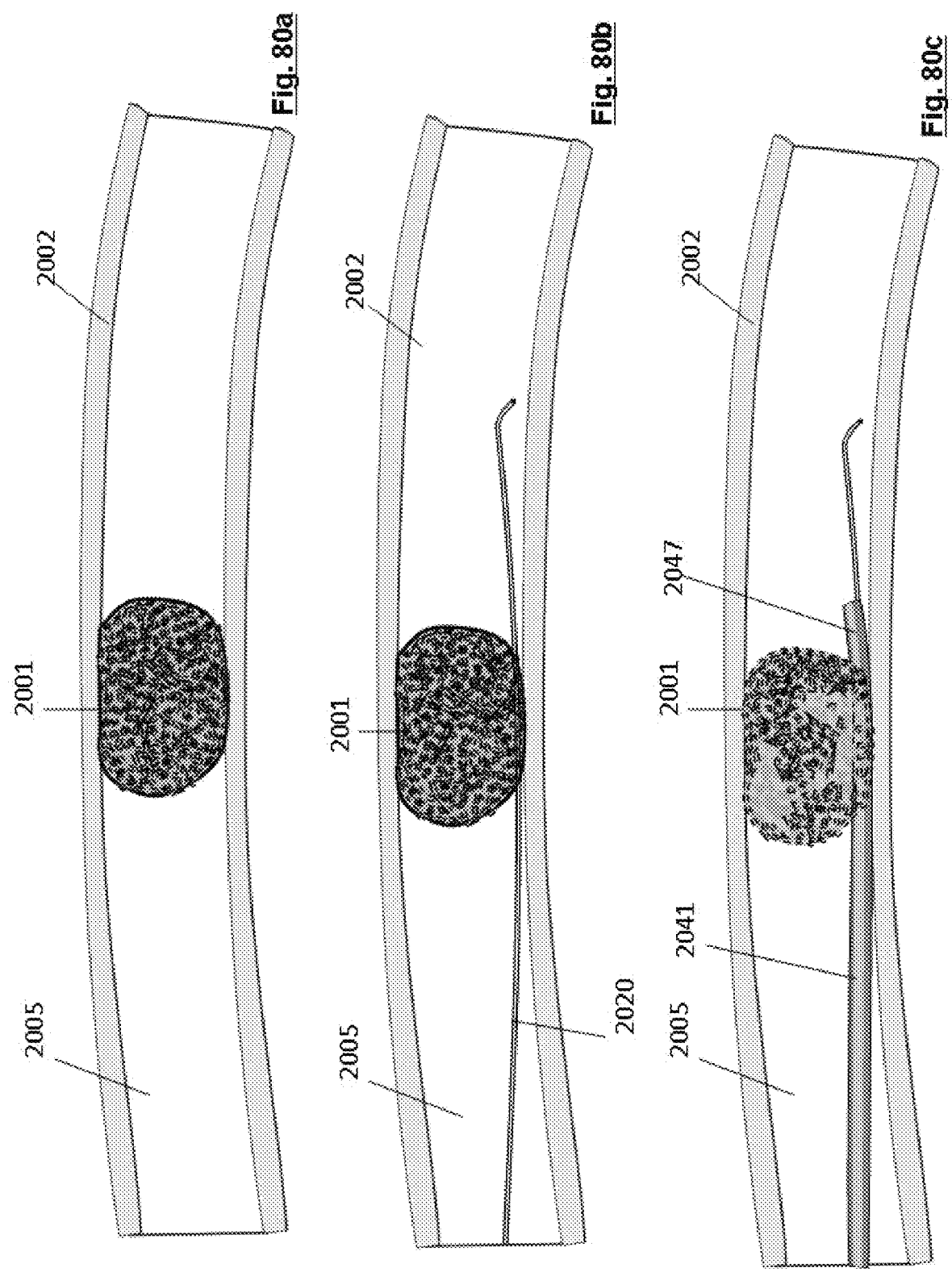

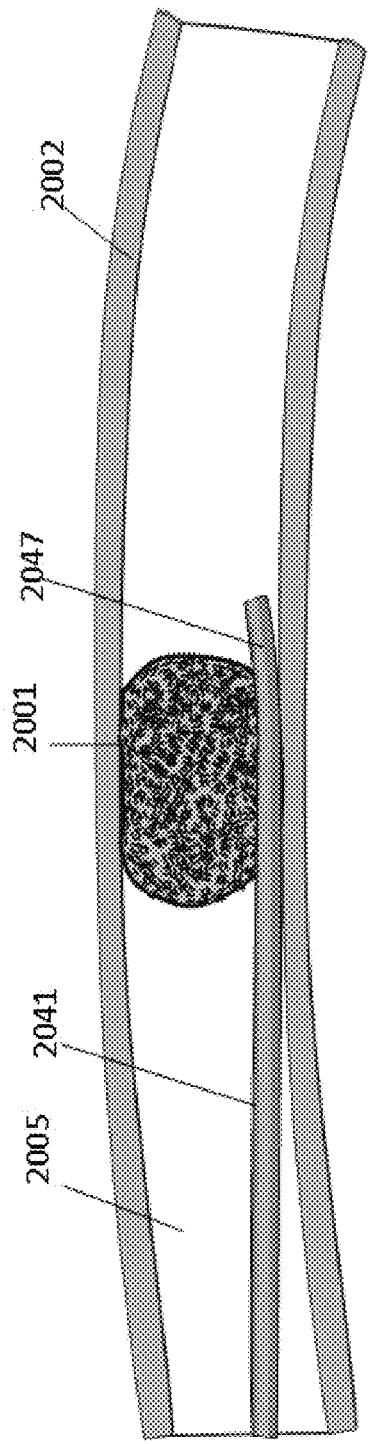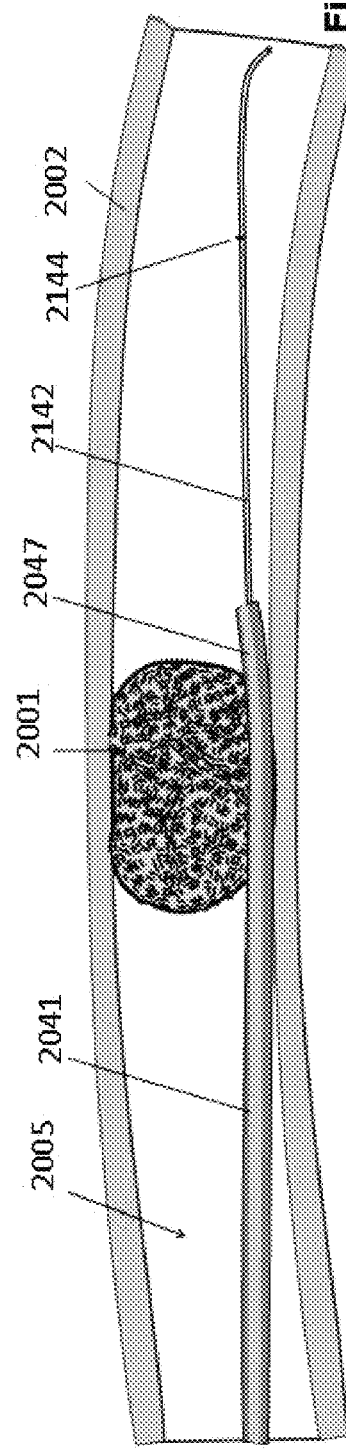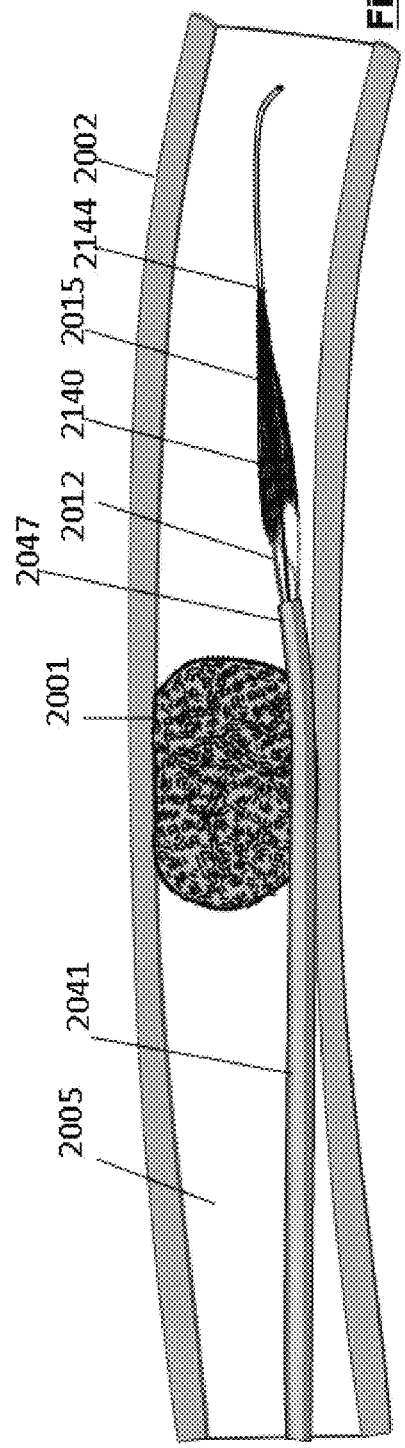

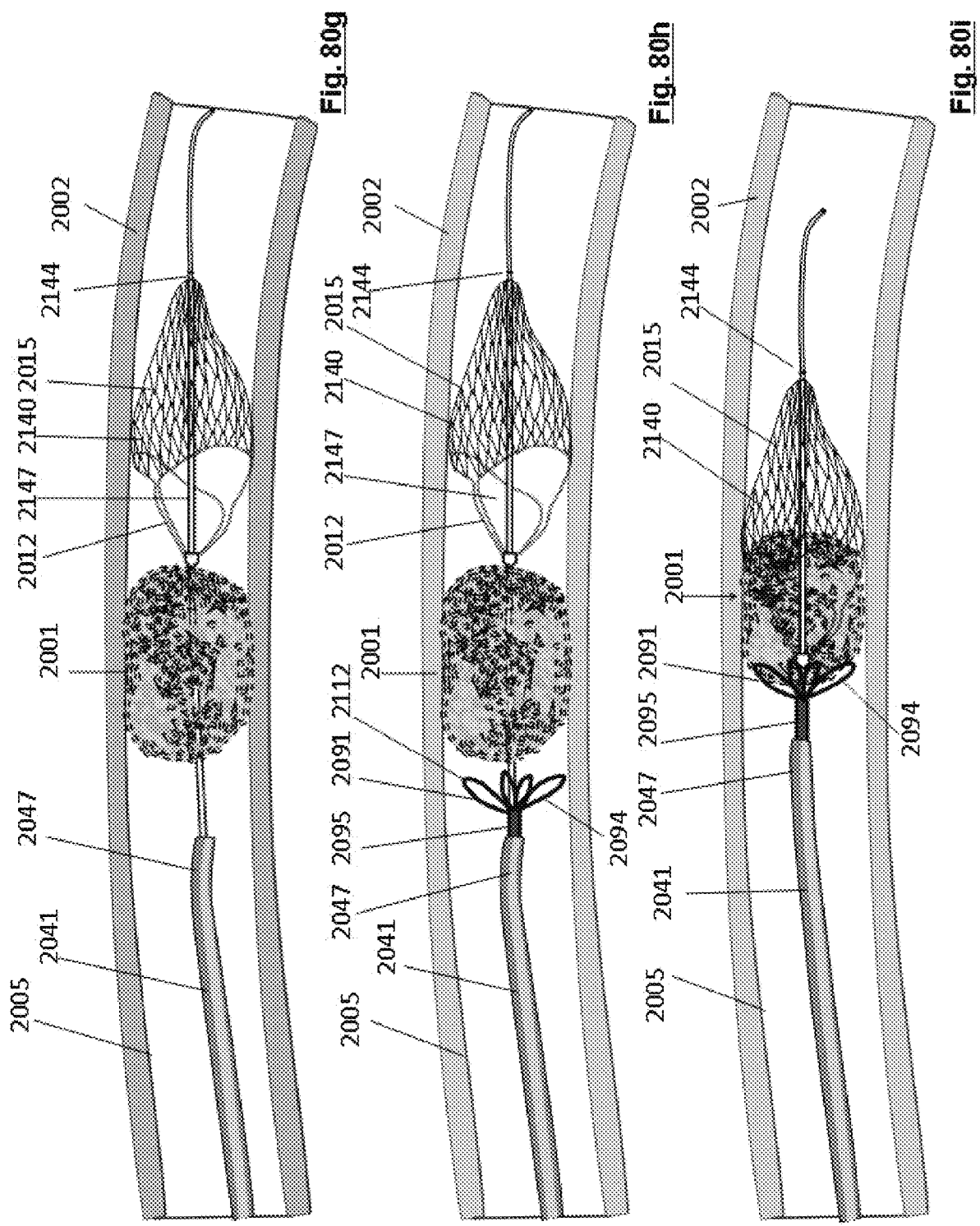

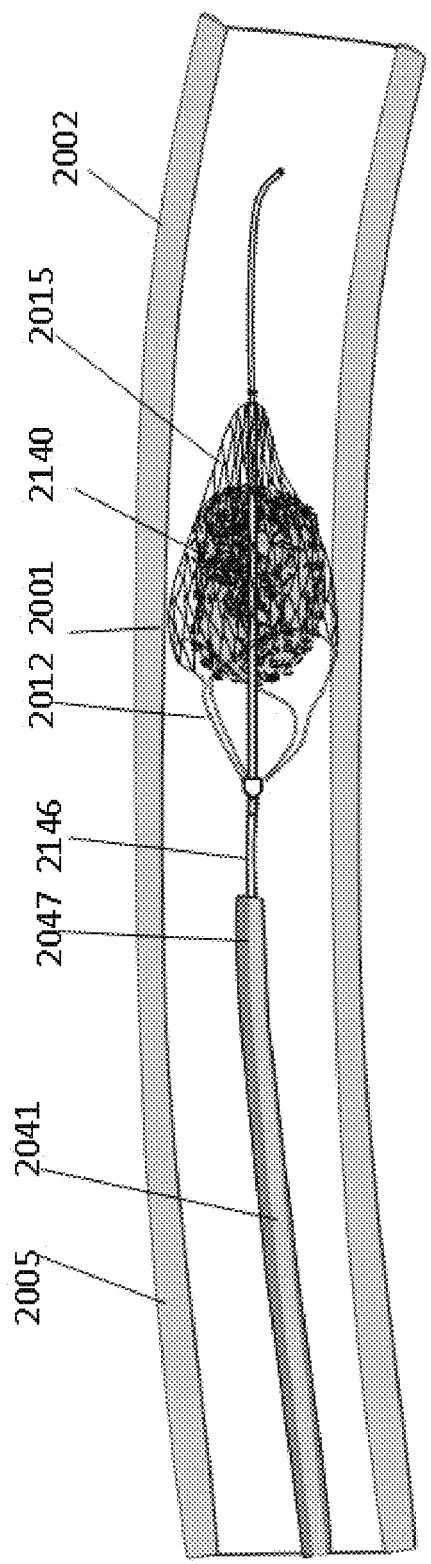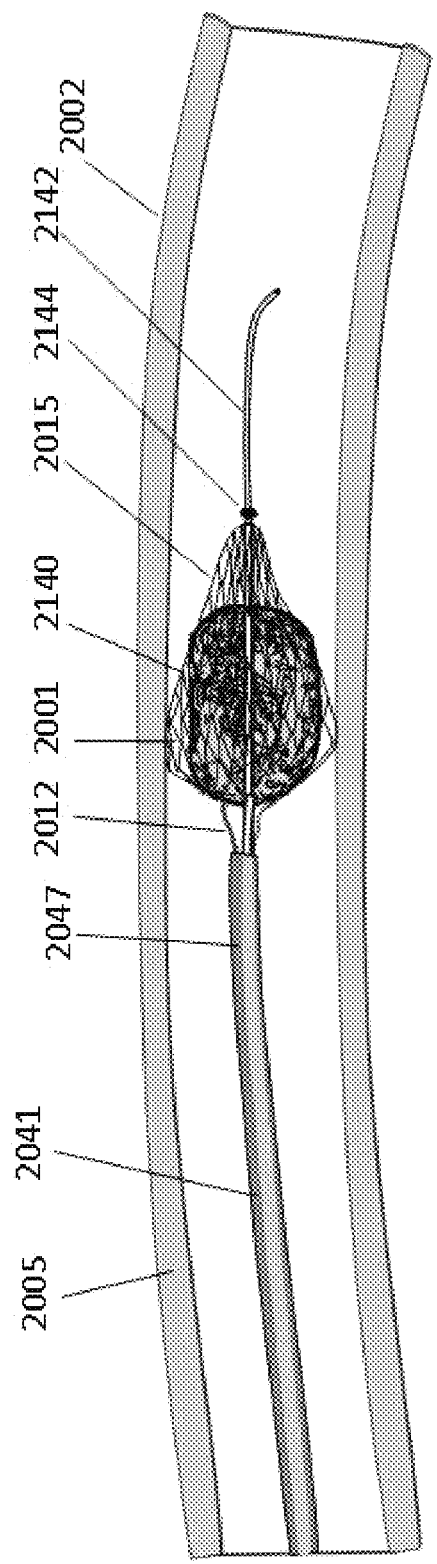

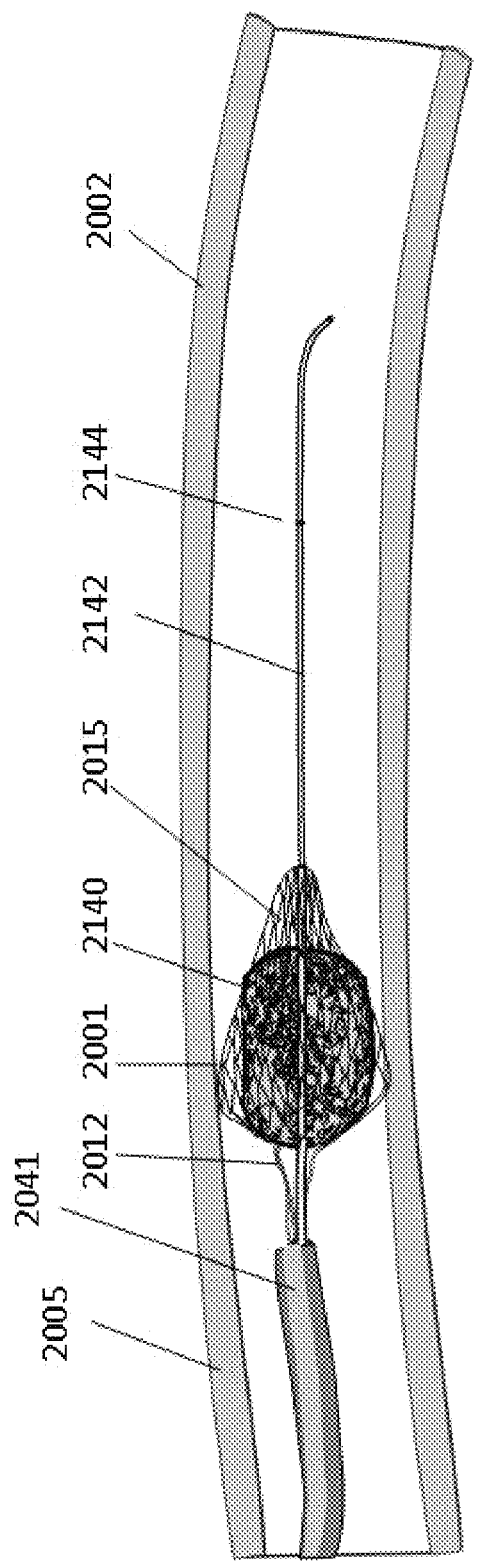
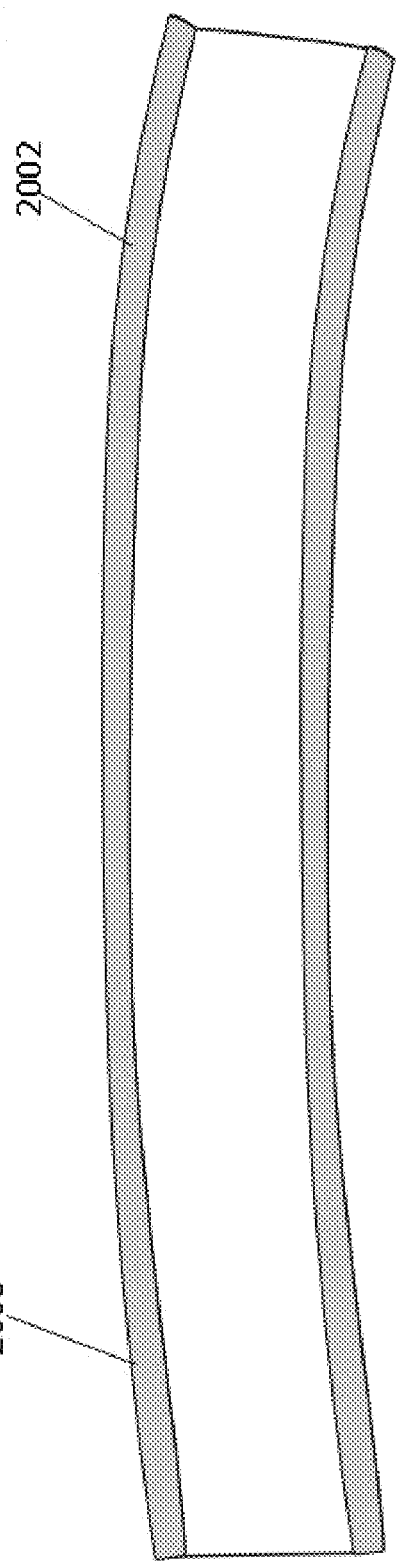
Fig. 80l
Fig. 80m

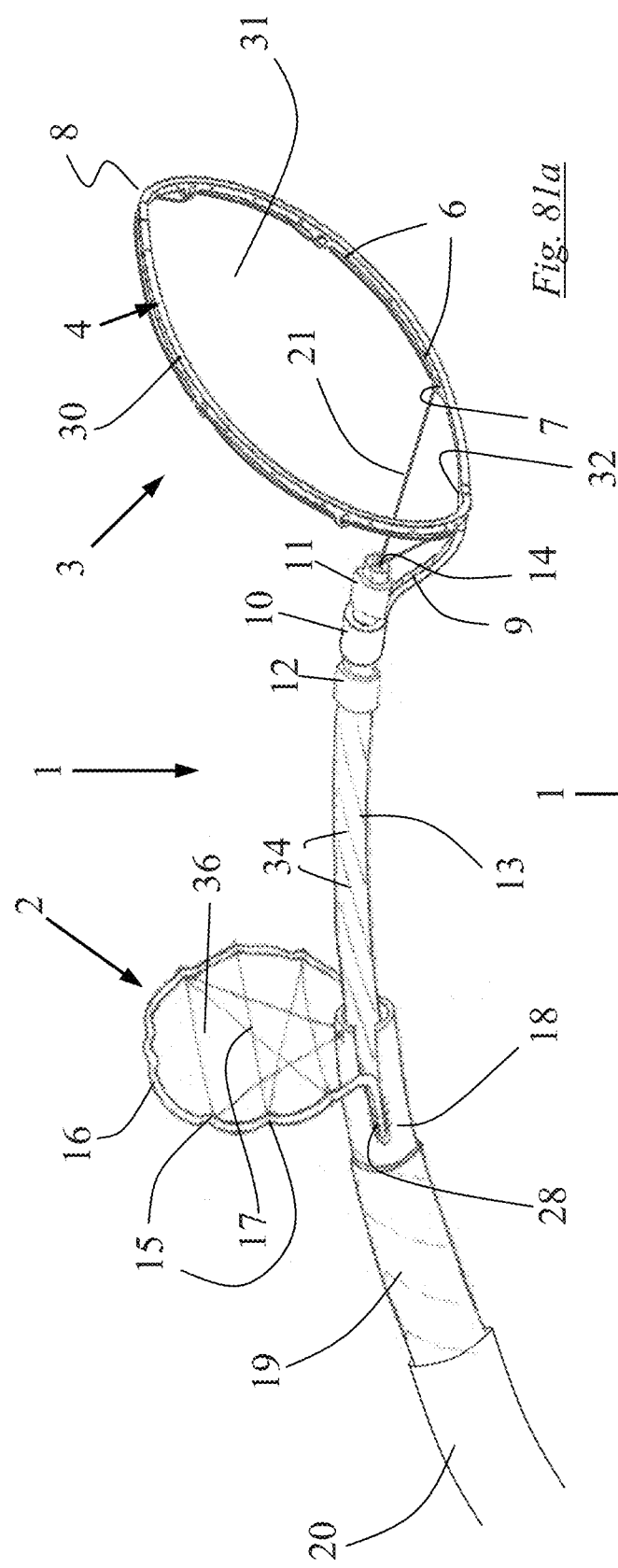
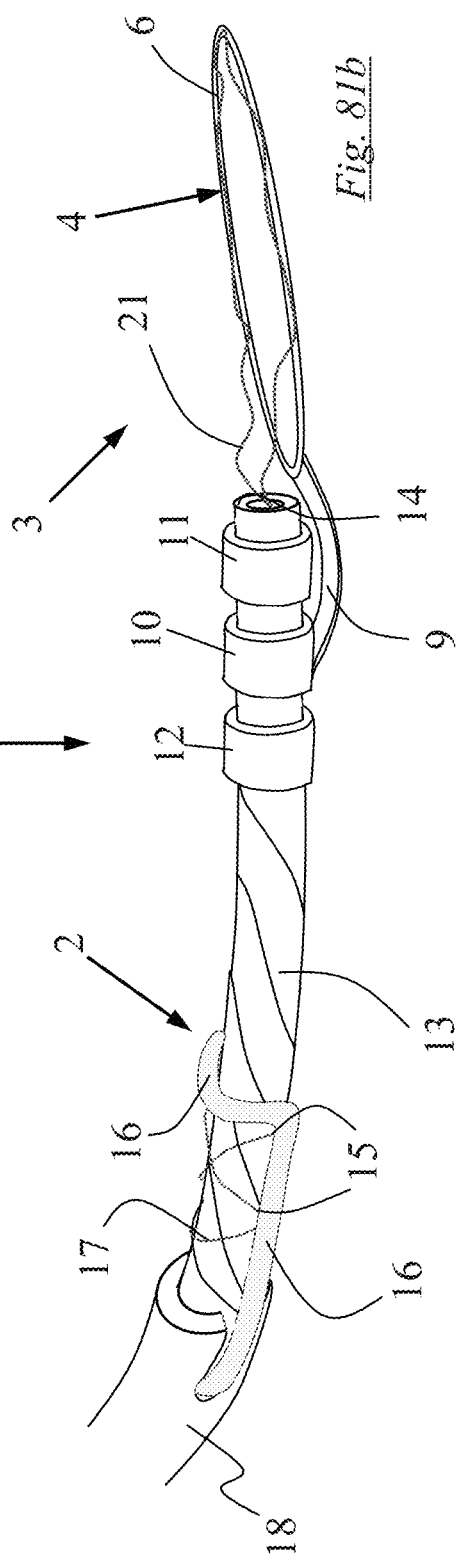
Fig. 81a
Fig. 81b

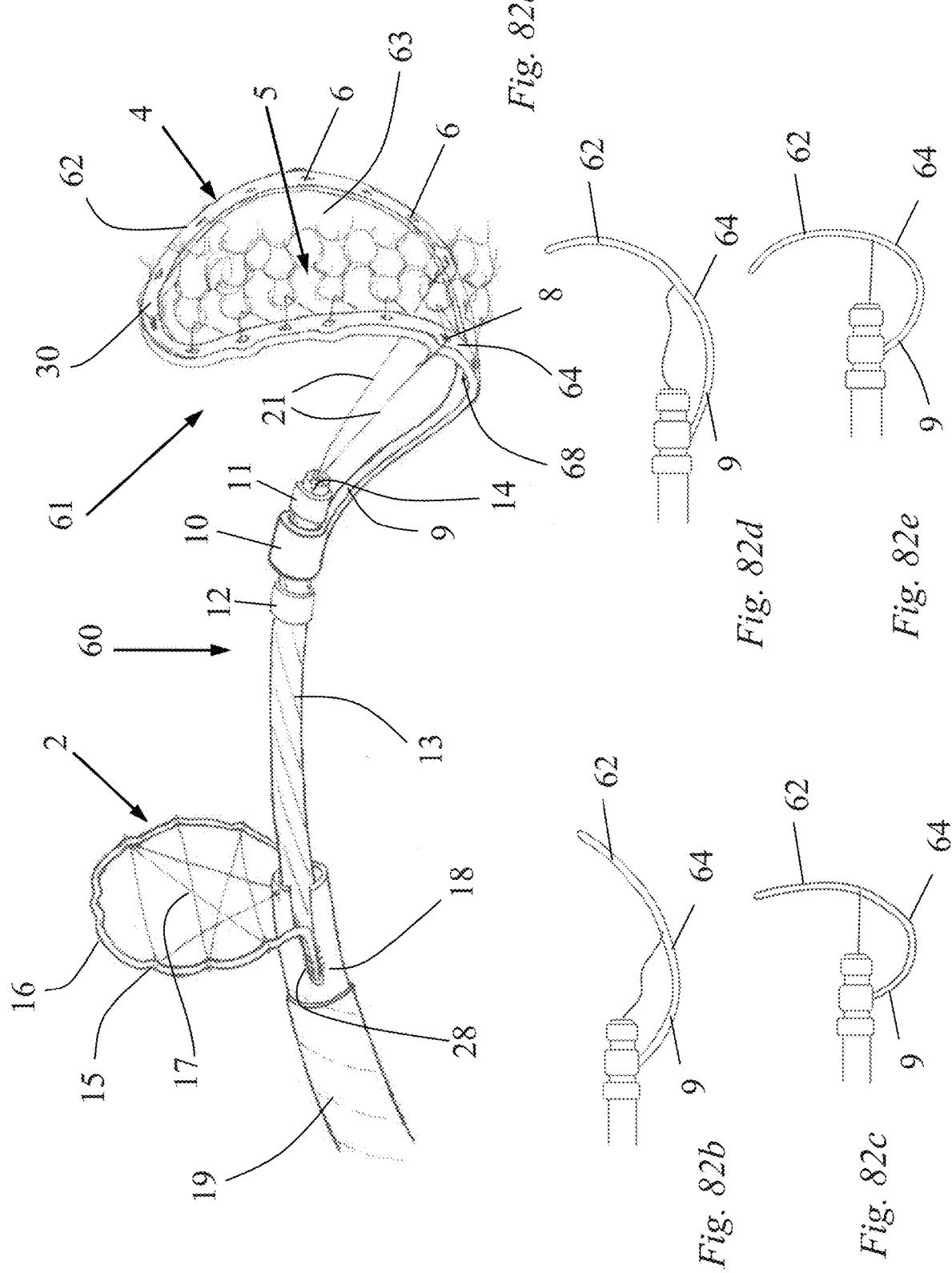

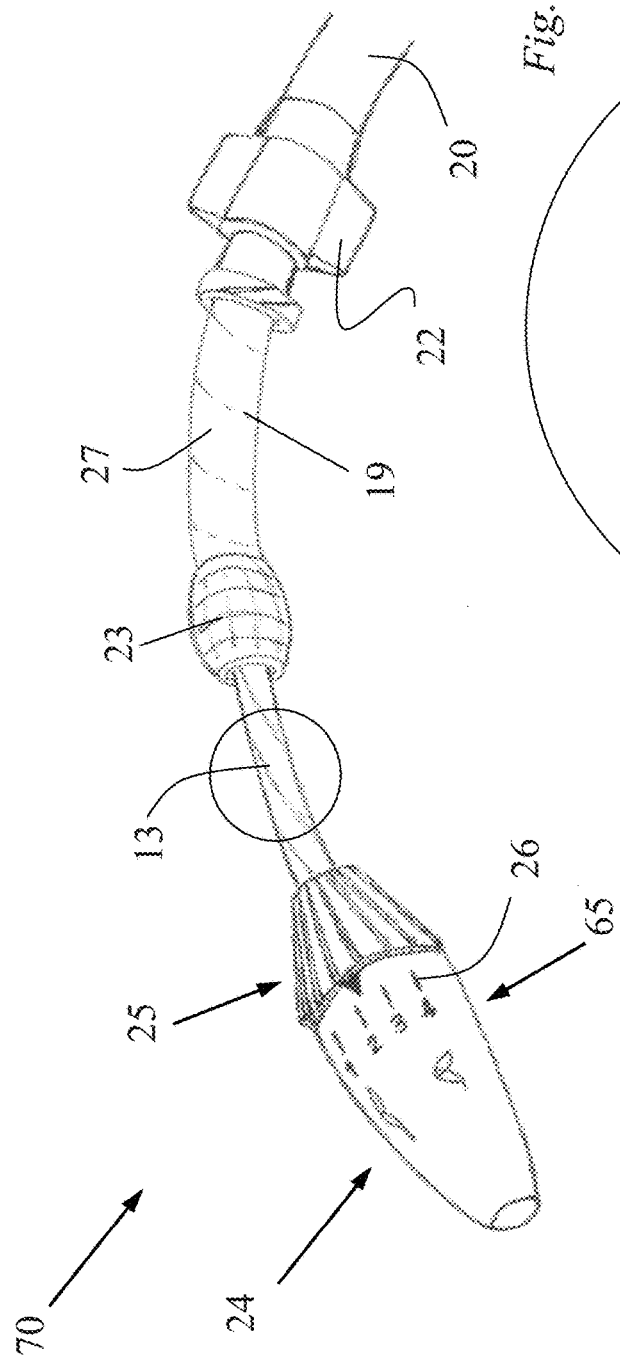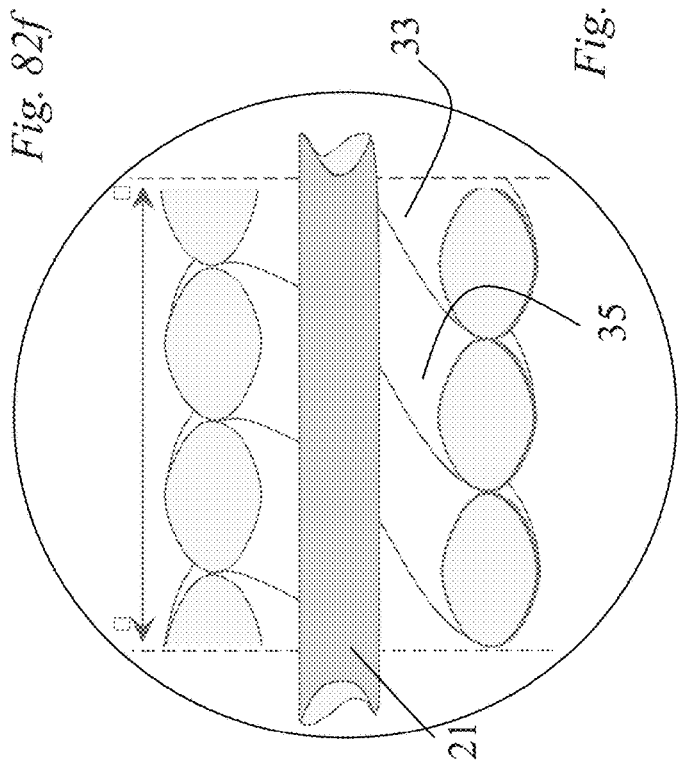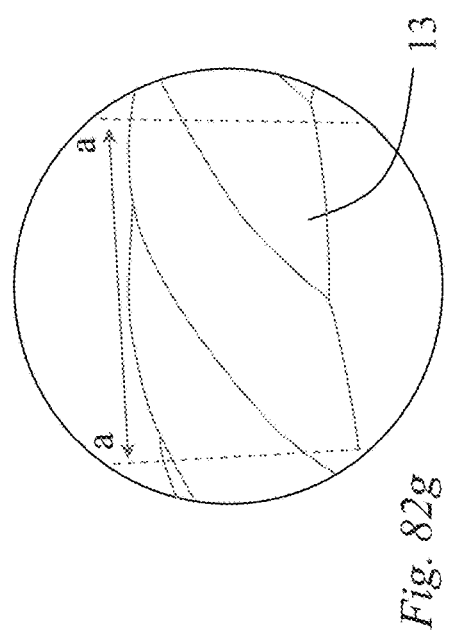

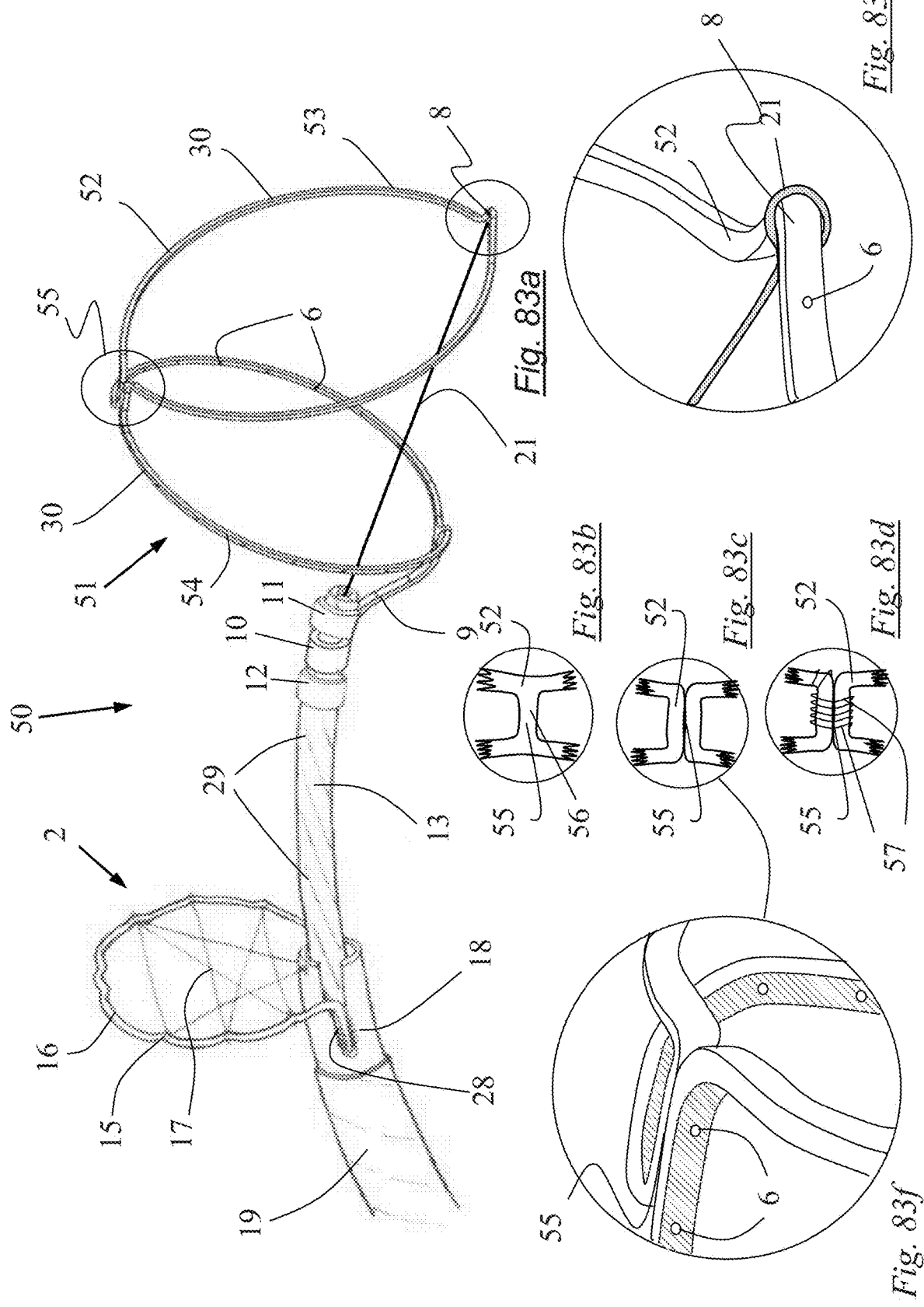

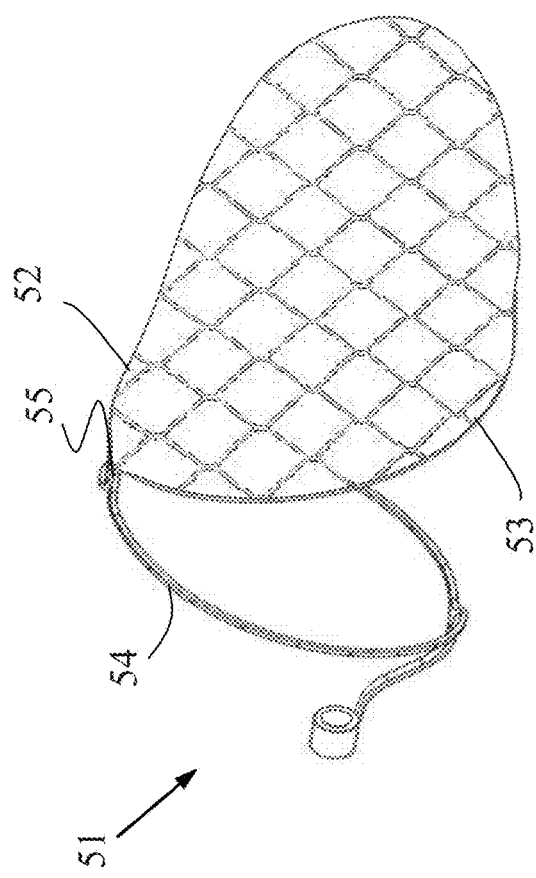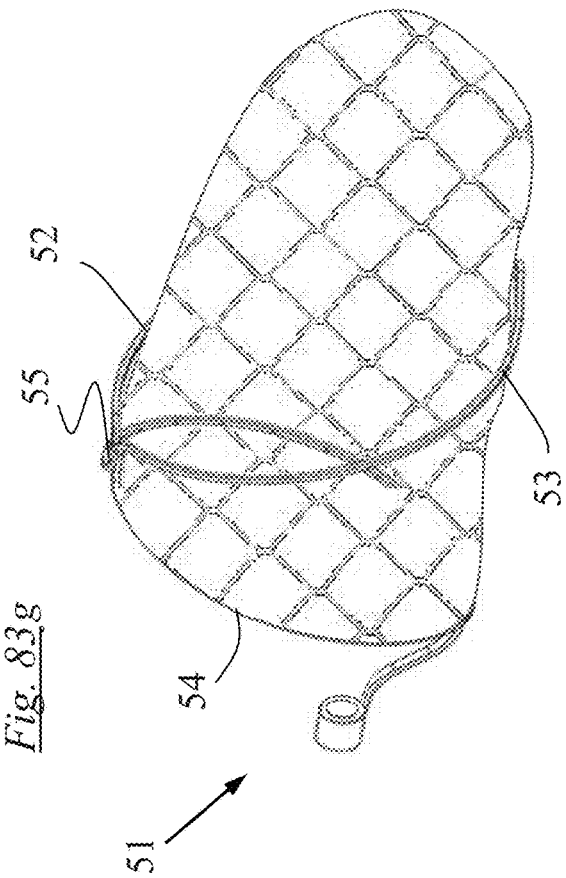

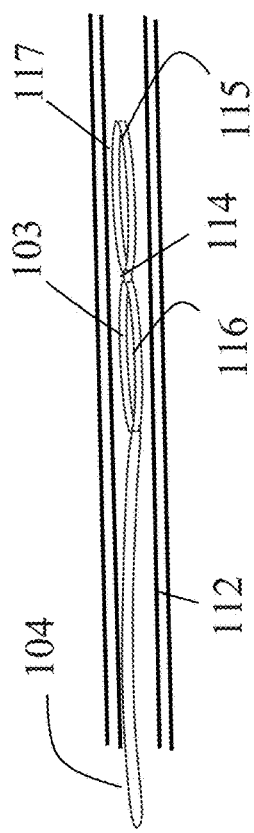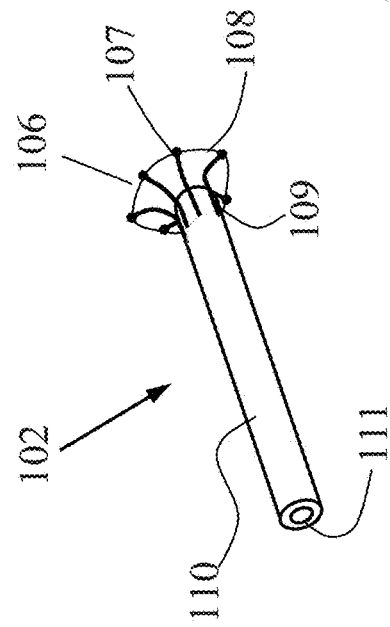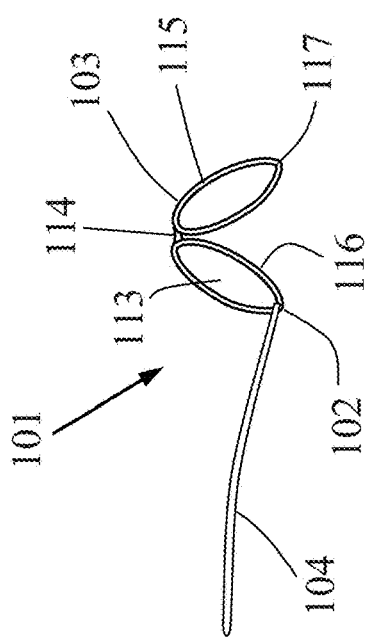

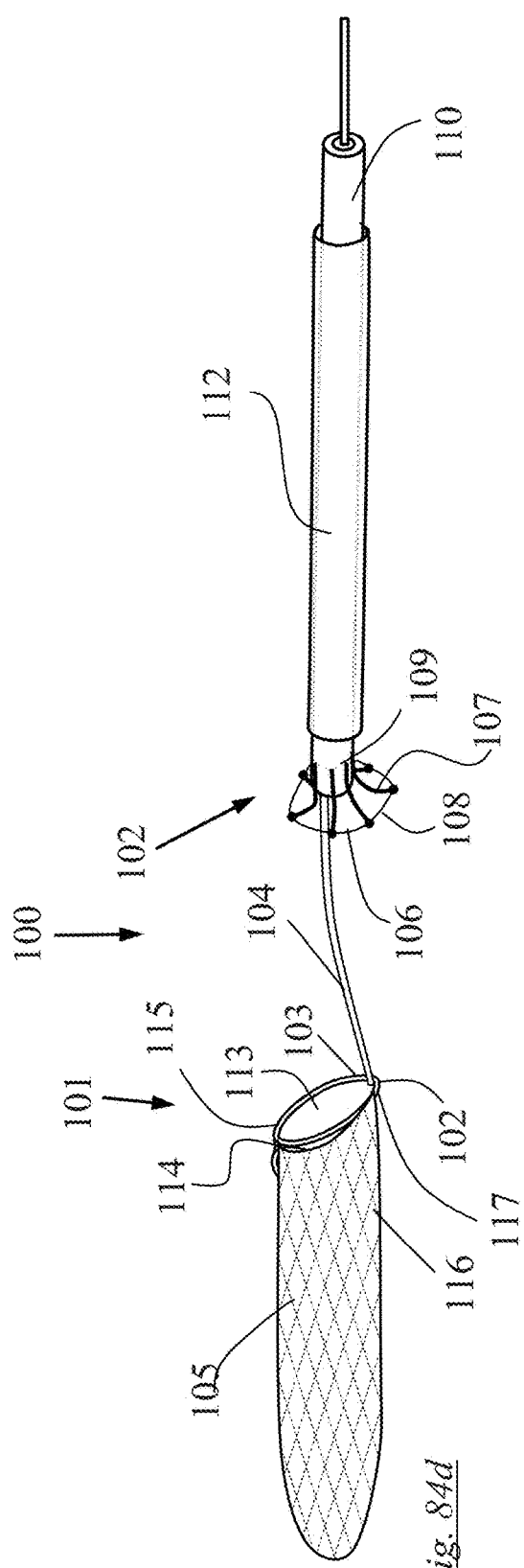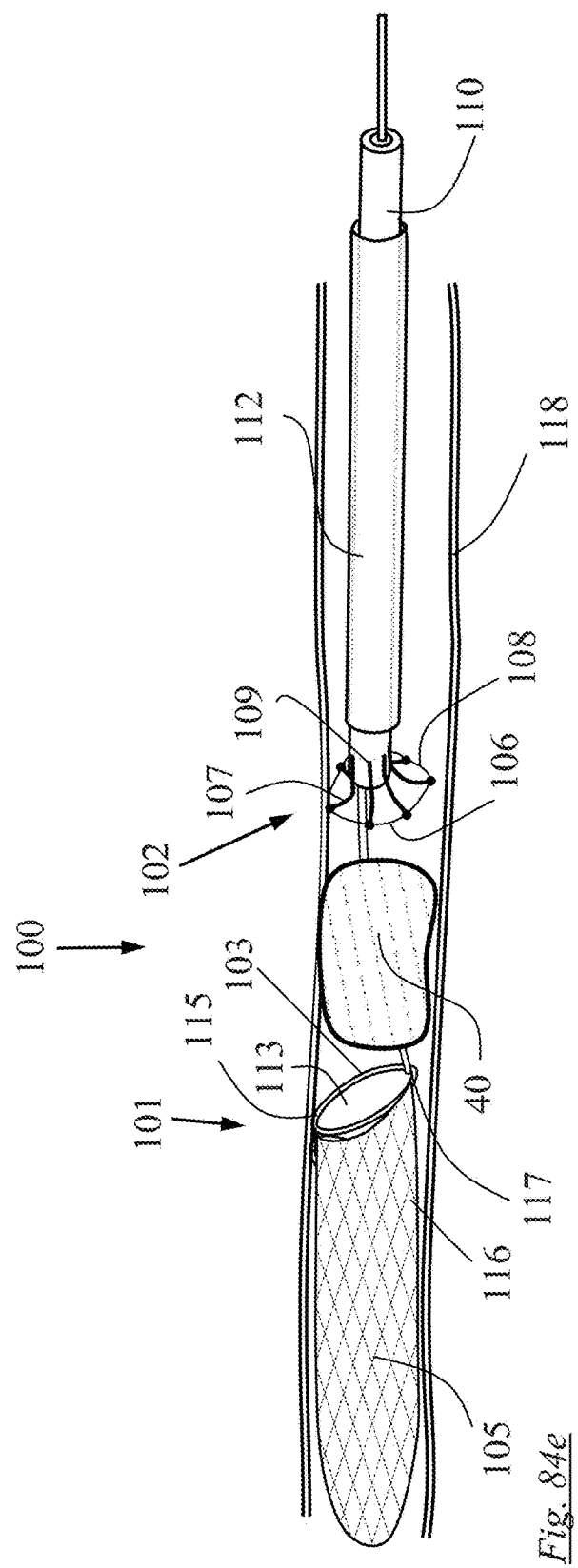

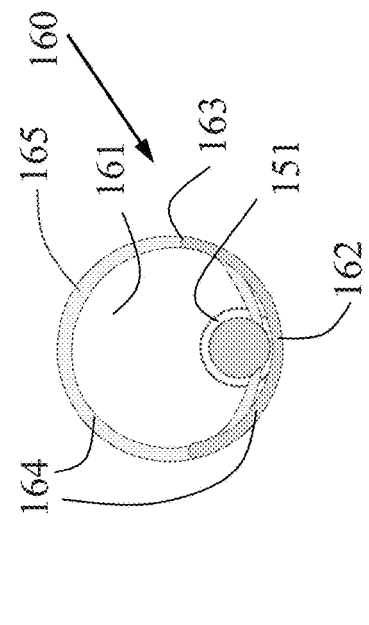
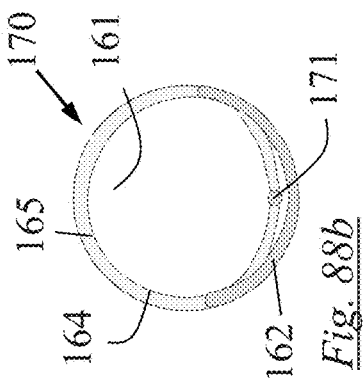
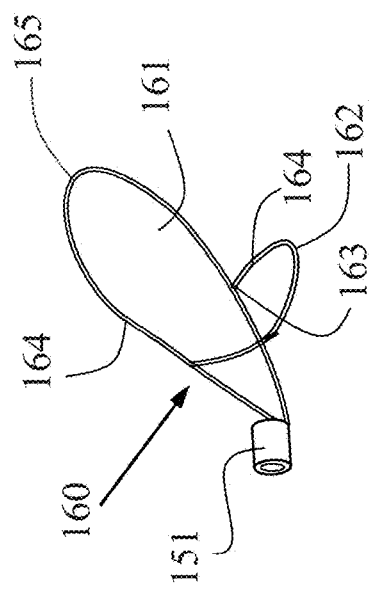
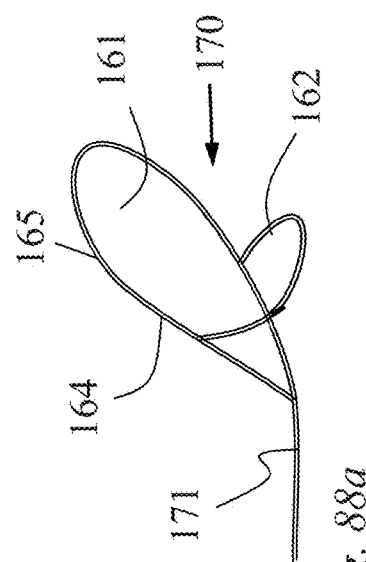
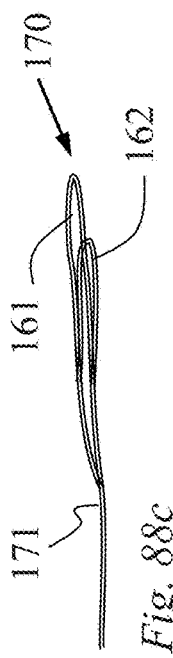
Fig. 87a
Fig. 87b
Fig. 88a
Fig. 88b
Fig. 88c

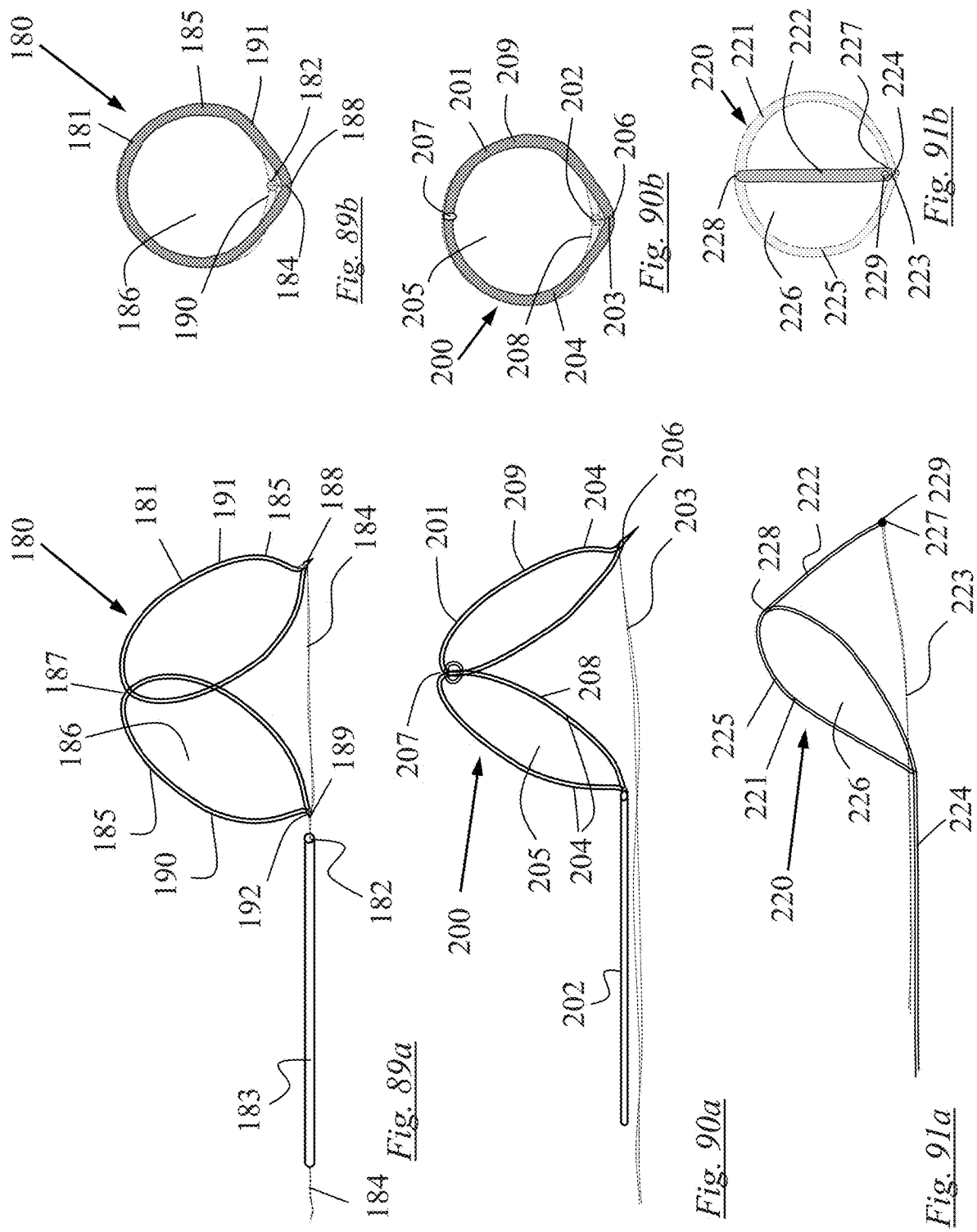

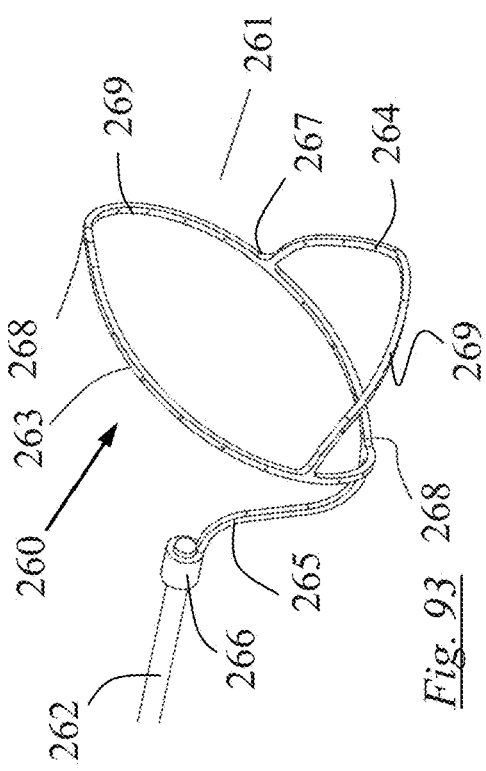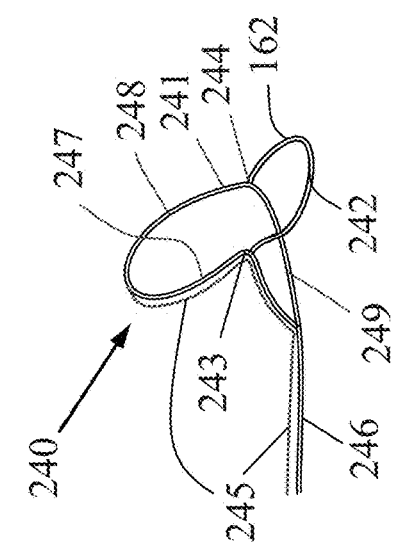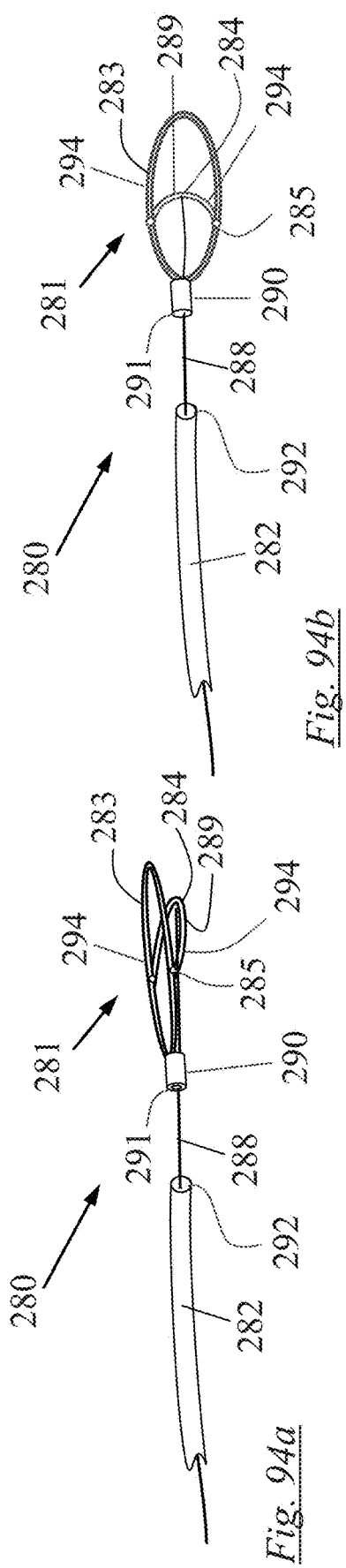
Fig. 93
Fig. 92
Fig. 94b
Fig. 94a

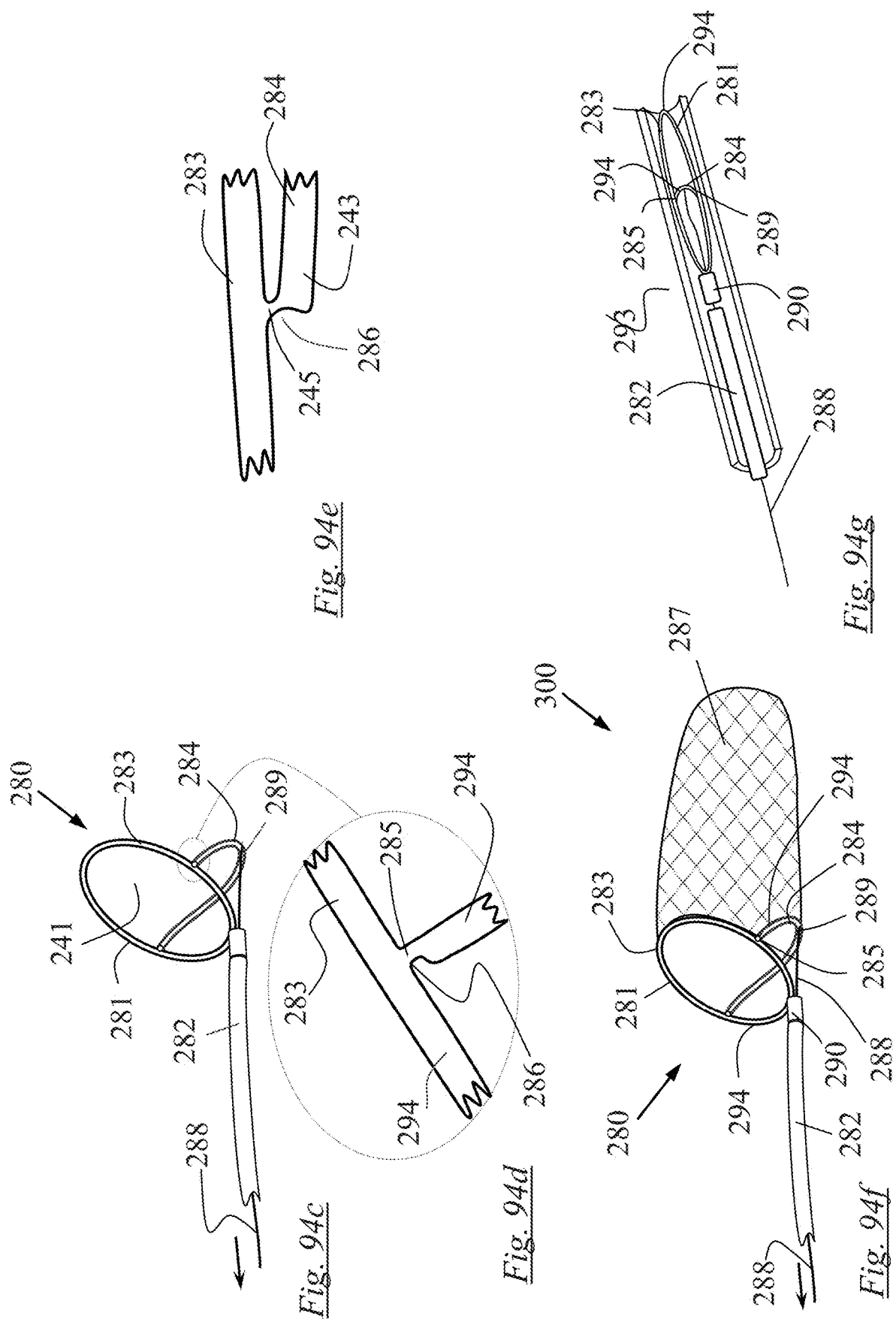

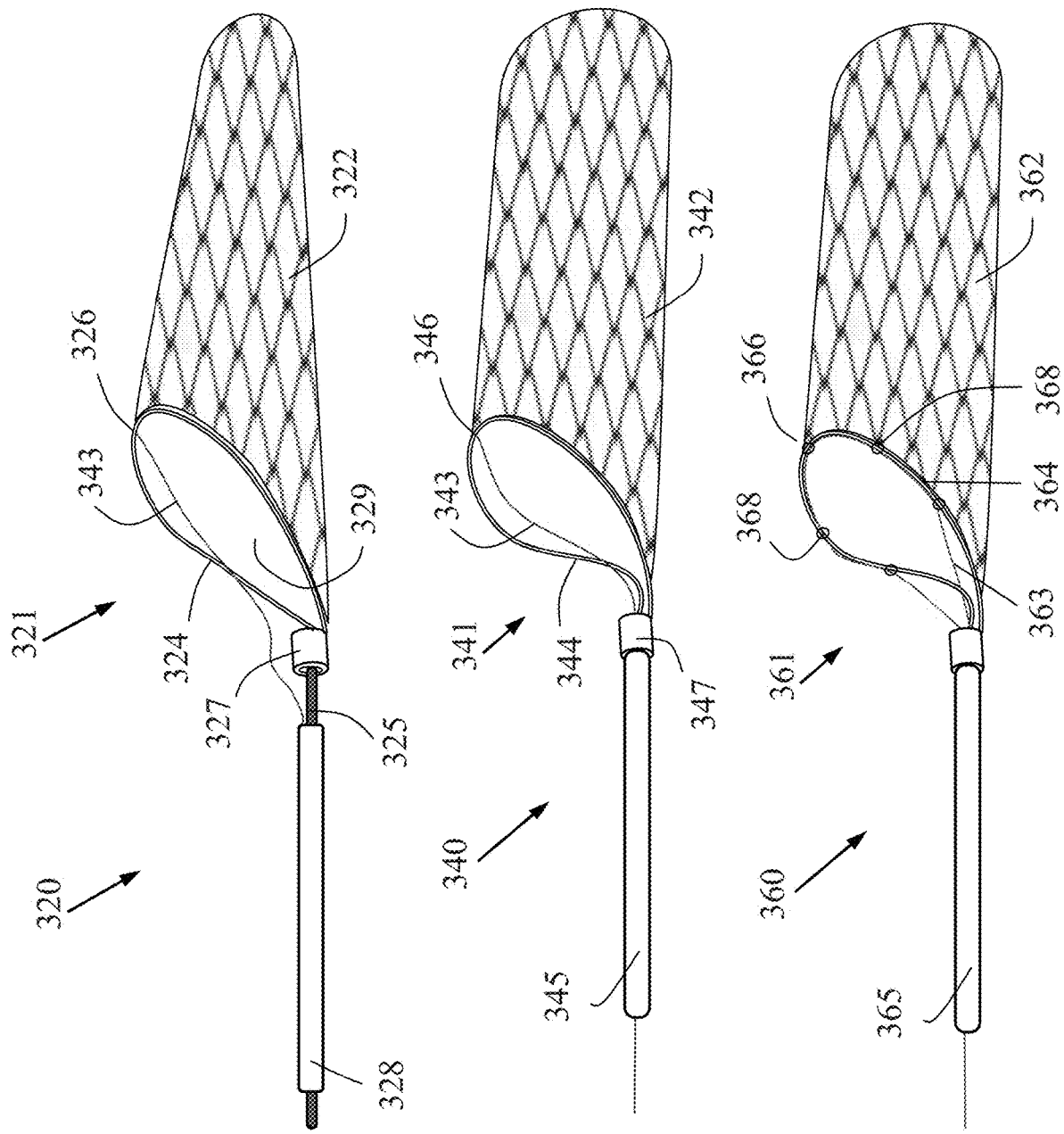

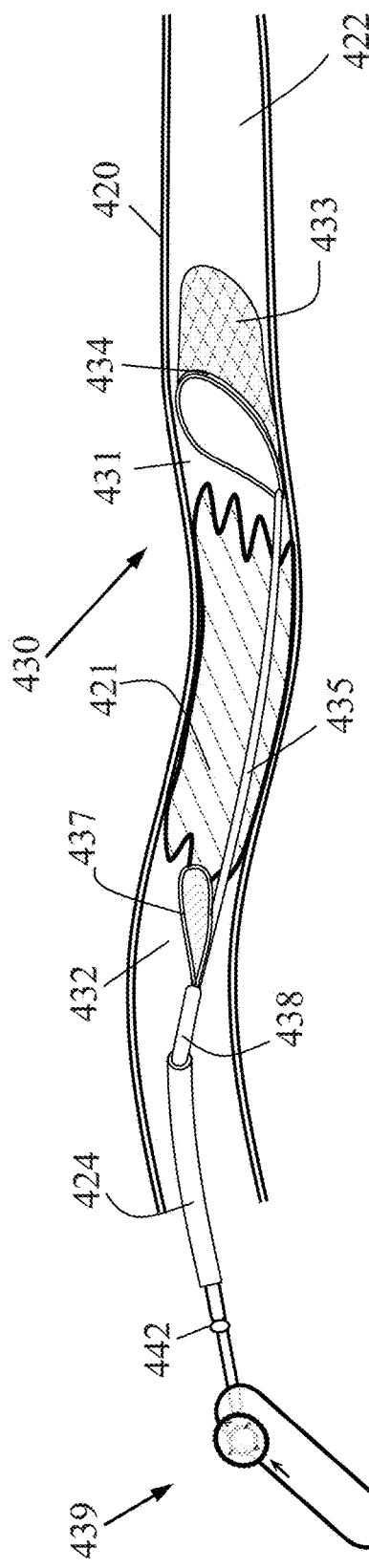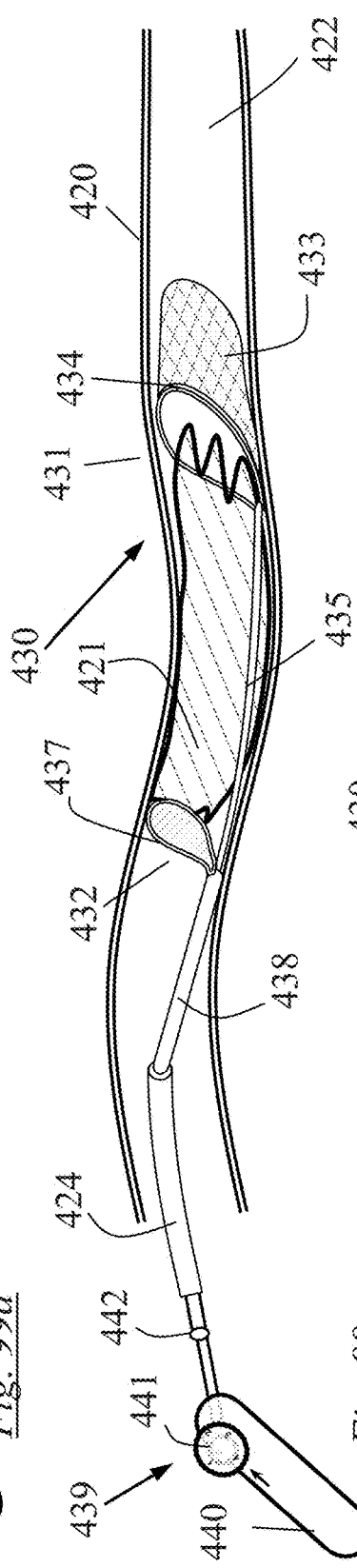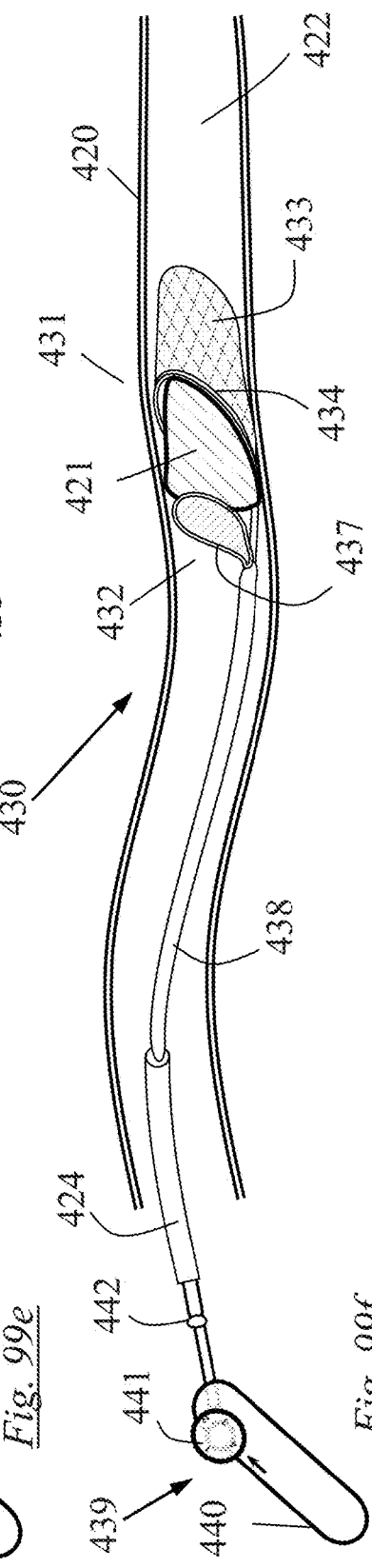

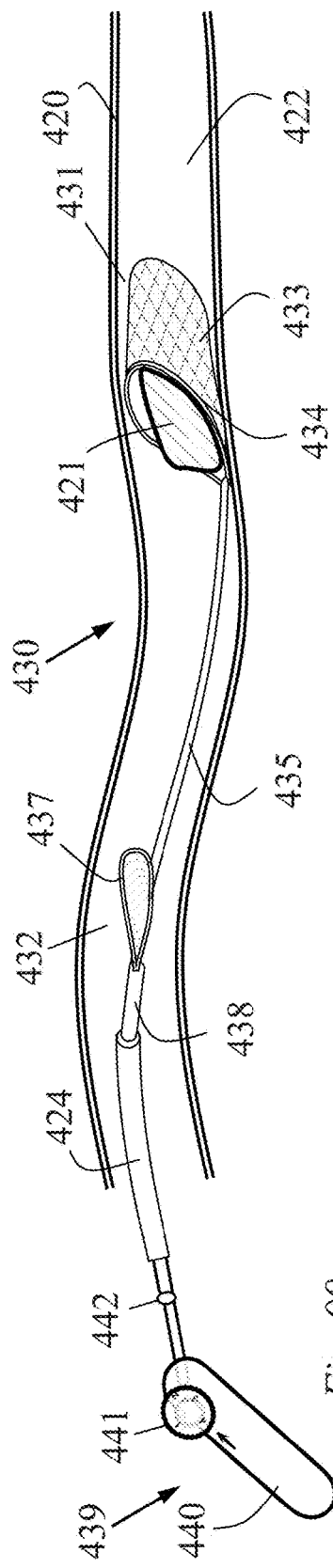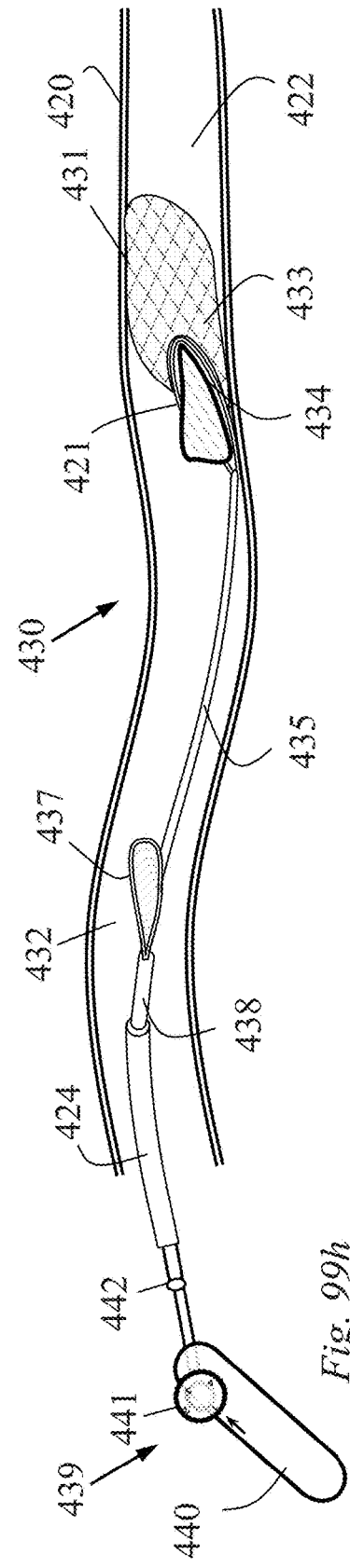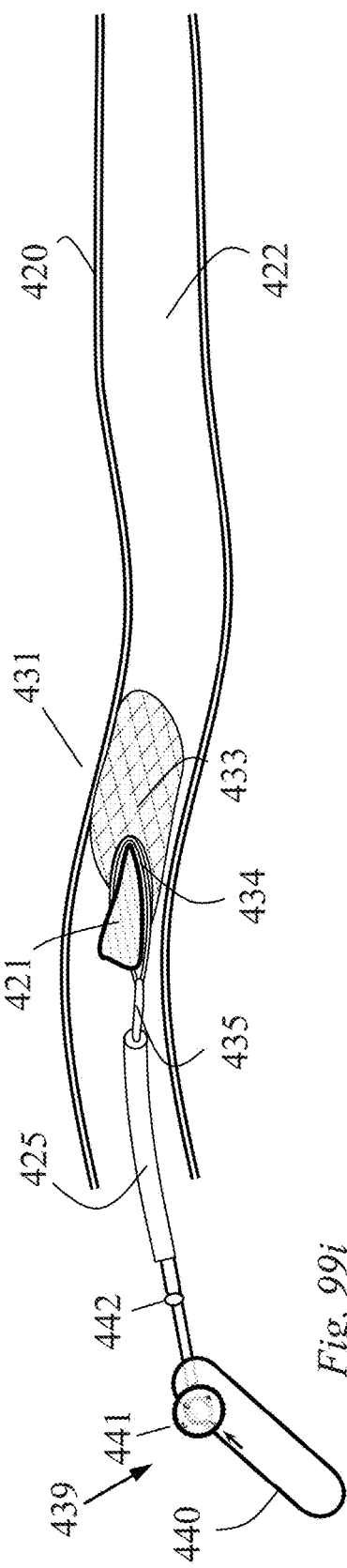

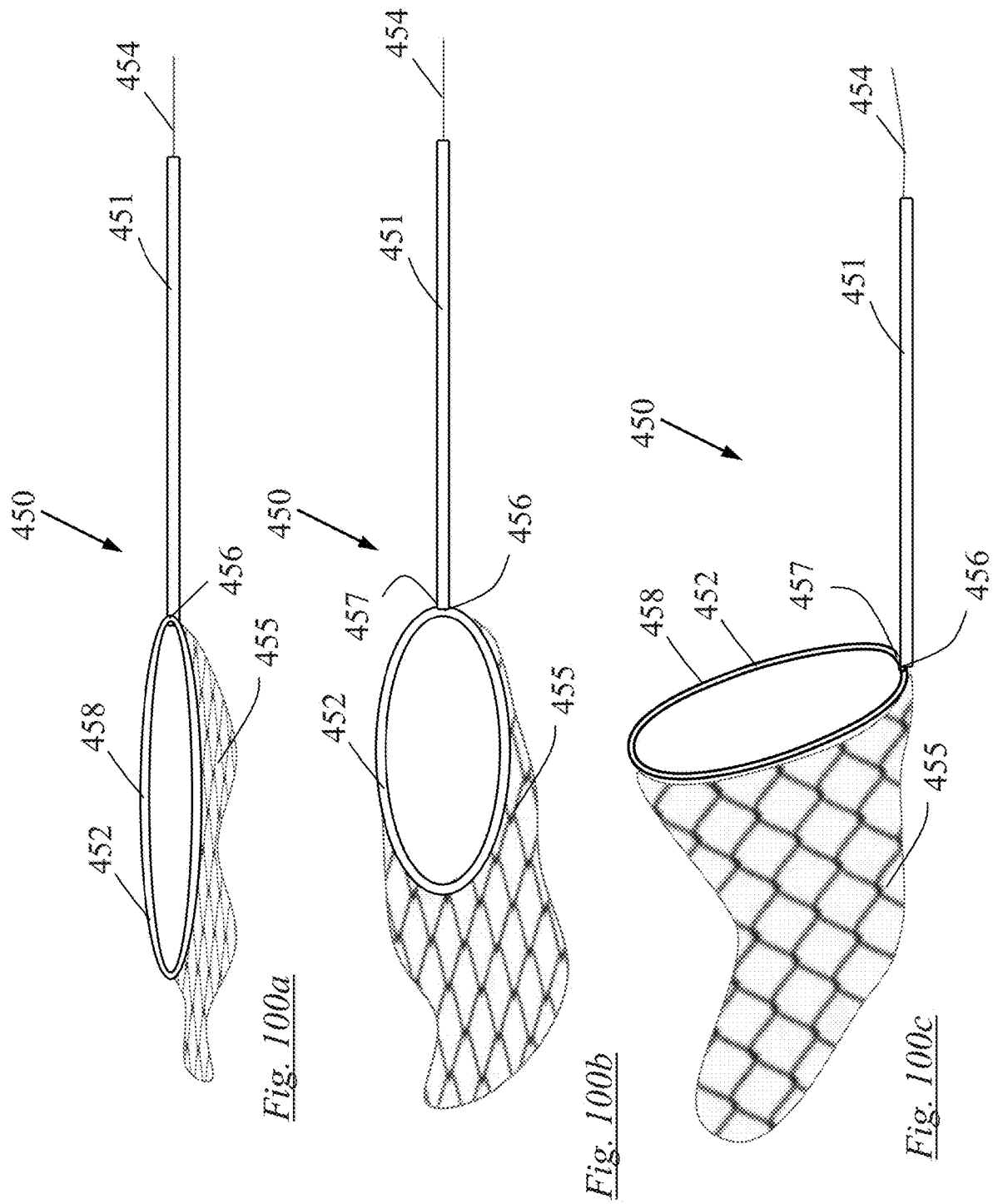

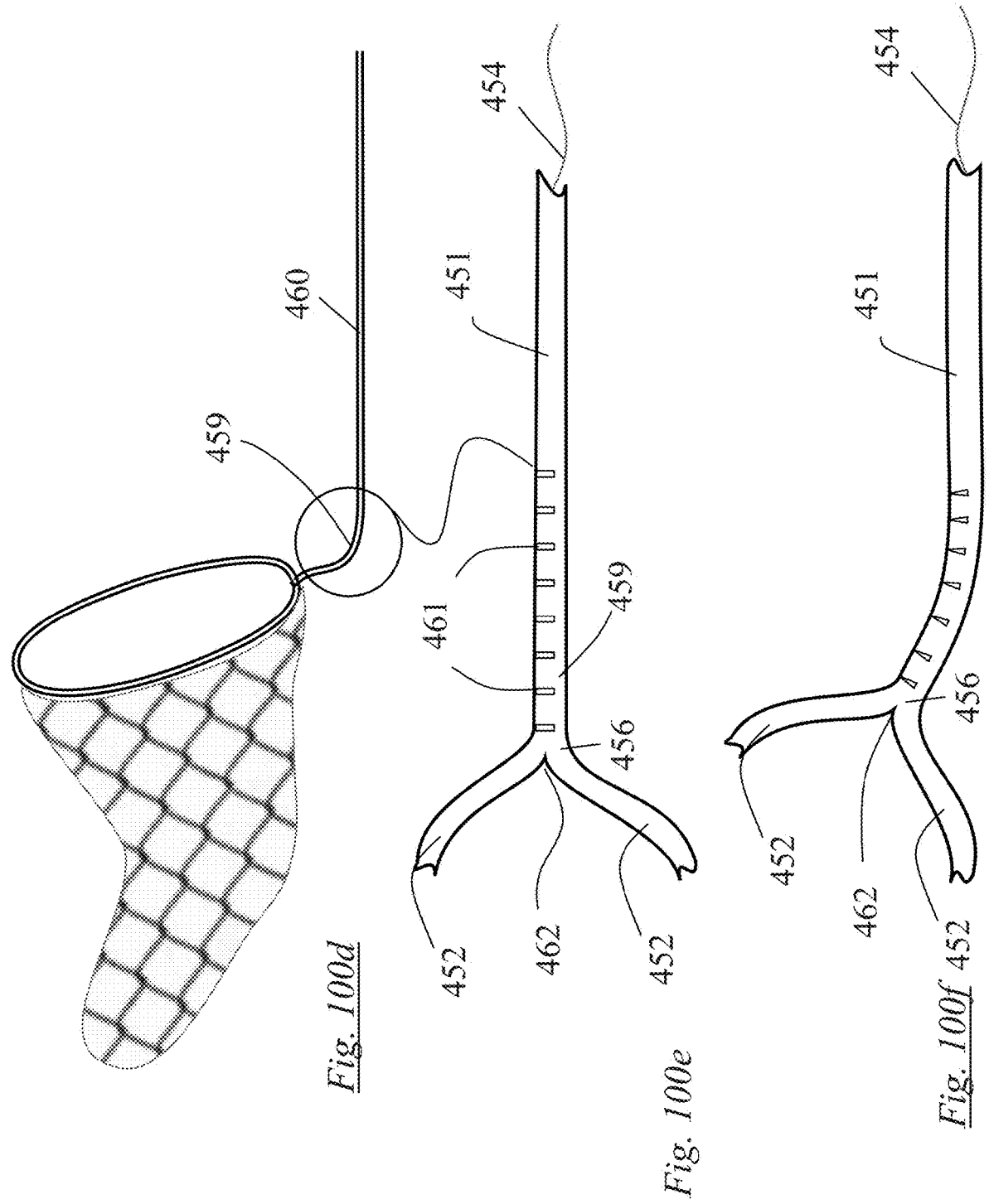

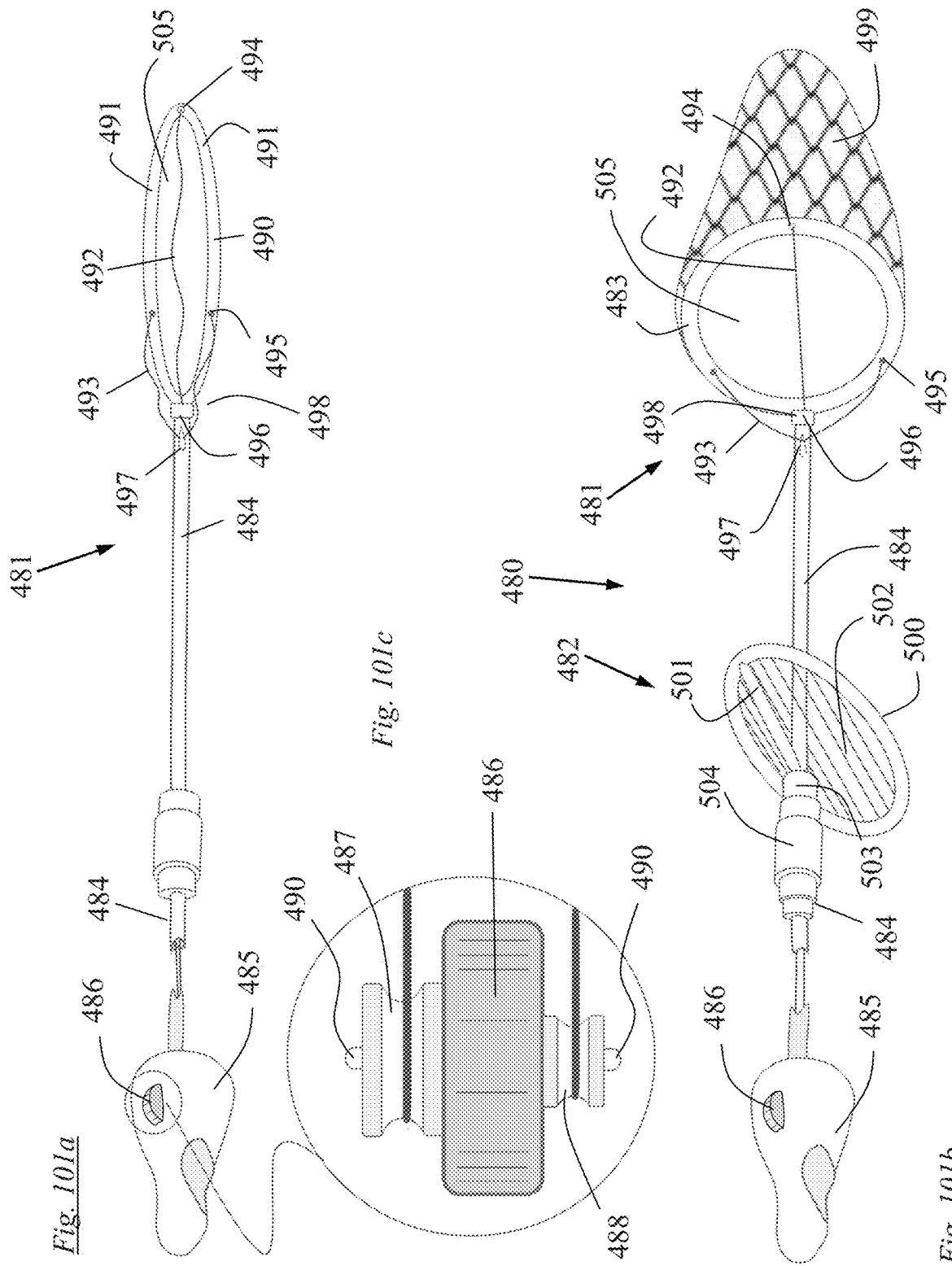

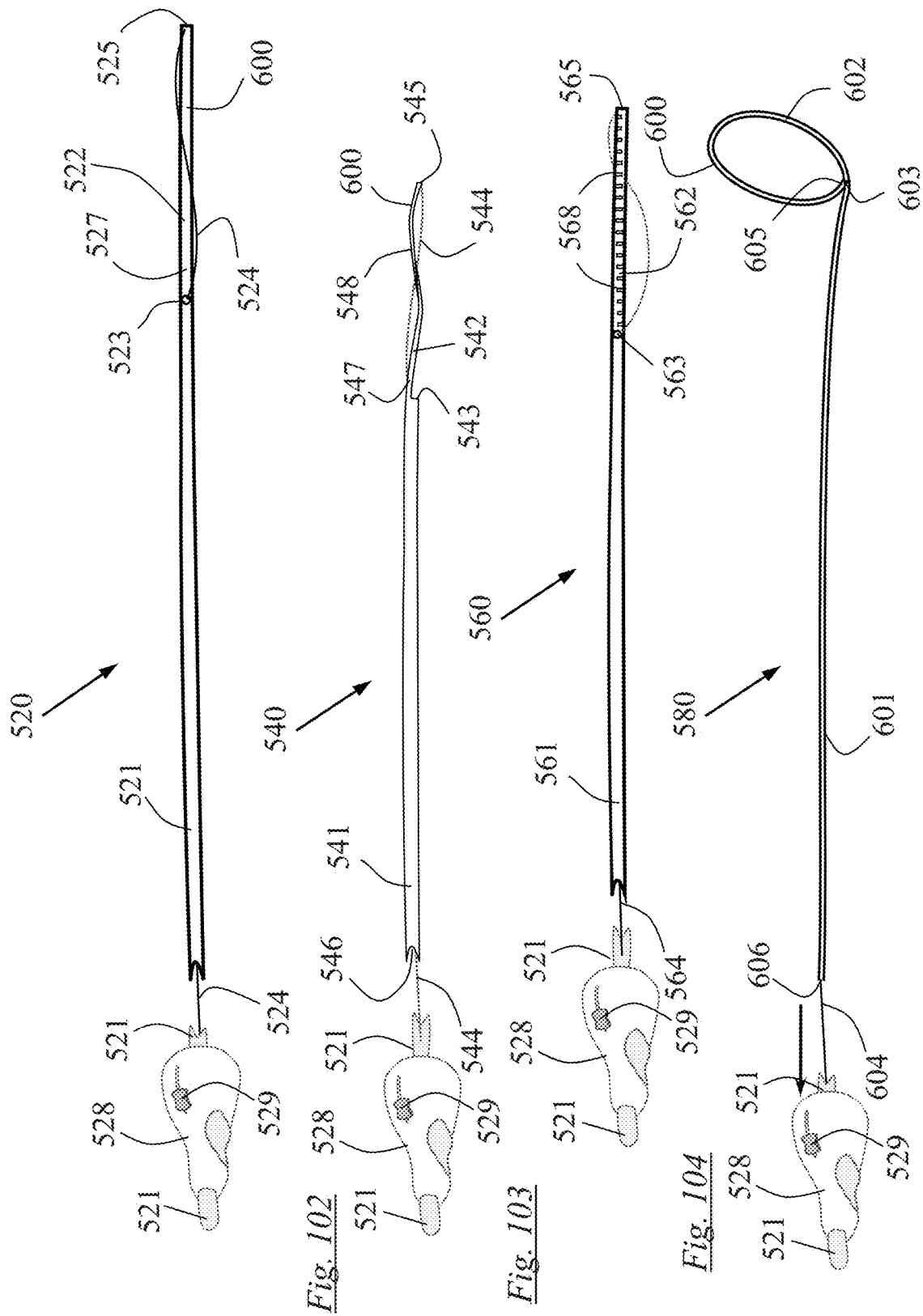

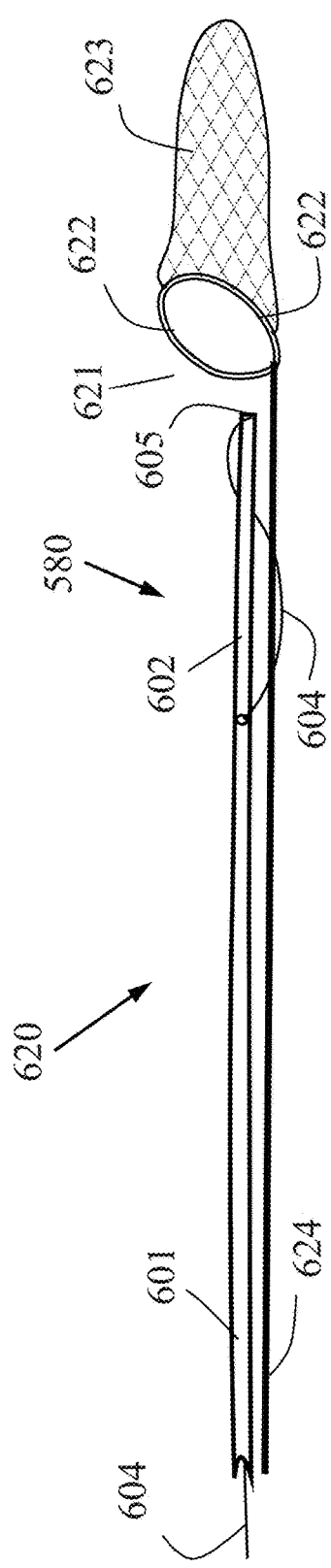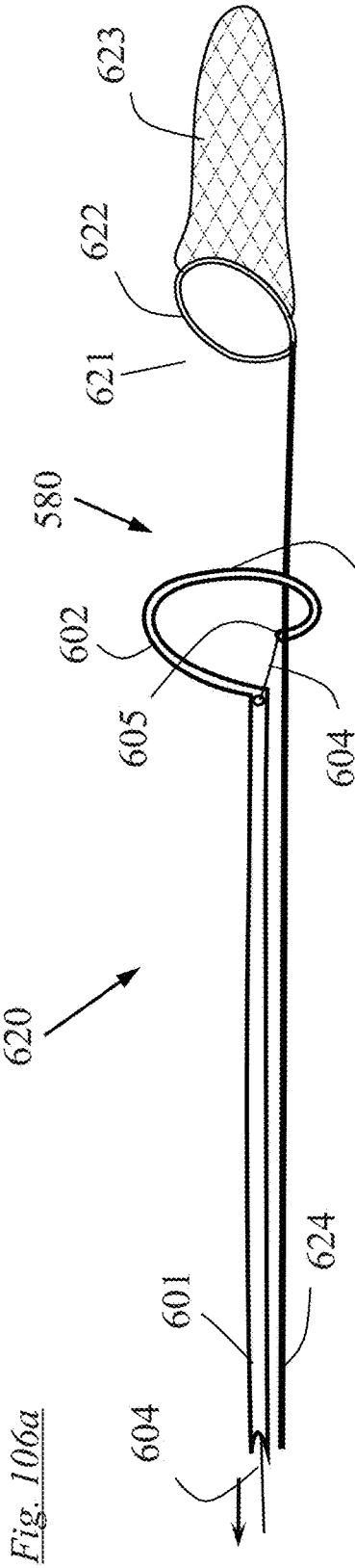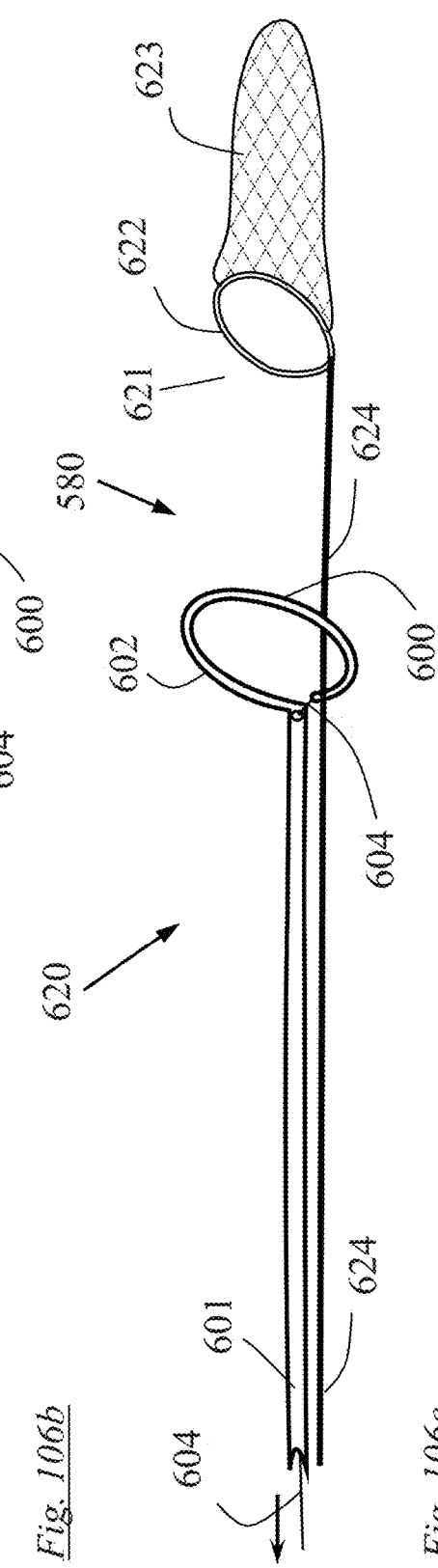

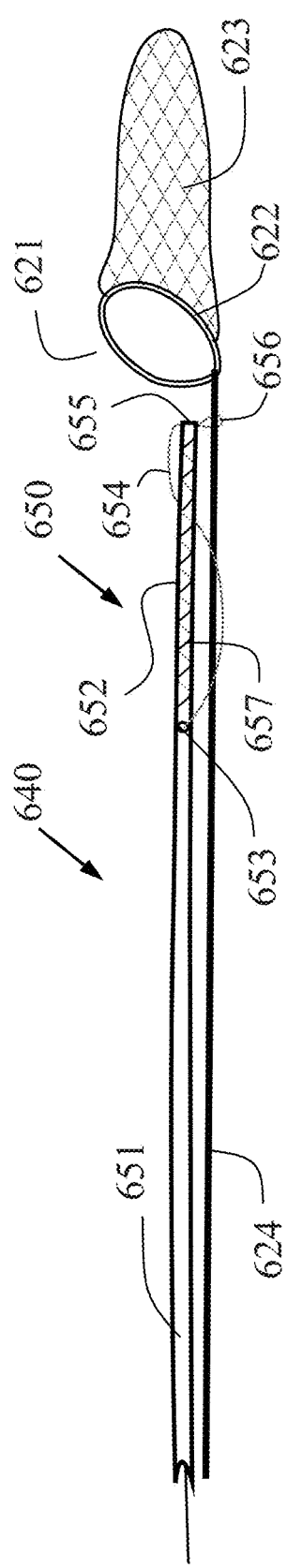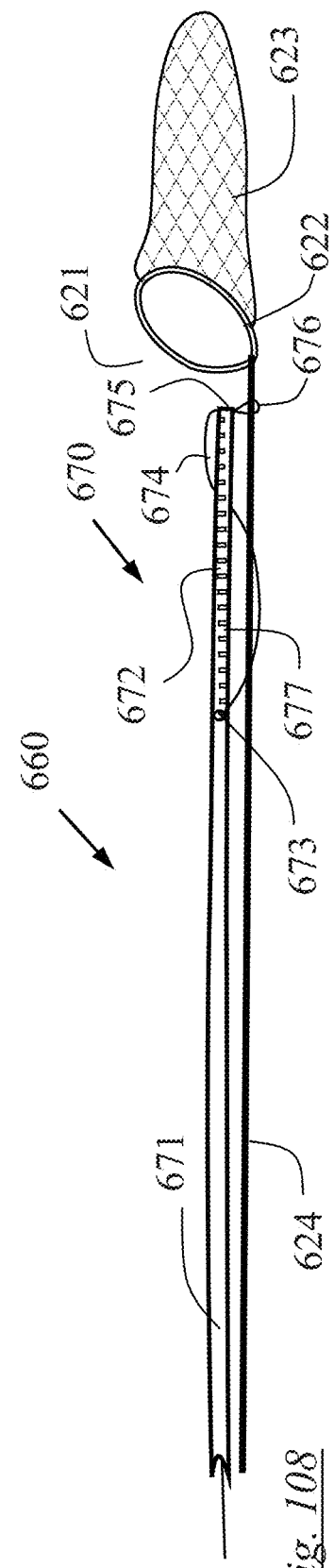

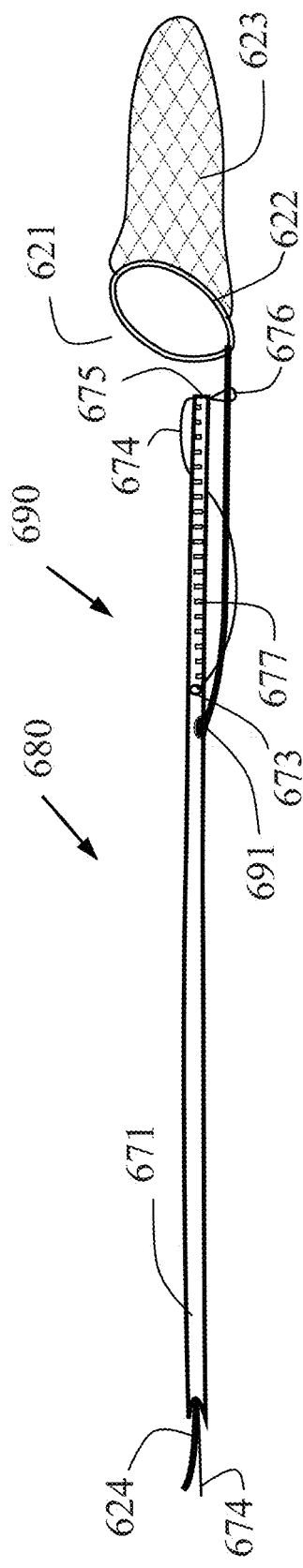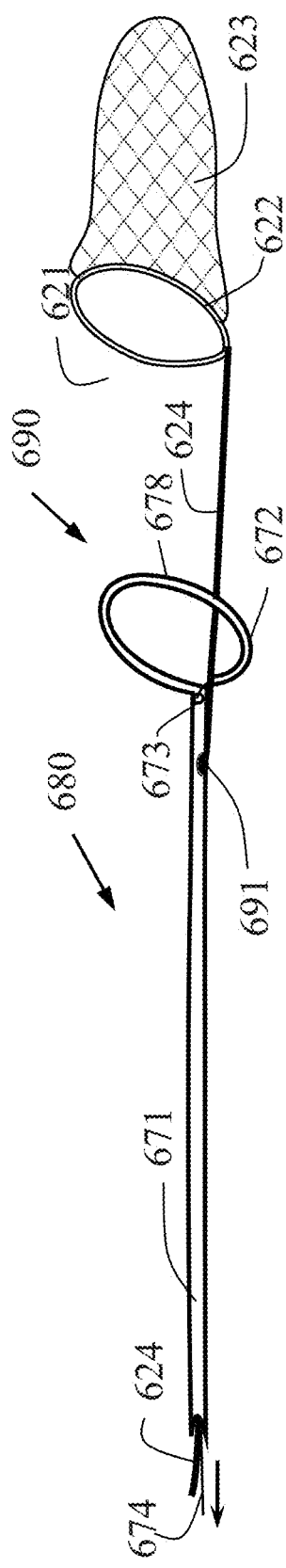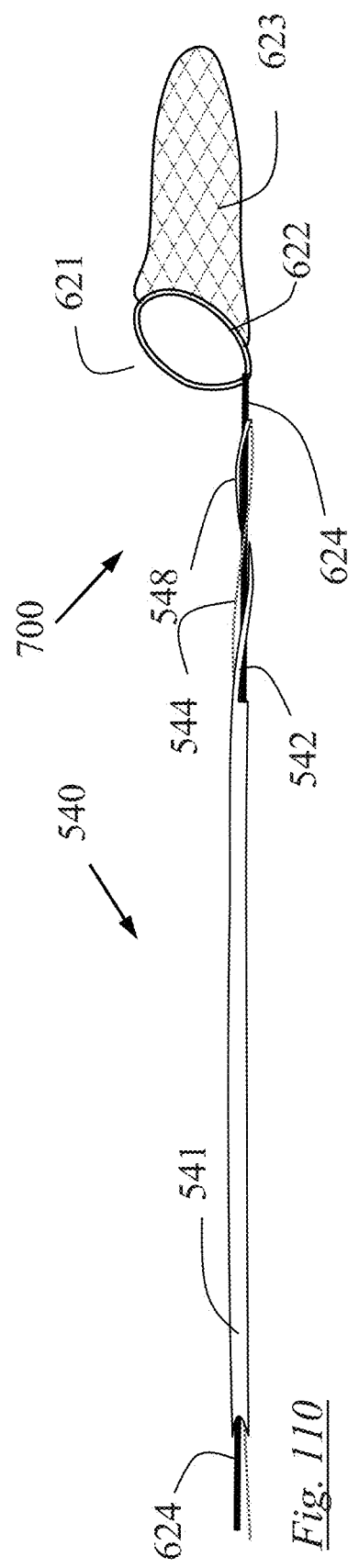

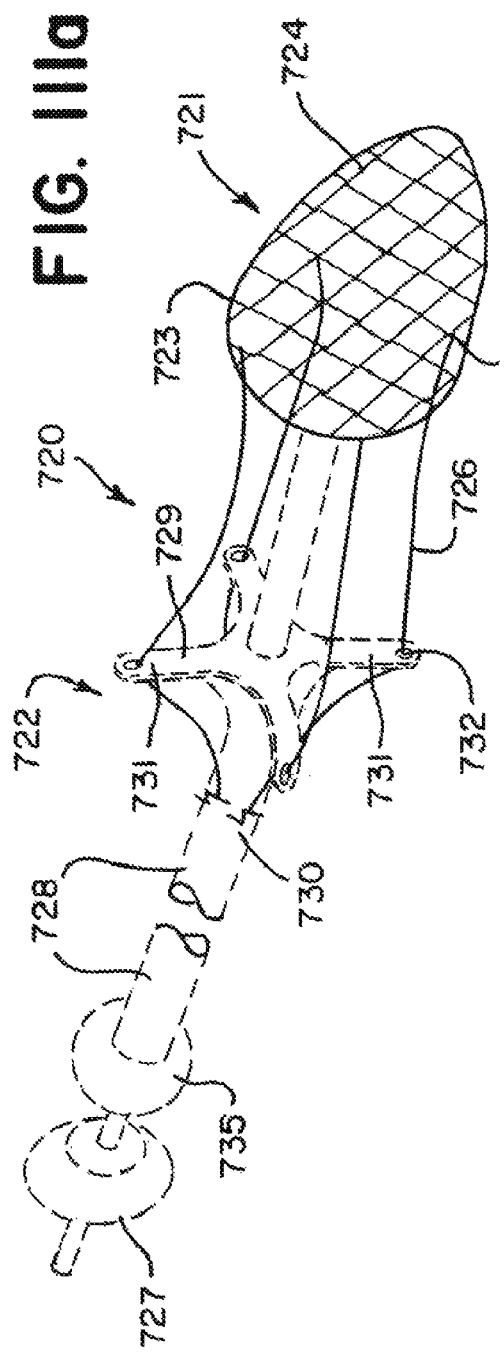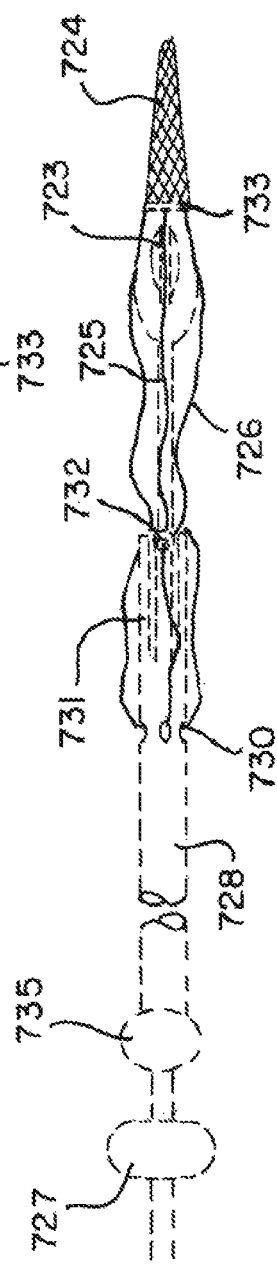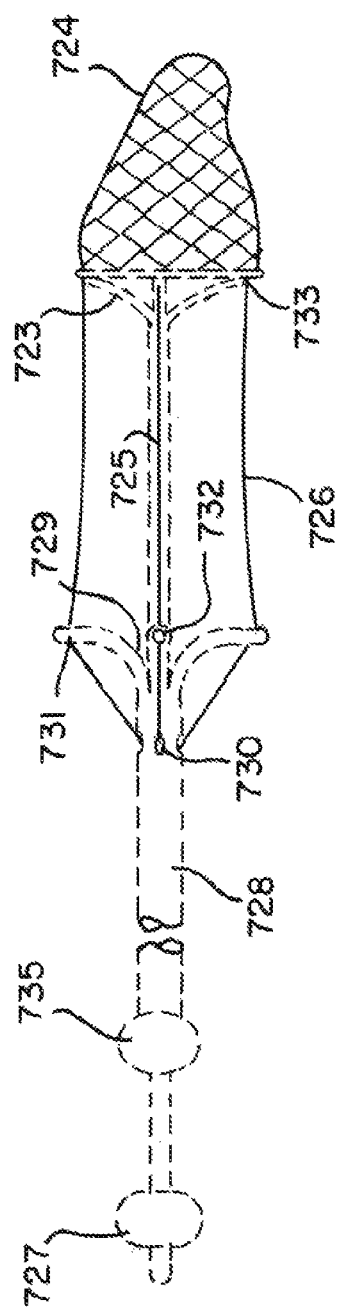

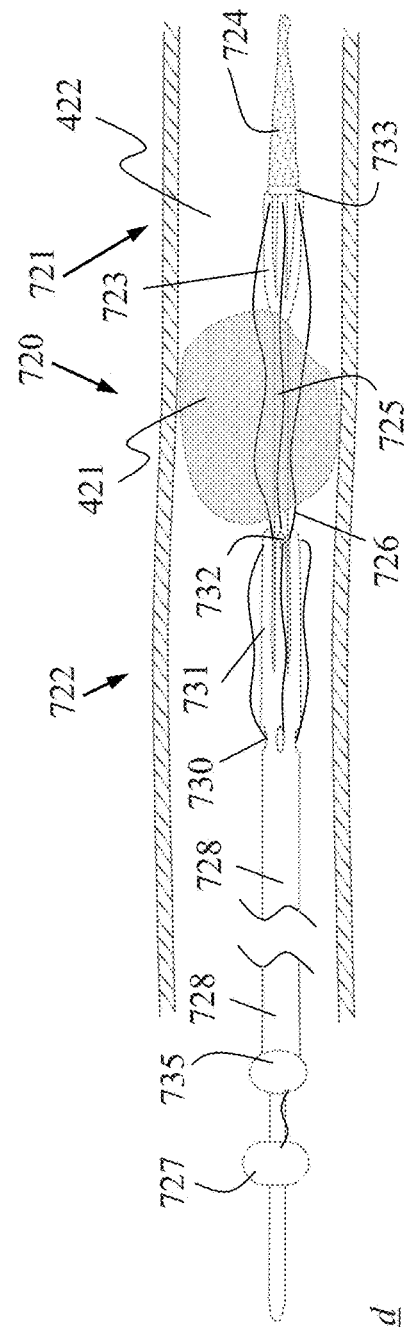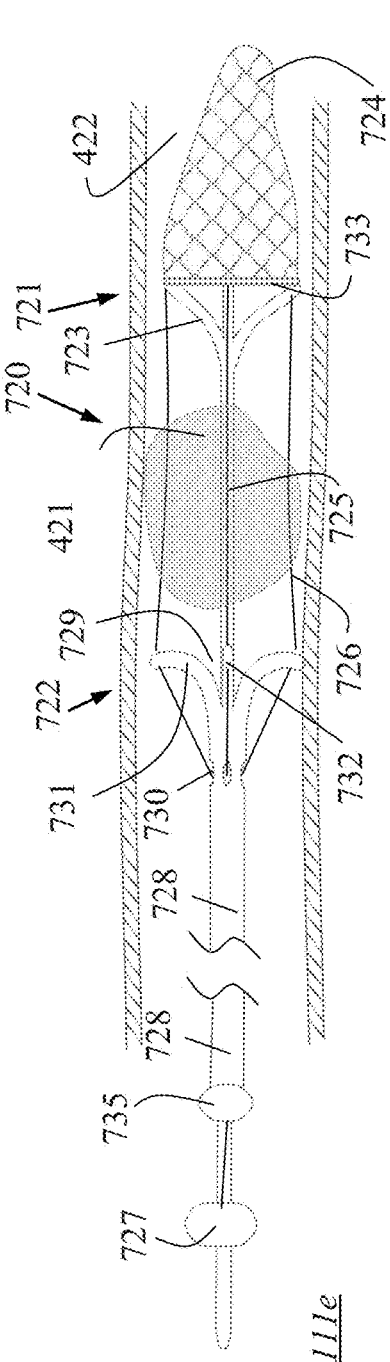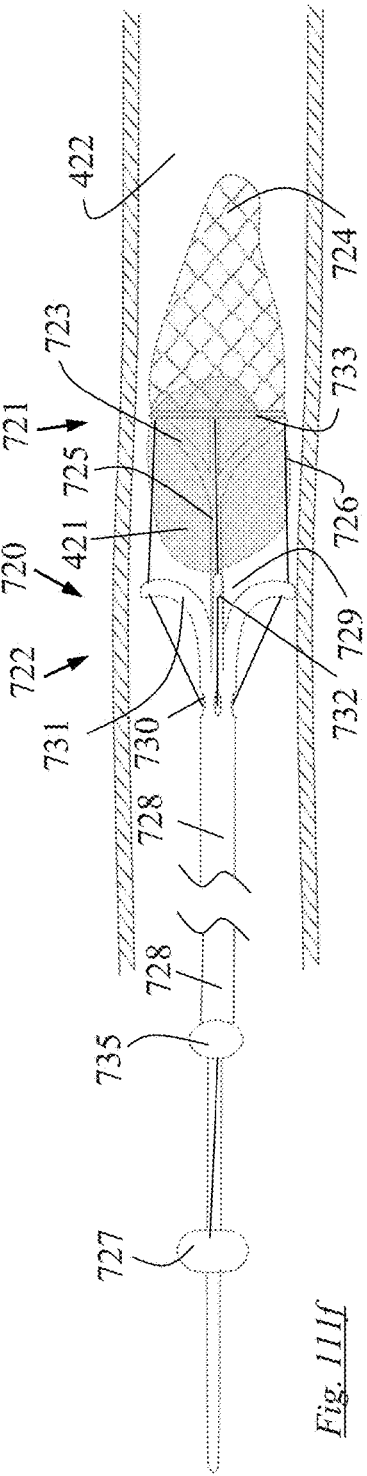
Fig. 111d
Fig. 111e
Fig. 111f

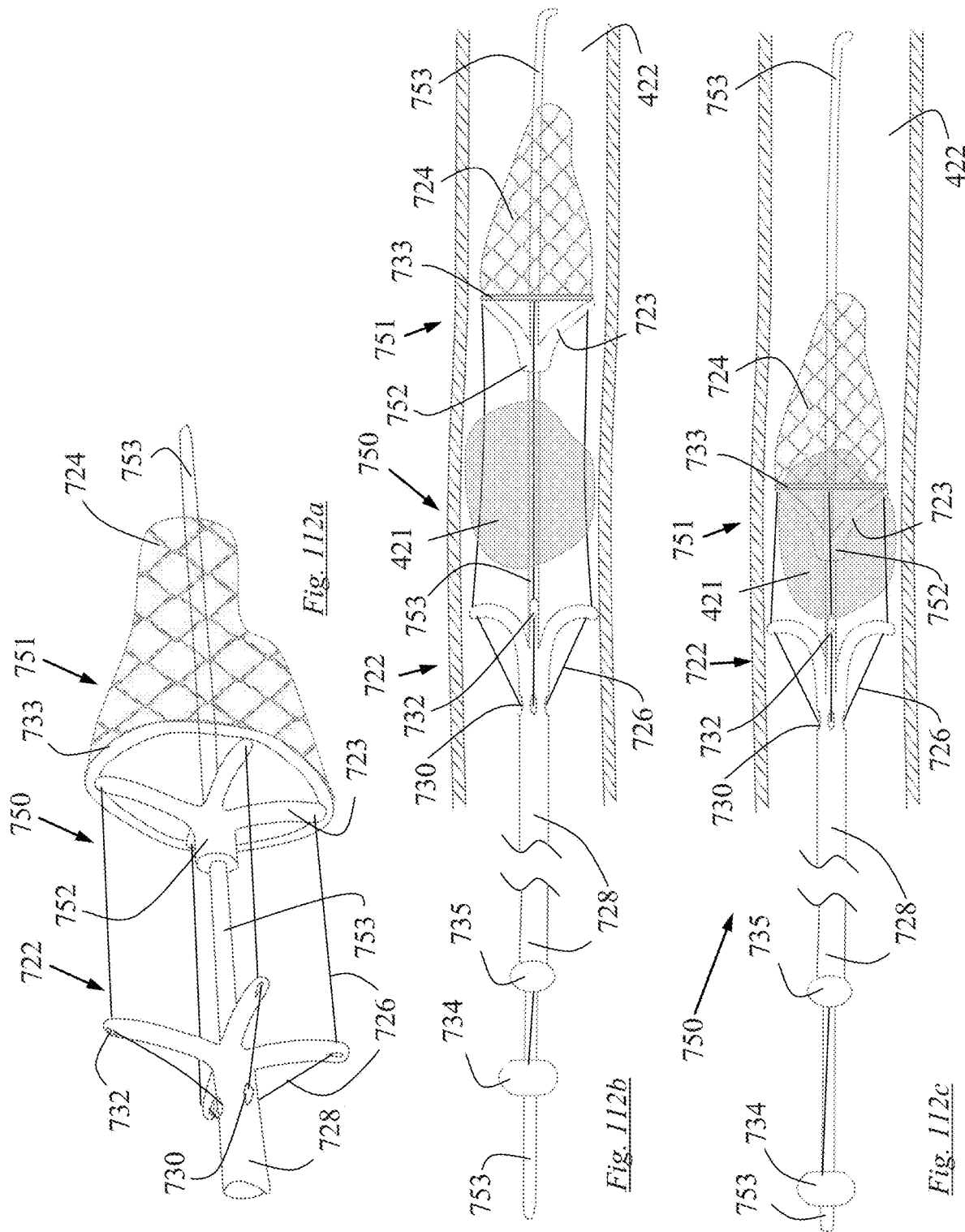

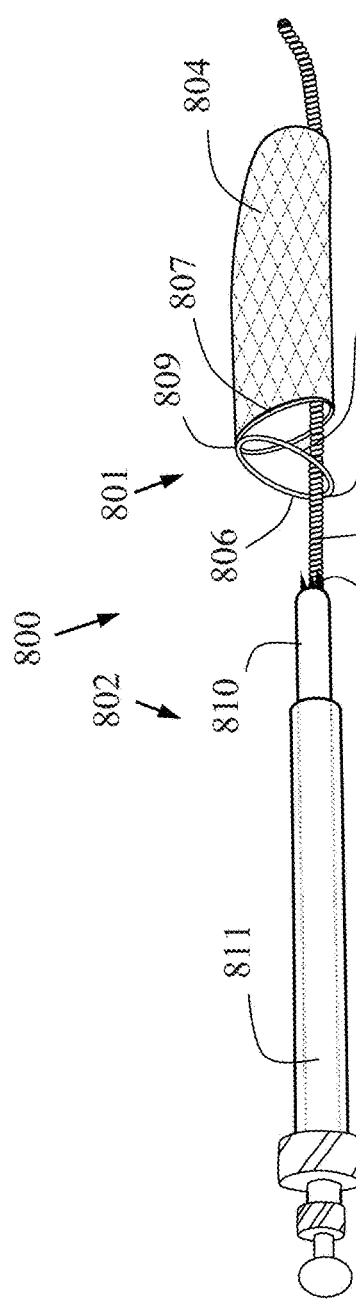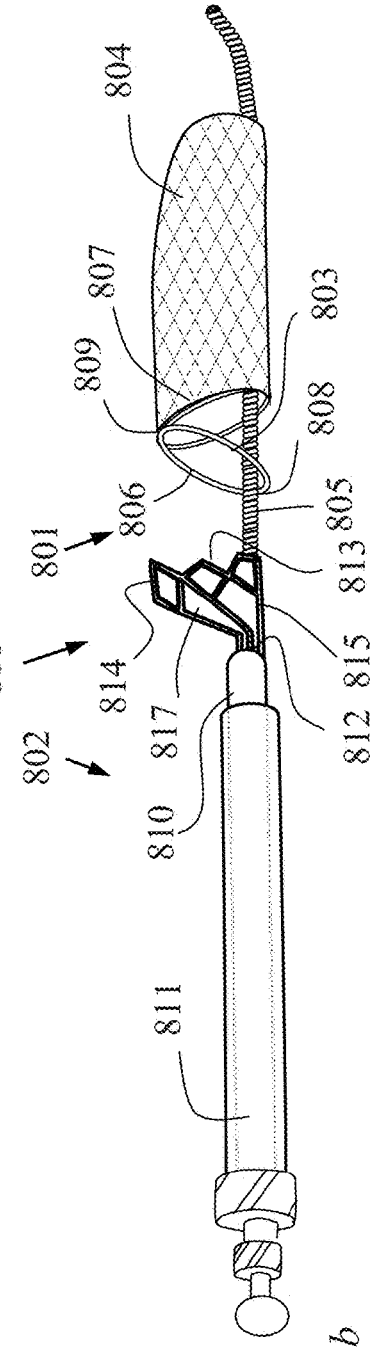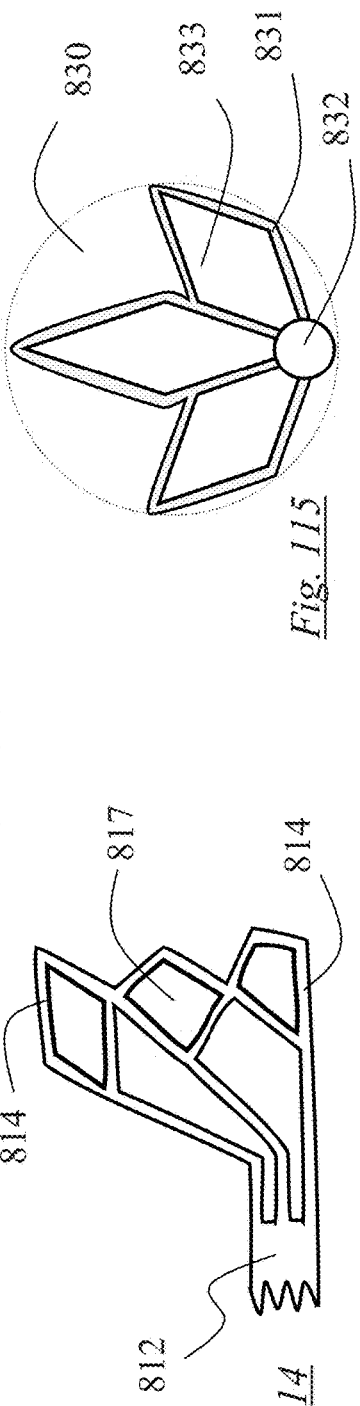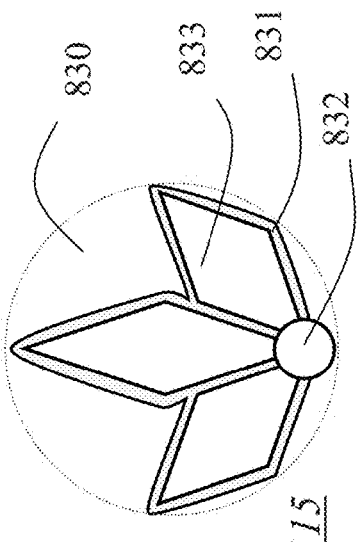

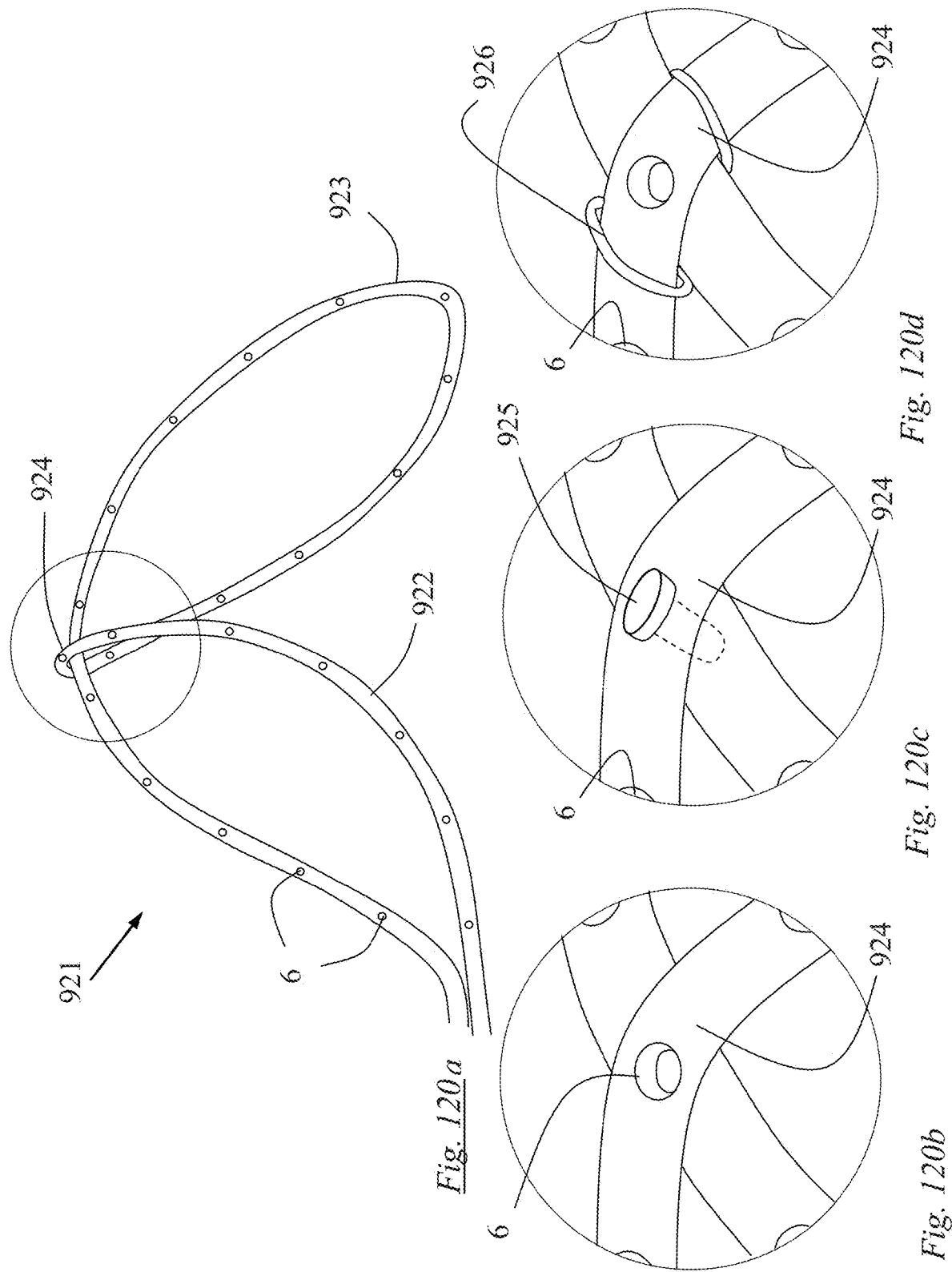

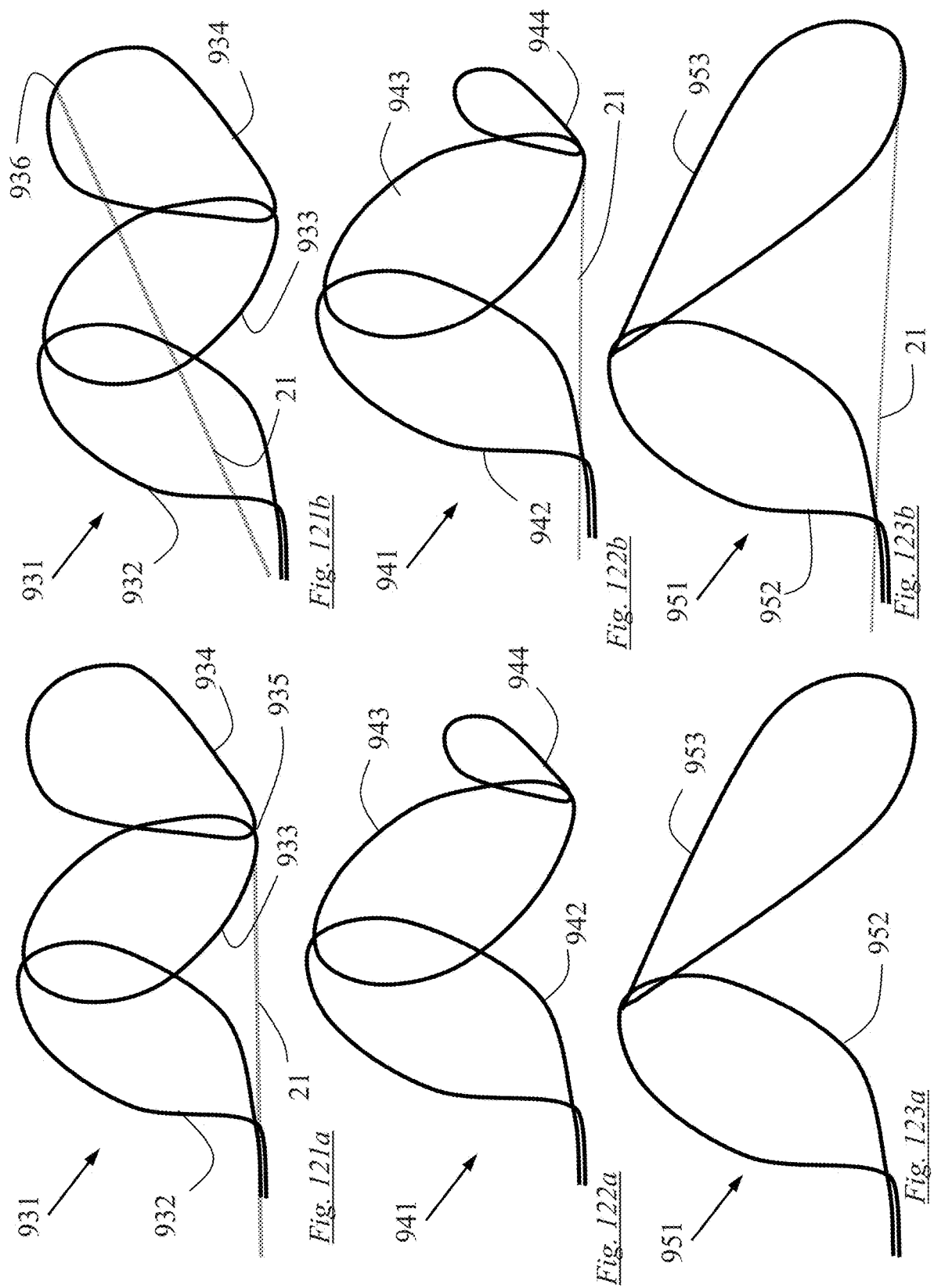

CLOT CAPTURE SYSTEMS AND ASSOCIATED METHODS

This application is a Continuation of U.S. application Ser. No. 13/662,299, filed Oct. 26, 2012, now U.S. Pat. No. 9,402,707, which is a Continuation-In-Part of U.S. application Ser. No. 12/737,527, filed Jan. 21, 2011, now U.S. Pat. No. 8,777,976, which is the National State of PCT/IE2009/000051, filed Jul. 22, 2009, which claims the benefit of U.S. Provisional Application No. 61/129,823, filed Jul. 22, 2008, and U.S. Provisional No. 61/202,612, filed Mar. 18, 2009. U.S. application Ser. No. 13/662,299, filed Oct. 26, 2012, is also a Continuation-In-Part of PCT/IE2011/000026, filed Apr. 28, 2011, which claims the benefit of U.S. Provisional 61/282,950, filed Apr. 28, 2010. The contents of all of the above-listed applications are herein incorporated by reference.

The invention relates to devices, and methods of removing acute blockages from blood vessels. The invention especially relates to removing acute obstructions from blood vessels. Acute obstructions may include clot, misplaced devices, migrated devices, large emboli and the like. More particularly the invention relates to removing clot from cerebral arteries in patients suffering acute ischemic stroke.

Accessing the neurovascular bed is difficult with conventional technology as the target vessels are small in diameter, are remote relative to the site of insertion and are highly tortuous. Despite the fact that there are over 600,000 acute ischemic strokes in the US each year, clot retrieval devices are used to treat patients in less than <1% of cases. The reasons for this are that conventional technology is either too large in profile, lacks the deliverability to navigate tortuous vessels or is not effective at removing clot when delivered to the target site.

There are significant challenges associated with designing clot removal devices that can deliver high levels of performance. Firstly there are a number of access challenges that make it difficult to deliver devices. In some patients the configuration of the aortic arch makes it difficult to position a guide catheter in the larger arteries that supply blood to the brain. These difficult arch configurations are classified as either type 2 or type 3 aortic arches with type 3 arches presenting the most difficulty. The tortuousity challenge is even more severe in the arteries approaching the brain. It is not unusual at the distal end of the internal carotid artery that the device will have to navigate a vessel segment with a 180° bend, a 90° bend and a 360° bend in quick succession over a few centimetres of vessel.

Secondly, neurovascular vessels are more fragile than similarly sized vessels in other parts of the body and are in a soft tissue bed. This issue is compounded by the fact that in many instances the clot is firmly wedged in the vessel. Typically a few hours have passed before the patent arrives at the hospital, is appropriately screened and arrives at the catheterisation lab for treatment. During this time a number of processes are in play that strongly bonds the clot to the vessel wall. Firstly the clot is under the influence of pulsing blood pressure and this pulsing blood pressure progressively force-fits the clot to the vessel. Some additional clot will also be laid down adjacent the occlusion. After the initial occlusion, endothelial cells between the clot and the vessel wall are compromised and bonds are formed between the vessel wall and the clot. All three of these mechanisms play a role in strongly adhering the clot to the vessel wall. Breaking these bonds without damaging these fragile vessels is a significant challenge. The high aspect ratio of the device and the vessel tortuousity make it difficult to transmit forces to the clot and for the user to feel reaction forces from the clot.

STATEMENTS OF INVENTION

In accordance with the present invention, device and methods for removing obstructions are described. The invention provides designs and systems for removing clot and other obstructions from the neurovascular arteries and veins as well as other vascular beds.

In one case the invention provides endovascular capture devices which capture obstructive elements and retrieve them from the vessel. The devices of the invention may be used in vessels that are small, tortuous and easily ruptured.

The invention provides a means for removing acute blockages or obstructions from blood vessels. Acute obstructions may include clot, misplaced devices, migrated devices, large emboli and such like. The invention is especially directed at removing clot from cerebral arteries in patients suffering acute ischemic stroke.

The invention provides a clot retrieval device that can be delivered through a micro catheter. The device has sufficient structure to engage the clot. The device provides a means for debonding the clot from the vessel wall. The device further provides means to prevent the fragmentation of the clot and effectively retrieve the clot from the vessel.

There are significant challenges associated with retrieving clot from cerebral vessels including: navigation of the highly tortuous pathways that often exist in the distal internal carotid artery and cerebral arteries, collapsing a device into a profile compatible with the tiny microcatheters typically used in cerebral vessels, disengaging the target clot from the vessel wall without applying painful or harmful forces to the cerebral vessels, and retaining adequate clot retaining scaffolding features in an ultra low profile device to remove the captured clot without fragmentation.

This invention provides a therapeutic device which can be collapsed to a very low profile, and which has a flexible configuration suitable for navigation beyond the Petris portion of the internal carotid artery to restore blood flow by the capture and removal of target clots from the cerebral vasculature. Features and methods that enable disengagement and capture of the target clots which are substantially equivalent in size to the target vessel and to the opening of the clot retrieval device itself are also disclosed.

The invention further provides a device for removing an obstruction from a vessel comprising: an elongate member, a frame with one or more openings and a plurality of fibre segments wherein the elongate element has a proximal end, a distal end and an intermediate segment, and in use the proximal end extends exterior of the patient the intermediate segment extends through the vasculature of the patient to the target vessel and the distal end is positioned in the target vessel with the frame connected to the elongate member adjacent the distal end.

The obstruction to be removed may be clot, with removal of this clot providing the therapeutic benefit of restoring blood flow to the vessel.

The device may comprise a proximal support frame; and a distal fibre net, the support frame having a retracted delivery configuration and an expanded deployed configuration, the proximal support frame in the expanded configuration defining a proximal inlet mouth for engaging or embracing a clot and the net confining the clot; and an elongate member to facilitate capture and/or withdrawal of a clot from a vessel.

The frame may comprise a collapsed state for delivery through the vasculature to the vessel and an expanded state for removing the obstruction from the vessel. The expanded state the frame may comprise a hoop.

The frame may be cut from a metallic tube and the cut frame may comprise a one piece construction. This one piece frame may comprise at least one connector element and a hoop element, and may also comprise a collar.

The frame may be connected to the elongate member and the point of attachment to the elongate member may be spaced apart from the hoop.

The connector element may extend between the points of connection to both the elongate member and the hoop, and may be fixedly connected to the elongate member.

One or more connector elements may be fixed to the elongate member so as to allow rotation between the elongate member and the connector element, or said connector elements may be indirectly fixed to the elongate member.

One or more connector elements may be coupled to a collar and said collar fixed to said elongate member.

The frame may be made of one piece and comprise regions of low strain and regions of high strain, wherein the regions of high strain comprise curved segments to relieve said high strain.

The frame may have an 'as cut' state and an expanded state wherein in the 'as cut' state the frame has a pattern cut through its wall and said pattern defines the collar, one or more connectors, the hoop and the struts that define the hoop.

The frame expanded state may be achieved by expanding the hoop and connector elements to the desired shape for clot retrieval and heat setting the frame in the expanded such that the expanded shape is remembered by the frame and the frame is relaxed in the expanded state.

The connector element may be parallel to the axis of the tube in the as cut state, or may be at an angle to the axis of the metallic tube.

The struts that define the hoop may be parallel to the axis of the tube in the as cut state, or may comprise a helix which traces a pathway around the axis of the tube. Said helix may trace a pathway of not greater than 180 degrees around the axis of the tube.

The cross section of the tube may comprise four quadrants and the at least one first strut and the at least one second strut may be situated either in adjacent quadrants or in the same quadrant over at least a portion of their length in the as cut state.

The hoop may comprise at least one first strut and at least one second strut and said at least one first strut and said at least one second strut may meet at a junction element and said junction element may be at the end of said at least one first and second struts. The at least one first strut and the at least one second strut may be diametrically opposite when the frame is in the as cut state.

The cut pattern of the junction element may comprise a smooth inner curve and a smooth outer curve.

The at least one first strut and the at least one second strut and the junction element may comprise a common neutral axis of bending in the as cut configuration.

The shape defined by the neutral axis of the at least one first strut and at least one second strut may be substantially linear and the shape defined by the neutral axis of the junction element may be curved.

The radius of curvature of the neutral axis of the junction element may be greater when the junction element is in the expanded state than when the junction element is in the as cut state.

The frame may comprise a collar, one or more connector elements and a hoop, and said collar may be fixed to the elongate member. Said collar may be slidable relative to the elongate member, and said elongate member may comprise at least one stop to limit the translation of the collar.

The distal end of the elongate member may comprise a frame, or the elongate member may comprise a shaped section adjacent its distal end and said shaped section comprises the frame.

The elongate member may comprise a tube and the elongate member and the frame may be integral.

The elongate member may comprise a guidewire.

The bending stiffness of the elongate member may decrease along the length of the elongate member.

The elongate member may comprise a plurality of circumferential slots adjacent its distal end, said slots reducing the bending stiffness of the elongate member. The distance between said slots may vary along the length of the elongate member.

The elongate member may comprise at least one continuous helical slot adjacent the distal end of the elongate member to reduce the bending stiffness of the elongate member.

The bending stiffness of the elongate member may decrease gradually along the length of the distal segment of the elongate member. Also the diameter of the elongate member may be less in the distal segment than in the proximal segment.

The elongate member may comprise a solid wire, a wire with a coating, a wire and an outer tube, a wire and a outer coil, a tubular member and an inner core, a tubular member and an inner cable, or a tubular member and an inner tube.

The elongate member may be offset relative to the axis of the vessel when the frame is in the expanded configuration, or the elongate member may be substantially concentric with the axis of the vessel when the frame is expanded in the vessel, or the elongate member may be adjacent the wall of the vessel when the frame is in the expanded configuration in the vessel.

The frame may comprise a collapsed state for delivery through the vasculature to the vessel and an expanded state for removing the obstruction from the vessel. The expanded state of the frame may comprise a hoop.

The wire of the hoop may comprise a round wire, a square wire, a rectangular wire, an elliptical wire a flattened wire or a multifilament.

The elongate member may comprise a wire and the distal segment of said wire is formed into a hoop. The distal end of said wire may be fixed to the wire in order to close the hoop. The fixing of the wire distal end to the wire may comprise a weld joint, a solder joint, an adhesive joint, a bifilar joint, a coupling, a compression joint, a snap fit, or an interlock.

The hoop may comprise a single piece hoop cut from a metallic tube or from a metallic sheet.

The distal section of the elongate member may comprise a tube and said hoop may be integral with said tube.

The elongate member distal end may comprise a machined section. The elongate member distal end machined section may comprise a hoop.

The elongate member cross-section may comprise four quadrants and the hoop may comprise at least two struts, each extending from a separate quadrant. The first strut may extend from said first quadrant and said second strut extend from said third quadrant. The first and second struts may be diametrically opposite. The first strut may extend from said first quadrant and said second strut may extend from said second quadrant. The first strut may extend from said first quadrant and said second strut may extend from said first quadrant.

The struts may comprise a plurality of net attachment features.

The hoop of the frame may be expanded by inserting a pin between the struts and heat treating the frame to set the shape. This pin diameter may be similar to the diameter of the target vessel.

The hoop may be cut from a large diameter tube, the diameter of which is similar to the diameter of the target vessel. Alternatively the hoop may be integral with the elongate member.

A plurality of connector elements may be attached to the hoop. This plurality of connector elements may be connected to the hoop at a series of spaced apart junction points around the circumference of the hoop and said spacings may be substantially equal.

In its expanded state the hoop may define an opening, and said opening may be elliptical or circular in shape, and may be similar in size to the cross-sectional area of the target vessel. The axis of the elongate member may pass through this opening created in the hoop in its expanded state.

The connector element may extend at least partially radially inward from the hoop and be connected to the collar, or the connector element may extend radially inward and proximally from the hoop and be connected to the collar, or the connector element may extend radially inward and distally from the hoop and be connected to the collar.

In the collapsed state the hoop may lie substantially parallel the elongate member, or may lie at an angle of approximately 90 degrees to the axis of the elongate member.

In the expanded state the hoop may make an angle of greater than 90 degrees to the axis of the elongate member, or may make an angle of less than 90 degrees to the axis of the elongate member. The angle between the hoop and the elongate member may be between 45 degrees and 135 degrees. The angle between the hoop and the elongate member may be between 60 degrees and 120 degrees. The angle between the hoop and the elongate member may be between 80 degrees and 100 degrees.

The hoop may comprise a number of struts wherein said struts are rectangular, square or circular in cross-section. The struts may be interconnected. These interconnections may be at the strut ends and said interconnections may comprise curved crown elements.

In the collapsed state said the curved crown elements may connect strut segments that are substantially parallel, or may connect strut segments that are angled relative to one another.

The hoop may comprise a plurality of curved segments. The plurality of curved segments of the hoop may be configured to from a single plane, or may be configured to form two planes with the curved segments interconnecting at a point of intersection of the planes.

The plurality of curved segments may comprise a plurality of struts and said plurality of struts may form a substantially circular hoop when viewed along the axis of the elongate member.

The frame may comprise at least two openings in the expanded state each opening defining an opening for the capture of clot. The two openings may comprise a circular shape.

Each opening may be defined by a strut section and a body strut section wherein the strut section comprises two radially projecting struts and the body strut section comprises a curved strut wherein the radius of curvature of said body strut section is substantially similar to the target vessel size for the device.

The body strut section may connect the ends of the two projecting radial struts. The two substantially parallel wires may be connected to each other at at least one end.

The elongate member may extend in use from the target vessel through the vasculature of the patient and further extend exterior of the patient.

The elongate member may comprise a distal end, said distal end may terminate adjacent the frame collar, or may terminate at the distal junction of the capture fibres. Or the distal end may terminate distal of said frame and net and comprise a soft atraumatic tip.

The elongate member may comprise an inner lumen said inner lumen may extend from the proximal end of the elongate member at least to an area adjacent the frame.

The elongate member may comprise an exit port, said exit port located in the distal region of the elongate member.

The elongate member may comprise an inner core and an outer tube. Said inner core may comprise a wire and said wire may comprise a tapered distal end. The inner core wire may comprise an atraumatic distal end.

The distal end of the inner core wire may be associated with the distal fibre junction. The fibre junction may be adjacent to the core wire. The fibre junction may be tethered to the core wire.

The fibre junction may be integral with the distal segment of the inner core, or may be moveable relative to the inner core, or may be moveable by the inner core.

The inner core may comprise a coil. This coil may be a radiopaque coil.

The frame may comprise at least one collar. The collars may be fixed relative to the elongate member, or the collars may be slidable relative to the elongate member.

The frame may comprise a first collar and a second collar. Said first collar may be fixed relative to the elongate member and said second collar may be slidable relative to said elongate member.

The collar may be integral with at least one first strut and the collar and first strut may comprise a collapsed state for delivery through the vasculature and an expanded state for capturing and removing said occlusive material.

The at least one integral collar strut may define an area of bending and said area of bending may comprise a relaxed state and a strained state wherein in the frame expanded state the area of bending is in the relaxed state and in the frame collapsed state the area of bending is in the strained state.

The frame may comprises at least one proximal connector strut and at least one distal connector strut where said at least one proximal connector strut is connected to the hoop at a point which is spaced apart from the point of connection of the at least one distal connector strut.

The cross-sectional dimensions of the connector struts may be different to the cross-sectional dimensions of the hoop struts.

The device may further comprise a third collar distal of previously mentioned first and second collars.

The frame may further comprise a formed collar wherein the collar comprises a C shaped section. This C shaped section may be formed by cutting a segment of the large diameter tube, and forming the tube section such that it's radius of curvature is greatly reduced and heat treating the section so as to permanently set the formed shape.

Any or all of these collars may comprise at least one longitudinal slot extending along at least a portion of the length of the collar, and/or at least one circumferential slot extending partially around the circumference of the collar.

The plurality of fibres may constitute a capture net, said net comprising a series of fibre segments arranged to create a three dimensional clot capture net. The net may be connected to the frame at a plurality of points or engagement features around the circumference of the frame.

The capture net may comprise a knitted, braided or crocheted structure, or may comprise a series of longitudinal fibre segments. This structure may comprise a tube. This tube may be cylindrical or conical in shape.

The net comprises an inner layer and an outer layer. The inner layer and the net outer layer may be integral The net may be connected to the frame with a fibre. The net may partially encircle the frame.

The net may comprise a fibre junction wherein a plurality of fibre segments are connected. The capture net may comprise a series of fibre segments extending between the frame and this fibre junction. The fibre junction may be spaced apart from the frame and the fibre segments may define a basket for restraining clot that has been debonded from the vessel.

The clot capture system may have a capture net wherein the net comprises a proximal end and a distal end, the proximal end of the net being attached to the frame. The capture net may have a low density structure where the area ratio of the fibres to the capture net pores is <20%.

At least one of the plurality of high tensile fibres may have an ultimate tensile strength of at least 1500 MPa, or at least 2000 MPa, or at least 2500 MPa, or 3000 MPa or greater.

At least one of the plurality of high tensile fibres may comprise polymer fibers such as Ultra High Molecular Weight Polyethylene or Kevlar, or metal fibers such as 302 stainless steel, 304 stainless steel, other stainless steels, MP35N, L604, 35N LT, or Nitinol.

Wherein a metal fiber is used it may be cold worked to at least 50%.

An Ultra High Molecular Weight Polyethylene (UHM-WPE) fiber may comprise a Dyneema, Celanese, Spectra or a Tekmilon fibre.

The frame may comprise a plurality of attachment points around its circumference, and the capture net may be secured to the frame at a plurality of points around the circumference of the frame.

The attachment features may be integral with the frame struts and comprise localised changes to the cross section of the struts. The localised change in cross section may comprise a hole in the strut wherein the hole is circular, oblong, elliptical, curved and the hole may be in the centre of the strut or is offset. The hole may extend through the wall of the frame.

The localised change in cross section may comprise a notch, a recess, a depression, or a groove in the outer surface of the strut of the frame. The attachment points may comprise a plurality of such localised changes in cross section. The plurality of attachment points may be spaced equally around the circumference of the frame.

The plurality of attachment points may comprise holes in the struts and said holes may be less than 50 microns in diameter, or less than 30 microns in diameter, or less than 25 microns in diameter, or less than 20 microns in diameter.

The holes may not be fully cylindrical, but may be less than 50 microns in one dimension, or less than 30 microns in one dimension, or less than 25 microns in one dimension, or less than 20 microns in one dimension.

The frame and holes may be polished by a polishing process selected from sand blasting or electropolishing or chemical etching.

The device may further comprise a fibre junction where a plurality of fibre segment ends are connected. This fibre junction may comprise a knot, a weld, an adhesive joint, a site of attachment, a laminated junction, a coupling, a bonded joint or an assembly joint.

The device may further comprise a distal collar and said distal collar may comprise a junction for a number of fibres of the fibre net.

The distal collar may comprise a reception space and said reception space may be configured to restrain the ends of said fibre segments.

The distal collar reception space may comprise an annular space, said annular space sized to allow fibres to be received in the space.

The distal collar reception space may comprise at least one hole wherein said hole is sized to receive at least one fibre. The distal collar reception space may also comprise a plurality of holes, said plurality of holes being sized to receive one or more fibres.

The distal collar reception space may comprise a feature such as a hole, a groove or an annular space in the wall of the collar wherein said feature is sized to receive at least one fibre. This feature may also be located between the collar and the elongate member.

The device may comprise an expansion cable which may be connected to the frame and extend in use exterior of the patient.

The expansion cable may comprise a relaxed state and a tensioned state wherein in the relaxed state the expansion cable exerts no force on the frame and in the tensioned state the expansion cable exerts an expansion force on the frame. This expansion force may assist in the expansion of the frame.

The expansion cable in use may extend from exterior of the patient through a lumen in the elongate member, through an exit port located in the distal region of the elongate member and terminate at a point of connection with the frame.

The expansion cable may comprise a polymeric or metallic cable, and may be a monofilament or multifilament. The material of the expansion cable may be a polymer, such as a polyester, Ultra high molecular weight polyethylene, a fluoropolymer, a nylon, or Kevlar, or may be metallic such as a stainless steel or nitinol, or may be a mixture of the above or may possess similar properties to the above.

The frame may comprise an expanded configuration and a collapsed configuration and may be naturally biased towards the collapsed configuration and may further comprise a restraining system, which allows the frame to be stored in the collapsed state (during delivery) by interconnecting elements of the frame to one another.

The restraining system may comprise restraining one or more struts to each other.

The restraining system may comprise restraining a frame hoop in a collapsed state substantially parallel with the axis of the elongate member.

The elongate member may comprise an inner core extending distal of the collar of the frame, and the restraining system may comprise fixing the hoop to the inner core in a collapsed state.

The frame may comprise a supporting strut extending distally from the collar and substantially parallel to the axis of the collar, and the restraining system may comprise fixing the hoop to the supporting strut in a collapsed state.

The supporting strut may comprise an engagement feature allowing the supporting strut and the hoop and/or a connector element to be fastened to the supporting strut.

The device may further comprise a micro-delivery catheter comprising a reception space and a shaft. This reception space may extend proximally wherein the frame and net are configured to be received in the reception space in the collapsed state for delivery to the site of occlusion. The reception space may comprise a tubular element.

The collar or collars of the frame may be mounted on a tubular member and the tubular member may be moveable relative to the guidewire. The tubular member may be connected to a control wire and said control wire may extend proximally to the user, allowing the user to move the frame relative to the guidewire, or the tubular member may extend proximally to the user, allowing the user to move the frame relative to the guidewire.

The frame of this invention may also compromise hinges and may comprise a plurality of struts with one or more hinges connecting at least a pair of said struts. The expansion of the frame from its collapsed state to its expanded state may comprise an articulation of one or more of these hinges. Said hinges may be configured to articulate without significant resistance.

The at least one pair of struts may comprise a first strut and a second strut and the first strut may comprise a first point wherein said first point is spaced apart from the hinge. The at least one hinge may be configured such that said first point is restricted to move through a segment of a substantially circular arc when said hinge is articulated. The at least one hinge may be configured such that said first point is restricted to move through a set of points defining a substantially spherical surface when said hinge is articulated.

The at least one hinge may each comprise a first strut and a second strut, the first and second struts comprising hinge attachment features and said first and second struts being coupled by a hinge coupling element.

The hinge attachment features may comprise a hole, a mounting, a loop, a cut profile or a formed shape.

The hinge coupling may comprise a monofilament fibre, a multifilament fibre, a pin, a loop, a C section, a ring, a tether, or an articulating coupling.

The hinge attachment feature may comprise a hole and the hinge coupling may comprise a fibre wherein said fibre is looped through the hole in said first and second struts so as to fix said struts to one another while allowing said struts to articulate in at least one direction.

The frame may comprise a hoop and at least one connector strut. This hoop may comprise a plurality of hoop struts. The at least one hinge may comprise a pair of hoop struts. The at least one hinge may comprise a hoop strut and a connector strut.

The frame may comprise a compound hinge wherein more than two struts are hinged relative to each other. The compound hinge may comprise three struts. The compound hinge may comprise two hoop struts and a connector strut.

The at least one connector strut may be connected to the elongate member. The connection between the connector strut and the elongate member may comprise a hinge. The connection between the connector strut and the elongate member may comprise a collar wherein said collar connects the connector strut to the elongate member.

The frame may comprise an arrangement of hinges and said hinges may comprise movement freedoms and movement constraints and said movement freedoms and movement constraints may be arranged such that the frame moves progressively between a collapsed state and an expanded state when activated and between an expanded state and a collapsed state when deactivated.

The frame may be expanded by advancing or retracting at least a part of the elongate member. The elongate member may be connected to at least one strut and advancing or retracting a portion of the elongate member may cause the articulation of the at least one hinge and the frame expands.

The elongate member may comprise a first portion and a second portion and the elongate member first portion may be connected to an at least one first strut and the elongate member second portion may be connected to at least one second strut and relative movement between the elongate member first portion and the elongate member second portion may cause expansion or collapse of the frame depending on the direction of relative motion.

The elongate member may comprise an inner shaft and an outer tubular member and said outer member may be slidable relative to said inner shaft. Movement of the outer tubular member relative to the inner shaft may cause the frame to expand and/or collapse.

Any of the frames disclosed herein may be expanded by the release of stored energy. Said stored energy may comprise the release of stored elastic energy wherein at least one element of the frame comprises an elastic component and said elastic component is restrained in a strained state during delivery. Upon removal of said constraint said elastic component relaxes to its unstrained state and in so doing the frame is expanded.

The elastic component may comprise a nitinol component, a shape memory component, an elastic component or a super-elastic component.

The elastic component may comprise a hoop strut, a connector strut, a connector or a combination of these elements or a junction between these elements.

This invention also comprises a clot debonding device which may be used in conjunction with the clot retrieval designs described herein. The clot debonding device is designed to assist in the removal of obstructions from a vessel by providing an abutment surface which may be used to appose one side of the obstruction so that a force may be applied to the other side of the obstruction without said force being transmitted to the vessel in which the obstruction is placed. It therefore enables a clot retrieval device or other similar device to more effectively engage and capture clot or other such vessel obstructions.

It will be appreciated that such a device also has applications beyond its use with the clot retrieval device described herein. Such a clot debonder may be effectively used to aid the disengagment and removal of vessel obstructions in conjunction with other clot retrieval devicesor thrombectomy devices or aspiration devices.

The invention further provides a clot capture system for disengaging a clot from a vessel wall and removing the clot from the vessel, the clot capture system comprising:—a clot capture device for placement on a distal side of a clot, the clot capture device having a retracted delivery configuration and an expanded deployed configuration; and a clot debonding device for placement on a proximal side of a clot, the clot debonding device having a retracted delivery configuration and an expanded deployed configuration and comprising a clot engagement element which defines a distal abutment in the deployed configuration for urging a clot into the clot capture device.

It will be understood that the above mentioned clot capture device may be any of the clot retrieval device embodiments previously described herein, and the clot capture system may comprise any combination of the permutations described below with those of the clot retrieval devices described above.

The abutment area of the clot debonding device may be configured to engage with the clot in its expanded configuration. The engagement of the abutment area with the clot may comprise a relative movement between the abutment area and the clot and said relative movement may at least partially disengage the clot from the vessel. The relative movement between the abutment area and the clot may comprise an axial movement or a rotational movement or a combination of both movements of the abutment area.

The clot retrieval device may be configured to engage the clot from a distal end and the clot debonding device may be configured to engage the clot from a proximal end. The clot debonding device may thus be configured to apply a debonding force to the clot to disengage the clot from the vessel, and the clot retrieval device may be configured to apply a reaction force to the clot wherein the reaction force is applied substantially in the opposite direction to the debonding force and the combination of said forces disengages the clot from the vessel wall.

The clot retrieval device may comprise an engagement element and a reception space said engagement element may be configured to engage the clot from a distal end and said reception space may be configured to receive said disengaged clot and to allow the removal of said clot from the vasculature.

The clot debonding device may be configured to at least partially protect the blood vessel from the forces of clot debonding.

The clot engagement element may extend substantially the width of the mouth of the capture device in the deployed configuration.

The clot debonding device is movable relative to the clot capture device in the deployed configuration.

The clot engagement element may have a longitudinal axis and the distal abutment may extend radially of the longitudinal axis. The longitudinal axis may be a substantially central axis and the distal abutment may extend radially outwardly of the substantially central axis, or the longitudinal axis may be an offset axis and the distal abutment may extend radially outwardly of the offset axis.

The engagement element may comprise an axially extending region and a radially extending region. The engagement element may further comprise a circumferential region extending from the radial region. The engagement element may also comprise a transition region between the axial region and the radial region.

The clot debonding device may comprise an axially extending collar.

The clot capture device may define an inlet mouth in the deployed configuration and the clot engagement element may extend substantially the width of the inlet mouth of the clot capture device.

The clot debonding device may be slidable relative to the clot capture device.

The clot debonding device may be rotatable relative to the clot capture device.

In the deployed configuration, the clot capture device may be located distal of the clot debonding device.

The clot capture device and the clot debonding device may be independently movable.

The clot capture system may comprise an elongate member. The clot capture system may comprise a first elongate member associated with the clot capture device. The clot capture system may comprise a second elongate member associated with the clot debonding device. The first elongate member may comprise a guidewire, and said guidewire may comprise a stop. This stop may comprise a distal stop.

The second elongate member may comprise a proximal shaft. The clot debonding device may be mounted to the proximal shaft. The clot bonding device may be fixedly mounted to the proximal shaft.

The clot capture system may comprise a delivery catheter for the clot capture device.

The system may further comprise a first access catheter and a second access catheter, the distal end of said first access catheter being placed in a proximal vessel and the distal end of said second access catheter being placed in a distal vessel wherein the second access catheter is delivered to said distal vessel through the lumen of said first access catheter. Said first access catheter may comprise a guide catheter or a guide sheath and said second access catheter may comprise a delivery catheter or a microcatheter, wherein the clot retrieval device is configured to be delivered through the second access catheter.

The clot debonding device may comprise a lumen extending from its distal end and a proximal shaft connected either directly or by a collar to the expandable engagement element. The clot debonding device may be configured as a rapid exchange catheter.

The distal end of the clot debonding device may comprise an abutment surface in the collapsed state for advancement of the clot retrieval basket through a catheter lumen.

The expandable engagement element may expand radially outward from a central axis and may comprise an inflatable element, a self expanding element, a shape memory element, a super elastic element, a remotely activated element, a coil or spring element.

The expandable engagement element may comprise a balloon, an inflatable cuff, a plurality of struts, a slotted section, a cell structure, a plurality of wire segments, a helical coil, a flare, a ring, a braided section, or a hoop.

The expandable engagement element may comprise a slotted tubular member, or a number of overlapping coaxial slotted tubular members. The slotted tubular members may be self expanding or may be expanded by retraction of an actuation element connected to their distal end.

The expandable engagement element may comprise elements which expand into a generally helical configuration, such as a coiled element which at least partially uncoils to expand from one diameter to a second larger diameter.

The expandable engagement element may comprise a number of curved wire struts or segments, which may have points of inflection, and/or which may be configured to create closed or open cells, or a mixture of both.

The expandable engagement element of the clot debonder may be made from a shape memory alloy or a super elastic alloy such as Nitinol, or from another metal such as stainless steel, or from a polymer such as PEEK, Nylon, PE or Polyimide.

The expandable engagement element may comprise a plurality of struts or segments cut from a tube. Said struts or segments cut from a tube with slots that run substantially parallel to the longitudinal axis of the tube, or with slots that are not parallel to the longitudinal axis of the tube.

Said struts or segments may overlap or may be non non-overlapping.

The engagement element may comprise a collapsed state wherein the engagement struts are aligned with the axis of the clot debonder and said plurality of struts comprise a tubular structure.

Said plurality of struts may be close packed in the delivery configuration.

In the expanded state the engagement element is preferably configured to transmit axial force of the user to the clot. The engagement element may comprise an engagement surface and said engagement surface may comprise a distally facing surface. In one embodiment the engagement surface comprises an annular surface. With this embodiment the engagement surface may have an outer diameter and an inner diameter. The outer diameter may be substantially the same or smaller than the diameter of the vessel. The outer diameter may be substantially the same or smaller than the diameter of the clot. The inner diameter may be substantially the same or larger than the diameter of the guidewire.

In one embodiment the engagement surface comprises a flared surface. In another embodiment the engagement surface comprises a plurality of struts said struts configured to apply pressure to the clot over a substantial portion of the cross-section of the vessel. In one embodiment the engagement surface is configured to apply an axial displacement to the entire body of the clot. The engagement surface of the clot debonding device may be configured to prevent clot fragmentation during debonding and capture.

In one embodiment the engagement element comprises a plurality of elongate struts. In the delivery configuration the elongate struts may be substantially aligned with the axis of the vessel. In the expanded configuration the struts may project radially outward from the axis of the clot debonder. In one embodiment the struts are interconnected. The struts may comprise regions of bending.

In one embodiment the struts of the engagement element comprise an outer ring member and a plurality of radial struts connected to said outer ring member. In another embodiment the strut arrangement of the engagement element comprises a plurality of cells. Each cell boundary may be defined by a strut. In another embodiment the engagement element comprises an outer ring member. The outer ring may comprise a plurality of struts configured in a circumferential ring. The engagement element may comprise an inner ring member. The inner ring member may be connected to or separate of the outer ring member. In one embodiment the outer ring member is connected to the collar by a plurality of radial struts. In one embodiment the outer ring member comprises a plurality of zig zag strut elements.

In one embodiment the struts are cut from a nitinol tube. The tube may comprise a cut pattern. The cut pattern may comprise a plurality of longitudinal slots and a plurality of struts. In one embodiment the cut pattern comprises a plurality of curved segments interconnecting said struts.

In another embodiment the engagement element comprises a plurality of wires. The wires may comprise a collapsed state and an expanded state. In the collapsed delivery state the wires may be substantially aligned with the axis of the vessel. In the expanded state the wires may project radially outwardly of the axis of the clot debonding device.

In the fully expanded state the engagement element may comprise an outer rim. The outer rim may comprise a plurality of curved segments.

In another embodiment the engagement element comprises a plurality of shaped wires. Each shaped wire may comprise a first wire end and a second wire end. The first wire ends and second wire ends may be fixed to a tubular member. The wire segment may comprise a first radial curve adjacent the collar and a second circumferential curve. The circumferential curve in the wire may comprise an atraumatic vessel interface.

In one embodiment the engagement element comprises an axial strut segment, a curved strut segment and a radial strut segment. With this embodiment the engagement element may be connected to a tubular member at the proximal end of the axial strut section. The struts of the axial segment may be oriented substantially parallel to the axis of the clot debonding device. The engagement element may comprise an immediate segment distal of the axial segment. The intermediate segment may comprise the radial curve. The intermediate section may comprise most of the engagement surface. The intermediate section may provide a high area surface for the transmission of force to the clot.

The clot debonding element may be designed to transmit force over the entire surface of the clot. The clot debonding element may be configured to debond the clot in one piece. The clot debonder may be configured such that the clot does not snag on its surface. The clot debonder may be configured to push the clot into the opening of the clot capture basket.

The clot debonder engagement element may be configured such that upon withdrawal it disengages from the clot without snagging, or fragmenting the clot and without removing the clot from the capture basket.

The connection between the wire and the collar may be configured so as to orient the wire parallel to the axis of the clot debonding device. The connection between the collar and the wire may comprise a hole in the collar. Immediately distal of the collar the wire may comprise a curve. The wire may be radially curved so as to create an abutment surface. The body of the wire may be substantially radial relative to the axis of the clot debonder. The clot engagement element may comprise a plurality of radial wire segments configured to deliver and distribute pressure to one face of the clot. The wires may comprise a second curved segment. This second curved segment may define an outer rim of the clot engagement element. The curved segment may also present an atraumatic surface to the vessel. This second curved segment may be curved in the circumferential direction.

The clot engagement element may comprise radial and circumferential engagement elements and may transmit force to the clot in a manner similar to that of a piston.

In another embodiment the struts or wires of the engagement element comprise an articulation region. The engagement element may assume the expanded state by an articulation of the struts or wires about the articulation region.

The invention also provides a method for removing clot from a vessel involving a clot capture device that comprises a frame, a net and an elongate member such as a wire and is capable of being advanced through a microcatheter comprising the steps of: advancing a crossing guidewire through the vasculature and across the clot, advancing a microcatheter over the guidewire such that the tip of the microcatheter is across the clot, removing the crossing guidewire from the microcatheter, advancing through the lumen of the microcatheter a collapsed clot capture device, deploying the clot capture device distal of the tip of the microcatheter, expanding the clot capture device distal of the microcatheter, retracting the clot capture device and engaging with the clot, applying a force to the clot over at least a portion of the outer circumference of the clot, applying shearing forces to the clot, disengaging the clot from the wall of the vessel, capturing the clot within the clot capture basket, removing the clot capture basket and the clot from the patient and taking a final angiogram of the recannalized vessel.

The step of removing the clot capture basket may comprise at least partially collapsing the basket and/or applying compressive forces to the clot.

The clot capture device may comprise a frame, a wire and a net wherein the frame is expandable and the net is attached to the frame and the frame is at least partially fixed to the guidewire.

The invention provides a further method for removing clot from a vessel involving a clot capture device that comprises a frame and a net and is capable of being advanced through a microcatheter and is further advancable relative to a guidewire comprising the steps of: advancing a guidewire through the vasculature and across the clot, advancing a microcatheter over the guidewire such that the tip of the microcatheter is across the clot, advancing the frame and net in a collapsed state over the guidewire, deploying the frame and net from the distal end of the microcatheter, expanding the frame and net distal of the clot, retracting the frame and net and engaging with the clot, applying a force to the clot over at least a portion of the outer circumference of the clot, applying shearing forces to the clot, disengaging the clot from the wall of the vessel, encircling at least a portion of the clot with the frame, restraining fragments of the clot with the net, removing the frame and net from the patient and taking a final angiogram of the recannalized vessel.

The clot capture device may comprise an advancement element and the step of advancing the frame and net over the guidewire may comprise advancing the advancement element parallel of and relative to the guidewire.

The invention provides a further method for removing clot from a vessel involving a clot capture device that comprises a frame, a net and an elongate wire and is capable of being advanced through a guide catheter comprising the steps of: advancing a guidewire through the vasculature and across the clot, advancing a guidecatheter into the target vessel and positioning the tip of the guidecatheter proximal of the clot, advancing the clot capture device in a collapsed state through the guidecatheter, advancing the frame and net and the distal portion of the elongate wire across the clot, deploying the frame and net distal of the clot, expanding the frame and net distal of the clot, retracting the elongate wire with the frame and net attached, applying a force to the clot over at least a portion of the outer circumference of the clot, disengaging the clot from the wall of the vessel, encircling at least a portion of the clot with the frame, restraining fragments of the clot with the net, removing the frame and net from the patient, taking a final angiogram of the recannalized vessel.

The invention also provides a further method for removing clot from a vessel involving a clot capture device that comprises a basket and a debonding element, the capture basket comprising a collapsed state for delivery through the vasculature and an expanded state for the capture of clot, the clot debonding element comprising a collapsed delivery state and an expanded state the method comprising the steps of: advancing a guidewire through the vasculature and across the clot, advancing a microcatheter over the guidewire such that the tip of the microcatheter is across the clot, advancing the basket through the microcatheter, deploying the basket from the distal end of the microcatheter, expanding the basket distal of the clot, retracting the microcatheter until the tip of the micro catheter is proximal of the clot, retracting the basket and engaging with the clot, advancing the clot debonder through the microcatheter, deploying the clot debonder proximal of the clot, advancing the clot debonder to engage with the clot from the proximal side, retracting the basket while holding the clot debonder steadfast, disengaging the clot from the wall of the vessel without applying force to the vessel wall distal of the occlusion, disengaging the clot from the wall of the vessel, encircling at least a portion of the clot with the frame, retracting the clot debonder, collapsing the clot debonder inside the lumen of the microcathater, restraining fragments of the clot with the basket, removing the basket and the clot from the patient and taking a final angiogram of the recannalized vessel.

The above methods may include applying a force to the clot over at least a portion of the outer circumference of the clot, and/or applying shearing forces to the clot and/or collapsing the clot debonder inside the lumen of the guidecatheter and/or expanding the clot debonder at the distal end of the microcatheter.

The step of expanding the clot debonder may comprise inflating the clot debonder, or inflating a sac at the distal end of the clot debonder.

The step of expanding the clot debonder may comprise removing an outer restraint from clot debonder and allowing the clot debonder to self-expand. The step of removing this restraint may comprise removing a pod from over the clot debonder.

The step of removing the restraint may comprise retracting the distal end of the microcatheter from over the clot debonder.

The invention further discloses a method for removing clot from a vessel comprising the steps of: providing a clot capture device comprising a basket and a debonding element, the capture basket comprising a collapsed state for delivery through the vasculature and an expanded state for the capture of clot, the clot debonding element comprising a collapsed delivery state and an expanded state; advancing the basket through the vasculature in the collapsed state; deploying the basket distal of the clot; advancing the clot debonder through the vasculature; deploying the clot debonder proximal of the clot; engaging the basket and/or the clot debonder with the clot; disengaging the clot from the wall of the vessel; capturing the clot in the basket; and removing the clot from the vasculature.

A number of embodiments of the invention are disclosed herein. In the statements above and below the main embodiments are firstly described as a whole, with a list of further embodiments relating to variants of specific features or uses appended the main embodiments. It will be appreciated that these further embodiments/feature variants may also be applicable to any of the main embodiments.

A device is disclosed for the removal of an occlusive clot from a vessel wherein the occlusion has substantially cut off blood supply to a distal vascular bed, the device comprising a basket and a clot holding assembly, the basket comprising a frame, a net and an elongate member, the frame comprising a first ring member and having a collapsed delivery configuration, a deployed configuration and an expanded configuration for dislodging clot from a vessel wall, the first ring member configured to be expanded distal of the occlusive clot, the basket further comprising a cable extending through the lumen of the elongate member, the cable attached to the first ring member, the cable comprising an activated state and a deactivated state, in the activated state the cable transmitting a force from the user to the frame, said force causing the deployed frame to assume the expanded state.

In other embodiments this invention may further include one or more of the following: The expansion of the frame may comprise an articulation of at least a portion of the frame.

The frame may further comprise a connector element and a collar arrangement.

The expansion of the frame may comprise an articulation of the first ring member.

The frame articulation may comprise an angular displacement of the frame.

The frame articulation may comprise a change in the shape of the frame.

The expansion of the frame may comprise an articulation of the connector member.

The deployed state may comprise a partially expanded state.

The frame may be biased towards the deployed state.

The frame may return to the deployed state when the cable is deactivated.

The frame may comprise a cable attachment to which the distal end of the cable is fixed.

The frame may comprise at least one cable guide.

The cable guide may at least partially encapsulate the cable.

The cable guide may comprise a channel which restrains the cable.

The channel of the cable guide may be configured such that the cable can slide in the channel.

The channel may comprise an eyelet.

The channel may comprise a restraining feature.

The axis of a portion of the cable may run substantially parallel to the neutral axis of the first ring along at least a portion of the circumference of the first ring.

In the expanded configuration the diameter of the frame may be substantially the same as the diameter of the vessel in a region of occlusion.

In the expanded configuration the diameter of the frame may be substantially the same as a diameter of the clot.

The elongate member may comprise a tubular member.

The elongate member may extend in use from the region of the occlusion through the vasculature to a user interface external of the patient.

The elongate member may comprise a spring, or a polymer tube, or a hypo tube over at least a portion of its length.

The elongate member may comprise a plurality of wire filaments wherein said filaments are arranged so as to define an inner lumen.

The wire filaments may be wound in a spiral arrangement.

The wire filaments may be packed tightly together and define an inner lumen.

The basket and the clot holding assembly may be configured to be delivered through the lumen of a microcatheter.

The basket and the clot holding assembly may be restrained in the collapsed state during delivery through the microcatheter.

The frame may be restrained in the collapsed state during delivery by a restraining element.

The restraining element may comprise a tether, or a tube, or a core to which the frame is fixed.

The restraining element may be removed distal of the clot and the frame deployed.

The restraining element may comprise the inner wall of the microcatheter.

The first ring member may be configured in the expanded state to engage with the occlusive clot at the interface between the clot and the vessel wall.

The clot holding assembly may be configured to provide an abutment.

The basket may be moveable relative to the holding assembly.

The clot holding assembly may be configured to provide a clot engaging surface.

The basket may not be moveable relative to the holding assembly.

The holding assembly may comprise an engagement frame and an elongate tube.

The holding assembly may be configured to be expanded proximal of the basket frame.

The holding assembly may be configured to transmit a holding force from the user to the proximal face of the clot.

The holding assembly may hold the clot in a fixed position while the first ring member of the basket is retracted over the clot.

The holding assembly may hold the vessel in a fixed position while the first ring member of the basket is retracted over the clot.

The basket may be held in a fixed position while the clot holding assembly is retracted with the clot.

The basket and clot holding assembly may be retracted together with the clot.

The first ring member of the basket may apply an action force to the clot to dislodge the clot from the vessel wall.

The holding assembly may apply a reaction force to the proximal end of the clot.

The reaction force may reduce the portion of the action force that is transmitted to the vessel wall.

The holding assembly may be configured to allow the user to apply a greater action force to the clot distal end.

The holding assembly may protect the vessel from force applied to the clot by the basket.

The abutment may comprise an abutment surface.

The abutment surface may comprise a plurality of tether segments.

The abutment surface may comprise a plurality of tethers lased to the second ring element.

The abutment surface may comprise a plurality of strut elements.

The abutment surface may comprise a plurality of strut elements and a plurality of tether segments.

The abutment surface may be configured to hold the clot stationary while the first ring dislodges the clot from the vessel wall.

The abutment surface may be configured to distribute the engagement force over the proximal surface of the clot.

The engagement frame may comprise a second ring element.

The plurality of tether segments may be lased to the second ring.

At least one of the plurality of tether segments may be taut when the engagement frame is in the expanded configuration.

The abutment may be configured to distribute force across a surface of the clot.

In the expanded configuration the second ring element may comprise a hoop.

The hoop may comprise a flat hoop.

The hoop may comprise a zig-zag hoop.

The abutment surface may comprise a flat surface.

The abutment surface may comprise an undulating surface.

The abutment surface may comprise two or more interpenetrating flat surfaces.

The abutment surface may comprise a complex 3 dimensional surface.

The abutment surface may be configured to grip the clot.

The abutment surface may be configured to engage with the clot on multiple planes.

The engagement frame may comprise a wire.

The engagement frame may comprise at least a pair of wire segments.

The wire may comprise a hoop in the expanded state and the wire may comprise a pair of substantially parallel wire segments in the collapsed configuration.

The engagement frame may comprise at least a pair of struts.

In one embodiment the pair of struts may comprise a first end and a second end.

The struts may be connected to one another at the first end.

The engagement frame may be connected to the tubular member adjacent the strut first end.

The struts may be connected to each other at the second end.

In the collapsed configuration the engagement frame may comprise a pair of substantially parallel struts.

In the collapsed configuration the pair of struts may lie along the surface of the elongate member of the basket assembly.

In the expanded configuration the struts may move apart between the first and second ends to form a hoop.

The basket may comprise a connector member which connects the first ring member of the basket to the elongate member.

The frame may comprise a collar arrangement.

The collar arrangement may be configured to allow the elongate member to rotate relative to the frame.

The collar arrangement may comprise a frame collar and a proximal and distal stop.

The frame collar may be disposed over the elongate member and may be rotatable relative the elongate member.

The proximal and distal stops may be fixed to the elongate member.

Axial movement of the frame collar may be restricted by said proximal and distal stops.

The frame collar may be connected to the connector member.

The connector member may comprise an articulating member.

The net may comprise a braided, knitted or filament wound net and the net may be tubular with an open end and a closed end.

The open end of the net may be attached to the ring member.

The net may be configured to capture dislodged clot.

The net may be configured to capture clot fragments.

The net may comprise a high tensile fibre.

The net may comprise a para-aramid, meta-aramid, a UHMWPE, a polyethylene naphthalate (PEN), a stainless steel, a nitinol, a tungsten alloy or a mixture of these.

The first ring may comprise a plurality of net attachments.

The net attachments may comprise eyelets, notches, contoured surface.

The cable may comprise a plurality of filaments.

The distal end of the cable may be branched and each branch may be fixed to the frame at a separate attachment point.

In one embodiment one of the cable branches may be attached to the net.

The elongate member may comprise an inner lumen.

The inner lumen of the elongate member may comprise a smooth undulating surface.

The device may comprise a user interface and said user interface may be configured to allow the user to control the frame assembly and the holding assembly.

The user interface may comprise a handle attached to the proximal end of the elongate member.

The handle may comprise a control mechanism.

The proximal end of the cable may be fixed to the control mechanism.

The control mechanism may be configured to apply or remove tension on the cable.

The control mechanism may be activated by a thumbwheel on the handle.

In another embodiment the device comprises a device for the removal of a thrombotic or embolic occlusion of a blood vessel the device comprising: a basket, a clot engagement element, a pull cable, and a user interface, the basket comprises a frame and a net, the frame configured to engage generally with the outer rim of the clot, the frame having a collapsed configuration and an expanded configuration, the clot engager being disposed proximal of the basket and configured to engage with the clot, the pull cable extending proximally from the basket to the user interface the pull cable comprising a relaxed configuration and a tensioned configuration, tensioning of the pull cable at least partially causing the frame to assume the expanded configuration.

In another embodiment the device comprises a device for the removal of clot obstructing the flow of blood through an arterial vessel, the device comprising an elongate member, a clot engaging element and a capture basket; the elongate member extending in use from a point adjacent the target treatment site interior of the patient to a point exterior of the patient; the capture basket comprising a frame and a net, and having an expanded and a collapsed configuration; the clot engaging element comprising a plurality of struts having an expanded and a collapsed configuration, the plurality of struts forming a first section and a second section, said first section tapering outward and distally from the elongate member and connected to the second section, said second section comprising a plurality of cells defined by a plurality of struts and arranged around at least a portion of the circumference of an axis substantially parallel to that of the elongate member; the clot engaging element and the capture basket being restrained in the collapsed configuration for delivery to the target site; and the clot engaging element being located adjacent the distal end of the elongate member and proximal of the capture basket and configured to engage with and dislodge clot from the vessel.

The capture basket frame may be self expanding.

The clot engaging element may be self expanding.

The elongate member may comprise a proximal section adjacent its proximal end and a distal section adjacent its distal end, said proximal section having a flexural stiffness greater than four times that of said distal section. The clot engaging element may comprise a central axis and a contact surface, said central axis being substantially parallel to the elongate member, said contact surface engaging with the clot and extending around at least a portion of the central axis.

The contact surface may extend around the entire circumference of the central axis.

The plurality of cells of the second section of the clot engaging element may be arranged around the entire circumference of an axis substantially parallel to that of the elongate member.

The elongate member may comprise an outer tubular element and an inner operating element.

The inner operating element may be movable relative to the outer tubular element and may extend both proximally and distally of the outer tubular element.

The clot engaging element may be attached to the distal section of the outer tubular element and the capture basket attached to the distal section of the inner operating element.

The capture net frame may be expandable to conform to the inner diameter of the vessel in which it is deployed.

The elongate member may contain an operating cable which may be connected to an element of the capture net frame and which can be advanced or retracted relative to the elongate member to control the degree of expansion of the frame.

The clot engaging element may be expandable to conform to the inner diameter of the vessel in which it is deployed.

The net may comprise a braided, knitted or filament wound net and may have an open end and a closed end.

The clot engaging element may comprise one or more tether segments which extend between some or all of the plurality of struts.

The clot engaging element may be laser cut from a tube or sheet.

The clot engaging element and the capture net may be restrained in the collapsed configuration by the inner lumen of a microcatheter during delivery.

The capture net frame may be self adjusting, and/or the expansion of the capture net frame may be adjustable by the user.

In another embodiment a device for the removal of a thrombotic or embolic occlusion of a blood vessel the device comprises a self expanding frame for use in the treatment of embolic or thrombotic disease of a blood vessel, the frame comprising a collapsed state for delivery, a partially expanded state and a fully expanded state wherein in the fully expanded state the frame comprises an unrestricted opening of substantially the same size as the cross-section of the target vessel, the frame further comprising at least one cable attachment point and at least one cable guide, wherein the cable guide restrains the cable in a path substantially parallel to the path of the strut but spaced apart from the neutral axis of the strut and allows the cable to slide relative to the cable guide.

In another embodiment a device for the dislodgement and removal of an occlusive clot in a blood vessel comprises a self expanding frame, the frame comprising a collapsed state for delivery, a partially expanded state and a fully expanded state wherein in the fully expanded state, the frame comprises a first hoop and a second hoop, the first hoop and the second hoop are connected at an articulating junction, the angle of the first and second hoops with respect to each other being variable.

The articulating junction may comprise a strut.

The first hoop, the second hoop and the articulating junction may be integral

The first hoop, the second hoop and the articulating junction may be cut from a self expanding tube.

The first hoop, the second hoop and the articulating junction may be cut from a self expanding sheet.

The first hoop, the second hoop and the articulating junction may comprise a shaped wire.

The device further may comprise an elongate member and the elongate member is connected to the frame adjacent the distal end of the elongate member.

In use the elongate member may extend from the region of the occlusion through the vasculature to the exterior of the patient.

The elongate member may comprise an inner lumen.

The device may comprise a cable, said cable fixed to an attachment point on the frame and extending through the vasculature to the exterior of the patient.

The cable may comprise an activated state wherein tension is applied to the cable by the user and a deactivated state wherein the cable is substantially free of tension.

In the cable activated state the frame may articulate.

The cable may comprise a plurality of activated states.

The frame may comprise a plurality of fully expanded states.

The frame may comprise two pairs of struts connected by the articulating junction in the collapsed state.

The frame may comprise a pair of elliptical rings in the deployed state.

The pair of elliptical rings may comprise a major axis and a minor axis.

The major axis of the pair of elliptical rings may be substantially aligned with the central axis of the vessel in the deployed state.

The cable attachment point may be adjacent the distal end of the distal ring when the ring is in the deployed state.

Activation of the cable may cause the both rings to rotate relative to the axis of the vessel.

Activation of the cable may cause the rings rotate in opposite directions.

Activation of the cable may cause the distal end of the distal ring moves towards the proximal end of the proximal ring.

The centre of the frame may comprise the crossing point of the major axis and the minor axis and the centre of the frame may be substantially coaxial with the central axis of the elongate member.

The centre of the frame may be spaced apart from the axis of the elongate member.

The frame may comprise a connector member, the connector member configured to connect the proximal hoop of the frame to the elongate member.

The net may be attached to the frame.

The net may be attached to the distal hoop of the frame.

The net may be attached to the proximal hoop of the frame.

The net may pass over the distal hoop of the frame.

The net may pass through the opening defined by the distal hoop of the frame.

The distal hoop may be slidable relative to the net.

The articulating junction may comprise an area where the thickness of the frame is reduced.

The articulating junction may comprise an area where the width of the frame is reduced.

The articulating junction may comprise a strut or a wire connecting the first and second hoops.

The articulating junction may comprise a pair of struts or wires connecting the first and second hoops.

The pair of struts or wires may be connected to each other.

The articulating junction may comprise a tether connecting the first and second hoops.

The articulating junction may comprise a weakened section.

The articulating junction may comprise a stress distributing region.

The frame may be fixed to the elongate member.

The frame may be rotatable relative to the elongate member.

The cable may extend parallel with the elongate member.

The cable may extend through the lumen of the elongate member.

Another embodiment of this device is for use in the dislodgement of an occlusive clot in a vessel the device comprising an expandable distal section and an elongate tubular member, wherein the expandable distal section comprises a collapsed configuration for delivery and an expanded configuration for dislodgement of the occlusive clot, the self expanding distal section comprising a plurality of self expanding members, said self expanding members projecting radially outward from the distal section of the elongate tube, each self expanding member comprising an atraumatic end, an engagement section and an attachment, the engagement section projecting substantially radially outwardly relative to the elongate tube and the attachment fixed to the elongate tube.

The elongate tube may comprise a lumen and said lumen may be configured to slidably receive a clot removal assembly, wherein the clot removal assembly comprises a shaft and a clot removal element and the shaft extends through the lumen of the tubular member and the clot removal element is distal of the expandable distal section of the device.

The clot removal element may comprise a basket.

The clot removal element may comprise a clot engagement device.

The expandable distal section may comprise a clot engagement device.

The atraumatic end of the at least one self expanding member may comprise a curved surface.

The atraumatic end of the at least one self expanding member may comprise an eyelet.

The atraumatic end of the at least one self expanding member may comprise a soft material.

The atraumatic end of the at least one self expanding member may comprise a curved member.

The self expanding distal section may comprise an abutment surface.

The abutment surface may comprise an annular surface.

The abutment surface may comprise a tapered surface.

The abutment surface may be concentric with the lumen of the elongate tube.

The abutment surface may be offset relative to the lumen of the elongate tube.

The abutment surface may comprise a plurality of tether segments.

At least one of the tether segments may comprise at least a partially circumferential segment.

At least one of the tether segments may comprise at least a partially radial segment.

At least two of the self expanding members may be connected.

In another embodiment a device for the dislodgement and removal of an occlusive clot in a blood vessel comprises a basket assembly, the basket assembly comprising a self expanding frame, a net and an elongate member, the frame comprises a hoop and a support ring segment, the hoop connected the elongate member and configured to appose a vessel circumference, the support ring segment is fixed to the hoop and the support segment is configured to appose a portion of a circumference of the vessel, the support segment providing an engagement support to the hoop.

The hoop may comprise a collapsed delivery configuration and an expanded configuration for engagement and dislodgement of the occlusive clot.

The hoop may be biased towards the expanded configuration.

The hoop may comprise a first strut and a second strut and each strut may be configured to form one half of the hoop.

The support ring segment may comprise a first end and a second end and the first and second ends may be attached to the first and second struts.

The centre of the hoop may be substantially coaxial with the axis of the elongate member.

The centre of the hoop may be spaced apart from the axis of the elongate member.

The elongate member of the basket assembly may be sized such that it can be interfaced with a clot debonding device.

In another embodiment a device for the dislodgement and removal of an occlusive clot in a blood vessel comprises a basket assembly, the basket assembly comprising a frame, a net, a cable and a tubular member, the frame comprising a self expanding hoop and a support, the support comprising a curved strut wherein the curve is configured to interact with the surface of the vessel, the ends of curved strut articulating with respect to the hoop and being fixedly connected to the hoop.

The curved strut may be integral with the hoop.

The frame may comprise a one piece self expanding structure cut from a tube.

The structure may comprise an articulation region connecting the curved strut to the hoop.

The articulation region may comprise a region wherein the wall of the tube is reduced.

The articulation region may comprise a region wherein the width of the section is reduced.

The curved strut may comprise a hinge at each of its ends.

The net may be attached to the hoop.

The frame may comprise a collapsed configuration, a deployed configuration and an expanded configuration.

The expanded configuration may comprise the clot dislodgement configuration.

The collapsed configuration may comprise the delivery configuration.

The deployed configuration may comprise the clot removal configuration.

In the collapsed configuration the struts that form the hoop may be compressed together to facilitate delivery.

In the collapsed configuration the curved strut may be collapsed to facilitate of the frame through a microcatheter.

In the deployed state the hoop may expand.

The cable may comprise an activated state and a deactivated state.

In the activated state the cable may be in tension and may cause the curved strut to articulate relative to the hoop.

In the activated state the cable may be in tension and may cause the expanded hoop to articulate relative to the elongate member.

In the deactivated state the cable may not be in tension and the frame may return to its deployed state.

The tubular member may comprise an abutment surface at its distal end.

The abutment surface may engage with the frame when the cable is activated.

The tubular member may be integral with the frame.

BRIEF DESCRIPTION OF THE DRAWINGS

The invention will be more clearly understood from the following description of some embodiments thereof, given by way of example only, with reference to the accompanying drawings, in which:—

FIG. 2 shows some of the anatomy of arteries above the aortic arch leading to the brain;

FIG. 4g shows the clot retrieval device being advanced proximally and capturing the obstructive clot with a removal catheter advanced from the proximal side;

FIG. 4h shows the clot retrieval device, the captured occlusive clot and the removal catheter being removed from the vessel;

FIG. 4i shows the target vessel with the obstructive clot and devices completely removed;

FIG. 5a shows a target vessel with an occlusive clot;

FIG. 5b shows a micro delivery catheter with a clot retrieval device collapsed within a distal lumen of the micro delivery catheter, the micro delivery catheter being advanced across the occlusive thrombus, the clot retrieval device having a guidewire that extends proximally and distally;

FIG. 5c shows the micro delivery catheter being removed with the clot retrieval device deployed in the target vessel distal of the occlusive clot with the guidewire extending across the lesion and proximal to the user;

FIG. 5d shows the clot retrieval device deployed in the target vessel distal of the occlusive clot with the guidewire extending across the lesion and proximal to the user;

FIG. 7a shows a clot retrieval device in its expanded capture state;

FIG. 7b shows the clot retrieval device of FIG. 7a inside a micro delivery catheter in its collapsed delivery state;

FIG. 8a shows a clot retrieval device frame constructed from a guidewire;

FIG. 8b shows a clot retrieval device frame attached to a guidewire;

FIG. 8c shows a clot retrieval device frame mounted between stops on a guidewire;

FIG. 8d shows a clot retrieval device frame connected to a tubular element mounted proximal to a stop on a guidewire;

FIG. 8e shows a clot retrieval device frame connected to a tubular element mounted a guidewire;

FIG. 8f shows a clot retrieval device frame connected to a tubular element with an exit port and proximal shaft, mounted on a rapid exchange guidewire;

FIG. 10b is a view of a clot retrieval device in which a proximal collar support struts and frame are cut from a single piece of tubing;

FIG. 10c is an elevational view of one piece frame component of FIG. 10b in a collapsed configuration;

FIG. 10d is an end view of a collar end of the device of FIG. 1.0c;

FIG. 10e is a cross sectional view on the line a-a in FIG. 10c;

FIG. 11a shows a clot retrieval device in its expanded capture state;

FIG. 11b shows the clot retrieval device of FIG. 11a inside a micro delivery catheter in its collapsed delivery state with the capture fibers removed (for illustration);

FIG. 11c shows the clot retrieval device of FIG. 11a inside a micro delivery catheter in its collapsed delivery state;

FIG. 12a shows a clot retrieval device in its expanded capture state without capture fibers being shown (for illustrative purposes);

FIG. 12b shows a clot retrieval device of FIG. 12a inside a micro delivery catheter in its collapsed delivery state with the capture fibers removed (for illustration);

FIG. 13a shows a clot retrieval device in its expanded state;

FIG. 18 shows a clot retrieval device in the deployed configuration distal of an occlusive clot;

FIG. 19 shows a clot retrieval device being withdrawn proximally to capture a clot;

FIG. 20a shows a first side view of a strut of the hinged frame of a clot retrieval device;

FIG. 20b shows a second side view of a strut of the hinged frame of a clot retrieval device;

FIG. 20c shows a strut of the hinged frame of a clot retrieval device. The strut has a preset curved shape;

FIG. 20d shows the joining of the ends of two struts in the construction of a hinged frame;

FIG. 20e shows a hinged frame with four struts forming a ring and four support elements supporting the frame;

FIG. 20f shows four struts of a hinged support frame configured into a ring;

FIG. 20g shows how the hinged support frame can collapse about the X axis;

FIG. 20h shows how the hinged support frame can collapse about the Y axis;

FIG. 20i shows how the hinges allow the support frame to collapse;

FIG. 20j shows the hinges in the collapsed state;

FIG. 20k is another view of a hinged support frame;

FIG. 21a shows an enlarged view of a hinged support frame with eyelets for fiber attachment;

FIG. 21b shows the frame of FIG. 20j integrated with proximal and distal frame supports;

FIG. 21c shows a clot retrieval device assembled and in a collapsed configuration with capture fibers included;

FIG. 23a shows a clot retrieval device with a hinged frame in the expanded configuration;

FIG. 23b shows a clot retrieval device with a hinged frame in the partially collapsed configuration;

FIG. 23c shows a clot retrieval device with a hinged frame in the fully collapsed configuration;

FIG. 24a shows a clot retrieval device with a hinged frame in the fully expanded configuration;

FIG. 24b shows a clot retrieval device with a hinged frame in the partially collapsed configuration;

FIG. 24c shows a clot retrieval device with a hinged frame in the fully collapsed configuration;

FIG. 26a shows an eyelet for capture fibre attachment to a strut;

FIG. 26b shows an eyelet for capture fibre attachment to a strut;

FIG. 26c shows an eyelet for capture fibre attachment to a strut;

FIG. 26d shows an eyelet in a strut section with a capture fibre in situ;

FIG. 26e shows an eyelet in a strut section with a capture fibre in situ;

FIG. 26f shows an eyelet in a strut section with a capture fibre in situ;

FIG. 28a shows a segment of a strut of a clot retrieval device;

FIG. 28b shows a cross section of a strut;

FIG. 28c shows a fixture for assembling capture fibres to struts;

FIG. 29a shows two eyelets for capture fibre attachment to a strut;

FIG. 29b shows an eyelet for capture fibre attachment to a strut;

FIG. 29c shows an eyelet for capture fibre attachment to a strut;

FIG. 29d shows a strut with curvature to define a capture fiber attachment location;

FIG. 29e shows a strut with raised features to define a capture fiber attachment location;

FIG. 29f shows a strut with recessed features to define a capture fiber attachment location;

FIG. 29g shows a strut with recessed features to define a capture fiber attachment location;

FIG. 29h shows a strut with bands to define a capture fiber attachment location;

FIG. 29i shows a strut with coils to define a capture fiber attachment location;

FIG. 30a shows a strut with a sleeve to create a capture fiber attachment location;

FIG. 30b shows a strut with a coating to create a capture fiber attachment location;

FIG. 30c shows a strut and a capture net with a connecting fiber joining the two;

FIG. 30d shows a strut and a capture net with connecting rings joining the two;

FIG. 30e shows a strut and a capture net with a connecting fiber joining the two;

FIG. 31a shows a capture net of a woven or braided construction;

FIG. 31b shows a capture net of a knitted construction;

FIG. 31c shows a sectional side view of the capture net of FIG. 31a or FIG. 31b inverted and mounted on a frame;

FIG. 32a shows a monofilament capture fiber;

FIG. 32b shows a multifilament twisted capture fiber;

FIG. 32c shows a multifilament braided capture fiber;

FIG. 32d shows a multifilament capture fiber with a cover sleeve;

FIG. 32e shows a multilayer capture fiber;

FIG. 33a shows a frame with a capture net with a porosity gradient;

FIG. 33b shows a frame with a capture net with a porosity gradient;

FIG. 33c shows a frame with capture fibers with a porosity gradient;

FIG. 33d shows a frame with capture fibers with a stiffening fiber;

FIG. 34a shows a clot retrieval device in the fully expanded configuration;

FIG. 34b shows a clot retrieval device in the collapsed configuration inside a catheter;

Figure 35A:
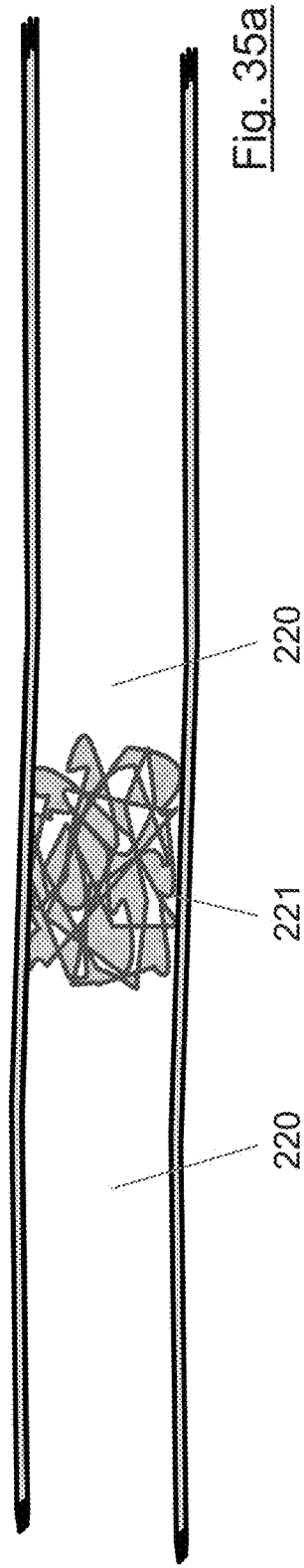
Figure 35B:
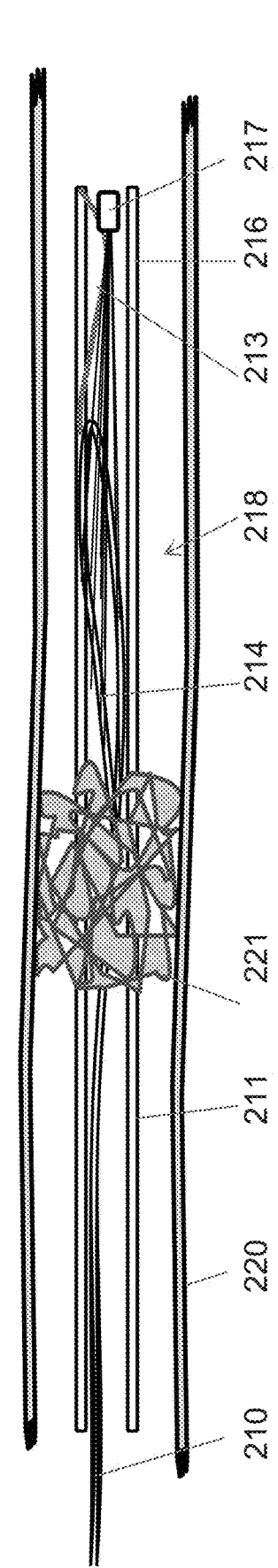
Figure 35C:
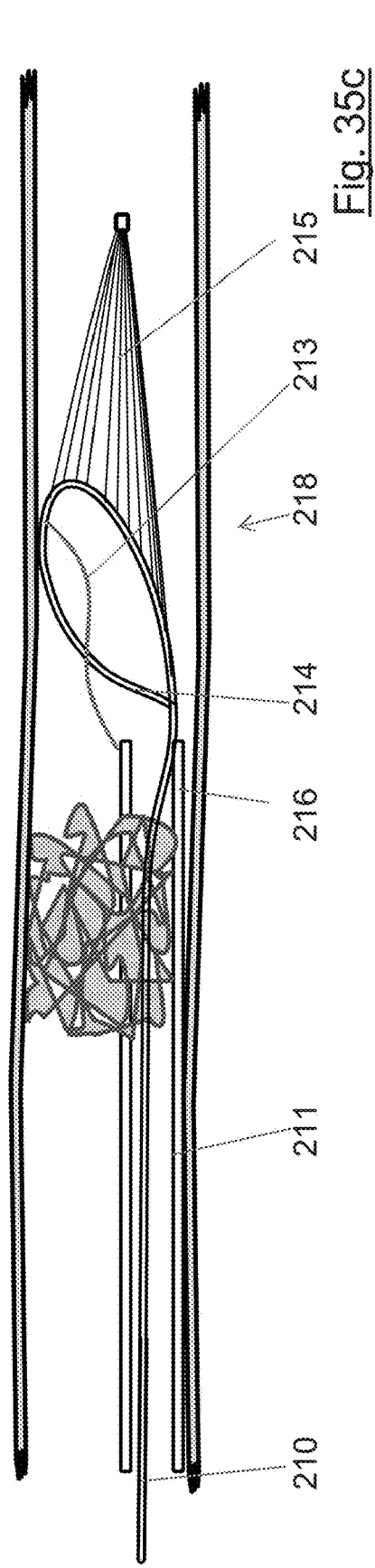
Figures 39A, 39B:
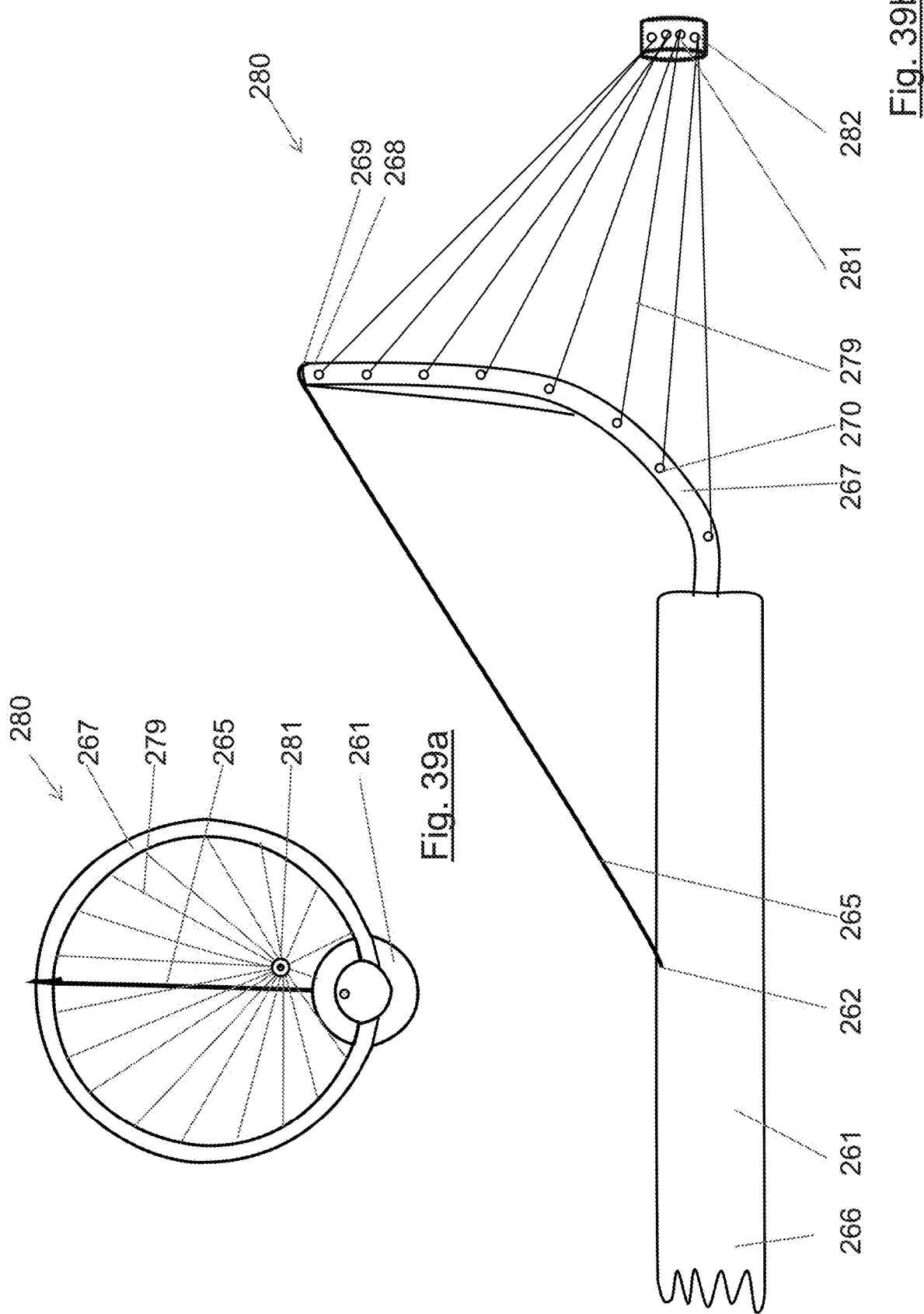
Figure 39C:
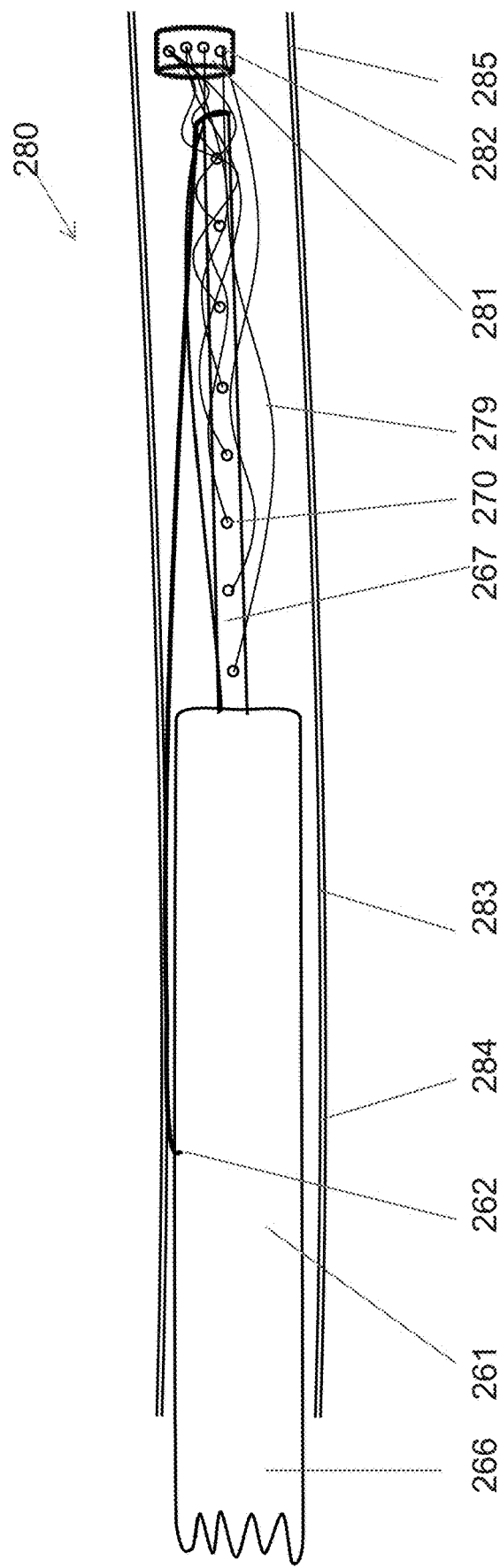
Figure 45A:
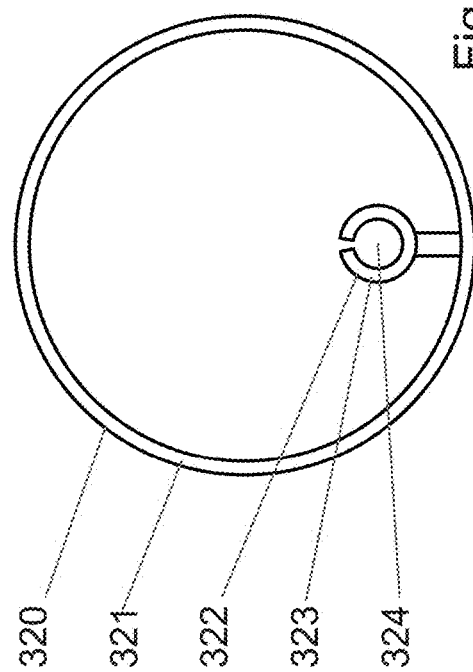
Figure 45B:
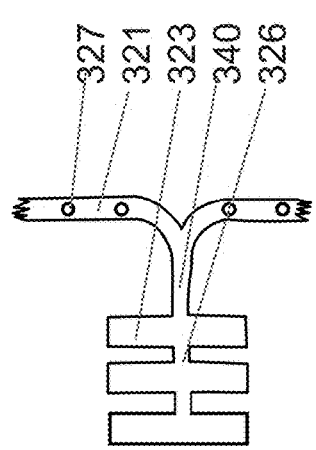
Figure 45C:
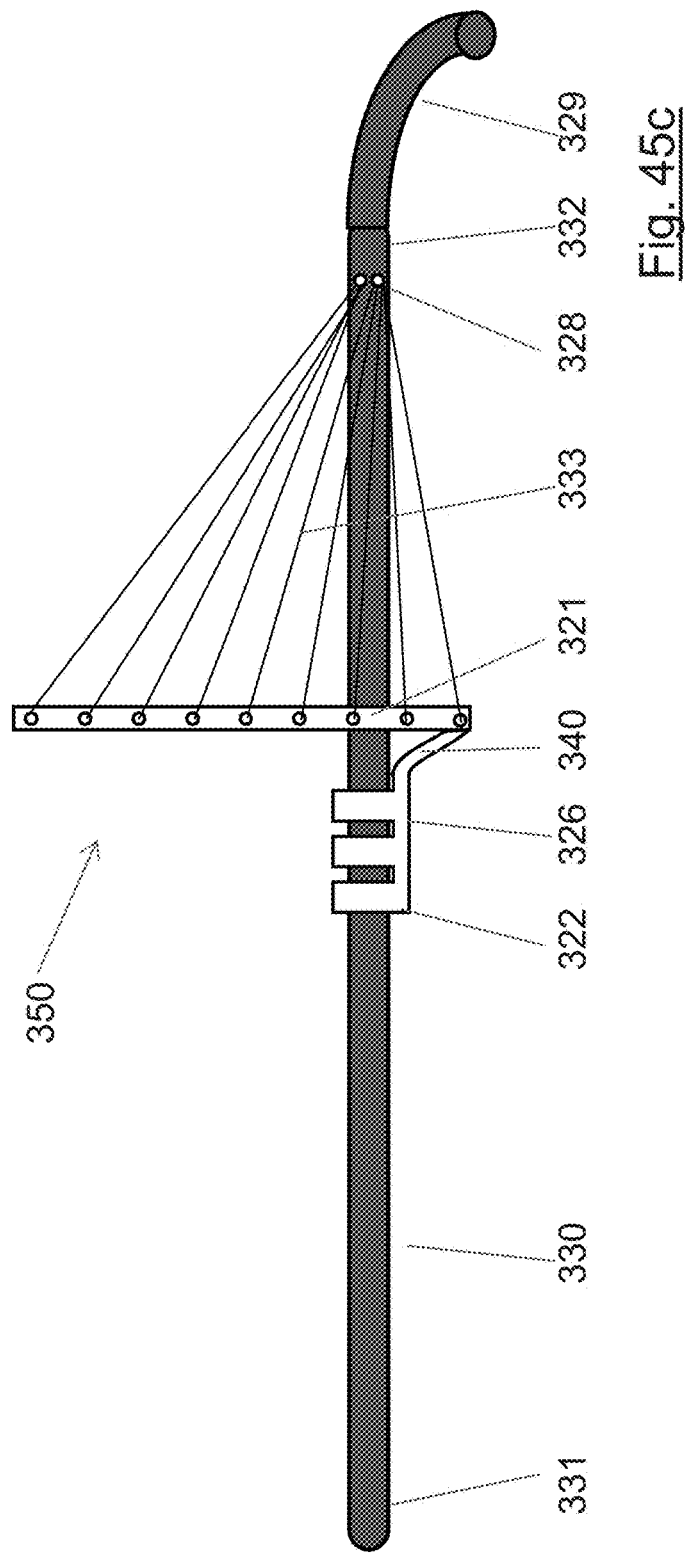
Figure 53:
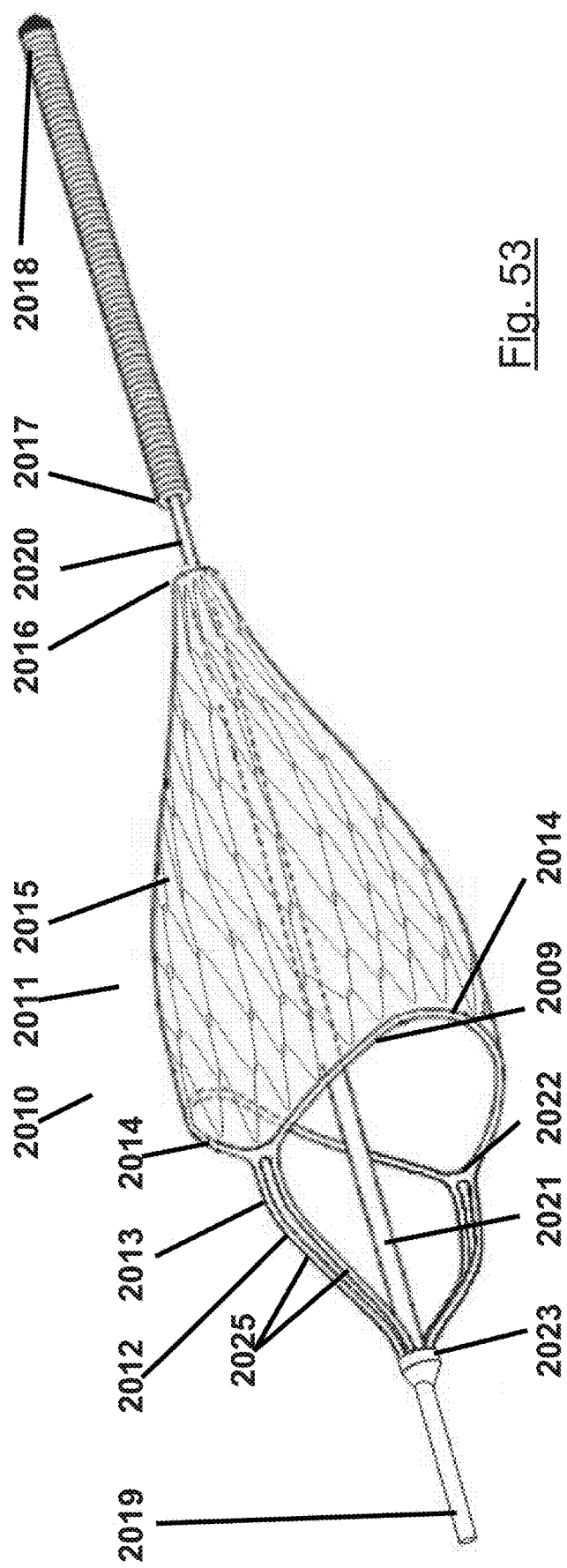
Figure 61A:
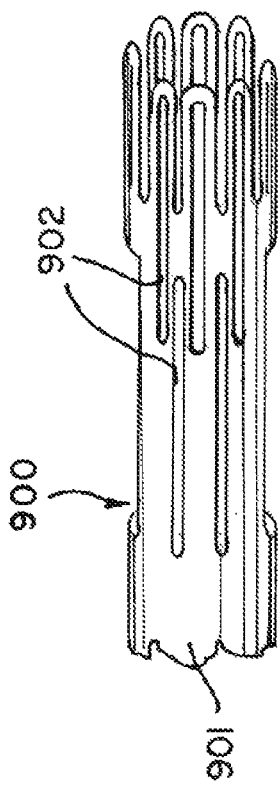
Figure 61C:
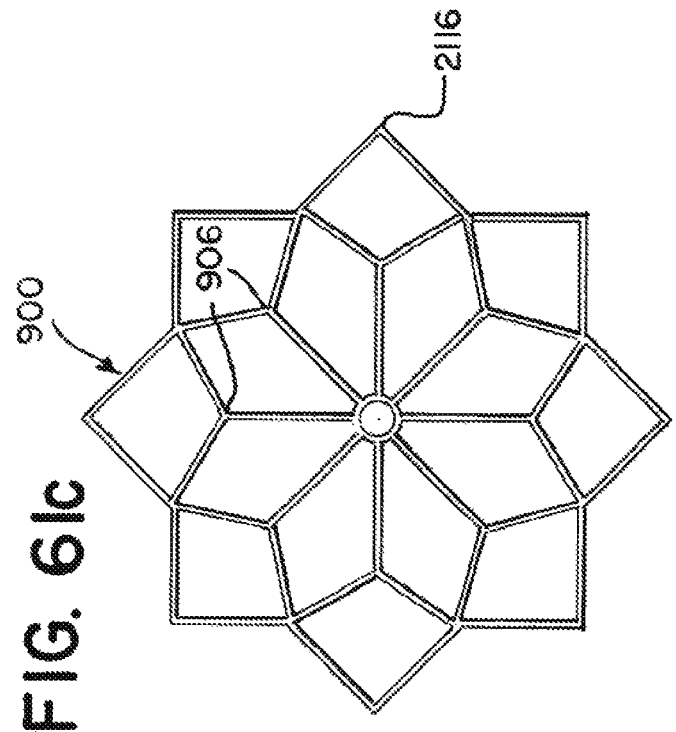
Figure 61B:
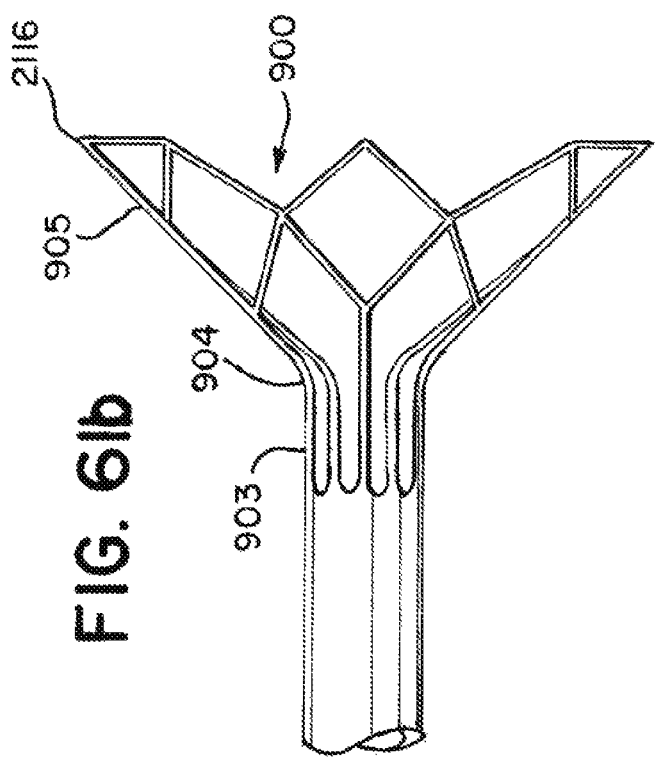
Figures 78A, 78B, 78C:
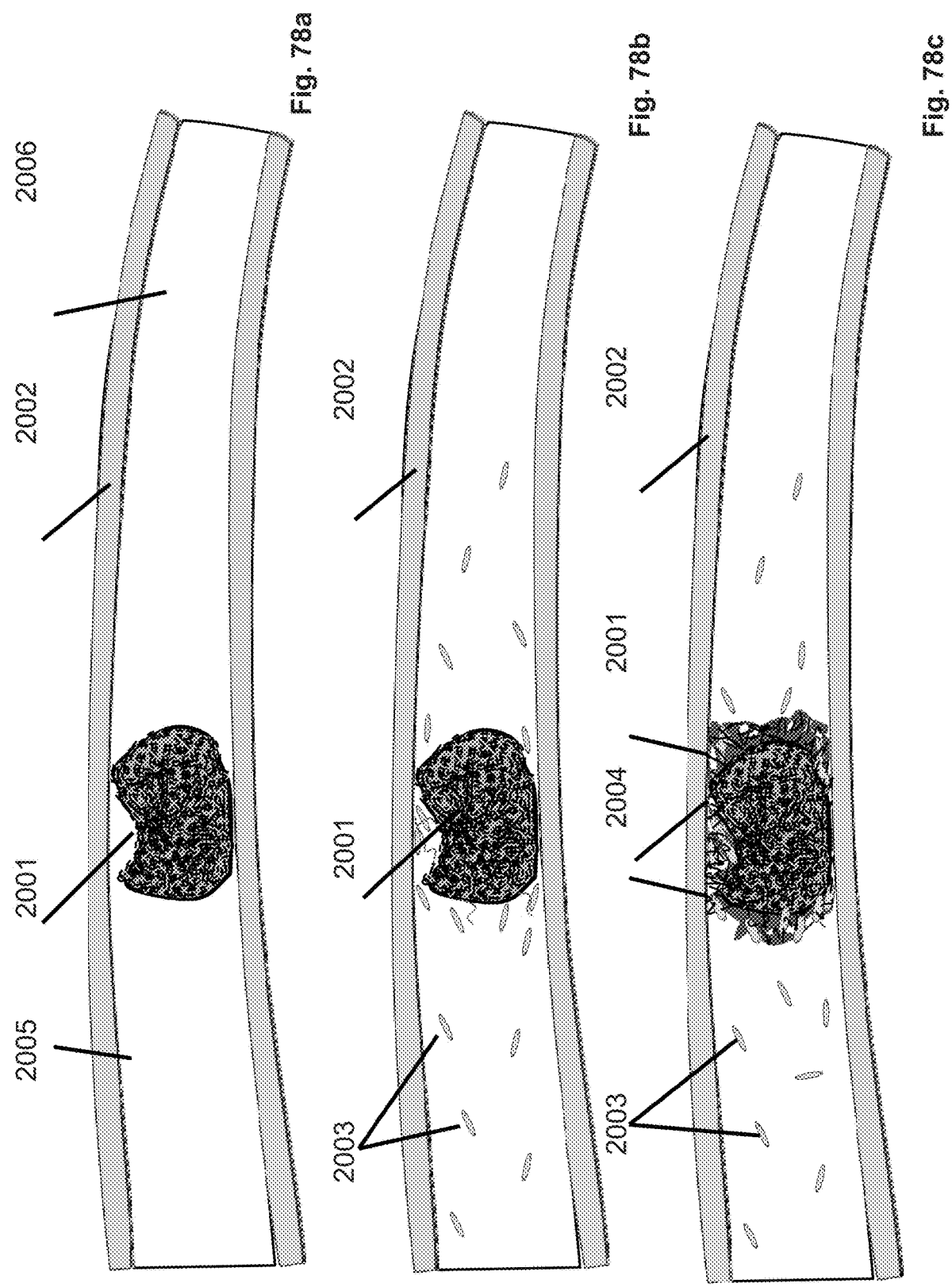
Figure 85B:
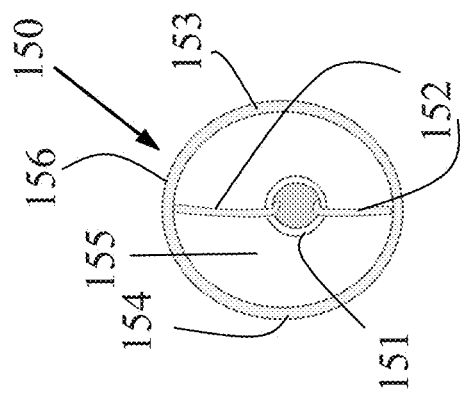
Figure 86B:
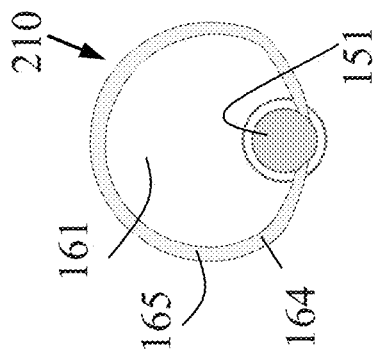
Figure 85A:
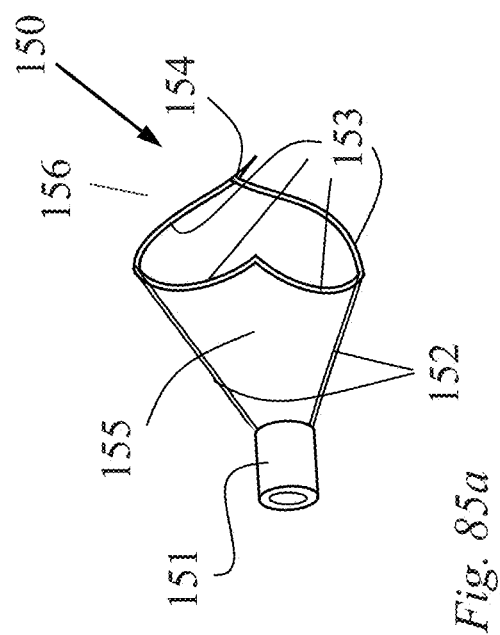
Figure 86A:
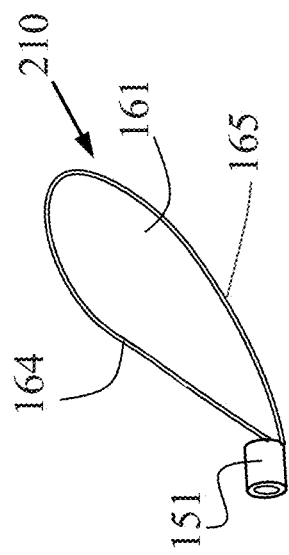

FIG. 34c shows a ring and guidewire of a clot retrieval device;

FIG. 34d shows a ring and guidewire of a clot retrieval device;

FIG. 34e shows a portion of a guidewire of a clot retrieval device;

FIG. 34f shows a portion of a guidewire of a clot retrieval device;

FIG. 35a shows a vessel with an obstructive clot;

FIG. 35b shows a clot retrieval device crossing an obstructive clot;

FIG. 35c shows a clot retrieval device being deployed in a vessel;

FIG. 35d shows a clot retrieval device deployed in a vessel;

FIG. 35e shows a clot retrieval device fully expanded in a vessel;

FIG. 35f shows a clot retrieval device capturing an obstructive clot;

FIG. 35g shows a clot retrieval device being collapsed;

FIG. 35h shows a clot retrieval device partially collapsed;

FIG. 35i shows a clot retrieval device being removed from a vessel;

FIG. 36a shows a clot retrieval device in the expanded configuration;

FIG. 36b shows a clot retrieval device in the collapsed delivery configuration;

FIG. 37a shows a conventional guidewire;

FIG. 37b shows a portion of a guidewire modified to create a clot retrieval device;

FIG. 37c shows a clot retrieval device in the expanded state;

FIG. 37d shows a clot retrieval device in the collapsed delivery configuration;

FIG. 37e shows an end view of a clot retrieval device;

FIG. 38a shows a portion of a guidewire modified to create a clot retrieval device;

FIG. 38b shows a portion of a guidewire modified to create a clot retrieval device;

FIG. 38c shows a cross sectional view of a guidewire modified to create a clot retrieval device;

FIG. 39a shows an end view of a clot retrieval device;

FIG. 39b shows a clot retrieval device in the expanded configuration;

FIG. 39c shows a clot retrieval device in the collapsed delivery configuration;

FIG. 40a shows an end view of a clot retrieval device;

FIG. 40b shows a clot retrieval device in the expanded configuration;

FIG. 41a shows an end view of a clot retrieval device;

FIG. 41b shows a clot retrieval device in the expanded configuration;

FIG. 42a shows an end view of a clot retrieval device;

FIG. 42b shows a clot retrieval device in the expanded configuration;

FIG. 43 shows a clot retrieval device in the expanded configuration;

FIG. 44a shows an end view of a frame design of a clot retrieval device;

FIG. 44b shows a view of a portion of frame of a clot retrieval device;

FIG. 44c shows a clot retrieval device in the expanded configuration;

FIG. 44d shows a clot retrieval device in the delivery configuration;

FIG. 45a shows an end view of a frame design of clot retrieval device;

FIG. 45b shows a view of a portion of frame of a clot retrieval device;

FIG. 45c shows a clot retrieval device in the expanded configuration;

FIG. 46 shows a clot retrieval device in the expanded configuration;

FIG. 47a shows a clot retrieval device in the expanded configuration;

FIG. 47b shows a clot retrieval device in the partially collapsed configuration;

FIG. 47c shows a clot retrieval device in the delivery configuration;

FIG. 47d shows a view of a portion of frame section of a clot retrieval device;

FIG. 48a shows a clot retrieval frame mounted on a guidewire;

FIG. 48b shows the device of FIG. 48a and a delivery device housed in a microcatheter;

FIG. 49a shows a clot retrieval device and a delivery catheter;

FIG. 49b shows the device of FIG. 49a loaded within its delivery catheter;

FIG. 50a shows a clot retrieval device;

FIG. 50b shows the device of FIG. 50a loaded within a catheter;

FIG. 50c shows the device of FIG. 50a partially withdrawn into a retrieval catheter;

FIG. 51a shows a clot retrieval device positioned over a full length guidewire;

FIG. 51b shows a clot retrieval device positioned over a rapid exchange length guidewire;

FIG. 52a shows a clot retrieval device;

FIG. 52b shows a guidewire of the clot retrieval device of FIG. 52a;

FIG. 53 shows another clot retrieval device;

FIG. 54 shows a frame cut from a hypotube for use as the frame of a clot retrieval device;

FIG. 55a shows another clot retrieval device delivered through a microcatheter;

FIG. 55b shows another clot retrieval device delivered through a microcatheter;

FIG. 56 shows a detailed view of the distal end of a clot retrieval device and a microcatheter delivery system;

FIG. 57 shows a detailed view of the distal end of another clot retrieval device and a microcatheter delivery and retrieval system;

FIG. 58a shows a detailed view of the distal end of another clot retrieval device and a microcatheter delivery and retrieval system;

FIG. 58b shows a detailed view of the clot retrieval device of FIG. 58a in another configuration;

FIG. 59a shows a guidewire with a step at the distal, the tip of the guidewire is placed in a vessel (not shown);

FIG. 59b shows a microcatheter being advanced over the guidewire;

FIG. 59c shows the clot retrieval device being delivered through the microcatheter and over the wire, a clot debonding device is also being advanced through the microcatheter;

FIG. 59d shows the clot retrieval device deployed from the distal end of the microcatheter and expanded in the vessel (not shown);

FIG. 59e shows the clot retrieval device deployed from the distal end of the microcatheter and the microcatheter advanced proximally;

FIG. 59f shows the clot debonding element deployed from the microcatheter;

FIG. 59g shows the clot debonding element retrieved back into the distal end of the microcatheter;

FIG. 59h shows the clot retrieval device collapsed back into the pod of the microcatheter;

FIG. 60a shows an end view of a clot debonding element;

FIG. 60b shows an end view of another clot debonding element;

FIG. 61a shows a side view of an unexpanded clot debonding element;

FIG. 61b shows a side view of the expanded clot debonding element from FIG. 61a;

FIG. 61c shows an end view of the expanded clot debonding element from FIG. 61a;

FIG. 62a shows an end view of another clot debonding element;

FIG. 62b shows a side view of a clot debonding device;

FIG. 62c shows a side view of another clot debonding device;

FIG. 62d shows a side view of yet another clot debonding device;

FIG. 62e shows a side view of an alternative clot debonding device;

FIG. 63a shows a side view of the end of an unexpanded clot debonding catheter;

FIG. 63b shows a side view of the end of an expanded clot debonding catheter from FIG. 63a;

FIG. 64a shows a side view of the end of an unexpanded clot debonding catheter;

FIG. 64b shows a side view of the end of an expanded clot debonding catheter from FIG. 64a;

FIG. 65a shows a side view of the end of an unexpanded clot debonding catheter;

FIG. 65b shows a side view of the end of an expanded clot debonding catheter from FIG. 65a;

FIG. 66a shows a side view of the end of an unexpanded clot debonding catheter;

FIG. 66b shows a side view of the end of a partially expanded clot debonding catheter from FIG. 66a;

FIG. 66c shows an end view of the expanded clot debonding catheter from FIG. 66a;

FIG. 67a shows a side view of the end of an unexpanded clot debonding catheter;

FIG. 67b shows an end view of the expanded clot debonding catheter from FIG. 67a;

FIG. 68a shows a side view of the end of an unexpanded clot debonding catheter;

FIG. 68b shows a side view of the end of a partially expanded clot debonding catheter from FIG. 68a;

FIG. 68c shows an end view of the expanded clot debonding catheter from FIG. 68a;

FIG. 69a shows the clot debonding catheter from FIG. 68a mounted over a microcatheter prior to deployment proximal to a clot and clot retrieval device;

FIG. 69b shows the clot debonding catheter from FIG. 69a post deployment;

FIG. 70 shows a clot retrieval device in the deployed configuration distal of an occlusive clot;

FIG. 71 shows a collector device being used with a clot retrieval device;

FIG. 72 shows a collector device with deployed elements being used to advance clot into a clot retrieval device;

FIG. 73 shows the collector device in an advanced position with most of the clot inside the clot retrieval device;

FIG. 74 shows an alternative clot advancement device;

FIG. 75 shows a clot advancement device with two coil elements;

FIG. 76a shows a side view of another clot advancement device;

FIG. 76b shows an end view of the clot advancement device of FIG. 76a;

FIG. 77 shows another clot retrieval device with an integral clot debonding element;

FIG. 78a shows an artery or vein with an occlusive clot acutely lodged in the vessel, the occlusive clot reduces or prevents distal blood flow;

FIG. 78b shows the occlusive clot of FIG. 78a with platelets being activated at the site of occlusion;

FIG. 78c shows bonds formed between the occlusive clot and the vessel wall;

FIG. 79a shows a vein or artery with an occlusive clot lodged therein;

FIG. 79b shows an occlusive clot with the tip of a guidewire advanced across the occlusive clot;

FIG. 79c shows a microcatheter advanced over the guidewire such that its tip is distal of the occlusive clot;

FIG. 79d shows the microcatheter tip distal of the occlusive clot with the guidewire removed;

FIG. 79e shows a clot retrieval device being advanced through the lumen of the microcatheter;

FIG. 79f shows the clot retrieval device expanded with the microcatheter partially withdrawn;

FIG. 79g shows a clot debonding element advanced through the microcatheter and in the deployed state;

FIG. 79h shows the clot being engaged by both the clot retrieval device and the clot debonding element;

FIG. 79i shows the clot captured in the net of the clot retrieval device with the clot debonding element removed through the lumen of the microcatheter;

FIG. 79j shows the clot retrieval device with the frame partially collapsed and the clot captured in the net;

FIG. 79k shows the clot retrieval device, the microcatheter and the captured clot being removed from the vessel;

FIG. 79l shows the vessel recannalized;

FIG. 80a shows a vein or artery with an occlusive clot lodged therein;

FIG. 80b shows an occlusive clot with the tip of a guidewire advanced across the occlusive clot;

FIG. 80c shows a microcatheter advanced over the guidewire such that its tip is distal of the occlusive clot;

FIG. 80d shows the microcatheter tip distal of the occlusive clot with the guidewire removed;

FIG. 80e shows a stepped guidewire advanced through the lumen of the microcatheter;

FIG. 80f shows a clot retrieval device being advanced through the lumen of the microcatheter and over the guidewire;

FIG. 80g shows the clot retrieval device expanded with the microcatheter partially withdrawn;

FIG. 80h shows a clot debonding element advanced through the microcatheter and in the deployed state;

FIG. 80i shows the clot being engaged by both the clot retrieval device and the clot debonding element;

FIG. 80j shows the clot captured in the net of the clot retrieval device with the clot debonding element removed through the lumen of the microcatheter;

FIG. 80k shows the clot retrieval device with the frame partially collapsed and the clot captured in the net;

FIG. 80*l* shows the clot retrieval device, the microcatheter and the captured clot being removed from the vessel;

FIG. 80*m* shows the vessel recannalized;

FIGS. 81*a* and 81*b* are isometric views of a device for removing an obstruction to a vessel, FIG. 81*a* is the device in an expanded configuration and FIG. 81*b* is the device in a collapsed configuration;

FIG. 82*a* is an isometric view of another device of the invention;

FIGS. 82*b* to 82*e* are side views of the distal end of the device of FIG. 82*a*;

FIG. 82*f* is an isometric view of the proximal end of a device of the invention;

FIG. 82*g* shows a portion of a frame support tube;

FIG. 82*h* is a cross section of a frame support tube;

FIG. 83*a* is an isometric view of another device of the invention;

FIGS. 83*b* to 83*f* are close up views of the basket frame of FIG. 83*a*;

FIGS. 83*g* to 83*h* are isometric views of basket constructions;

FIG. 84*a* is an isometric view of a basket frame;

FIG. 84*b* is a partial cross section of a basket in a microcatheter;

FIG. 84*c* is an isometric view of a debonder;

FIG. 84*d* is an isometric view of the device;

FIG. 84*e* is a partial cross section view of the device inside a vessel;

FIG. 85*a* is an isometric view of a basket frame;

FIG. 85*b* is an end view of the basket frame of FIG. 85*a*;

FIG. 86*a* is an isometric view of a basket frame;

FIG. 86*b* is an end view of the basket frame of FIG. 86*a*;

FIG. 87*a* is an isometric view of a basket frame;

FIG. 87*b* is an end view of the basket frame of FIG. 87*a*;

FIG. 88*a* is an isometric view of a basket frame;

FIG. 88*b* is an end view of the basket frame of FIG. 88*a*;

FIG. 88*c* is an illustration of a basket frame in a collapsed configuration;

FIG. 89*a* is an isometric view of a basket frame;

FIG. 89*b* is an end view of the basket frame of FIG. 89*a*;

FIG. 90*a* is an isometric view of a basket frame

Figure 98A:
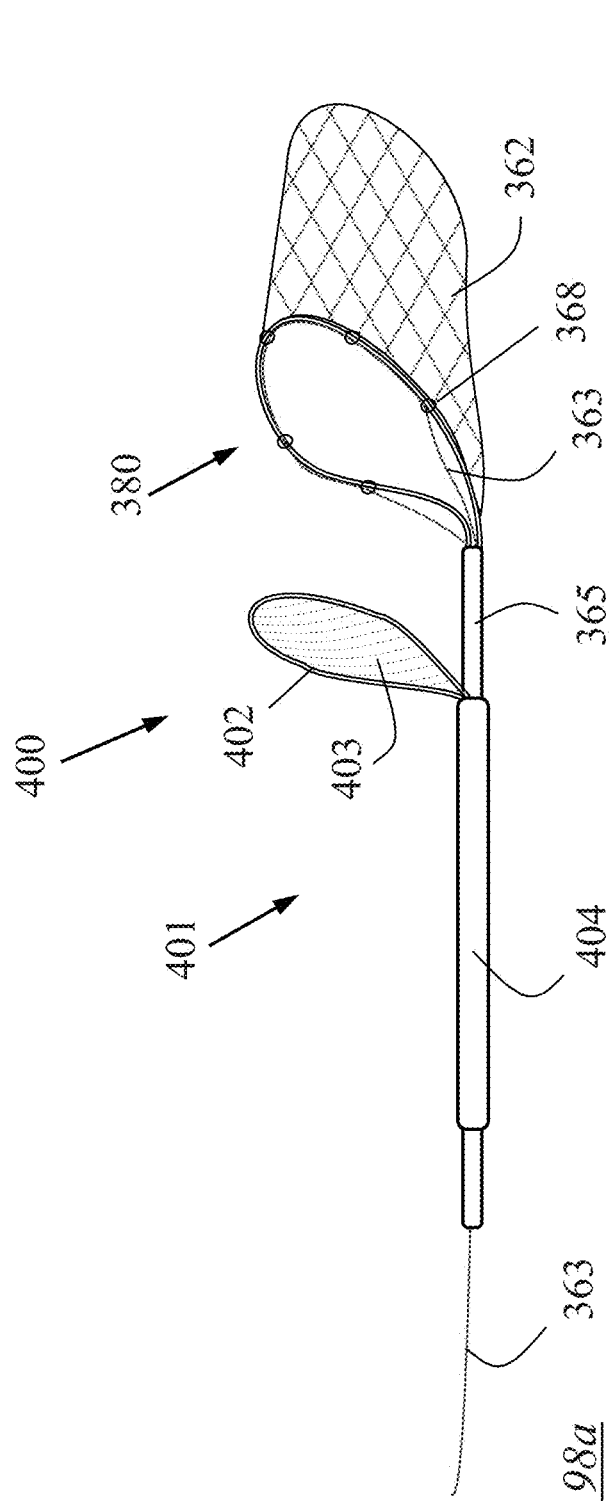
Figure 98B:
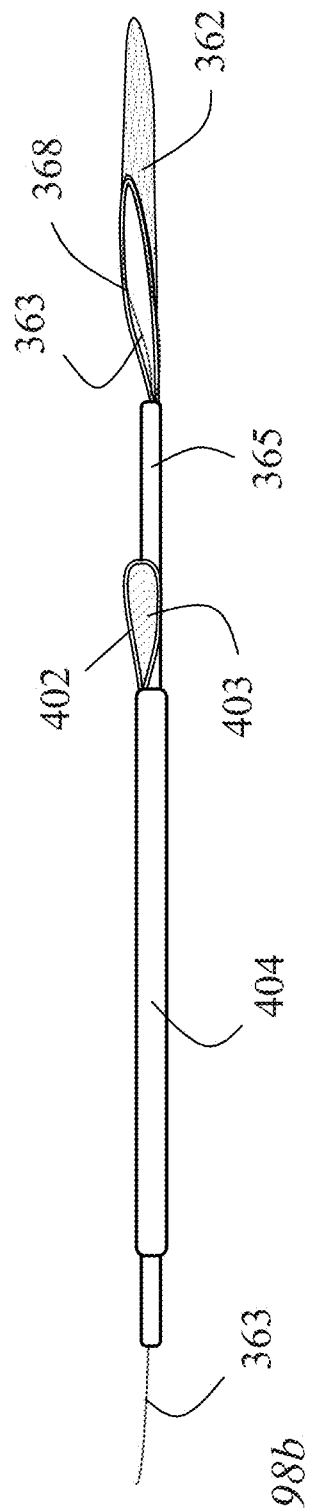
Figure 117A:
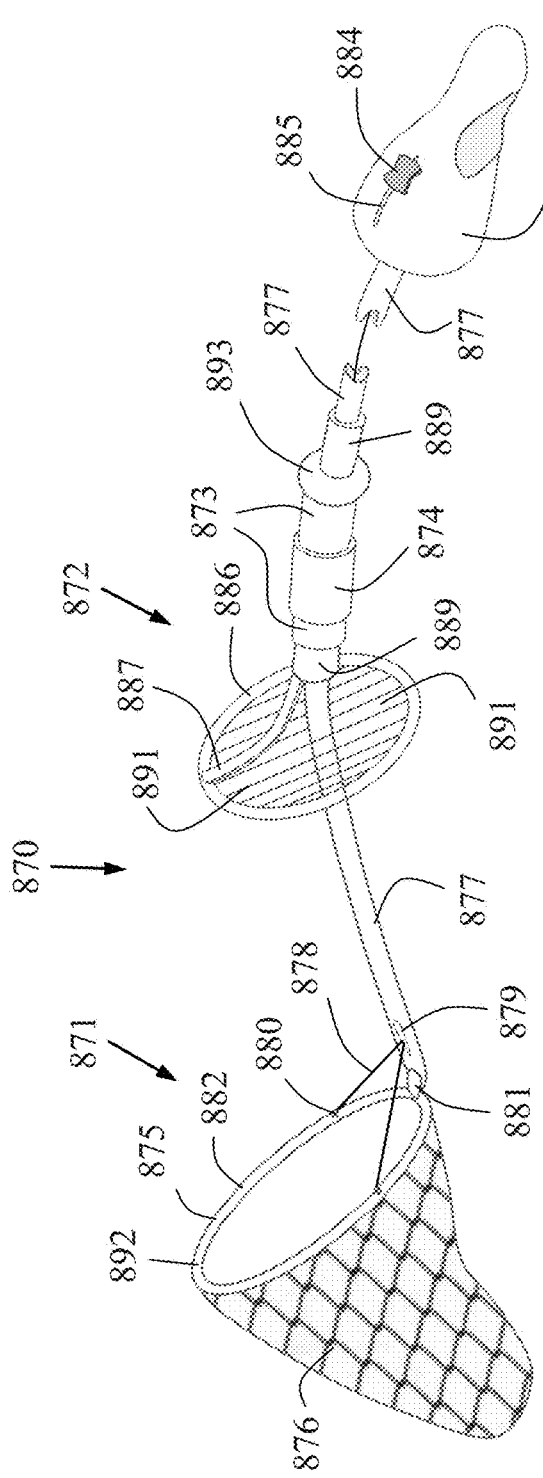
Figure 117C:
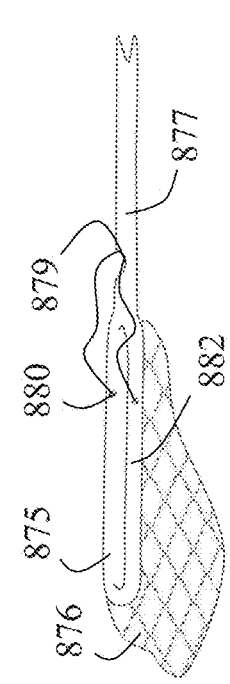
Figure 117E:
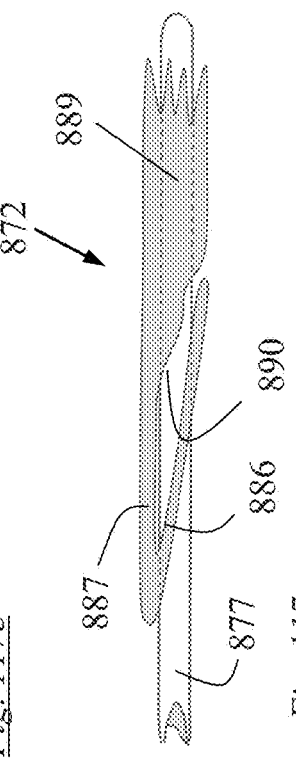
Figure 117B:
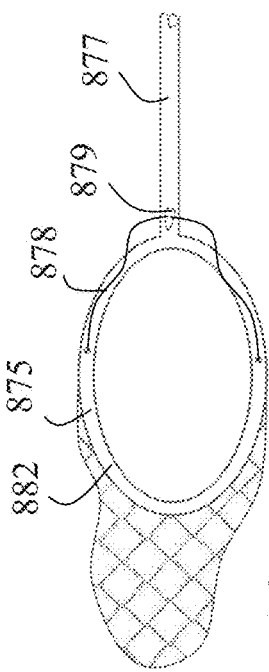
Figure 117D:
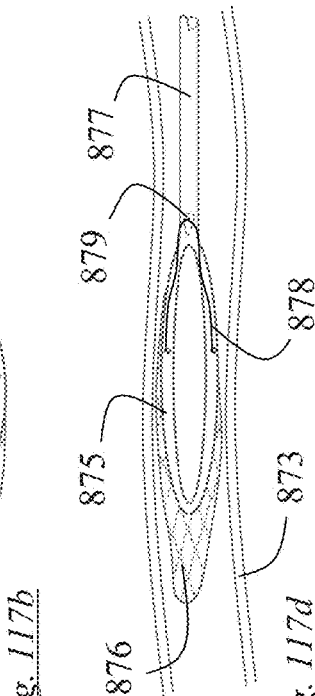
Figure 118B:
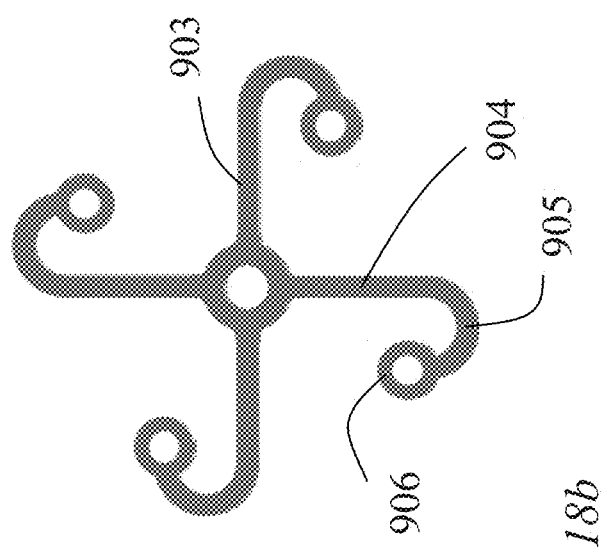
Figure 118A:
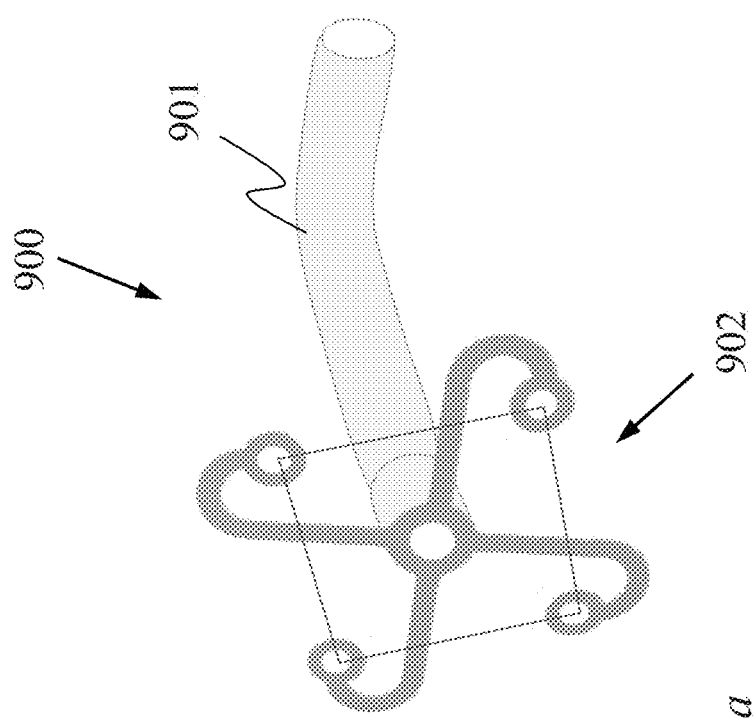
Figure 119A:
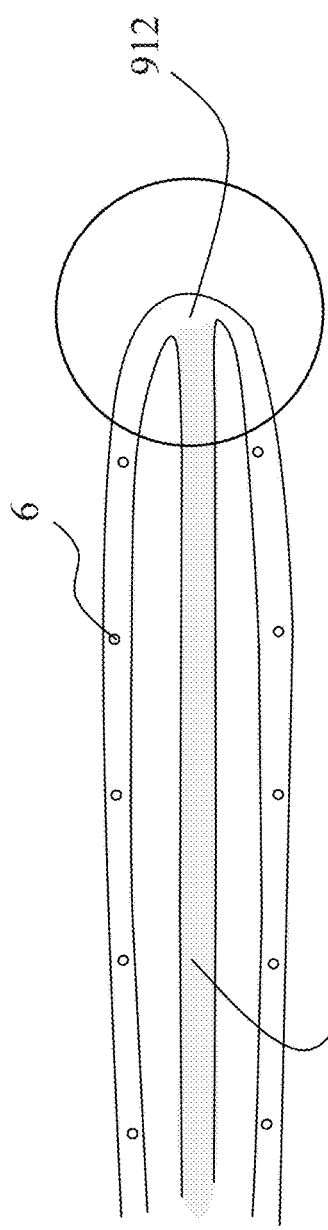
Figure 119B:
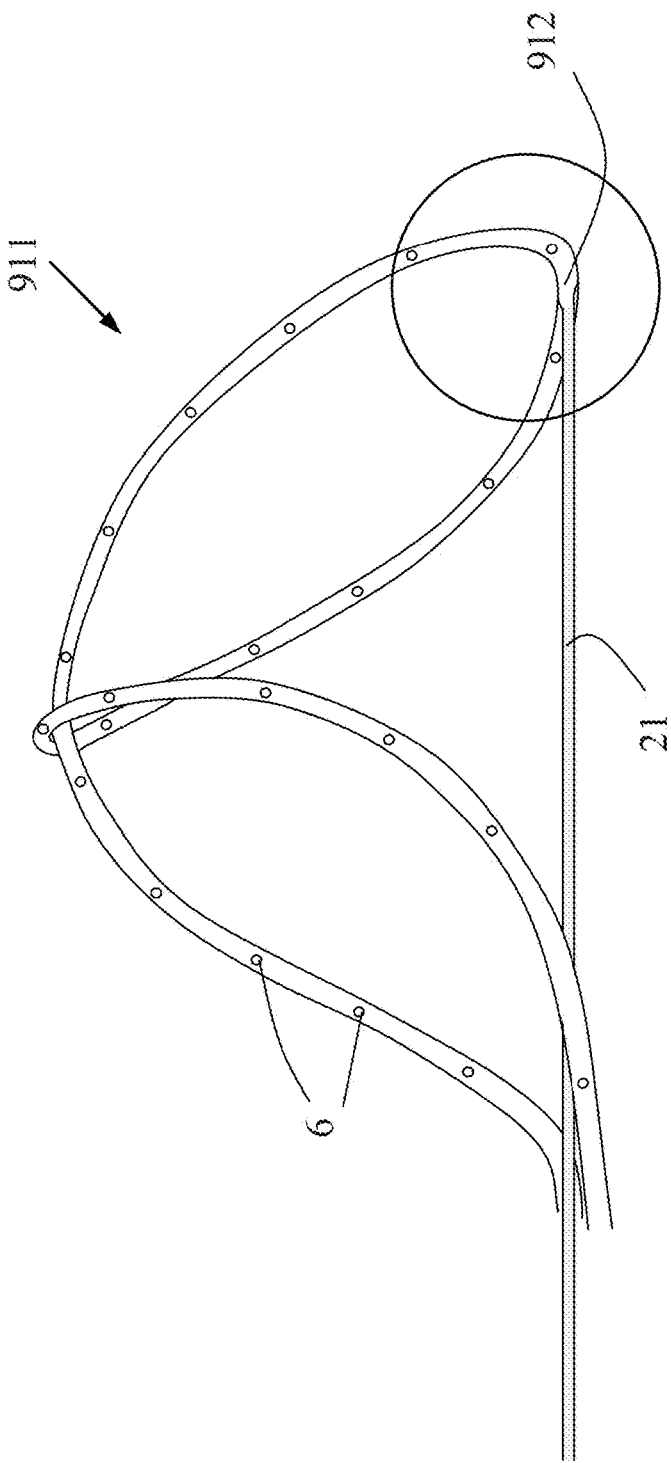

FIG. 90*b* is an end view of the basket frame of FIG. 90*a*;

FIG. 91*a* is an isometric view of a basket frame;

FIG. 91*b* is an end view of the basket frame of FIG. 91*a*;

FIG. 92 and FIG. 93 illustrate two basket frames of this invention;

FIGS. 94*a* to 94*g* are isometric views of another device of this invention;

FIGS. 95 to 97 are isometric views of other devices of this invention;

FIG. 98*a* is an isometric view of another device of the invention in an expanded configuration;

FIG. 98*b* is an isometric view of the device of FIG. 98*a* in a collapsed configuration;

FIGS. 99*a* to 99*i* illustrate a method of use for the devices described in FIGS. 95-98;

FIGS. 100*a* to 100*d* are isometric views of a basket assembly;

FIGS. 100*e* and 100*f* are close up views of FIG. 100*d*;

FIG. 101*a* is an isometric view of another device of the invention in a collapsed configuration;

FIG. 101*b* is an isometric view of the device of FIG. 101*a* in an expanded configuration;

FIG. 101*c* is a top-view of an activation mechanism of the device of FIG. 101*a*;

FIGS. 102 to 105 are partial cut away views of a debonding assembly;

FIG. 106*a* to FIG. 106*c* are views of another the device of the invention;

FIGS. 107, 108, 109*a*, 109*b*, and 110 are isometric views of a device of the invention in various configurations;

FIG. 111*a* is an isometric view of a device of the invention;

FIG. 111*b* is an elevation view of the device of FIG. 111*a* in a collapsed configuration;

FIG. 111*c* is an elevation view of the device of FIG. 111*a* in an expanded configuration;

FIGS. 111*d* to FIG. 111*f* illustrate the device of FIG. 111*a* in use;

FIG. 112*a* is an isometric view of another device of the invention;

FIG. 112*b* and FIG. 112*c* illustrate the device of FIG. 112*a* in use;

FIG. 113*a* is an isometric view of another device of the invention with a debonder in a delivery configuration;

FIG. 113*b* is the device of FIG. 113*a* with the debonder assembly in an expanded configuration;

FIGS. 114 and 115 are close up views of two debonders;

FIGS. 116*a* to 116*i* show a device of the invention in use;

FIG. 117*a* is an isometric view of another device of the invention;

FIG. 117*b* is a plan view of the untensioned basket frame of FIG. 117*a*;

FIG. 117*c* is a side view of the untensioned basket frame of FIG. 117*a*;

FIG. 117*d* shows the basket of FIG. 117*a* in a collapsed configuration;

FIG. 117*e* shows the debonder of FIG. 117*a* in a collapsed configuration;

FIG. 118*a* is an isometric view of a debonder assembly;

FIG. 118*b* is and end view of the debonder of FIG. 118*a*;

FIG. 119*a* is a close up view a basket frame;

FIG. 119*b* is an isometric view of a basket frame;

FIG. 120*a* is an isometric view of a basket frame;

FIGS. 120*b* to 120*d* are close up views of a basket frame of FIG. 120*a*; and

FIGS. 121*a*, 121*b*, 122*a*, 122*b*, 123*a*, and 123*b* are isometric views of basket frames according to the invention.

Sheet 92 of drawings: Eccentric Basket & Debonder. Hoop type debonder (self expanding). Basket frame with tether guides. Net connection eyelets. Hoop debonder. Slotted tube type debonder.

Sheet 93 of drawings: Eccentric Basket & Debonder. Hoop type debonder with strings. Swivel hoop basket with net and activation tethers. Control handle to tension tethers Sheet 95 of drawings: Eccentric Basket and Debonder. Hoop type debonder (self expanding). Double hoop basket with tether activation Sheet 97 of drawings: Double Hoop Eccentric Basket with radially projecting strut type debonder. Method of use.

Sheet 99 of drawings: Basket Frames. Tether activated. Eccentric with support strut.

Sheet 102 of drawings: Tether Activated Baskets. Collapsed and expanded. Structural elements. Self expanding/hinged.

Sheet 104 of drawings: Tether Activated Baskets. Tether connected centrally to frame. Tether guided along frame and connected to distal end of hoop.

Sheet 105 of drawings: Tether Activated Baskets. With hoop type debonder.

Sheet 106 of drawings: Tether Activated Baskets. With hoop type debonder. Method of use.

Sheet 107 of drawings: Tether Activated Baskets. With hoop type debonder. Method of use.

Sheet 108 of drawings: Tether Activated Baskets. With hoop type debonder. Method of use.

Sheet 109 of drawings: Tether Activated Baskets. Flat hoop frame Frame. articulated by tether. Distal end of wire articulated by tether.

Sheet 110 of drawings: Tether Activated Baskets. Detailed construction of articulating end of frame wire.

Sheet 112 of drawings: Debonder. Hoop style debonder. Tether activated. Constructions.

Sheet 113 of drawings: Debonder. Hoop style debonder. Configuration when used with basket.

Sheet 114 of drawings: Debonder. Hoop style debonder. Configuration when used with basket.

Sheet 115 of drawings: Debonder. Hoop style debonder. Configuration when used with basket Sheet 116 of drawings: Basket and Debonder. Slotted tube debonder. Slotted tube basket frame.

Sheet 119 of drawings: Double Hoop Basket. Eccentric basket. Eccentric clot debonder. Delivery and deployment.

Sheet 120 of drawings: Double Hoop Basket. Method of use.

DETAILED DESCRIPTION

The present invention is related to an apparatus and methods for the removal of obstructions in vessels. More particularly the present invention relates to devices and methods for the removal of obstructive clot from cerebral vessels.

Figure 1:
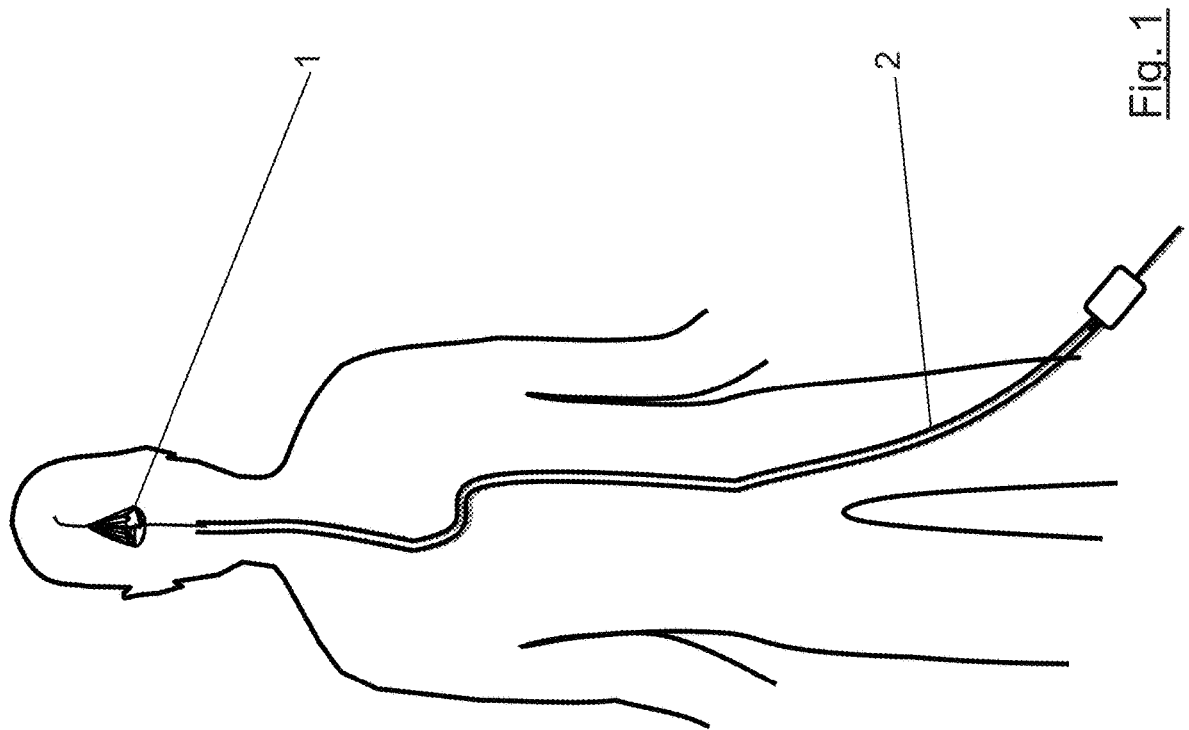
FIG. 1 shows a patient catheterized via femoral access with a clot retrieval device positioned in a cerebral vessel using the arterial system for its delivery.

With reference to FIG. 1 there is shown a schematic representation of the catheterization of a patient with a clot retrieval device 1 according to the invention. The patient is catheterized via the femoral artery with a catheter 2 in accordance with standard interventional technique.

FIG. 2 shows a schematic representation of some of the arteries supplying blood to the brain. The arteries shown are on the anterior circulation. Vessel 400 is the Aorta. Vessel 401 is the brachio-cephalic artery. Vessel 402 is the subclavian artery. Vessel 403 is the common carotid artery.

Figure 3D:
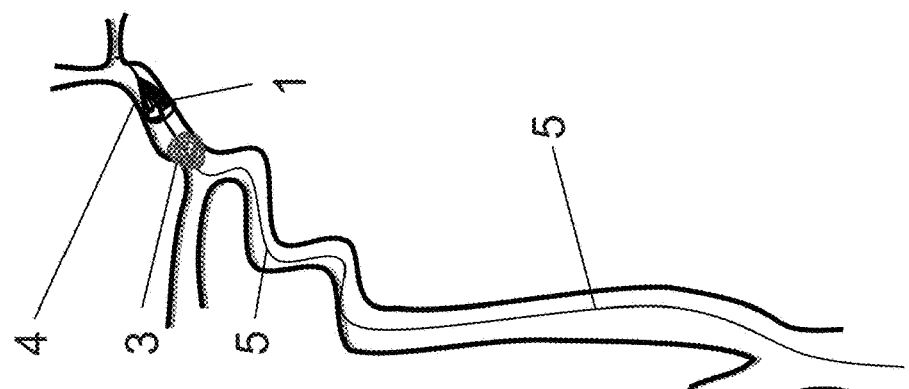
FIG. 3d shows the micro-catheter removed with the clot retrieval device placed distal of the obstructive clot.
Figure 3C:
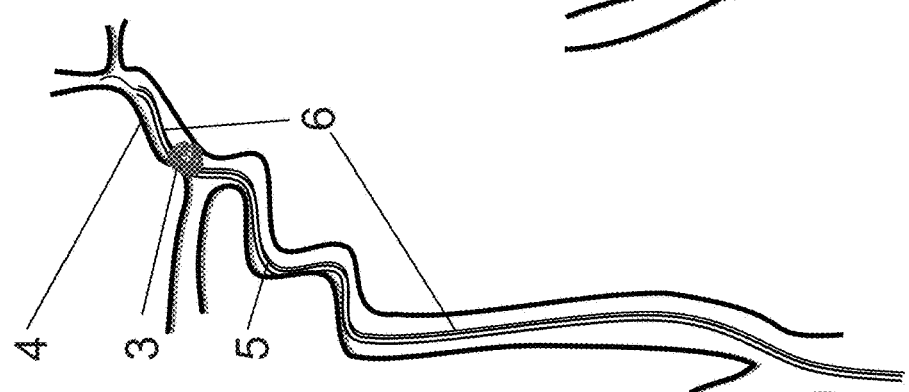
FIG. 3c shows a micro-catheter with the clot retrieval device of the invention crossing the obstructive clot.

Vessel 404 is the internal carotid artery. Vessel 405 is the external carotid artery. Vessel 406 is the middle cerebral artery. Vessel 407 is the anterio-cerebral artery. A catheter 2 is shown with its distal end in the common carotid artery. In the more detailed drawings of the invention the details of the access site will not be shown but in general access and delivery is in accordance with FIG. 1 and/or FIG. 2. It will be appreciated that the devices and methods disclosed in this invention relate to all of femoral access, radial access, direct stick access, carotid access even where only one variation is shown or described Now with reference to FIG. 3a to FIG. 3g a first method of using the devices of the invention is highlighted. FIG. 3a shows an obstructive clot 3 located on a cerebral vessel 4. The first step in treating this obstruction is to cross the obstruction 3 with a guidewire 5. The guidewire 5 is inserted into the arterial system through conventional techniques and is advanced to the obstruction. The tip of the guidewire 5 is advanced across the obstruction 3, FIG. 3b. A micro delivery catheter 6 can then be advanced over the guidewire 5 and across the obstructive clot 3. The clot retrieval device 1 is expanded in the target vessel distal of the clot 4. The micro delivery catheter is withdrawn until its tip is proximal of the occlusive clot. Alternatively it can be completely removed from the patient. The clot retrieval device is positioned at the distal end of guidewire 5 and is fixed thereto. The obstructive clot 3 is captured in the device by advancing the device proximally (FIG. 3e). A removal catheter 7 is advanced over the guidewire 5 to assist in the removal of the clot 3. The removal catheter 7 may be a micro-catheter, a guide catheter, a sheath or a special recovery catheter. Aspiration may be employed through the lumen of the recovery catheter to assist in clot removal. FIG. 3g shows the target vessel recannalised after the removal of the obstructive clot 3.

FIG. 3a shows part of the cerebral circulation with an obstructive clot 3 positioned in the Anterior Cerebral Artery 4, distal of the Middle Cerebral Artery branch.

Figure 3B:
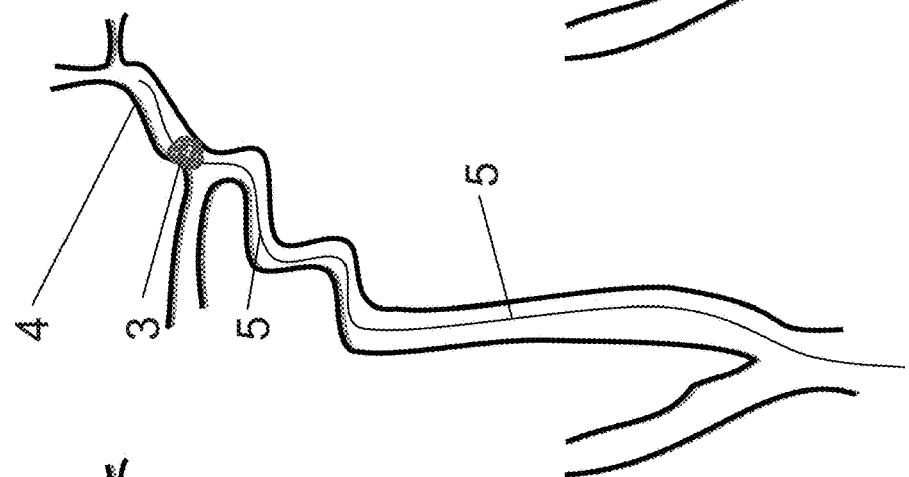
FIG. 3b shows a guidewire being placed across the obstructive clot.
Figure 3A:
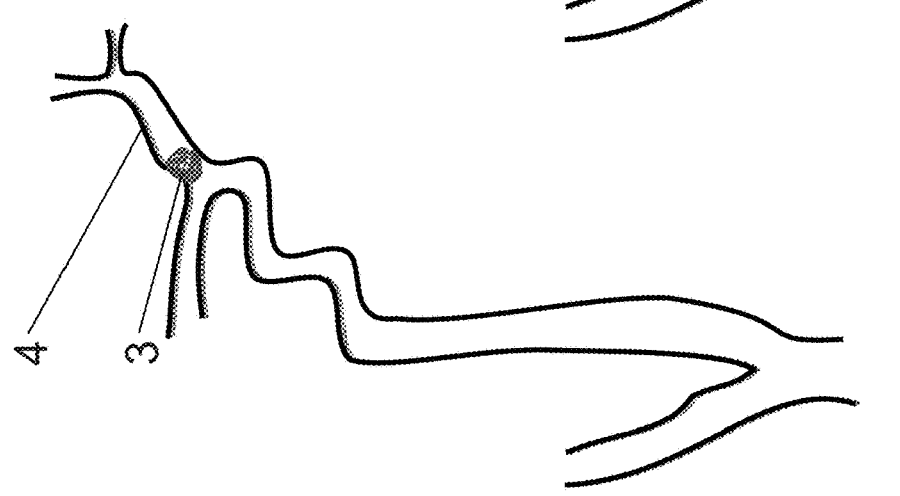
FIG. 3a shows part of the cerebral circulation with an obstructive clot positioned in the Anterior Cerebral Artery, distal of the Middle Cerebral Artery branch.
Figure 3G:
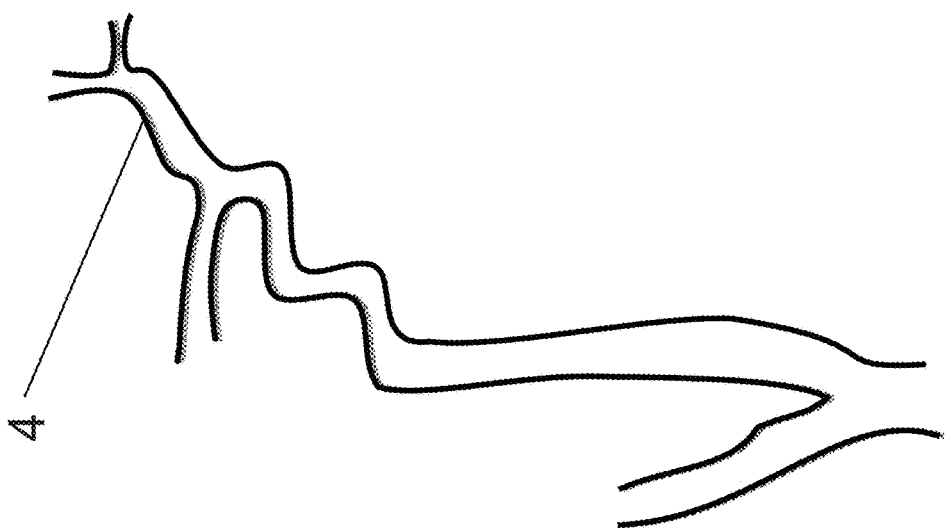
FIG. 3g shows the target vessel with the obstructive clot and devices completely removed.

FIG. 3b shows a Guidewire 5 being placed across the obstructive clot 3.

FIG. 3c shows a micro-catheter 6 with the clot retrieval device 1 of the invention crossing the obstructive clot 3.

FIG. 3d shows the micro-catheter removed with the clot retrieval device 1 placed distal of the obstructive clot 3.

FIG. 3e shows the clot retrieval device 1 being advanced proximally and capturing the obstructive clot 3 with a removal catheter 7 advanced from the proximal side.

Figure 3F:
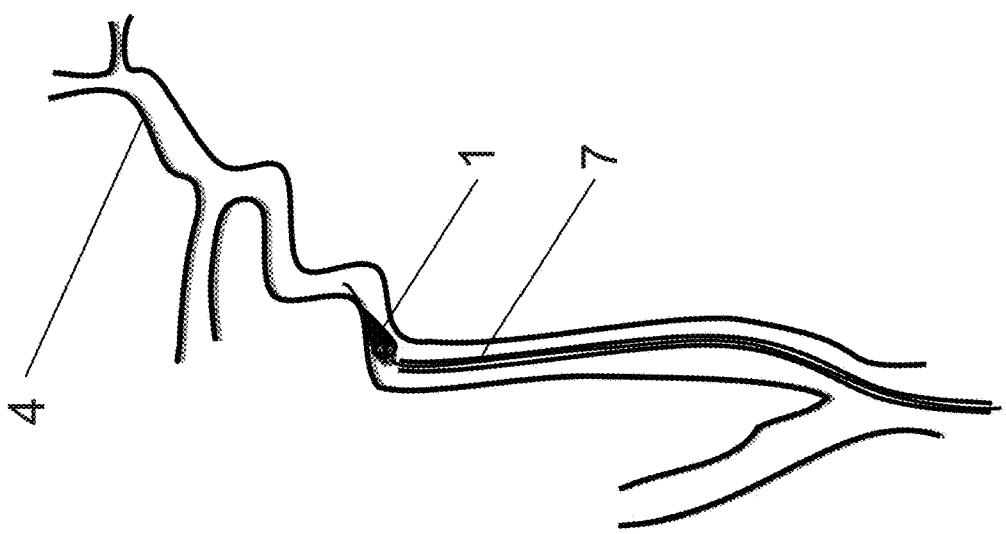
FIG. 3f shows the clot retrieval device, the captured occlusive clot and the removal catheter being removed from the vessel.
Figure 3E:
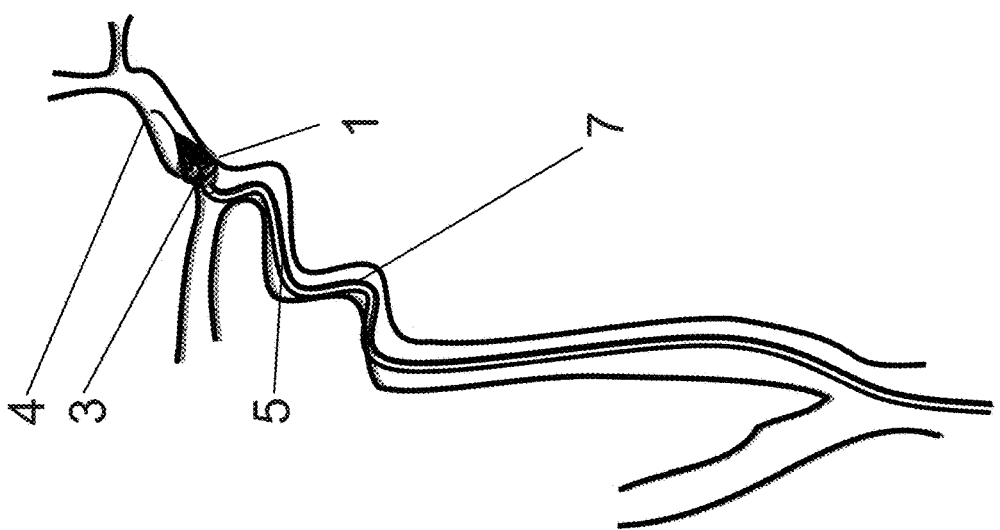
FIG. 3e shows the clot retrieval device being advanced proximally and capturing the obstructive clot with a removal catheter advanced from the proximal side.

FIG. 3f shows the clot retrieval device 1, the captured occlusive clot 3 and the removal catheter 7 being removed from the vessel.

FIG. 3g shows the target vessel 4 with the obstructive clot and devices completely removed.

Figure 4C:
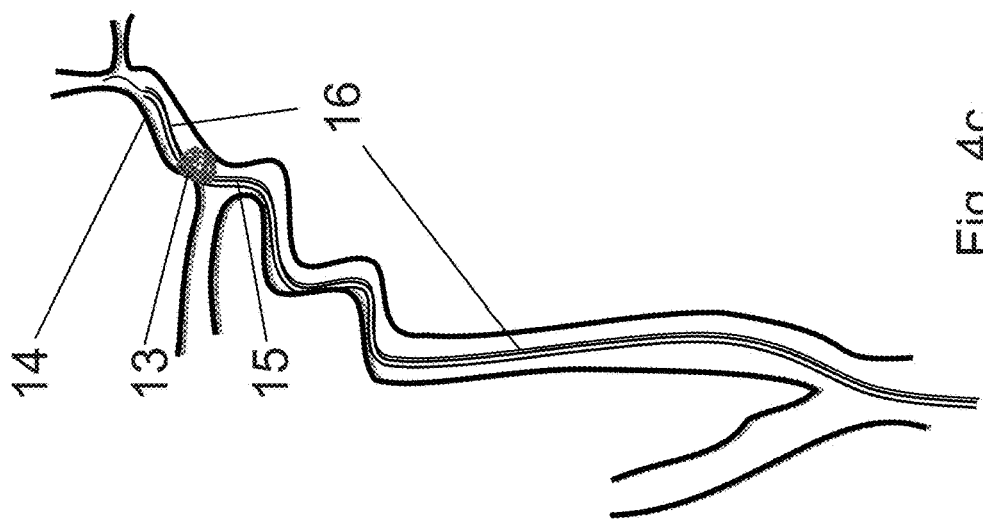
FIG. 4c shows a micro-catheter advanced over the guidewire until its distal end is across the obstructive clot.

With reference to FIG. 4a to FIG. 4i another method of employing the clot retrieval devices of this invention is described. With this method an access guidewire 15 is used to cross the obstructive clot 13. A micro catheter 16 is advanced over the access guidewire 15 and across the clot 13. The access guidewire 15 is removed from the lumen of the micro-catheter 16. A clot retrieval device 11 is advanced through the lumen of the micro-catheter 16 in a collapsed state. It will be appreciated that the clot retrieval device was collapsed in order to access the proximal end of the lumen of the micro-catheter 16. The clot retrieval device 11 expands distal of the tip of the micro-catheter 16 and clot 13. The micro-catheter 16 is advanced proximally until its tip is proximal of the clot. Alternatively the micro-catheter 16 can be removed from the patient (as shown FIG. 4d). The clot retrieval device 11 is advanced proximally with the aid of guidewire 18 to capture the obstructive clot 13. The guidewire 18 of the clot retrieval device 11 extends proximally of the expanded section of the device 11 and allows the physician to control the clot retrieval device 11. A removal catheter 17 is advanced over the guidewire 18 to assist in the removal of the clot 13. The removal catheter 17 may be the same micro-catheter that was used to deliver the clot removal device or it may be different size micro-catheter, or a guide catheter, or a sheath or a balloon catheter or a special recovery catheter. The recovery catheter 17 may also be used by the physician to assist with the clot capture by preventing the clot 13 from migrating proximally. Aspiration may be employed through the lumen of the recovery catheter to assist in clot removal. FIG. 4i shows the target vessel recannalised after the removal of the obstructive clot 13.

Figure 4B:
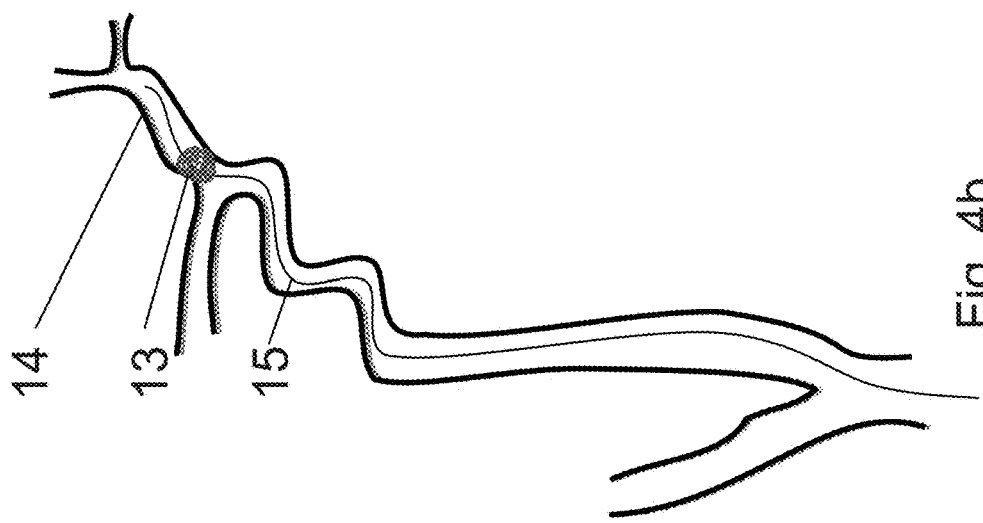
FIG. 4b shows a guidewire with its distal tip across the obstructive clot.
Figure 4A:
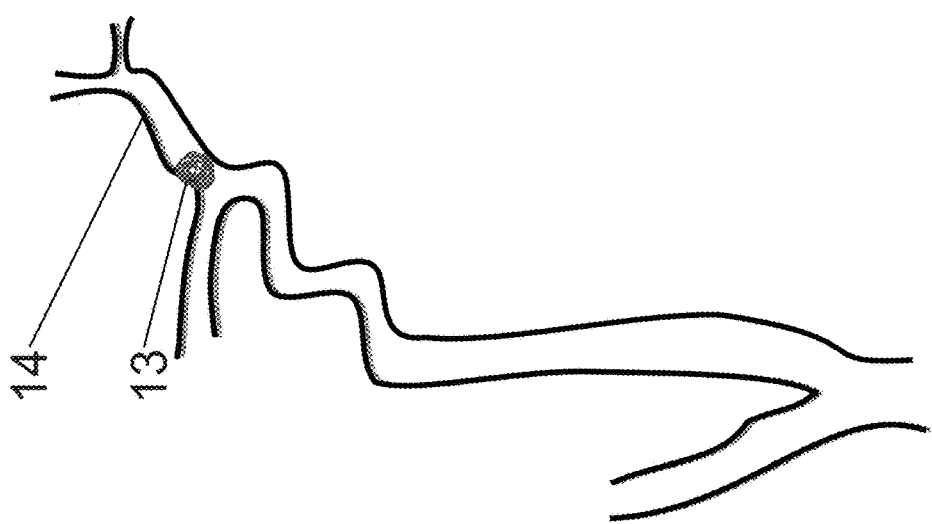
FIG. 4a shows a target vessel with an occlusive clot.

FIG. 4a shows a target vessel 14 with an occlusive clot 13.

FIG. 4b shows a guidewire 15 with its distal tip across the obstructive clot 13.

FIG. 4c shows a micro-catheter 16 advanced over the guidewire 15 until its distal end is across the obstructive clot 13.

FIG. 4c shows the preplaced micro-catheter 16 with its distal end across occlusive clot 13 and a clot retrieval device 11 being advanced through its inner lumen, guidewire 18 having being removed from the microcatheter.

Figure 4F:
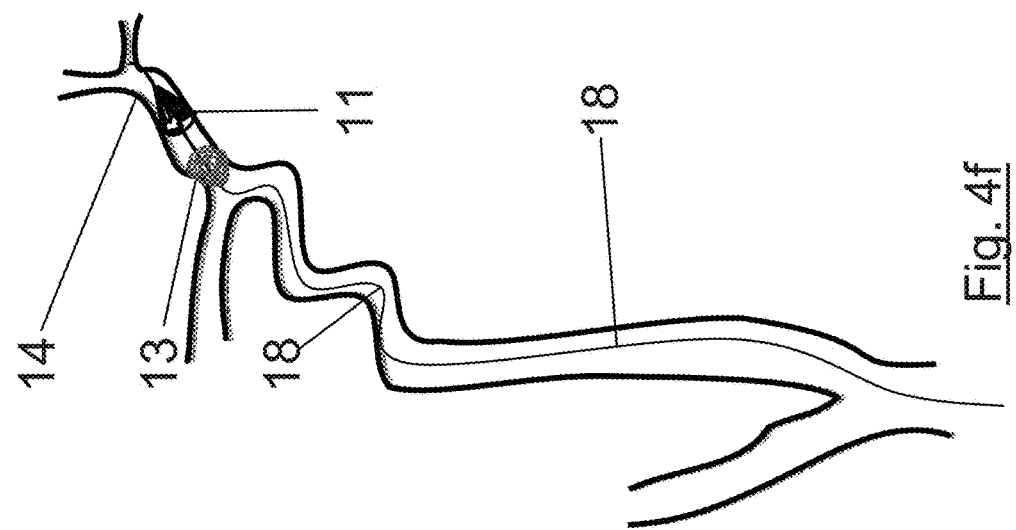
FIG. 4f shows the clot retrieval device deployed distal of the occlusive clot.
Figure 4E:
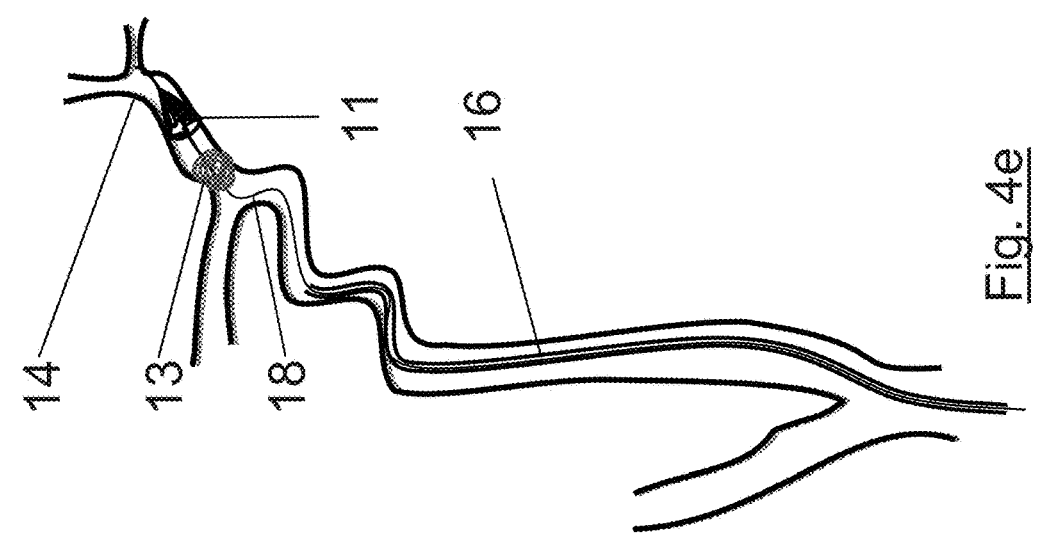
FIG. 4e shows clot retrieval device deployed distal of occlusive clot with the micro-catheter being withdrawn, the clot retrieval device being connected to a wire and the proximal end of the wire exiting the patient and being controlled by a physician.
Figure 4D:
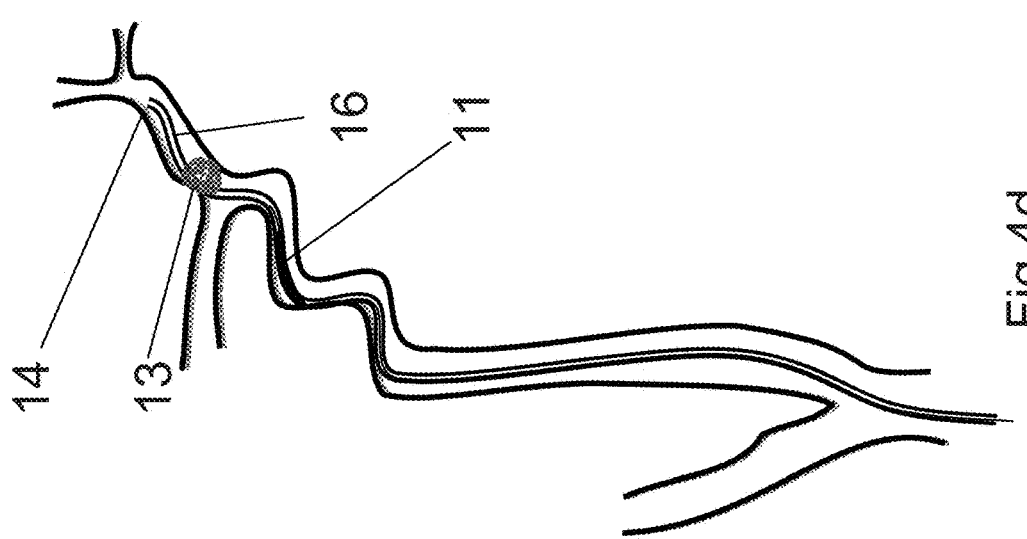
FIG. 4d shows the preplaced micro-catheter with its distal end across occlusive clot and a clot retrieval device being advanced through its inner lumen.

FIG. 4d shows clot retrieval device 11 deployed distal of occlusive clot 13 with the micro-catheter 16 being withdrawn. Clot retrieval device is connected to wire 18 and proximal end of wire 18 exits the patient and is controlled by the physician.

FIG. 4e shows the clot retrieval device 11 deployed distal of occlusive clot 13 with the micro-catheter being removed.

FIG. 4f shows the clot retrieval device 11 deployed distal of occlusive clot 13.

FIG. 4g shows the clot retrieval device 11 being advanced proximally and capturing the obstructive clot 13 with a removal catheter 17 advanced from the proximal side.

FIG. 4h shows the clot retrieval device 11, the captured occlusive clot 13 and the removal catheter 17 being removed from the vessel.

FIG. 4i shows the target vessel 14 with the obstructive clot 13 and devices completely removed.

Referring now to FIG. 5a to FIG. 5g another method of employing the clot retrieval devices of this invention is described. With this method the obstructive clot 23 in target vessel 24 is crossed directly with a clot retrieval micro-delivery catheter 26. The clot retrieval micro delivery catheter 26 has a reception space at its distal end and the collapsed capture device 21 resides in this reception space during delivery. In one embodiment the distal end of the guidewire 28 of the clot retrieval device 21 extends distally of the micro-delivery catheter 26 and assists the device in crossing the occlusive clot 23. When the distal end of the micro-delivery catheter is across the clot 23, the clot retrieval device 21 is deployed and the micro delivery catheter 26 advanced proximally.

The clot retrieval device 21 is advanced proximally with the aid of guidewire 28 to capture the obstructive clot 23. The guidewire 28 of the clot retrieval device 21 extends proximally of the expanded section of the device 21 and allows the physician to control the clot retrieval device 21. A removal catheter 27 is advanced over the guidewire 28 to assist in the removal of the clot 23. The removal removes the clot and capture device as described above.

FIG. 5a shows a target vessel 24 with an occlusive clot 23.

FIG. 5b shows a micro delivery catheter 26 with a clot retrieval device 21 collapsed within a distal lumen of the micro delivery catheter. The micro delivery catheter is advanced across the occlusive thrombus 23. The clot retrieval device 21 has a Guidewire 28 that extends proximally and distally.

FIG. 5c shows micro delivery catheter 26 being removed with the clot retrieval device 21 deployed in the target vessel 24 distal of the occlusive clot 23 with Guidewire 28 extending across the lesion and proximal to the user.

FIG. 5d shows the clot retrieval device 21 deployed in the target vessel 24 distal of the occlusive clot 23 with guidewire 28 extending across the lesion and proximal to the user.

Figure 5G:
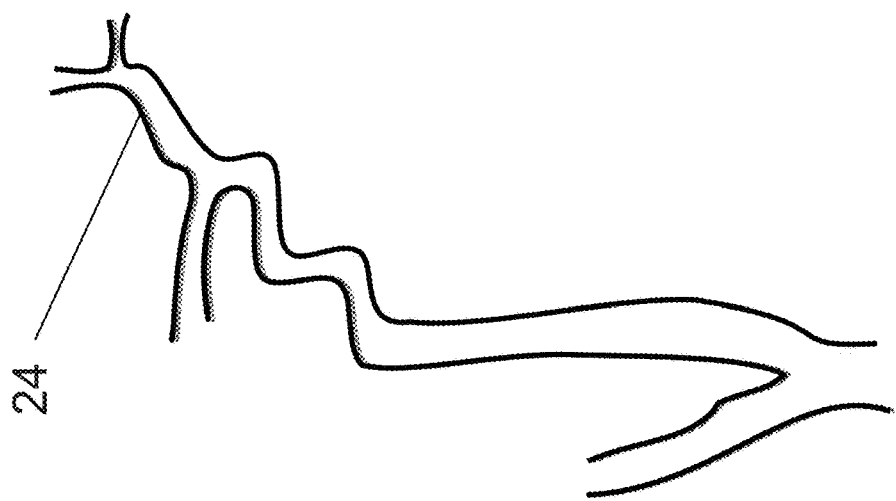
FIG. 5g shows the target vessel with the obstructive clot and devices completely removed.
Figure 5F:
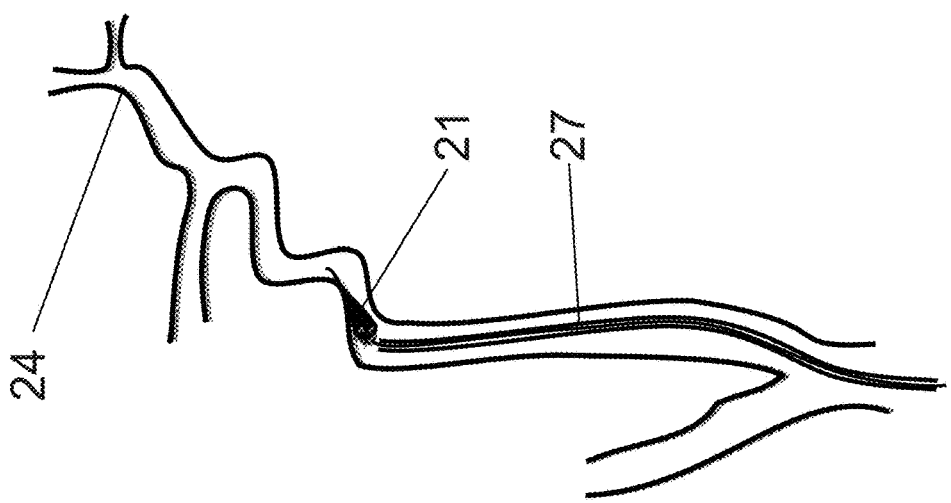
FIG. 5f shows the clot retrieval device, the captured occlusive clot and the removal catheter being removed from the vessel.
Figure 5E:
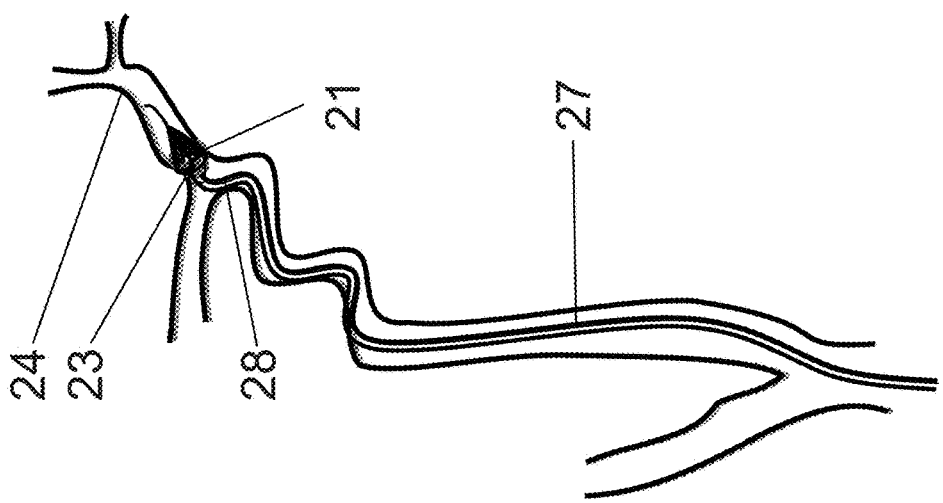
FIG. 5e shows the clot retrieval device being advanced proximally and capturing the obstructive clot with a removal catheter advanced from the proximal side.

FIG. 5e shows the clot retrieval device 21 being advanced proximally and capturing the obstructive clot 33 with a removal catheter 27 advanced from the proximal side.

FIG. 5f shows the clot retrieval device 21, the captured occlusive clot 23 and the removal catheter 27 being removed from the vessel.

FIG. 5g shows the target vessel 24 with the obstructive clot 23 and devices completely removed.

In one embodiment (not shown) the removal catheter comprises a balloon catheter wherein the guidewire lumen of the balloon catheter is larger than the guidewire diameter. The distal end of the balloon catheter lumen provides a reception space for a portion of the collapsed clot capture device. The balloon may be inflated during the clot capture step to prevent the clot from migrating proximally.

Figure 6:
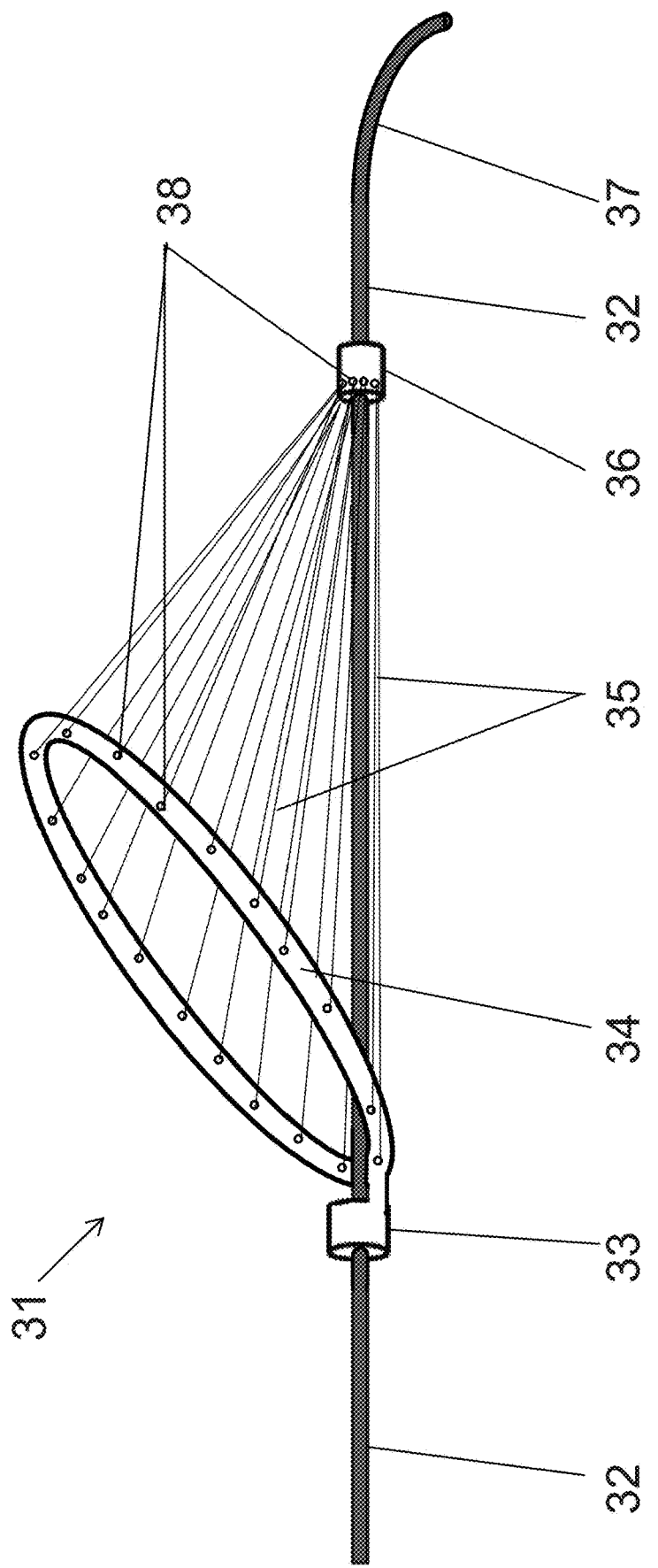
FIG. 6 is a detailed view of the distal end of a clot retrieval device in its expanded clot capture state.

With reference to FIG. 6 an example of the clot retrieval device of this invention is shown. The device 31 comprises a frame 34, a proximal collar 33, a distal collar 36, capture fibers 35, and a guidewire 32. Frame 34 comprises a metallic elliptical hoop. The hoop 34 is subtended at an acute angle relative to the guidewire 32 in the expanded configuration. In the collapsed state the hoop 34 sits substantially parallel to the guidewire 32. The frame 34 further comprises eyelets 38 that allow for a low profile interconnection between the capture fibers 35 and the frame 34. The eyelets 38 are shown as circular eyelets positioned substantially in the center of the struts. Multiple eyelets are located around the frame. Corresponding eyelets 38 are located on distal collar 36. The capture fibers are looped through the eyelets either in a simple single loop or using multiple loops. Where two or more loops are employed the loops act like a knot and prevent fiber slippage. In the embodiment shown the capture fibers 35 are not interconnected with each other but form straight line connections between the frame and the distal collar. This configuration means that there are no knots or fiber overlaps in the entire capture net which improves the wrapping profile of the device. In one embodiment the fibres are looped through the eyelets of the collar and the eyelets of the frame and this avoids the need for knots thus reducing the profile. The eyelets 38 of the distal collar 36 are arranged around the circumference of the distal collar 36. In one embodiment the distal collar is fixed to the guidewire 32. In another embodiment the distal collar 36 is slidable relative to the guidewire 32. In another embodiment the distal collar is rotatable relative to the guidewire. The proximal collar and the frame are preferably connected. In one embodiment the proximal collar and the frame are integral. In another embodiment both the frame and collar are machined from a hypotube. In this embodiment the hypotube diameter corresponds to that of the collar and the frame is laser cut in a configuration that corresponds closely to the shape of the frame when it is collapsed for delivery. The proximal hypotube is mechanically connected to the wire. This mechanical connection allows the memory in the metal to act to generate an angle between the frame and the guidewire in its expanded state. In one embodiment the mechanical connection comprises a closely tolerance fit between the collar inner diameter and the wire. In another embodiment the collar is fixed to the wire. It may be fixed by gluing, welding, or other well known means. The tip 37 of guidewire 32 is soft and flexible to allow the delivery system (not shown) to steer through the anatomy.

With reference to FIG. 7a another clot capture device 41 of the invention is shown. This device employs a similar arrangement to the device of FIG. 6, however in this instance the capture fibers 45 are interconnected. It will be noted that the fibers 45 are connected in a series of interconnecting loops 49. These loops 49 can be crafted by hand and have the advantage of avoiding the need for knots, bonds or other features that will significantly impact the profile of the device in the delivery configuration. The loops mean that the interconnected fibres can slide relative to one another and this allows the net to change its shape in response to an irregularly shaped clot. Alternatively the net may be knitted or braided so as to create a regular net structure. With both knitting and braiding it is also possible to create fibre interconnections without rigidly fixing the fibres at the cross over points. Attachment fibres are used to connect the net to the frame. In one case the proximal collar 43, distal collar 46 and guidewire 42 have similar features to those of FIG. 6.

The clot capture device of FIG. 7a is shown in the delivery configuration in FIG. 7b. The frame 44 lies substantially parallel to the guidewire 42 inside the lumen of delivery catheter 50. The delivery catheter 50 comprises a proximal shaft 51, a distal shaft 52 and a distal tip 53. The clot retrieval device sits inside a reception space at the distal end of the delivery catheter 50. The distal tip of the delivery catheter is preferably a soft tip material. The proximal end 51 of the delivery catheter 50 extends back to the user. In one embodiment the delivery catheter is a rapid exchange catheter.

In another embodiment the shaft 50 comprises a loading system. The distal tip 53 of the shaft 50 is engaged with the proximal end of a micro-catheter. The micro-catheter has had its distal end preplaced at a target treatment site. With the distal tip 53 engaged with the proximal end of the micro-catheter the clot retrieval element 41 is advanced into the lumen of the micro-catheter. When the proximal collar 43 has entered the micro-catheter the shaft 50 can be removed and the clot retrieval device 41 advanced through the micro catheter to the target location. It will be appreciated that the features of the loading system described with respect to the clot retrieval device 41 could be applied to other clot retrieval devices of the invention. It will also be appreciated that the method steps described can be applied with the methods described in FIGS. 3 to 5.

FIGS. 8a-f show a variety of frame mounting constructions that could be employed in the creation of a device similar to that described in FIG. 6. FIG. 8a shows a frame 501 constructed from a guidewire 502. FIG. 8b shows a frame 503 fixedly attached to guidewire 504 at proximal collar 505. FIG. 8c shows a frame 506 connected to a guidewire 507 in such a way that the collar 508 of the frame can translate and rotate along and around the guidewire between the two stops 509, which are fixedly attached to the guidewire, or an integral part of the guidewire. FIG. 8d shows a frame 510 whose proximal end is attached to tube 511, which is slideably mounted on guidewire 513 proximal to stop 512. FIG. 8e shows a frame 514 which is attached to tube 516, which is slideably mounted on guidewire 515 such that the tube and frame can be advanced or retracted over the guidewire and the guidewire can be moved or exchanged through the tube. FIG. 8f shows a variant of the design shown in FIG. 8e, in which frame 517 is attached to tube 518 and tube 518 is connected to a proximal shaft 519 at the guidewire exit port 520. Such a design would facilitate the deployment of the device over a shorter "rapid exchange" guidewire In other embodiments alternative stop configurations to those shown in FIG. 8c may be employed, in order to facilitate and control movement of the clot retrieval device relative to the guidewire, and/or in order to control the manner in which force may be transmitted to the device during delivery, retrieval and general use. Some of these alternative configurations are shown in various figures throughout this document. It will also be understood that the many other frame designs disclosed in previous and subsequent figures, although illustrated in a certain configuration, may be configured in any of the other configurations depicted in FIGS. 8a-f.

Figures 9A, 9B, 9C, 9D, 9E, 9F, 9G, 9H, 9I:
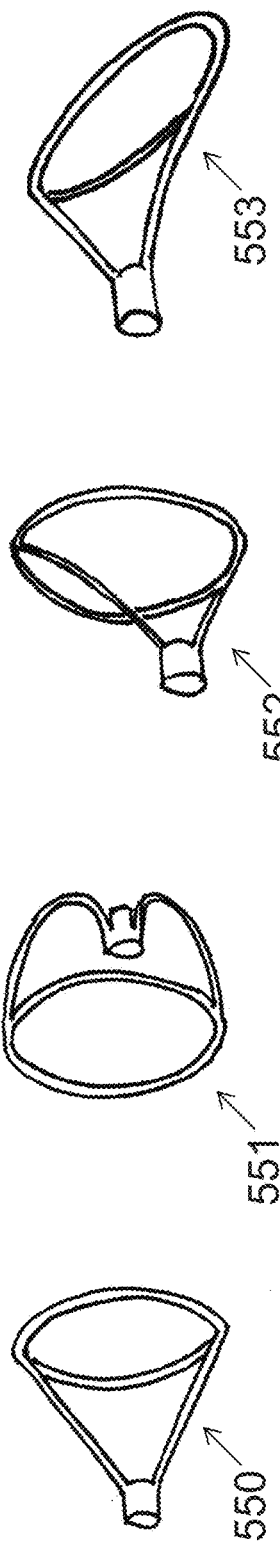
FIG. 9a shows the frame of a clot retrieval device in the expanded state.
FIG. 9b shows the frame of a clot retrieval device in the expanded state.
FIG. 9c shows the frame of a clot retrieval device in the expanded state.
FIG. 9d shows the frame of a clot retrieval device in the expanded state.
FIG. 9e shows the frame of a clot retrieval device in the expanded state.
FIG. 9f shows the frame of a clot retrieval device in the expanded state.
FIG. 9g shows the frame of a clot retrieval device in the expanded state.
FIG. 9h shows the frame of a clot retrieval device in the expanded state.
FIG. 9i shows the frame of a clot retrieval device in the expanded state.

FIGS. 9a-i show a variety of frame designs that could be employed in the creation of a clot capture device. Frame 550 in FIG. 9a has a generally circular perimeter with which to appose the vessel wall, and two proximal arms which taper outward distally from a proximal terminus. Such a design could be constructed from wire or from a cut tube or by other means, and could be made from any of the materials described later as suitable for the manufacture of frame 64 in FIG. 10a. Frame 551 in FIG. 9b is similar to frame 550 except that the inner terminus of the proximal arms is positioned distal to the outer circumferential portion of the frame. Frame 552 in FIG. 9c is similar to frame 550 except that the frame arms are of unequal lengths and/or angles, such that an offset is created between the centreline of the vessel and the proximal neck of the frame. Frame 553 in FIG. 9d is similar to frame 550 except that the frame arms are of unequal lengths and/or angles, such that the circumferential portion of the frame is inclined at an angle relative to the centreline of the vessel. Frame 554 in FIG. 9e is similar to frame 553 except that the frame has only one proximal arm. Frame 555 in FIG. 9f is similar to frame 550 except that the frame has three proximal arms. Frame 556 in FIG. 9g is similar to frame 550 except that the frame has four proximal arms. Frame 557 in FIG. 9h is similar to frame 554 except that the frame has an additional arm that tapers distally inwards from the outer circumferential portion. Frame 558 in FIG. 9i is similar to frame 501 of FIG. 8a except that the frame is not constructed directly from the guidewire itself, but from a separate material.

Another clot retrieval device 61 is shown in FIG. 10a-e. The clot retrieval device 61 shown in FIG. 10a comprises a frame 64, a guidewire 62, proximal collar 63, distal collar 66, support struts 60 and capture fibers 65. With this embodiment the frame 64 forms a three dimensional shape in its expanded configuration. The three dimensional shape is such that the outer surface of the frame in its expanded configuration can oppose the wall of a generally cylindrical vessel. The frame is preferably cut from a hypotube and is preferably metallic. Preferably the frame is nitinol, stainless steel, tantalum, MP35N, L604, a memory material, spring steel, or another high strength alloy. The frame comprises a number of segments 67. In a preferred embodiment the frame comprises pairs of segments. Each pair of segments are arranged at an angle and the angle of arrangement gets smaller as the frame is collapsed and increases as the frame is expanded. The pairs of segments are interconnected to from a 3D structure. In the embodiment shown two pairs of segments are shown. Three pairs of segments or more is also possible. The frame 64 is connected to the guidewire with support struts 60. In the embodiment shown the support struts 60 are attached to the frame 64 at its proximal end. The support struts 60 however are positioned underneath the frame 64 in the expanded configuration. This ensures that the frame 64 has maximum support when the guidewire 62 is being advanced proximally as the support struts 60 act generally to expand the frame. With this embodiment the frame is advanced proximally with a push force transmitted from the distal side. The force is transmitted along support struts 60 and has two components. One component acts to push the frame in the proximal direction while the other force acts to push the frame against the wall of the vessel. This makes it difficult for clot to escape around the outside of the frame 64. The support struts 60 are connected to the guidewire 62 through proximal collar 63. The support struts 60 may be connected to the frame in a number of ways. The support struts 60 may be laser cut from the same tube as the frame 67 and as such would be integral with the frame 67.

Figure 10A:
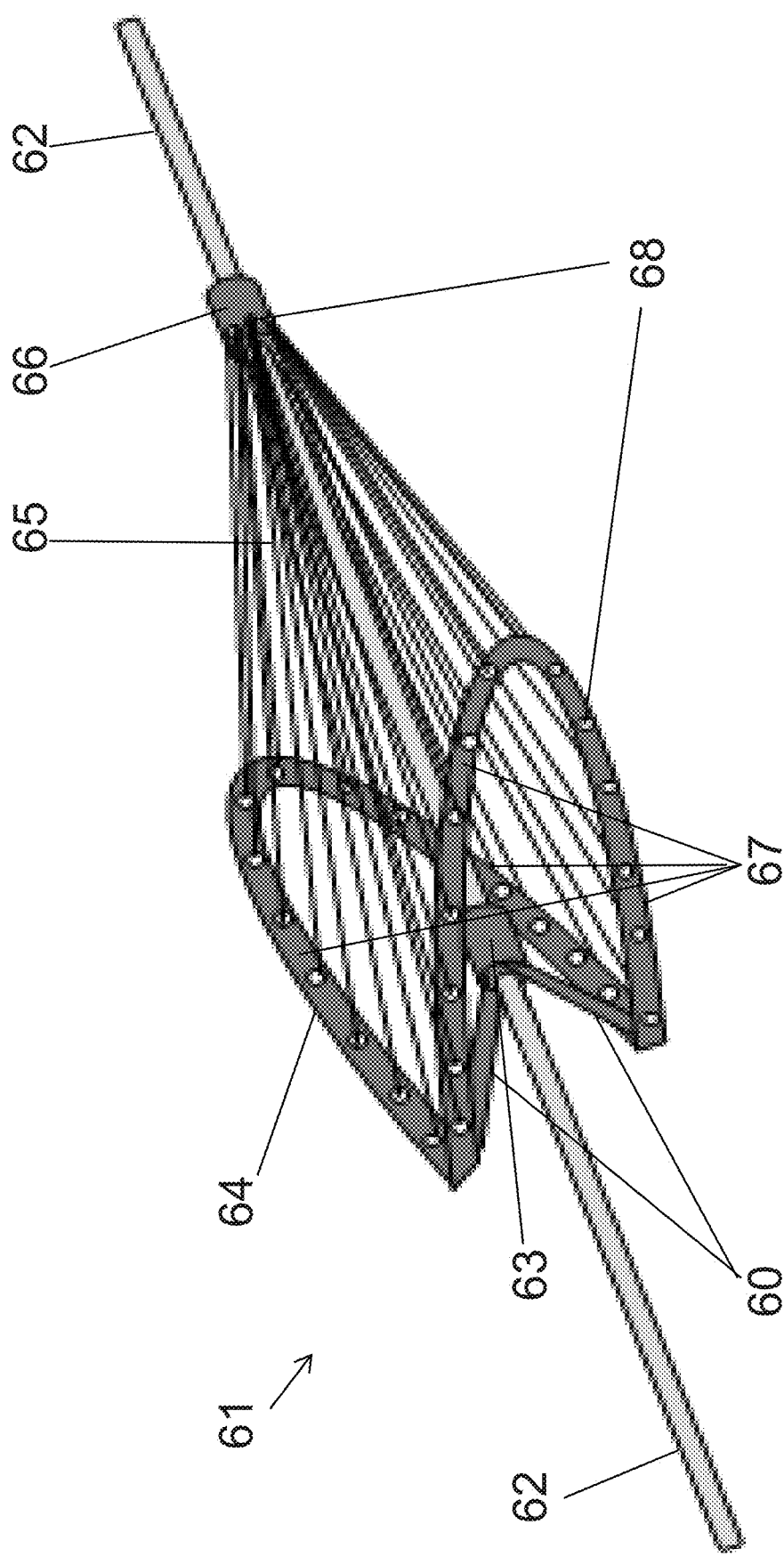
FIG. 10a shows a clot retrieval device in its expanded state.

FIG. 10b-e show a clot retrieval device 61 where the proximal collar 63, the support struts 60, and the frame are cut from a single piece of tubing which may be a hypotube. FIG. 10b is similar to FIG. 10a except that the proximal collar, the support struts and the frame are a single component. In order to manufacture such a complex component the metal used may be elastic. In one embodiment spring steel or a nitinol alloy is used. Preferably nitinol is used to make the frame.

FIG. 10c shows an elevation of the one piece frame component 64 in the collapsed (as cut) configuration. The proximal collar 63 is simply a segment of the original hypotube and should be kept as short as possible. A pair of support struts 60 extends from proximal collar 63 and connects the proximal collar 63 with the struts 67 of the frame 64. The support struts 60 are positioned diametrically opposite (thus only one is visible in the elevation view). The interface 87 between the support struts 60 and the collar 63 is an area of high strain when the device is expanded. The wall thickness of the support struts 60 may be locally thinned to reduce strain in this area. At the distal end each support strut 60 bifurcates to form two struts 67 of frame 64. The two struts are of the same length and reconnect at their distal end. The bifurcation 85 is also an area of high strain during expansion and the stress is relieved in this area by reducing locally the width of the struts. The junction 86 at the distal end is another area of high stress during expansion and the stress is relieved in this area by locally reducing the width of the strut in the region of the junction 86. FIG. 10d shows an end-view looking at the collar 63 end. FIG. 10e shows a sectional view at a-a. This sectional view shows the arrangement of the four struts 67, and the cut gap 88 between the struts. The construction of junction area 86 where neighboring struts 67 are connected is further highlighted.

In another embodiment the support struts 60 may be separate components that are joined to the frame 67. The support struts 60 may be connected to the frame by a hinge. The resistance of the hinge to movement is much less than the resistance of the frame or support struts to bending movements. The hinge may be formed by an interconnection between the support strut 60 and the frame 64. In another embodiment a suture or fiber(s) is used to create the hinge. With this embodiment the flexibility of the suture/fiber allows the strut to move relative to the frame while their points of connection are relatively constrained.

The capture fibers 65 of this embodiment are of similar size to those described earlier. The capture fibers 65 are attached to the frame 64 and the distal collar 66 through eyelets 68. Preferably the fibers are highly oriented fibers. This high orientation results in fibers that are anisotropic and these fibers are particularly preferred. These fibers are very strong along the axis of the fiber and less strong in other directions. The distal collar 66 contains eyelets 68 through which the capture fibers are threaded. In one embodiment the distal collar 66 is fixed to the guidewire. In another embodiment the distal collar 66 is integral with the guidewire. In yet another embodiment the guidewire is a hypotube and the eyelet holes are made in the guidewire hypotube thus eliminating the need for a separate distal collar. In yet other embodiments the fibres are attached to a collar or directly to the guidewire or to each other by bonding, welding or other methods.

Yet another embodiment of the invention is shown in FIG. 11a-11c. The clot retrieval device 71 comprises a frame 74, a guidewire 72, proximal collar 73, intermediate collar 70 a distal collar 76, support struts 79 and capture fibers 75. With this embodiment the frame comprises a hoop subtended at an angle relative to the guidewire 72. The hoop is held relative to the wire by two support struts 79 a proximal collar 73 and an intermediate collar 70. In one embodiment the proximal collar is fixed and the distal collar slides on the guidewire. In another embodiment the distal collar is fixed and the proximal collar slides on the Guidewire. In yet another embodiment both collars are slidable on the guidewire and a stop or stops are used to enable a force to be applied through the guidewire to either collar, such as illustrated in FIGS. 7, 48 and 50. FIG. 11b shows the clot retrieval device 71 in the collapsed crossing configuration. In this illustration the capture fibers 75 are not shown (for clarity). The support struts 79 are positioned distal and proximal of the frame in the collapsed configuration. The crossing catheter 80 is preferably a micro-catheter. Preferably the crossing catheter 80 is 2.3 French or less in its distal diameter 82. Preferably the crossing catheter 80 has a distal diameter 82 of 1.9 French or less. More preferably the crossing catheter 80 has a distal diameter 82 of 1.6 French or less. The tip 83 of the crossing catheter is preferably made of a soft material and has a smooth transition. FIG. 11c shows the clot retrieval device 71 and the crossing catheter 80 of FIG. 11b, with the exception that the capture fibers 75 are also shown. The diameter of the capture fibers 75 is so small as they exert only a minor influence on the profile.

FIG. 12a and FIG. 12b show another embodiment of the invention. This embodiment is similar to that of FIG. 11a-11c except that the frame 94 is circular rather than elliptical and the support struts 99 make an angle with the guidewire that is closer to a right angle. In the expanded position the proximal collar 93 and the intermediate collar 90 are adjacent each other. The support struts 99 are connected to the frame in a hinged configuration. This hinged configuration is important as the support strut moves through a large angle during device expansion. In one embodiment the support strut moves through an angle of greater than 60'. Preferably the support strut moves through an angle of at least 80'. More preferably the support strut moves through an angle of at least 90'. This large angle of movement has the effect of reducing the length of the device in the collapsed configuration and this shorter device is more deliverable.

For example: For a device with an expanded diameter of 3 mm, changing the strut angle from 45' to 90' has the effect of shortening the device by 1.24 mm. In the neurovascular territory where vessel diameters are small and vessel tortuousity is high this is a very significant reduction. In one embodiment the hinge comprises three elements, a strut element 99 a frame element 94 and a hinge element 104. The frame element 94 and the strut element 99 are connected with the hinge element 104. The hinge element allows the frame 94 and strut 99 to change angle relative to each other with little resistance. In one embodiment the hinge element is a pin. In another the hinge element 104 is a fiber, a filament, a multifilament or a suture. In another embodiment the strut 99 and the frame 94 are connected and the hinge is integral of the connection. In another embodiment the hinge comprises a weakness in the structure at the area where the strut 99 and frame 94 meet. In another embodiment the hinge between the strut 99 and frame 94 is adjacent a hinge in the frame.

In one embodiment the intermediate collar is fixed to the wire. With this embodiment the intermediate collar 90 provides a movement stop to the proximal collar 93. This configuration provides a particularly stiff frame construction even for a low profile device. In another embodiment the proximal collar is fixed and the intermediate collar 90 can move axially. In one embodiment the proximal collar 93, intermediate collar 90 and distal collar are radiopaque. With this embodiment the collars are made from or coated with a material that absorbs X-Rays. Typically this involves using materials that have a high atomic mass. Materials with a concentration of gold, platinum, iridium, tungsten, and tantalum are especially suited. It will be appreciated that a variety of other metals, alloys or compounds could be employed. Such radiopaque features may be used in any of the devices described herein.

FIG. 12b shows the clot retrieval device 91 in the delivery configuration. A crossing catheter 100 is used to constrain the device 91 in the collapsed state during delivery and crossing of the obstruction. The catheter has a proximal end 101 and a distal end 102. The guidewire extends proximally through a lumen of the crossing catheter 100 and exits at either the proximal end of the crossing catheter 100 or through an exit port in the wall of the crossing catheter 100. The capture fibers are arranged as previously described although they are not shown in FIG. 12a or 12b.

Figure 13D:
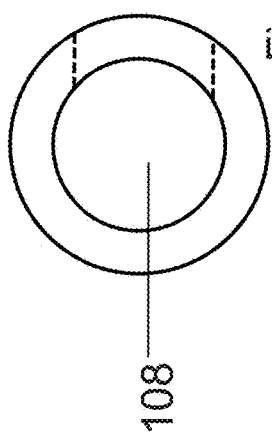
FIG. 13d shows an end view of a collar and strut arrangement for use with a number of frame designs of the invention with the strut in its collapsed state.
Figure 13E:
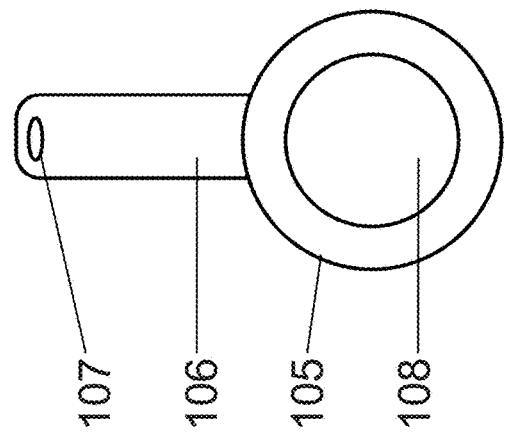
FIG. 13e shows an end view of a collar and strut arrangement for use with a number of frame designs on the invention with the strut in its expanded state.
Figure 13B:
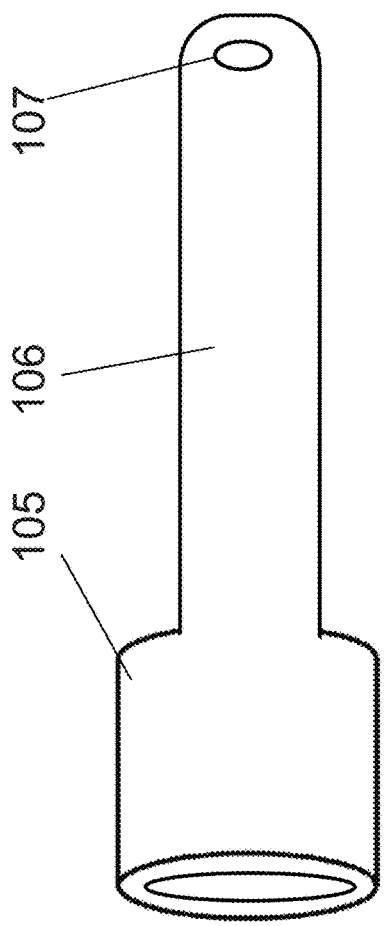
FIG. 13b shows a view of a collar and strut arrangement for use with a number of frame designs of the invention.
Figure 13C:
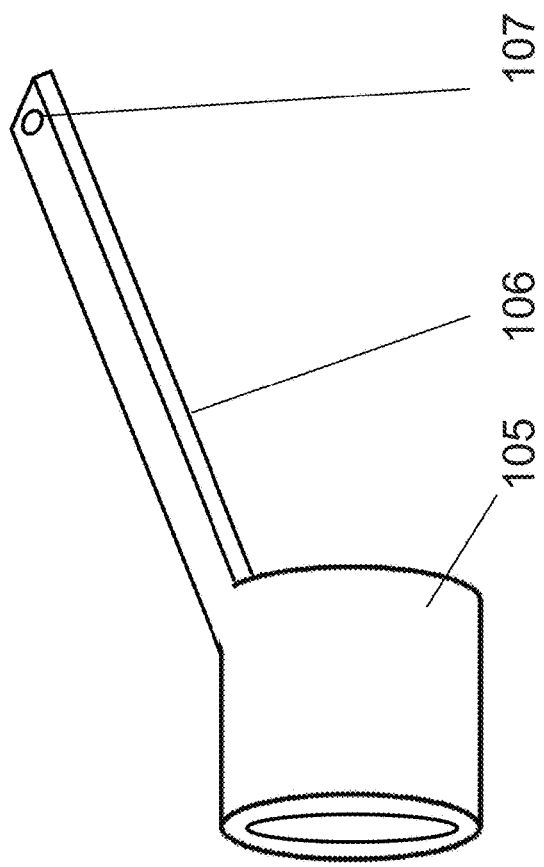
FIG. 13c shows another view of a collar and strut arrangement for use with a number of frame designs on the invention.
Figure 15:
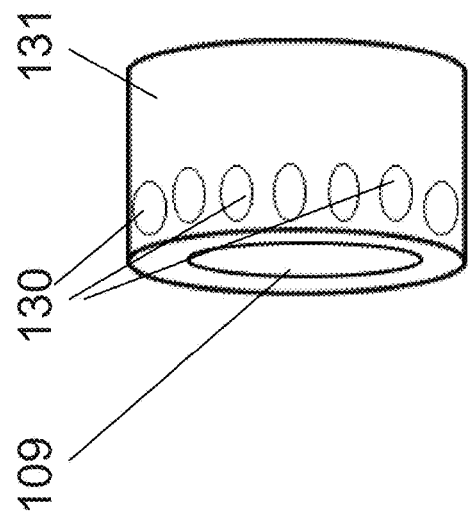
FIG. 15 shows a distal collar with eyelets for fiber alignment and/or attachment.

FIG. 13a shows the clot retrieval device of FIG. 12 except that the capture fibers 95 are shown. FIG. 13 also shows the collar arrangement whereby the intermediate collar 90 is fixed relative to guidewire 92 and the proximal collar 93 is slidable relative to guidewire 92. In another embodiment the proximal collar 93 and intermediate collar 90 are rotatable relative to guidewire 92. FIG. 13b to FIG. 13e show views of the proximal collar, intermediate collar and support struts of FIG. 12 and FIG. 13. The collar 105 could be either a proximal collar or an intermediate collar. In the embodiments shown the strut 106 and collar 105 are integral. In one embodiment they are formed from a single piece of hypotube. Preferably the tube is nitinol and the shape of the strut 106 is set by heat treatment. FIG. 13b and FIG. 13d show an arrangement where the strut is in the delivery configuration. This is also the pre-heat treatment configuration. The lumen 108 is sized to fit over the guidewire of the earlier embodiments. FIG. 13d and FIG. 13e show the collar 105 and strut 106 in the expanded configuration. The hole 107 allows for the creation of a hinge feature with the frame of earlier embodiments.

Figure 17:
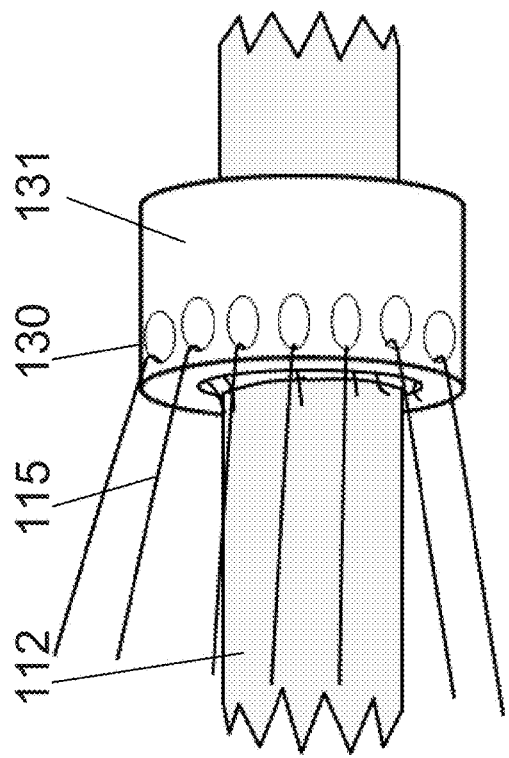
FIG. 17 shows a distal collar mounted on a guidewire with eyelets for fiber alignment and/or attachment.
Figure 14:
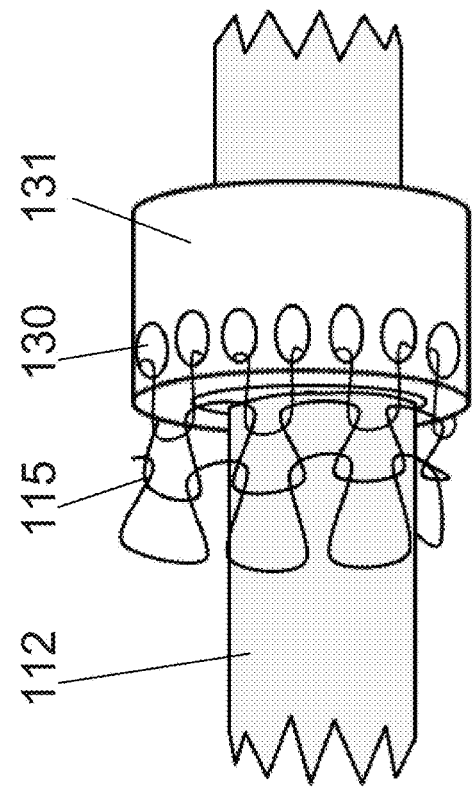
FIG. 14 shows a distal collar mounted on a guidewire with eyelets for fiber alignment and/or attachment.
Figure 16:
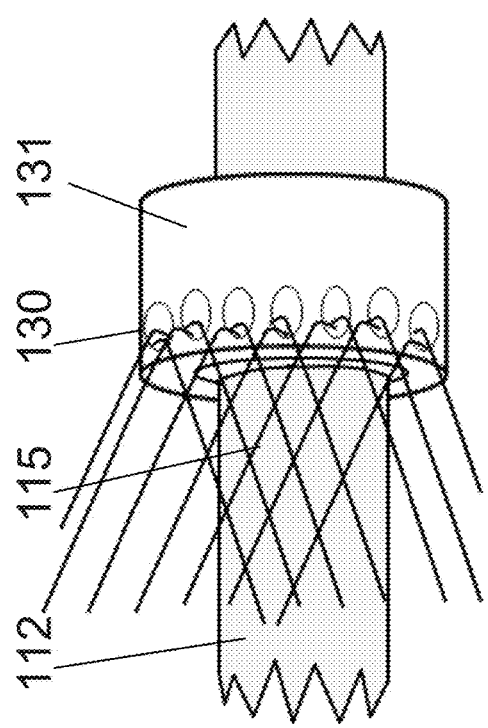
FIG. 16 shows a distal collar mounted on a guidewire with eyelets for fiber alignment and/or attachment.

Some examples of intermediate or distal collars 131 associated with the clot retrieval devices of the invention are shown in FIG. 14 to FIG. 17. FIG. 14, FIG. 16 and FIG. 17 shows collar 131 with lumen 109 mounted on guidewire 112. The collar comprises eyelets 130 for attachment of capture fibers 115. In FIG. 14 the capture fibers form a knitted structure and are connected to the collar in a series of loops through the eyelets 130. In FIG. 16 the capture fibers 115 are arranged in a weaved configuration and are attached to the eyelets through a series of loops. The capture fiber may be looped between one eyelet 130 and a neighboring eyelet or it may be looped through the eyelet and the body of the collar 131.

FIG. 18 and FIG. 19 show the clot retrieval device 91 of FIG. 12 and FIG. 13 in use. The device 91 is shown deployed distal of obstructive clot 100. The device is advanced proximally in order to capture the clot as shown in FIG. 19.

Now with reference to FIG. 20 through to FIG. 23 there is shown another clot retrieval device of the invention. This device is constructed from a series of sub-elements that work together through a series of hinge elements. For the purpose of describing the hinge features of this invention, hinges will be classified in terms of the number of axis of freedom available to the hinge. One axis of freedom shall mean that the hinge movement is limited to a single plane of movement. An example of a hinge with one axis of freedom is the human knee joint. Two axis of freedom shall mean that the hinge movement is limited to a two planes of movement and the two planes are normal to each other (X,Y). An example of a hinge with two axis of freedom is the human hip joint.

With reference to FIG. 20a-h there is shown a number of sub-elements to the frames of the clot retrieval devices of the invention. FIG. 20a and FIG. 20b show a strut element 150 with curved ends 152 and a hinge hole 151 located concentric with curved ends. Curved ends 152 may be curved in one axis or two axes depending on whether the hinge has one axis of freedom or two axis of freedom. FIG. 20c shows the strut 150 in a curved configuration. FIG. 20d shows a schematic of the construction of a hinge between two struts 150. The end curves 152 of two struts are brought into contact and a hinge element 153 secures the strut ends 152 relative to each other. Since both ends are curved in two planes this configuration creates a hinge with two axis of freedom. In one embodiment the hinge element 153 is a ring element. In another embodiment the hinge element 153 is a fiber, monofilament, multifilament, a wire or a suture. FIG. 20d also shows eyelets 154 on the strut for attachment of capture fibers.

FIG. 20e shows another hinge configuration of the clot retrieval devices of the invention whereby two struts or a strut and a support member are joined in a hinged configuration. The strut 150 has two curved ends 152 and each curved end 152 has two hinge holes 151. Each hinge hole is fastened to its neighboring hinge hole to create a hinge that has one axis of freedom. A frame 164 for a clot retrieval device is shown in FIG. 20f and FIG. 20g. The frame comprises four struts 150 configured in a circular arrangement. Each strut comprises curved ends 152 and hinge holes 151 adjacent said curved ends. The frame 164 is supported by support members. In one embodiment proximal support members 157 and distal support members 156 are employed. Proximal support members 157 are connected to the guidewire proximally. Distal support members 156 are connected to the guidewire distally. In one embodiment the proximal support member 157 and/or the distal support member 156 is connected to the guidewire 172 via a collar 155. In one embodiment the support member 156/157 is integral with the collar 155. In another embodiment the support member 156/157 is connected to the collar with a hinge arrangement. Preferably the hinge arrangement comprises a hinge with one axis of freedom. In one embodiment the support member 156/157 and the collar are integral and the hinge is made by thinning out the wall of the support member in the plane of bending adjacent the collar. Thinning the wall reduces plastic strain in the wall during hinging and allows large angles of movement. In one embodiment the support member 156/157 contacts the frame on its inner surface. In another embodiment the support member 157 contacts the frame intermediate the inner and outer surfaces.

FIG. 20h shows the arrangement of a frame support 165. The frame support comprises a collar 155 and support members 157. The collar comprises an inner lumen 166 and an outer surface. The support members 157 comprise a curved end 158 and a hinge hole 151.

FIG. 20h and FIG. 20i show how the hinges 167/168 allow the support frame to collapse. It will be noted that pairs of hinges facilitate most efficient collapse of the frame of the clot retrieval device. In the delivery configuration the curve of the struts 150 is straightened. This is illustrated in FIG. 20j where all of the hinges 168/167 are in the collapsed state and the struts 150 are straightened and lie substantially parallel to the axis of the guidewire 172.

FIG. 21a-c shows the frame elements of FIG. 20a-j assembled and mounted on a guidewire. FIG. 21a shows the frame 164 of FIG. 20j integrated with proximal and distal frame supports 165 of FIG. 20h. FIG. 21b shows the frame 164 of FIG. 20j integrated with proximal and distal frame supports 165 of FIG. 20h and all of this mounted on guidewire 172. FIG. 21c shows the clot retrieval device 175 assembled and in the collapsed configuration with capture fibers 171 included.

The hinges 167/168 associated with the body of frame 164 provide no bias for the frame. The hinges 167/168 thus provide no significant resistance to either expansion or collapse. The frame can thus be expanded from a collapsed state in one of the following ways.

In one embodiment the frame 164 is expanded and collapsed by movement of the more proximally located collar 155a relative to the more distal collar 155b. In one embodiment either the more proximally located collar 155a or the more distally located collar 155b is fixed to the guidewire 172. If the more distally located collar 155b is fixed longitudinally, then, advancing the more proximally located collar 155a distally expands the frame 164. In one embodiment movement of the collar 155a is achieved using a bumper catheter 173 as shown in FIG. 21c. The bumper catheter 173 has an outside diameter, a lumen and a distal face. The bumper catheter 173 is advanced over the Guidewire 172 until its distal face is adjacent the proximal end of collar 155a. The bumper catheter is further advanced and engages with the collar 155a and causes collar 155a to advance distally. As collar 155a advances distally the frame 164 expands. With the frame 164 in the expanded state, and the bumper catheter 173 held in position the clot retrieval device 175 and bumper catheter 173 are advanced proximally to capture the clot. When the clot is captured the bumper catheter 173 is disengaged from the collar 155a. The clot retrieval device 175 is retrieved. This may be achieved using a retrieval catheter, a micro-catheter, a sheath or guide catheter or the lumen of another catheter. Alternatively the clot retrieval device 175 can be withdrawn proximally into the procedural catheter.

In another embodiment the bumper catheter is connected to the collar 155a. In this way advancing the bumper catheter distally causes the frame 164 of the clot retrieval device 175 to expand, while advancing the bumper catheter proximally causes the frame 164 to collapse. In another embodiment the bumper catheter 173 is detachably coupled to the clot retrieval device 175 through collar 155a.

In another embodiment the support members 157/156 of frame support 165 are biased to the expanded state. For delivery the frame 164 is stored inside the pod of a delivery catheter. Upon deployment distal and proximal frame supports 165 acts on hinge points 167/168 and cause these to move radially outward. As these move outward the frame 164 of the clot retrieval device expands. On full expansion the frame 164 assumes a 3 dimensional ring-like configuration. With this embodiment, when the clot retrieval device 175 is deployed and the frame 164 is expanded the clot is captured by proximally advancing the clot retrieval device 175. After the clot is captured the clot retrieval device 175 is retrieved using a retrieval catheter, a micro-catheter, a sheath or guide catheter or the lumen of another catheter. Alternatively the clot retrieval device 175 can be withdrawn proximally into the procedural catheter.

A capture fiber collar 169 is located distal of the collars 155a/155b and this collar 169 provides an anchor site for the capture fibers distally. The capture fiber collar 169 may be fixed on the wire 172 or may be slidable and/or rotatable on the wire 172. In a preferred embodiment the capture fiber collar 169 has a limited range of movement. The movement may be limited proximally by abutment with the collar 155b of the frame support 165, or it may be limited by a stop (not shown) on the Guidewire 172. The movement of the capture fiber collar 169 may be limited distally by the capture fibers or by a stop on the wire 172. In yet another embodiment the distal tip of the guidewire ends proximal of collar 169, and collar 169 is therefore not engaged with the guidewire, but still acts as a distal terminus for the capture fibers.

Figure 22:
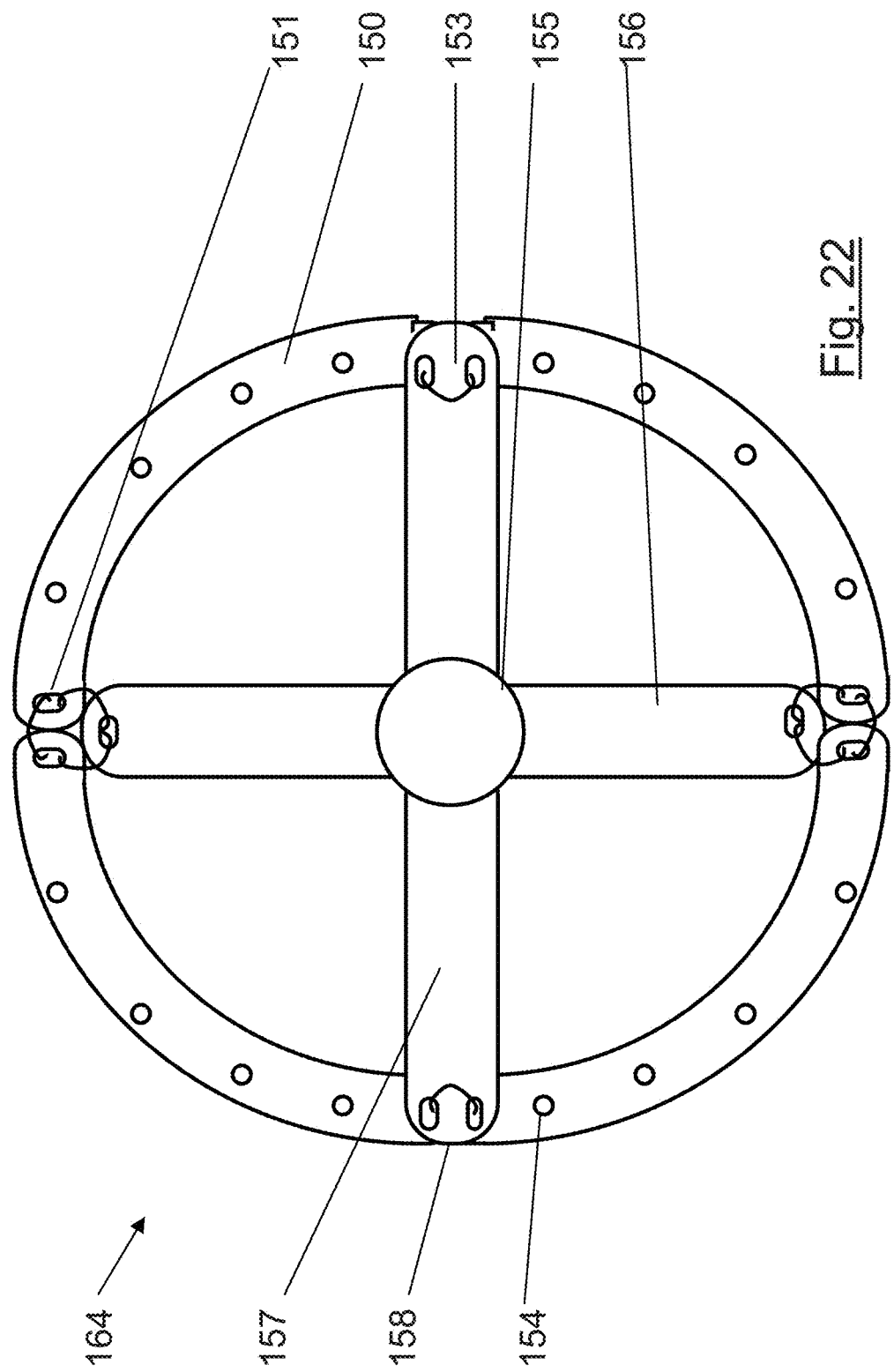
FIG. 22 shows a clot retrieval device with a hinged frame in the expanded configuration.
Figure 25A:
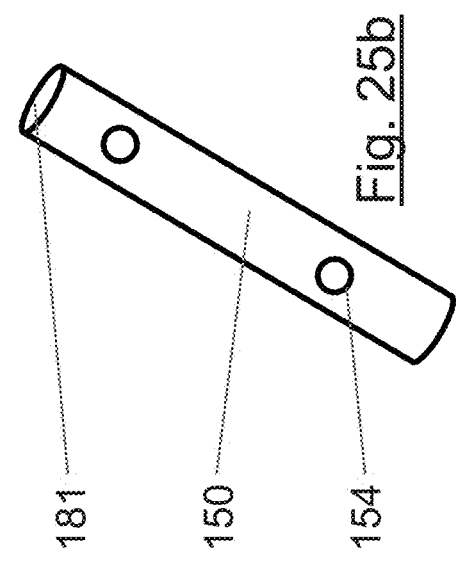
FIG. 25a shows a section of a strut of a clot retrieval device.
Figure 25B:
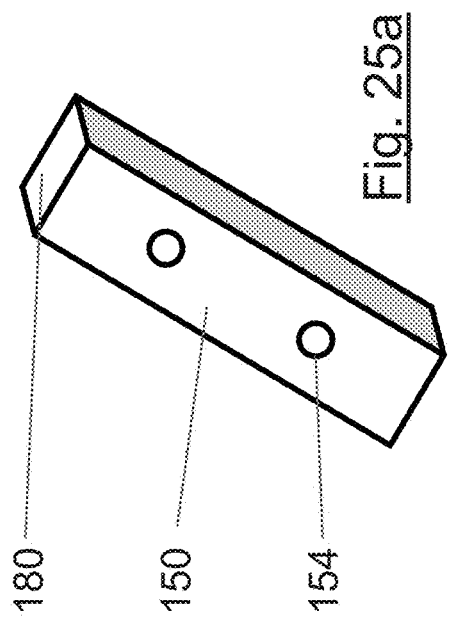
FIG. 25b shows a section of a strut of a clot retrieval device.
Figure 25C:
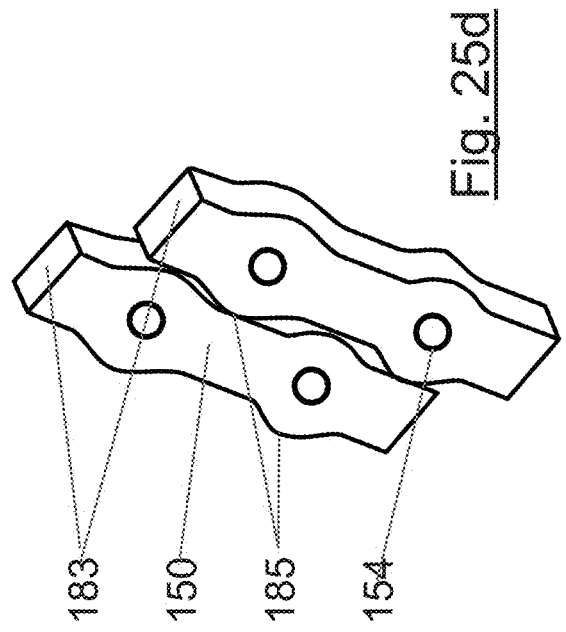
FIG. 25c shows a section of a strut of a clot retrieval device.
Figure 25D:
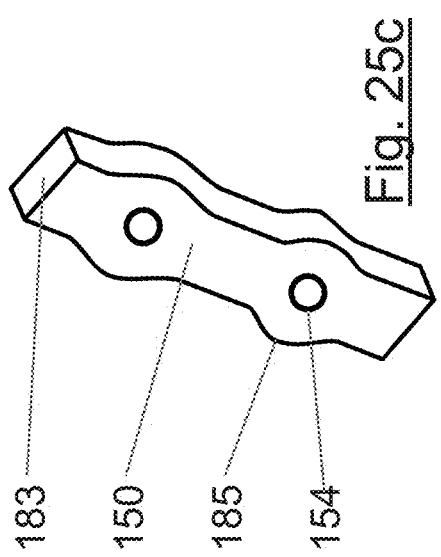
FIG. 25d shows two sections of two adjacent struts of a clot retrieval device nesting together.

FIG. 22 shows the frame 164 of the invention when viewed from the proximal end in its expanded configuration. The struts 150, the support members 157/156 and the collars 155a/155b/169 are preferably manufactured from a metal. Preferably the material is nitinol, stainless steel, MP35N, L604, Tantalum, a mixture of the above or another alloy with similar mechanical attributes. The optimum choice of materials is dependant on the design and operating mechanism of the frame. In the case of a self expanding frame as illustrated in FIGS. 10a-d it will be advantageous to select a material which can recover from the high strains that may be induced in collapsing the frame for delivery through a small diameter catheter. Such strains will be design dependant, but selection of a superelastic material such as nitinol, which can recover from strains as high as 8%, will enable more compact geometries for areas 85 and 86 to be adopted. In the case of a frame that is expanded by an external force as described in relation to FIG. 21c, greater flexibility in material choice is made possible. In the case of hinged designs, as for example is shown in FIG. 22, still greater material choice is afforded, as significant strains are not induced in the hinged areas.

A frame 164 of a clot retrieval device of the invention is shown in FIG. 23a-23c at various levels of expansion. In FIG. 23a the frame 164 is shown in the fully expanded configuration. Struts 150 form a circular ring and these are supported by support members 157/156. The proximal collar 155a and support member 157 support the frame 164 at two opposing hinge points 168. The more distally located collar 155b and support members 156 support the frame at the two remaining opposing hinge points 167. The frame 164 is shown in the partially collapsed state in FIG. 28b. The proximal collar 155a has moved proximally relative to the more distally located collar 155b. In the partially collapsed (or expanded) configuration the struts form a zigzag pattern in three dimensions. The zigzag pattern is defined on a cylindrical surface in 3D space.

The frame 164 is shown in the fully collapsed state in FIG. 23c. The collar 155a has moved even more proximally and the strut 150 is substantially parallel to the axis of the guidewire 172.

FIG. 24a-24c shows the device of FIG. 23 with the capture fibers 171 in place. It will be appreciated that other capture fiber arrangements described in this invention could be used with the frames 164 and clot retrieval devices of FIG. 20-28.

FIG. 25a-d and FIG. 26a-f show more detailed views of aspects of the struts 150 of the frames 164. In one embodiment the struts are rectangular in cross-section 180. In another the cross-section 181 of the struts 150 is circular. In another embodiment the strut 150 comprises a number of eyelets 154 and the strut 150 comprises a thickened section 185 adjacent the eyelet 154. The eyelets 154 and thickened sections 185 are staggered on neighboring struts such that the struts stack more efficiently in the collapsed configuration. In one embodiment the eyelets 154 are circular. In another embodiment the eyelets 154 are centered on the neutral axis 195 of the strut 150. The neutral axis 195 of the strut 150 is defined as the portion of the strut that undergoes zero strain when the strut is loaded in bending. In another embodiment the eyelets 190 are elliptically shaped and the major axis of the elliptical eyelets 190 is substantially parallel with the neutral axis 195 of the strut 150. In another embodiment the eyelet 191 is elongated and the axis of elongation is approximately parallel to the neutral axis 195 of the strut 150. Capture fibers 192 are looped through eyelets 150. In one embodiment the capture fiber 192 makes a single loop through the eyelets 150. In another embodiment the capture fiber 193 makes a double loop through the eyelet 190. In another embodiment multiple capture fibers are looped through eyelets 191 or a single capture fiber 194 is looped multiple times.

The eyelets of this invention could be configured in a variety of shapes including elliptical, square, oblong, rectangular, polyhedral, or combinations or variations of the above. The eyelets are typically very small in diameter and are preferably processed by laser machining. The eyelets have a minor axis and a major axis. For the purpose of this invention the dimension of the minor axis is defined as the largest diameter of cylindrical pin guage (gage) that will fit into the eyelet without deforming the eyelet. Per this invention it is desired that the eyelet dimension be as small as possible. Preferably the eyelet has a minor axis that is less than 100 micrometers. More preferably the eyelet has a minor axis that is less than 50 micrometers. More preferably the eyelet has a minor axis that is less than 30 micrometers. Most preferably the eyelet has a minor axis that is less than 20 micrometers. When the major axis of the eyelet is positioned on the neutral axis of the strut then it is the size of the minor axis that dictates the loss of mechanical properties of the strut. It is therefore an object of this invention to minimize the loss of mechanical integrity of the struts while allowing high strength fibers to be secured to the frame. In another embodiment the capture fiber has a flattened aspect. The fiber may be elliptical or flattened in cross section or the fiber may be multifilament fiber.

The capture fibers used with the clot capture devices of this invention have special properties. In order to deliver the capture device through a micro catheter the capture fibers are exceedingly small. Fibers with a diameter of less than 100 micrometers are desired. More preferably the diameter of the fibers is less than 50 micrometers. Even more preferably the diameter of the fiber is less than 30 micrometers. Most preferably the diameter of the fiber is less than 20 micrometers.

The capture fibers 35 of this invention are exceptionally strong in order to achieve the really low delivery profiles of the invention. Suitable fibers include Ultra High molecular weight polyethylene fibers, PET fibers, stainless steel fibers, MP35N fibers, PTFE fibers, Polypropylene fibers, nylon fibers, Kevlar fibers and PEEK fibers. More preferably the fibers are polymeric fibers. More preferably the fibers are Nylon, PET, Kevlar or UHMWPE. Most preferably the fibers are made from ultra high molecular weight polyethylene (UHMWPE) or Kevlar. UHMWPE has a very long molecular chain and can therefore have molecular weights from 3 million to as high as 10 million atomic units, as opposed to approximately 500,000 atomic units for standard HDPE. This gives it excellent abrasion resistance as well as strength, making it an excellent choice for a capture net fiber. An exemplary UHMWPE capture fiber is supplied by DSM Dyneema BV, Urmond, The Netherlands.

Tables land 2 below compare the properties of a range of material fibers. The strength of a specific fiber strand is proportional to ultimate tensile strength of its material and to the square of the fiber diameter. Therefore a big reduction in strength is caused by a relatively small reduction in diameter. For example with reference to table 1, reducing the diameter of a Dyneema UHMWPE fiber from 30 microns to 15 microns results in a four-fold decrease in fiber strength from 1.86 N to 0.46 N. For this reason while it is desirable for profile reasons to use a low fiber diameter, it is also desirable to use a fiber with a high ultimate tensile strength.

The fibers used are sufficiently strong to withstand the loads that will be experienced during device delivery and clot retrieval, and also to facilitate device manufacturability. Inadequate fiber strength in manual, automated or semi-automated assembly processes is likely to result in frequent breakages and low yields. Preferably an individual fiber strength will be greater than 0.25 N. More preferably an individual fiber strength will be greater than 0.35 N. Most preferably an individual fiber strength will be greater than 0.5 N. While PET is generally considered a high strength polymer, particularly when highly oriented, it can be seen from Table 2 that to achieve a 0.5 N fiber strength a PET fiber diameter of over 25 microns is required, while the same strength can be achieved with UHMWPE or Kevlar fibers in diameters of less than 20 microns.

TABLE 1

Fiber Strengths (in Newtons) for specific fiber diameters

| Fiber material | Fiber diameter (microns) | | | | | UTS (Mpa) |
|---|---|---|---|---|---|---|
| | 15.00 | 20.00 | 25.00 | 30.00 | 50.00 | |
| UHMWPE - Dyneema | 0.46 | 0.82 | 1.29 | 1.85 | 5.14 | 2620 |
| UHMWPE - Celanese | 0.23 | 0.41 | 0.64 | 0.92 | 2.55 | 1300 |
| UHMWPE - Spectra 1000 | 0.51 | 0.90 | 1.41 | 2.03 | 5.64 | 2870 |
| UHMWPE - Tekmilon | 0.43 | 0.77 | 1.20 | 1.73 | 4.81 | 2450 |
| PET | 0.18 | 0.31 | 0.49 | 0.71 | 1.96 | 1000 |
| Nylon | 0.14 | 0.25 | 0.39 | 0.57 | 1.57 | 800 |
| Kevlar | 0.53 | 0.94 | 1.47 | 2.12 | 5.89 | 3000 |
| 302 SS (50% CW) | 0.27 | 0.48 | 0.74 | 1.07 | 2.98 | 1516 |
| 302 SS (90% CW) | 0.42 | 0.75 | 1.17 | 1.68 | 4.67 | 2378 |
| MP35N (95% CW) | 0.44 | 0.78 | 1.22 | 1.76 | 4.90 | 2495 |
| 35NLT (90% CW) | 0.45 | 0.80 | 1.25 | 1.80 | 5.01 | 2551 |
| L604 (50% CW) | 0.40 | 0.70 | 1.10 | 1.58 | 4.40 | 2241 |
| Nitinol | 0.26 | 0.45 | 0.71 | 1.02 | 2.84 | 1448 |

TABLE 2

Fiber diameters (in microns) for specific fiber strengths

| Fiber material | Fiber strength required (N) | | | | | UTS (Mpa) |
|---|---|---|---|---|---|---|
| | 0.20 | 0.50 | 1.00 | 5.00 | 10.00 | |
| UHMWPE - Dyneema | 9.86 | 15.59 | 22.04 | 49.29 | 69.71 | 2620 |
| UHMWPE - Celanese | 14.00 | 22.13 | 31.30 | 69.98 | 98.97 | 1300 |
| UHMWPE - Spectra 1000 | 9.42 | 14.89 | 21.06 | 47.10 | 66.61 | 2870 |
| UHMWPE - Tekmilon | 10.19 | 16.12 | 22.80 | 50.97 | 72.09 | 2450 |
| PET | 15.96 | 25.23 | 35.68 | 79.79 | 112.84 | 1000 |
| Nylon | 17.84 | 28.21 | 39.89 | 89.21 | 126.16 | 800 |
| Kevlar | 9.21 | 14.57 | 20.60 | 46.07 | 65.15 | 3000 |
| 302 SS (50% CW) | 12.96 | 20.49 | 28.98 | 64.80 | 91.64 | 1516 |
| 302 SS (90% CW) | 10.35 | 16.36 | 23.14 | 51.74 | 73.17 | 2378 |
| MP35N (95% CW) | 10.10 | 15.97 | 22.59 | 50.51 | 71.44 | 2495 |
| 35NLT (90% CW) | 9.99 | 15.80 | 22.34 | 49.96 | 70.65 | 2551 |
| L604 (50% CW) | 10.66 | 16.85 | 23.84 | 53.30 | 75.38 | 2241 |
| Nitinol | 13.26 | 20.97 | 29.65 | 66.31 | 93.77 | 1448 |

While UHMWPE fibers are extremely strong they are difficult to bond. The present invention overcomes these difficulties by allowing one single fiber to be used to manufacture the entire capture net. Furthermore the arrangement of the frame eyelets and collar eyelets allows a single fiber to be threaded over and over. Single loops can be made through the eyelets or multiple loops can be made. Multiple loops can be used to terminate a fiber. A small drop of adhesive can be used to fix the end of the fibers in the eyelets. Even though it is difficult to bond to the surface of UHMWPE fibers the adhesive acts as a mechanical constraint that prevents the loops from unraveling. Further since the load is carried by multiple fibers and multiple loops it is dispersed.

In another embodiment the capture fiber is a multifilament fiber. In yet another embodiment the fiber is a flat fiber or an oblong fiber.

In one embodiment the eyelets are positioned on the neutral axis of the strut of the frame. The neutral axis is generally at the center of the strut and corresponds to the line or plane in the strut that sees zero strain when the strut is loaded in bending. The advantage of putting the eyelet on the neutral axis is that it reduced the weakening effect of the eyelet. Where the eyelet has a major and a minor axis it is preferred that the major axis is as close to the neutral axis of the strut as possible.

Figure 27A:
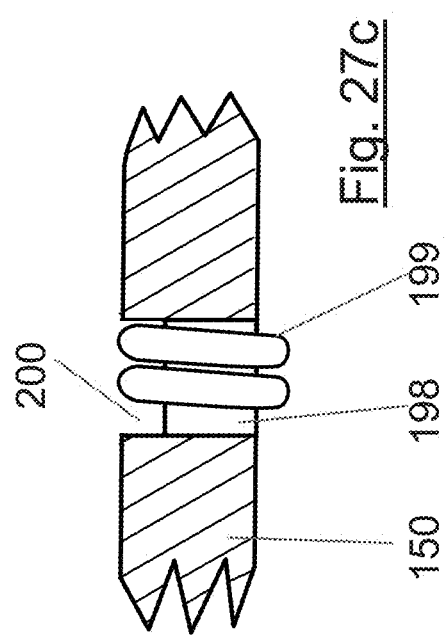
FIG. 27a shows a cross section of a strut with a capture fibre threaded through an eyelet.

FIG. 27a shows a cross-sectional view of a strut 150. The cross section shows an eyelet 197 and a capture fiber threaded through the eyelet. FIG. 27b shows a plan view of the same strut 150, eyelet 197 and capture fiber 196 arrangement.

Figure 27C:
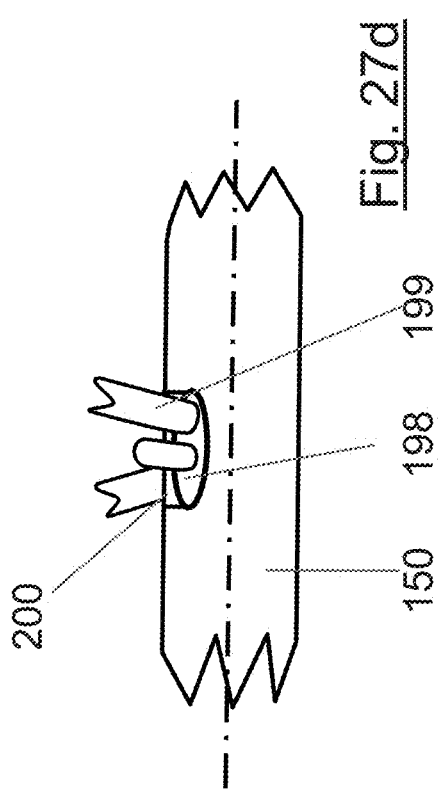
FIG. 27c shows a cross section of a strut with a capture fibre threaded through an eyelet.
Figure 27B:
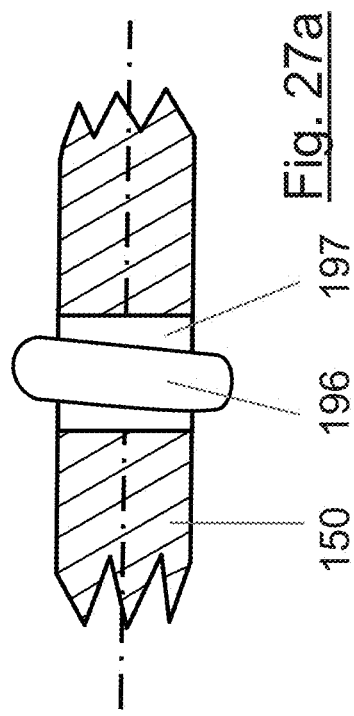
FIG. 27b shows a strut with a capture fibre threaded through an eyelet.
Figure 27D:
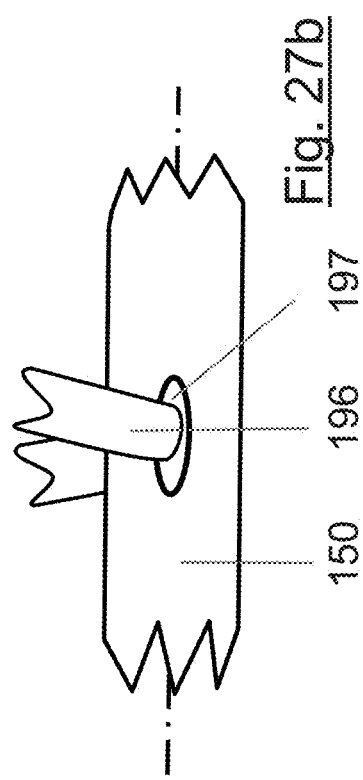
FIG. 27d shows a strut with a capture fibre threaded through an eyelet.

FIG. 27c shows another arrangement of strut 150, eyelet 198 and capture fibers 199. This time the eyelet is offset relative to the neutral axis of the strut 150. The eyelet is positioned close to one wall of the strut. A relief section 200 is also shown. This relief section 200 is created by partially machining material in the area where the capture fiber lies. In the embodiment shown the relief section 200 is created on the outer surface of the device. This ensures that the capture fibers do not add to the profile of the device as they loop about the frame. A plan view of the strut 150, eyelet 198, capture fiber 199 and relief section 200 is shown in FIG. 27d. It will be noted that the capture fiber 199 loops around the strut section twice in this schematic.

It will be appreciated that the capture fibers of this invention and the eyelets of the invention are both very small and assembling both presents a challenge. FIG. 28a shows a view of a segment of a strut 150 with eyelet 154. FIG. 28b shows a cross sectional view of the strut 150 taken through eyelet 154 along section line a-a. FIG. 28c shows a representation of a fixture device that allows the assembly of the capture fibers In another embodiment the eyelet is positioned close to the edge of the strut. With this embodiment the strut may be thickened on the side opposite the eyelet to compensate for any weakening.

FIGS. 29a-i show additional eyelets and fiber path defining features to those previously described in FIGS. 25-28. The purpose of these features is to provide points or areas of engagement between the frame and the fibers that help to define the configuration of the fiber or fibers. Frame 600 in FIG. 29a has eyelets 601 and 602 similar to those described in frames 26a and 26b. Frame 603 in FIG. 29b has a circular offset eyelet 604. Frame 605 in FIG. 29c has an assymetrical offset eyelet 606. Frame 607 in FIG. 29d has an inflexion 608 which creates a feature to provide a preferential seat for fiber attachment. FIG. 29e shows two variations of raised features 610 and 611, pairs of which may be used to define a fiber attachment point to the frame 609. FIG. 29f shows recessed features 613 which may be used to define fiber attachment points to the frame 612. FIG. 29g shows recessed features 615 which may be used to define fiber attachment points to the round wire of frame 614. Frame 616 in FIG. 29h is similar to frame 614, except that its raised features are separate components, which in one embodiment are radiopaque marker bands, and in another embodiment are of other metallic or polymeric materials. Element 619 in FIG. 29i is wrapped around frame 618 in such a way as to leave defined spaces 620 in which to attach fibers to the frame. In one embodiment element 619 is a radiopaque platinum wire, but in other embodiments may also be of other materials or in the shape of a coil. The recesses and raised areas illustrated may be created by a laser machining process, or by other mechanical, electrical or chemical means.

Now with reference to FIGS. 30a-e there are shown various frame features which may assist the attachment of a distal fiber or fiber structure to a frame structure. FIG. 30a illustrates a frame 650 with an external sleeve 651, which provides an attachment surface to which fibers may be more easily bonded or a higher friction surface on which fibers will slip less easily if tied in place. Attachment surface 651 may be a polymer sleeve, which may be placed prior to forming the frame shape and may also be bonded or heat shrunk into position. Alternatively the attachment surface may be a coating 652, as shown in FIG. 30b. FIGS. 30c-e describe variants in which connection elements are used to join distal fibers to a frame. These connection elements may be fibers also, and may be used with any of the frame designs disclosed elsewhere, particularly those with features as shown in FIGS. 25-30. Fiber 655 in FIG. 30c is connected to frame 653 by connection element 654, which is itself wrapped around frame 653. Fiber 655 is shown connected to the eyelets of frame 656 by discrete connection elements 657 in FIG. 30d, and by a continuous connection element 658 in FIG. 30e.

FIGS. 31a and 31c show two fiber configurations that may be employed to reduce the size of embolus that can pass through the fiber net. The weave or braid configuration 700 shown in FIG. 31a is constructed from multiple fibers, which is advantageous in that if one fiber breaks the integrity of the entire structure is not significantly affected; however this structure leaves multiple loose fiber ends 701 at each end. FIG. 31b shows a design which deals with this challenge by folding the woven net around the frame 703 and joining the loose ends together at a distal junction 704. In another embodiment the woven net may be folded around a connecting element which is in turn connected to the frame, or may be connected to the frame in a similar fashion to that described in FIGS. 30c-e. FIG. 31c shows a knitted net 705, which can be formed from a single fiber, and thus does not have the disadvantage of multiple loose ends. Such a net may be joined to the frame in a multitude of ways, many of which have been previously described in FIGS. 25-30.

FIG. 32a-e illustrates a number of fibre types that may be employed in the construction of a fiber net. A monofilament fiber 750 is shown in FIG. 32a. A multifilament twisted fiber 751 is shown in FIG. 32b. A multifilament braided fiber 752 is shown in FIG. 32c. A multifilament fiber with an outer sleeve 753 is shown in FIG. 32d. A multilayer fiber 754 is shown in FIG. 32e. Any of these fibers may be used to construct the net designs shown in FIGS. 33a-d. FIGS. 33a and 33b show how a porosity gradient may be created with either a knitted 756 or braided 757 design, which may be advantageous in efficiently balancing wrapped profile and effective particle retention. FIGS. 33c and 33d show a clot retrieval device constructed with axial fibers 758, which also create a similar porosity gradient. FIG. 33d illustrates a similar design to FIG. 33c, except that a stiffening element 759 is provided, which serves to control the wrapped configuration of the net during delivery and retrieval.

Now with reference to FIG. 34a-f there is shown a clot retrieval device 218 which comprises a frame assembly 225 and a catheter 211. The frame assembly 225 further comprises strut section 214 with eyelets 212, capture fibers 215, a fiber junction 217, an expansion cable 213, and a guidewire 210. The frame assembly 225 is shown in its expanded state in FIG. 34a and in its delivery state in FIG. 34b. The strut section 214 lies substantially parallel to the axis of the catheter 211 in the delivery configuration. The strut section 214 expands to a ring shape when it is not constrained. The strut section 214 is deployed from the catheter 211 by advancing the guidewire 210 relative to the catheter 211. In order to deliver the device 218 into very small vessels it is necessary that the profile (diameter) of the device is very small. In retrieving obstructive clots from the brain it is desired that the device can be delivered through a micro-catheter. Typical commercially available micro catheters have profiles of 1.2 F to 1.9 F (1 F=0.333 mm=0.013"). The inner lumen of a 1.9 F micro-catheter is approximately 0.016" (0.41 mm). In order for the clot retrieval device to fit into this space the cross-sectional area of the strut section needs to be very small. However in order to capture clot effectively larger strut sections are desired. The strut section 214 of FIG. 34 has a cross sectional area that can fit into a micro-catheter. The expansion cable 213 is a flexible yet strong cable and it is fastened to the strut section 214 at anchor point 223. The anchor point 223 is at the distal most portion of strut section 214. The other end of expansion cable 213 is fastened to the distal end 216 of catheter 211. The expansion cable is strong, flexible and very small in diameter. The cable may be manufactured from polymeric or metallic cable materials. Preferably the cable is made from polyester, nylon, olefin, fluoropolymer, stainless steel or other similar cables. The expansion cable may be monofilament or multifilament. PET, Nylon, UHMWPE, Kevlar and PEN fibers are especially preferred. When the strut section 214 is deployed it expands to form a ring. The strut section 214 is connected to the guidewire section 210 at the distal section 229 of guidewire. The strut section 214 and distal section 229 of guidewire are adapted such that the strut section 214 sits at an angle transverse to the axis of the vessel. In one embodiment the strut section 214 and/or/not the distal section of guidewire 210 have a preset shape that causes the strut section 214 to sit transverse to the axis of the vessel. In another embodiment the expansion cable 213 is tensioned by advancing the catheter 211 proximally relative to frame assembly 225. When the expansion cable is tensioned it causes the strut section 214 to move more transversely in the vessel. It will be appreciated that this mechanism allows the user to modify the shape of the strut section 214 as well as controlling the resistance of the strut section to collapse during clot capture. It will also be appreciated that this allows the device to be delivered through micro-catheters as the cross sectional area of the strut section can be reduced significantly. In another embodiment more than one expansion cable 213 is employed. With this embodiment the expansion cables are preferably attached to opposite sides of the strut section 214. Both cables are attached to the distal end of catheter 211 and both cables are tensioned by a proximal advancement of the catheter 211 relative to the frame assembly 225. With two cables the position of attachment 223 to the strut section can be varied. However some displacement relative to distal section 229 of guidewire is desired as this reduces the force required to bias the strut section 214.

In another embodiment the tensioning of the expansion cable 213 is controlled by a handle at the user end. The handle comprises means for locking to the guidewire, means for locking to the catheter 211 and a mechanism to control fine axial motion of the catheter 211 and guidewire 210.

In one embodiment the fine axial motion is controlled by a helical mechanism such as a thread or coil. In another embodiment the fine axial motion is achieved with a gear arrangement such as a rack and pinion. In one embodiment the guidewire locking mechanism comprises a pin vice. In another embodiment the expansion cable is fastened to the proximal end of catheter 211. In another embodiment the expansion cable is releasably attached to the proximal end of catheter.

In yet another embodiment the expansion cable 213 can be released from catheter 211 and catheter 211 can be removed from the guidewire 210 leaving the frame assembly and the expansion cable behind. With this embodiment the strut section can be activated directly by the user by tensioning the expansion cable. In another embodiment the expansion cable has a grip section attached to its proximal end.

In the embodiment shown in FIG. 34a-b the strut section 214 is shown delivered inside the distal end 216 of catheter 211. The catheter 211 with strut section 214 collapsed are delivered to the target location through a procedural catheter. The lumen at the distal end 216 of catheter 211 is sized to accommodate the frame assembly 225 in its collapsed state.

With reference to FIG. 34c-f there is shown some detailed embodiments of the frame assembly 225 of the invention. FIG. 34c shows a frame assemble 225 comprising a strut section 214 and guidewire 210. The strut section 214 is ring shaped and is integral with the distal end 228 of guidewire 210. The guidewire 210 comprises a proximal section 226 and a distal section 228. The proximal and distal segments are joined at junction section 227. In one embodiment the proximal section at least partially comprises a tube and said tube engages with junction section 227 to connect the proximal 226 and distal 228 sections of the guidewire 210. The joint between the proximal 226 and distal 228 sections of the guidewire may be further reinforced by any of a variety of conventional joining techniques including screw joint, welding, soldering brazing, adhesive bonding, crimping, swaging or combinations of the above. The guidewire 210 extends from the strut section 214 back to the user in use and is thus much longer than depicted. The strut section 214 may be any of a variety of cross-sectional shapes including circular, elliptical, rectangular, square, polyhedral, and multifilament. Circular or rectangular are preferred. The strut section further comprises eyelets 212. The eyelets 212 are as described earlier in FIG. 30-33. The expansion cable 213 is connected to the strut section 214 at its distal end. An eyelet 223 may be used to effect cable attachment. The cross sectional area of the distal end of the guidewire 210 may be locally modified to improve the shaping of the frame by the expansion cables. The guidewire 210 may be flattened so as to create a directional bias for strut section 214 when expansion cable 213 is activated. A flattened cross section in this area has the effect of keeping the strut section 214 in plane during expansion. The strut section 214 of FIG. 34c may be cut from a hypotube. The shape may be cut from a small diameter tube and expanded or it may be cut directly from a large diameter tube.

FIG. 34d shows an alternative construction of the frame assembly 225. The guidewire 210 and frame assembly 214 are manufactured from a single piece of wire. The strut section 214 forms a ring shape and comprises eyelets 212 and an expansion cable 213 attachment eyelet 223. The strut section 214 is made from a wire that is looped and joined to itself. The joint area 219 is at the distal end of guidewire 210. A smooth transition 224 is effected between the joint area 219 and the distal end of the guidewire 210. The distal portion 229 of the joint area 219 may be locally thinned or flattened to create a bias for strut section expansion. FIG.

34*e-f* show segments of strut sections 214 of the invention wherein the strut sections 214 have either a circular or rectangular cross section.

The method of use of clot retrieval device 218 of FIG. 34*a-f* is highlighted in FIG. 35*a-i*. FIG. 35*a* shows a vessel 220 and an obstructive clot 221. The clot retrieval device 218 is shown in its collapsed state crossing the obstructive clot 221. The distal tip 216 of catheter 211 is advanced across obstructive clot 221 with strut section collapsed inside the lumen of the catheter distal tip 216. The guidewire extends proximally and is operably moveable relative to catheter 211 to deploy the strut section 214. The strut section 214 is deployed by advancing catheter 211 proximally while holding the guidewire 210 fixed (FIG. 35*c-d*). The strut section assumes its remembered ring shape in the vessel. The clot retrieval device is advanced proximally until its strut section 214 is adjacent the obstructive clot 221. At this point the catheter 211 is advanced proximally relative to the guidewire 210 until the expansion cable 213 is tensioned (FIG. 35*e*). This step can be controlled with a handle mechanism at the proximal end as described elsewhere. Increasing the tension in expansion cable 213 changes the angle that the strut frame 214 makes relative to the axis of the vessel 220. This in effect changes the size of the capture opening of the clot retrieval device 218. As the capture opening increases the strut frame 214 achieves better apposition with the walls of the vessel 220. It will be appreciated that these features allow the user to achieve very efficient clot capture. However overly tensioning the expansion cable 213 is not desirable as this will induce trauma to the vessel. Rather the expansion cable 213 is tightened to the point where the strut section 214 has achieved apposition with the vessel and the catheter 211 is then locked relative to the guidewire at the user end. The clot retrieval device 218 is now advanced proximally to capture obstructive clot 221 (FIG. 35*f*). With the obstructive clot captured the lock between catheter 211 and guidewire 210 is released. The guidewire is advanced proximally relative to catheter 211 and at least the proximal portion of strut section is drawn into the lumen at the distal end 216 of catheter 211 (FIG. 35*g-h*). This step reduces the diameter of the strut section and makes removal of the clot 221 and clot retrieval device 218 easier. The clot retrieval device 218 and clot 221 are removed from the body (FIG. 35*i*).

In another embodiment the lumen at the distal end 216 of catheter 211 is sized only to accommodate guidewire 210. With this embodiment the strut section 214 cannot be collapsed inside catheter 211. Instead, the frame assembly 225 and catheter 211 are delivered through the lumen of a micro catheter. The tip of the micro-catheter is placed across the obstructive clot. The strut section 214 is collapsed and while restrained in the collapsed state the frame assembly 225 and catheter 211 are advanced into the proximal lumen of the micro-catheter. The clot retrieval device is advanced through the lumen of the micro-catheter and deployed distal of the tip of the micro-catheter. When the device is deployed the micro-catheter is advanced proximally. Subsequently the clot retrieval device is advanced until the strut section is adjacent the obstructive clot. The catheter 211 is advanced proximally and expansion cable 213 is activated. When the frame section is expanded to the desired shape, the expansion cable 213 and catheter 211 are locked relative to guidewire 210. The clot retrieval device 218 is advanced proximally to capture the clot. The micro-catheter is again advanced until its distal tip engages with the strut section 214 of the clot retrieval device 218. The micro catheter is advanced further and partially collapses the strut section. The micro-catheter and clot retrieval device 218 are withdrawn from the vessel together.

Yet another embodiment is shown in FIG. 36*a-b*. The clot retrieval device 218 is the same as the clot retrieval device of FIG. 35. However in the embodiment shown in FIG. 36 the lumen of catheter 211 accommodates a separate crossing guidewire 222. The crossing guidewire 222 runs parallel the guidewire 210 of the clot retrieval device. The crossing guidewire 222 may sit side by side with the collapsed clot retrieval device. Alternatively catheter 211 has a separate lumen for crossing guidewire 222. The crossing guidewire is free to move axially and rotationally relative the clot retrieval device. The crossing guidewire 222 is preferably a conventional guidewire and its tip can be shaped to access target vessels. This allows the crossing guidewire 222 to be used in conjunction with catheter 211 to access difficult to reach locations by advancing the crossing guidewire 222 relative to the catheter 211 and torqueing it as necessary to achieve access. When the tip section of crossing guidewire 222 has accessed a side branch the catheter 211 can be advanced over the crossing guidewire. When the clot retrieval device 218 is delivered to the target location the crossing guidewire may be removed. Alternatively the crossing guidewire may be left in the target vessel.

FIG. 36*a* shows a crossing guidewire 222 with its distal tip across the capture fibers 215 of clot retrieval device 218. The capture fibers are arranged in a fashion that a small diameter device can be pushed through the gaps in the capture fibers 215. The ability of low profile devices to cross the capture fibers allows other devices to be used with the clot retrieval device.

Another embodiment of the invention is shown in FIG. 37*a-e*. FIG. 37*a* shows a conventional guidewire 230. The guidewire comprises a proximal end 231, a distal end 232 and a tip 234. The tip 234 is flexible and atraumatic to vessels. Many of the features of the clot retrieval device 250 of this embodiment are achieved by modifying the area 233 adjacent the tip 234 of conventional Guidewires 230. With reference to FIG. 37*b* there is shown a guidewire 233 which has been modified proximal of the tip in order to create clot retrieval device 250. The guidewire 233 comprises an inner shaft 235 and an outer shaft 236. The inner shaft and the outer shaft are fixed together. Proximal of the tip of the guidewire 230 the outer shaft 236 has substantially longitudinal cuts 238 so as to create strut elements 237. The strut elements 237 are cut so as to create ring elements 247. One or more ring elements may be created with strut elements 237. In the embodiment shown two ring elements 247 are created by cutting two pairs of strut elements 237 and connecting the strut elements 237 at their distal ends. In one embodiment the segment of the outer shaft 236 adjacent the tip 234 is made from an elastic, a super elastic or a shape memory material. Preferably said elastic material is nitinol or a spring steel. Most preferably the outer shaft 236 is made from nitinol. FIG. 37*c* shows the clot retrieval device 250 in its expanded state. It can be seen that a number of elements have been added to the modified guidewire of FIG. 37*b* to create the clot retrieval device 250. The strut elements 237 have a collapsed state and an expanded state. FIG. 37*b* shows the strut section 237 in it's as machined (laser cut) state. The strut section 237 is shown in its expanded state in FIG. 37*c*. In the expanded state the strut sections 237 form a capture frame 247. In the embodiment shown the capture frame 247 comprises two D-shaped elements. The capture frame comprises radial strut sections 246 and body strut sections 248. The body strut sections interface with the vessel wall in the expanded state and provide a line of apposition around the circumference of the vessel. The radial strut section 246 connects the body strut section to guidewire shaft 236. Eyelets 244 are provided on at least the body strut section 248 and capture fibers 241 are fixed to the capture frame 247 using said eyelets 244. The capture fibers 241 are fixed to collar 243 distally. Collar 243 is fixed to the distal portion of the guidewire. In another embodiment the distal eyelets are cut into the outer shaft 236 of the guidewire 230. This eliminates the need for collar 243 and reduces the distal profile of the device. When the strut section 237 is in the expanded state a recess area 240 is created in the wall of the guidewire. The integrity of the guidewire is maintained by the presence of connector elements 242. The connector element 242 is a portion of the outer shaft 236 that lies adjacent the recess area and connects the distal part 232 of the outer tube 236 with the proximal part 231 of the outer shaft 236. The connection between the proximal portion 231 and the distal portion 232 of the guidewire 230 is further reinforced with the inner shaft 235. In one embodiment the inner shaft 235 is fixed to the outer shaft 236. In one embodiment the connector element 242 is fixed to the inner shaft 235. When the strut section 237 is in the collapsed state it packs into the recess area 240. This keeps the delivery profile of the clot retrieval device 250 extremely low. Since the capture fibers are made from a highly oriented fiber such as Dyneema (UHMWPE), and since the recess space 240 is larger than the strut section the attachment of the capture fibers to the strut section 237 will not adversely impact the profile of the strut section 237 of the clot retrieval device 250 in the collapsed configuration.

The clot retrieval device 250 is shown in the delivery configuration in FIG. 37d. The delivery catheter 245 is of an extremely low profile. Preferably the delivery catheter is less than 2 F (0.66 mm). More preferably the delivery catheter profile is less than 1.9 F. Even more preferably the delivery catheter is less than 1.6 F.

FIG. 37e shows an end view of the device 250 in the expanded state. The view is as seen from distal of the expanded strut section 237. The inner core 235 is visible with two connector elements 242 diagonally opposite. The strut section 237 is shown expanded to from capture frame 247. The capture frame 247 comprises a double-D shape. The capture frame 247 further comprises radial strut sections 246 and body strut sections 248. The strut sections 237 are provided with eyelets 238 for capture fiber attachment.

In yet another embodiment the clot retrieval device 250 is delivered to the target site without the need for a delivery catheter. With this embodiment the inner shaft 235 and the outer shaft 236 are moveable relative to each other. The strut section 237 is connected to the inner shaft 235 in the delivery configuration and said connection restrains the strut section 237 in the collapsed state. Upon reaching the target site relative movement of the inner shaft relative to the outer shaft releases the connection and allows the strut section 237 to expand. In one embodiment the connection comprises a tether that is attached to both the strut section 237 and the inner shaft 235. In the collapsed configuration the tether is under tension as it restrains the strut section 237. The inner shaft 235 is either advanced or rotated to relax the tension in the tether and this allows the strut section 237 to expand. In another embodiment an engagement between the inner shaft 235 and the strut section 237 retains the strut section 237 in the collapsed state. The inner shaft 235 is either rotated or advanced to disengage with the strut section 237 and this allows the strut section 237 to expand. The engagement may be a frictional engagement, a snap engagement, a clip engagement feature, a hook engagement or other similar engagements.

Now with reference to FIGS. 38-39 there is shown another low profile clot retrieval device 280. FIG. 38a-b shows modifications to guidewire 260 necessary to create clot retrieval device 280 of FIG. 39a-b. The modified guidewire 260 comprises a tubular shaft 261 which has aproximal end 266 and a distal end, an outer surface and an inner lumen. The distal end of tubular shaft 261 comprises a strut section 267 and an expansion cable 265. The strut section is shown in the 'as cut' state in FIG. 38a-b. The strut section 267 comprises at least one pair of generally longitudinal struts 264 and a strut connection 268 at the distal end of longitudinal struts 264. Where the strut segment 267 comprises a single pair of longitudinal struts 264 then in the expanded configuration the axis of the outer shaft adjacent the strut section 267 will be offset relative to the axis of the vessel (as shown in FIG. 39a-b). However where the strut segment 267 comprises two pairs (or more) of longitudinal struts 264 then in the expanded configuration the axis of the outer shaft adjacent the strut section 267 will be generally coaxial with the axis of the vessel. In one embodiment the strut connection is a short strut like element. In a preferred embodiment the strut connection 268 has a curved aspect. The curved aspect helps to distribute stress as the strut section is expanded to from a ring. Preferably the strut connection has an inner curve and an outer curve wherein the inner curve has a smaller radius than the outer curve. Preferably the difference in radius of the inner curve versus the outer curve is less than the width of the strut sections 267. Preferably the strut connection comprises a strain relief feature. In another embodiment the strut connection 268 comprises an element that is curved in at least two dimensions.

The expansion cable is attached to the frame section 267 at attachment point 269 and extends proximally to the user. The expansion cable 265 enters the lumen of the tubular shaft 261 at port 262 and extends through the lumen back to the user. The expansion cable can be tensioned by the user at the proximal end of the guidewire shaft 261. In one embodiment the expansion cable is attached to a fine adjustment mechanism at the user end. This allows the user to control the level of tension in the expansion cable 265 and thus the resistance of the strut section 267 to collapse during clot capture. The port 262 position along the tubular shaft 261 may be varied. In one embodiment the distal opening of the lumen of the tubular shaft 261 is used as the port 262.

In the embodiment shown in FIG. 38 the eyelets 270 are shown along the length of strut section 267. Eyelets may also be placed at the distal end of the tubular shaft 261. The eyelets 270 may be created in a variety of configurations as previously described. Likewise, the attachment of the capture fibers 279 is as described earlier.

In another embodiment the width of struts 264 is sufficiently great that an expansion cable is not needed in order for the strut section 267 to effectively capture the obstructive clot.

The clot retrieval device 280 is shown assembled and in the expanded state in FIG. 39a-b. The capture fibers and the distal collar 282 have been added to FIG. 38 and the strut section 267 has been expanded. The strut section 267 is preferably made from an elastic material, a super elastic material or a shape memory material. The strut section 267 forms a ring in the expanded state and the ring shaped strut section 267 apposes the vessel in the expanded state. In use the expanded strut section 267 is advanced proximally to capture the clot. The expansion fiber 265 is used to add stiffness to the frame and prevent its partial collapse during clot capture. The large open mouth of the strut section in the expanded state makes this embodiment an effective clot capture device. The capture fibers are terminated at a distal junction 281 with a collar as previously described. The distal collar comprises eyelets for capture fiber attachment. In another embodiment the distal junction 281 is formed by the joining of the distal ends of the capture fibers 280 to each other. In one embodiment a knot arrangement is used, in another embodiment the capture fibers are bonded or welded together.

In the embodiment shown in FIG. 39 the distal junction 281 is free to move proximally as it is not constrained relative to the guidewire 261. In another embodiment at least one of the capture fibers has a bias. Preferably said bias generally pushes the distal junction 281 distal of the strut section. Preferably the biased capture fiber is elastic, super elastic or shape memory. Preferably said biased capture fiber is metallic. Preferably said capture fiber is nitinol, or stainless steel.

FIG. 39c shows the clot retrieval device 280 in the delivery configuration. The strut section 267 is shown in the collapsed configuration inside a pod 285 of delivery catheter 284. The guidewire shaft 261 extends proximally through the lumen of catheter 284. In one embodiment the catheter 284 and guidewire 261 are arranged in an over the wire fashion. In another embodiment the catheter 284 and guidewire 261 are arranged in a rapid exchange fashion. The catheter shaft is preferably made from a thin walled flexible material. Preferably the catheter is made from an olefin, nylon, a PEBAX, polyester, polyurethane or a fluoropolymer. The delivery catheter may be made from a combination of these materials. The catheter may be made with two or more layers and at least one of these layers comprise at least one of the above list of materials.

FIG. 40a-b shows a clot retrieval device 290 that is very similar to the clot retrieval device 280 of FIG. 39. The clot retrieval device 290 has a first difference in that the distal junction is connected to strut tip 287. The strut tip is created during the machining of the strut section 267. The strut tip is formed from a portion of the wall of the tubular shaft 261 that lies between longitudinal struts 264. The strut tip is designed to be mechanically similar to the core of a guidewire tip. The strut tip tapers distally and has an atraumatic element 287 at its distal end. The strut tip 287 provides a site upon which the distal junction 281 can be connected. In the embodiment shown a collar is used as the distal junction 281 and the collar has limited movement relative to the strut tip 287. In one embodiment the collar is fixed relative to the strut tip. A second difference between the clot retrieval device 280 of FIG. 39 and clot retrieval device 290 of FIG. 40 is that the distal end of the tubular shaft 261 has machined slots 286 to improve the trackability of the device. In one embodiment the slots run transverse to the axis of the tubular shaft and run only part of the circumference. In another embodiment pairs of transverse slots 286 are arranged on opposite sides of the tubular shaft 261. In another embodiment the slots 286 are arranged in a continuous helix along a portion of the distal end of the tubular shaft 261. In another embodiment the clot retrieval device comprises a supporting strut 288. The supporting strut 288 extends distally and substantially parallel of the axis of the tubular shaft 261 and comprises a restraining feature. The supporting strut 288 is configured to restrain the strut section 267 in the collapsed state during delivery. The restraining feature may comprise a tether arrangement, an interconnection between the supporting strut and the strut section 267, an interlock between the supporting strut and the strut section 267, or a coupling between the supporting strut 288 and the strut section 267. The restraining feature may be deactivated when the clot retrieval device 290 is at the site of the occlusion causing the strut section 267 to expand to its remembered expanded state. The deactivation may be brought about by means of a release cable, use of an inner core which may be advanced or retracted to free the strut section or advancement or retraction of an outer tubular member or a combination of these mechanisms. In another variant the restraining feature may be configured such that the strut section is firstly restrained to itself and secondly restrained to the supporting strut and that both restraints are decoupled either simultaneously or in series when the clot retrieval device 290 is at the site of occlusion. The clot retrieval device 290 is otherwise the same as clot retrieval device 280 and similar numbers shall have the same meaning for both devices.

The clot retrieval devices of FIG. 41-43 are very similar to the clot retrieval devices shown in FIG. 39 and FIG. 40. With FIG. 41 the strut tip is cut substantially parallel to the longitudinal struts 264 of strut section 267. The longitudinal strut extends distal of the strut section and connects the tubular shaft proximally 261 with a distal segment of tubular shaft 291. The distal segment of the tubular shaft 291 is modified to make it atraumatic to vessels. The modification may comprise a spiral cut or slots as described previously. The distal tip 293 of the tubular shaft 291 is smooth soft and atraumatic. The distal junction 268 is connected to the distal shaft 291 as previously described.

FIG. 42a-b shows an inner core 301 adapted to from a guidewire like tip to the clot retrieval device 300. The inner core has proximal diameter that allows it to fit inside the lumen of the tubular shaft 261. The inner core 301 may be fixed relative to outer shaft 261 or it may be moveable relative to outer shaft 261. The distal portion of the inner core tapers distally and has an atraumatic tip 302. The atraumatic tip 302 comprises a rounded tip 304 and a coil segment 303. The rounded tip 304, the distal tip of the inner core 301 and the coils are preferably fastened together. The distal junction 268 is positioned proximal of the distal end of the core wire. In one embodiment the distal junction comprises a collar with eyelets for capture fiber attachment. The proximal end of inner core may be terminated distal of port 262. Alternatively the inner core extends proximally but provides clearance for the expansion cable. In yet another embodiment the inner core 301 and the expansion cable 265 are connected proximal of port 262 and the inner core 301 movement is used to tension the expansion cable 265. In another embodiment the inner core 301 distal end is shapeable.

In another embodiment the clot retrieval devices of this invention are adopted for use as embolic protection devices. With this embodiment the delivery catheter is removed after deployment and the guidewire is employed to deliver treatment devices. A greater number of capture fibers are employed and the capture fibers are arranged so as to create distal pores of less than 200 microns.

Another embodiment of the invention is shown in FIG. 44-46 wherein the clot retrieval device comprises a guidewire 330, a clot capture ring 320, and capture fibers 333. With reference to FIG. 44a there is shown a clot capture ring 320 of clot retrieval device 350. The clot capture ring is characterized in that it is cut from a tube and formed. The strut section 321 is shown in its as cut configuration and provides strong vessel apposition. The strut section is attached to the guidewire with a collar element 322. The collar element is cut from the same tube as the strut section 321 but it is formed into a collar after cutting. The collar element 322 comprises at least one finger element 323. The finger element is formed into a tubular segment such that it can be attached to the guidewire. Preferably one or more finger elements wrap around the guidewire diameter and make a secure attachment. Multiple finger elements are preferred over one wide finger element to ensure the device is trackable while distributing forces to the guidewire. The collar element may be welded or bonded to the guidewire. Alternatively the collar element may be a force fit with the guidewire. FIG. 44b shows a view of the collar element 322 and a portion of the strut section 321 in the as cut configuration. In this embodiment pairs of fingers 323 are located on either side of member 326. The collar element 322 is connected to the strut section by a connector element 325. The connector element 325 has a curved interface with the strut section 321. The connector element 325 is designed such that it distributes strain loads it has to endure during collapse and delivery. The curved interface helps to distribute the loads. Preferably the connector element comprises strain distributing features as described. The eyelets 327 are shown on the strut section and these function as previously described.

FIG. 44c shows the clot retrieval device 350 in the expanded configuration mounted on guidewire 330. The guidewire comprises a shaft, a proximal end 331, a distal end 332 and a tip 329. The capture ring 320 is connected to the guidewire adjacent the distal end 332. The capture ring is secured to the guidewire 330 using collar element 322. Capture fibers 333 are attached to the strut section using eyelets 327 and are attached to the distal end of the guidewire at distal attachment point 328. Distal attachment point comprises at least one eyelet in the guidewire. The guidewire may be tubular in this area or at least one micro-hole may be drilled through the wall of the guidewire to create an attachment. Alternatively the capture fibers may be bonded or mechanically fastened to the guidewire.

The clot retrieval device 350 is shown in the collapsed configuration inside the distal lumen of delivery catheter 335 in FIG. 44d. The clot retrieval device is deployed by advancing the guidewire 330 relative to the delivery catheter 335.

FIG. 45a-c shows a variation in the embodiments shown in FIG. 44. This time the connector element 340 is longer than previously described. This allows better strain relief to be achieved in the area of bending during collapse and it also allows the offset of the guidewire position to be controlled. In the embodiment shown the guidewire position is close to the strut frame but there is still a gap between the guidewire and the wall. This partial offset feature allows for a large capture opening.

Another variation of the embodiments described in FIG. 44-45 is shown in FIG. 46. This time an expansion cable 341 is employed to help frame expansion. The device is shown with the expansion cable in the tensioned configuration with the frame expanded into a ring. The expansion cable allows the angle of the ring to the vessel to be controlled by the user. In the embodiment shown the angle is greater than 90'. This makes the resistance of the frame to collapse very difficult during clot capture. The guidewire shaft has a port 342 and an inner lumen 343 through which the expansion cable runs. The proximal end of the expansion cable exits the lumen 343 at the proximal end of the guidewire 331.

With reference to FIG. 47a-d there is shown another clot retrieval device 360 which is constructed from a guidewire 364, capture fibers 365 and a fiber anchor 367. The guidewire comprises a proximal end 363, a distal end 368, a distal tip 369 and a frame section 361. The proximal end of the guidewire 363, comprises a tube section with an expansion cable 362 extending from the frame section 361 to a point proximal and external of the guidewire 364. The proximal end of the guidewire 363, in use, is external of the patient. The expansion cable is attached to the distal end of the distal frame section 371. The distal tip 369 has an atraumatic tip to prevent vessel injury. The frame section 361 further comprises a distal frame section 371 and a proximal frame section 370. The frame section 361 has an expanded configuration and a collapsed configuration. In the collapsed configuration the frame section comprises an elongate element. In the expanded configuration the proximal frame section 370 and distal frame section 371 forms a ring that orients transverse to the axis of the vessel.

In a first embodiment the frame section 361 is a substantially elongate element in its relaxed state. When the expansion cable 362 is tensioned the shape of frame section 361 changes from its relaxed elongate state to its expanded ring configuration. This shape change is controlled by compression slots 375 in the tubular wall of the guidewire shaft 364. The compression slots 375 allow the shaft 364 to compress preferentially on one side and this allows the shaft to adopt a curved configuration. Where all the slots are on one side of the tube then the tube will bend into a simple curve when loaded in compression. Complex curves can be achieved by using multiple slots and moving the position of the slots around the axis of the tube. FIG. 47d shows a section 364 of a guidewire shaft with slots designed to create both simple and complex curves. In the center of the slotted section all the slots 375 are in a line and this construction will allow for a simple curve when the shaft is compressed. At both the proximal and distal end of the section, the slot position changes as we move along the shaft. This creates a curve in two dimensions (Y & Z). In order to create the ring shown in FIG. 47a two complex curves ('a' in FIG. 47d) at either end of a simple curve ('b' in FIG. 47d) are required.

In another embodiment the frame section 361 is ring shaped in its relaxed state. In this configuration the device is collapsed for delivery using a delivery catheter 372. The collapsed device is stored in the lumen of the delivery catheter and advanced across the obstruction. It is deployed distal of the obstruction and opposes the vessel wall. The expansion cable may be employed in order to improve the stiffness of the device in the expanded configuration. Since the expansion cable effectively locks the distal end of the distal frame section 371 to the proximal end of the proximal frame section it greatly increases the resistance of the frame section to collapse.

In another embodiment two or more expansion cables are used. The first expansion cable is used as described above. The second expansion cable is attached to the frame section 361 between the distal frame section 371 and the proximal frame section 370. The expansion cable extends proximally until it enters the lumen of the guidewire 364 proximal of the frame section through a port in the wall. This second expansion cable when tensioned prevents the frame from collapsing distally when capturing clot.

With each of these embodiments the capture fibers 365 are attached to the frame section 361 at the proximal end and to the fiber anchor 367 at the distal end. Preferably the capture fibers 365 are slidably attached to the fiber anchor 367. In one embodiment the capture fibers 365 are connected to the compression slots 375. In another embodiment the frame section 361 comprises eyelets as previously described and the capture fibers are attached to the eyelets. In either scenario the attachment points of the capture fibers 365 are spaced apart along the length of the frame section 361. Preferably the capture fibers 365 are evenly spaced apart along the frame section 361. The fiber anchor 367 at the distal end provides for secure fiber attachment to the distal shaft 368 while allowing the capture fibers 365 to slide at the fiber anchor. The ability of the fibers to slide is important in allowing the frame section to collapse efficiently. Fibers attached to the distal part of distal frame section 371 require very little slack in order to allow that portion of the frame to move from an expanded state to a collapsed state. However, fibers at the proximal end of the proximal section of the frame 370 require considerable slack in order to allow that portion of the frame to collapse unconstrained. In order to minimize the amount of capture fiber 365 slack it is preferred that fibers connected to the distal section of the distal frame section 371 be looped through the fiber anchor and connected back to the proximal end of the proximal frame section 370. By taking this approach throughout the frame the level of capture fiber slack can be minimized. It will be appreciated that in order to allow for this fiber slack to be distributed the fibers need to slide through the fiber anchor with ease. Preferably the size of the opening on the distal anchor for fiber attachment is a clearance fit for the capture fibers. In one embodiment the anchor 367 comprises a ring with an inner diameter. The inner diameter is larger than the diameter of the guidewire and one or more attachment legs 376 fix the ring relative to the guidewire.

FIG. 48*a* shows a clot Retrieval device 800 in the expanded state. FIG. 48*b* shows the same device loaded into a microcatheter 812 for delivery to the target site. Frame 804 is similar to frame 361 in FIG. 47*a*, but in this case is not formed from the guidewire. Frame 804 expands to a generally circular shape in end view, but elongates and twists into a longitudinal element when collapsed for delivery and retrieval as shown in FIG. 48*b*. The proximal 807 and distal 806 ends of the frame 804, are mounted to tubular elements 808 and 805 respectively. These elements are mounted on the guidewire 809, allowing rotation and translation of the frame relative to the guidewire. Stops 801, 802 and 803 are positioned on the guidewire to allow the user to apply a push or pull force to appropriate elements of the device to facilitate its advancement or withdrawal. Stop 803 prevents the frame from elongating during clot retrieval, and together with stop 802 acts against the frame during clot capture and retrieval. Stop 802 apposes element 805 during device advancement through and from a delivery microcatheter 812 as shown in FIG. 48*b*. Apposing the distal end of the frame in this way keeps the frame 804 in tension rather than compression as would be the case if force were applied to element 807 to facilitate advancement. Keeping the frame in tension reduces the lateral forces applied to the lumen of the microcatheter, and thus reduces the force required to advance the clot retrieval device through the microcatheter. In one embodiment of this design a delivery assist catheter 811, with proximal element 810, may be used to transmit a push force to stop 801, which in turn transmits a push force through the guidewire to stop 802 and thus to the distal end of the frame. This method of advancement eliminates the need for that element of the guidewire proximal of stop 801 to transmit push, and therefore permits the use of a more flexible wire. In another embodiment (not shown) stop 801 is not present and delivery assist catheter 811 is not required as push force can be transmitted through the guidewire to stop 802 and thus to the frame.

FIGS. 49*a*-*b* illustrate another clot retrieval device 850 similar to device 360 shown in FIG. 47*a*, but employing an additional tether element 853. Frame 851 is configured to tend to adopt a curved profile and appose the vessel wall when released from the constraints of the delivery microcatheter 854 shown in FIG. 49*b*. When placed in tension the tether element 853 provides additional integrity to the frame, and acts against the tendency of the frame to elongate when meeting resistance such as during clot capture. Once the target clot has been successfully captured the tether element may be relaxed so as to allow the frame to elongate again for ease of retrieval. Alternatively the tether element may be kept in tension to maintain the frame and capture net 852 in a more preferential configuration for retention of captured clot during retrieval from the body.

FIGS. 50*a*-*c* show another clot retrieval device 870. FIG. 50*a* shows the device in its deployed state. Frame 871 is connected to guidewire 875 by element 873, which allows the frame to rotate and translate relative to the guidewire. Distal capture net 872 is connected to frame 871 and is also connected at its distal end to collar 874. FIG. 50*b* shows the device encapsulated in microcatheter 878 just prior to deployment from the microcatheter. To effect deployment the guidewire 875 on which the device is mounted is fitted with a stop 877, which apposes collar 874 when the microcatheter is retracted, preventing the clot retrieval device from retracting with the catheter. This configuration also holds the capture net in tension, with the associated benefits described previously in relation to FIGS. 48*a* and *b*. In the embodiment shown a second guidewire stop 876 is provided, which apposes proximal frame element 873 during retraction and retrieval of the device. Such a design allows the length of guidewire protruding distal to stop 877 to be limited or eliminated. In another embodiment (not shown) only one guidewire stop is provided which acts in both deployment and retrieval.

FIG. 51*a* shows a clot retrieval device 890 configured in such a way that it may be used in conjunction with a variety of suitably sized guidewires 891. The device 890 has a shaft 892 which is sized to be able to advance or retract over guidewire 890. FIG. 51*b* shows a similar device 894 mounted on a shaft 895 which has a guidewire exit port 896, so that the device may be used with any suitably sized short length guidewires.

FIG. 52*a* shows a clot retrieval device 2010. The clot retrieval device 2010 comprises guidewire 2020 and a clot capture basket 2011. The clot capture basket comprises a frame 2012, and a net 2015. The clot retrieval device 2010 has an expanded state for engagement and capture of clots and a collapsed state for delivery through the vasculature. The frame 2012 comprises a collar 2023 for mounting the frame 2012 on the guidewire 2020, a hoop 2014 composed of struts 2009 and at least one connector element 2013 to connect the collar 2023 and the hoop 2014. Preferably the frame 2012 is made from a superelastic or shape memory material. The frame further comprises a bifurcation point 2022 where the connector 2013 splits to form two struts 2009. In this embodiment the connector 2013 has greater width than the struts 2009. In another embodiment the connector 2013 has greater width over most of its length than tha strut 2009 except in the region just proximal to the bifurcation. In this area the width of the connector 2013 is significantly reduced. This allows the connector 2013 to hinge at this point and so respond to vessel asymmetry or asymmetry in the guidewire access.

In one embodiment the clot capture basket 11 is fixed to the guidewire. In another embodiment the clot capture basket 2011 is slidable on the guidewire 2020.

FIG. 53 shows another clot retrieval device 2010 which is almost identical to the clot retrieval device of FIG. 2002 except that the connector comprises a pair of parallel struts 2025. The pair of parallel struts 2025 allows the connector to contribute strongly to the engagement force of the device while providing greater lateral flexibility. The capture basket 2011 further comprises a basket mounting tube 2019. The basket mounting tube 2019 extends from the proximal end of the basket 2011 to the distal end of the net 2015. The net is attached to the mounting tube 2019. The mounting tube may be fixed relative to the collar 2023 or it may slide relative to the collar 2023. The distal end of mounting tube is configured to engage with the stop 2017.

FIG. 54 shows a frame 2012 of FIG. 52 as a subcomponent. The frame 2014 comprises three segments; the proximal segment comprises a collar 2023 which is a short tube for mounting on the guidewire 2020, the intermediate segment comprises two connectors 2013 and the distal segment comprises a plurality of struts that form a hoop 2014. Ideally there are four struts that each form a quadrant of the hoop. The frame 2014 is preferably made from a super elastic or a shape memory alloy.

FIG. 55 shows another clot retrieval device 2030, which is similar to the clot retrieval devices of FIG. 52-54, and similar numerals are used to describe similar elements. The clot retrieval device is shown with a microcatheter 2031. The clot retrieval device is delivered through the lumen of a microcatheter and is moveable relative to the microcatheter 2031. The movement of the clot retrieval device 2030 relative to the microcatheter is effected by the movement element 2019. In one embodiment movement element 2019 comprises a tubular element which is slidable over the guidewire. The tubular element may be fixed to the collar 2023 of the capture basket 2011 and can thus control movement of the capture basket 2011 in both directions relative to the guidewire or the microcatheter. Alternatively the tubular element 2019 is separate fro the capture basket and advances the capture basket as a bumper tube. With this embodiment the bumper tube can advance the clot capture basket 2011 but can not withdraw the basket. In this embodiment the capture basket is withdrawn by engaging the step at the distal end of the guidewire.

Alternatively the movement element 2019 is a guidewire. With this embodiment the capture basket 2011 if fixed to the guidewire 2019 and thus movement of the capture basket is controlled by the guidewire. Forward and backward movement of the capture basket 2011 are controlled by the guidewire 2019.

FIG. 56 shows another clot retrieval device 2040, which is similar to the clot retrieval devices of FIG. 52-55, and similar numerals are used to describe similar elements. With this embodiment the capture basket 2011 is deployed from a reception space 2046 at the distal end 2047 of the microcatheter 2041. The guidewire 2020 is moveable relative to the capture basket 2011. The microcatheter is connected to the capture basket 2011 by a telescoping tube 2048 which is fixed the collar 2023. The telescoping tube 2048 further comprises a stop 2043 which engages with a microcatheter stop 2044 to prevent complete separation of the basket 2011 and the microcatheter 2041. A bumper tube (not shown) is used to deploy the capture basket 2011 from the reception space 2046. The capture basket 2011 is removed at the end of the procedure by withdrawing the guidewire 2020 so as to engage the guidewire distal stop 2017 with the body tube 2021. This forces the telescoping tube 2048 and the capture basket back into the reception space for removal.

FIG. 57 shows another clot retrieval device 2060, which is similar to the clot retrieval devices of FIG. 52-56, and similar numerals are used to describe similar elements. With this embodiment a bumper tube 2048 is used to advance the clot capture basket 2011 over the guidewire. The bumper tube further comprises a rapid exchange feature. The bumper tube comprises a lumen with a proximal exit port 2061 from which the guidewire exits. A control element 2063 is connected to the proximal end of bumper tube 2048. The control element 2063 extends proximal of the microcatheter 2041 and out of the patient. The user controls the position of the clot capture basket 2011 using a control handle 2065 at the proximal end 2064 of the control element 2063.

FIG. 58 shows another clot retrieval device 2080, which is similar to the clot retrieval devices of FIG. 52-57, and similar numerals are used to describe similar elements. With this embodiment a tether 2042 extends between the collar 2023 of the capture basket 2011 and the microcatheter 2041. The tether 2042 has a relaxed configuration as shown in FIG. 58a and a taut configuration as shown in FIG. 58b. The proximal end of the tether 2042 extends proximally. In one embodiment the tether 2042 is controlled by the user. In another embodiment the proximal end of the tether 2042 is connected to the microcatheter. The tether 2042 allows the capture basket 2011 to move relative to the microcatheter within a certain limit.

FIG. 59a-h shows the devices as described in FIG. 52-58 and similar numerals are used to describe similar elements. FIG. 59a-h also shows some of the methods of use of the clot retrieval devices described in the earlier drawings. These figures also disclose a clot debonding device 2091, which may be used in conjunction with the clot retrieval designs described herein. The clot debonding device is designed to assist in the removal of obstructions from a vessel by providing an abutment surface which may be used to appose one side of the obstruction so that a force may be applied to the other side of the obstruction without said force being transmitted to the vessel in which the obstruction is placed. It therefore enables a clot retrieval device or other similar device to more effectively engage and capture clot or other such vessel obstructions.

It will be appreciated that such a device also has applications beyond its use with the clot retrieval device described herein. Such a clot debonder may be effectively used to aid the disengagment and removal of vessel obstructions in conjunction with other clot retrieval devices or with thrombectomy devices or aspiration devices.

FIG. 59a shows a guidewire 2020 with a step 2017 at its distal end. The tip of the guidewire is placed in a vessel (not shown) distal of an occlusive clot (not shown). In FIG. 59b a microcatheter 2041 is advanced over the guidewire 2020 until its tip is also distal of the occlusive clot. A clot retrieval basket 2011 is advanced through the lumen of the microcatheter 2041 in FIG. 59c. In FIG. 59c the clot capture basket 2011 is being advanced using the distal end of a clot debonding device 2091. The clot debonding device 2091 comprises an expandable engagement element 2093 at its distal end. The expandable engagement element 2093 has an expanded configuration for engaging with a clot and debonding the clot and a collapsed state for delivery through a microcatheter. The expandable engagement element 2093 comprises a number of struts or wire segments 2094. In one embodiment the clot debonding element is cut from a hypo tube and the struts are expanded to the desired expanded shape and heat treated to remember that shape. Preferably the expandable engagement element 2093 is made from a shape memory alloy, a super elastic alloy. In one embodiment the expandable engagement element 2093 is made of Nitinol. The clot debonding device 2091 comprises a lumen extending from its distal end. The expandable engagement element 2093 comprises a channel or a lumen in both the expanded and collapsed states. In one embodiment the struts or wires of the expandable engagement element 2093 assume a collapsed state which maintains a channel (or lumen) over the distal end of the expandable engagement element 2093. In another embodiment the expandable engagement element 2093 comprises a collar 2095 and said collar comprises a lumen.

The clot debonding device 2091 further comprises aproximal shaft 2096. The proximal shaft 2096 is connected to the expandable engagement element 2093 and facilitates advancing and withdrawing the expandable engagement element 2091. In one embodiment the proximal shaft is connected directly to the expandable engagement element 2093. In another embodiment the proximal shaft 2096 is connected to the collar 2095 which in turn is connected to the expandable engagement element 2093. In one embodiment the expandable engagement element is integral with the collar 2095. In another embodiment the expandable engagement element is integral with the proximal shaft 2096. The proximal shaft 2096 comprises a lumen 2099 which is connected with the lumen or channel of the expandable engagement element and extends proximally to an exit port 2100. In FIG. 59 the exit port is shown at the proximal end of the shaft 2096. However, it will be appreciated that the exit port could be distal of the proximal end of the shaft 2096. The exit port may be towards the distal end of the shaft 2096. In one embodiment the exit port comprises an opening in the sidewall of the shaft. In another embodiment the shaft 2096 comprises a construction of at least two elements. The distal element comprises a tubing with a lumen and the proximal end comprises a connector element to connect the user with the distal lumen.

In one embodiment (not shown) the clot capture basket is advanced with a bumper tube which is removed upon deployment. When the clot capture basket 2090 is deployed distal of the occlusive clot then the clot debonding device is advanced over the proximal section of the guidewire 2020 and through the lumen of the microcatheter 2041 and it is deployed proximal of the occlusive clot. With this embodiment the rest of the procedure is as described in FIG. 59*a*-59*h*.

The clot debonding device 2091 comprises an engagement surface. The engagement surface is configured to engage with clot and comprises an expanded state and a collapsed state. The engagement surface is configured to achieve a low profile in the collapsed state and it is further configured to be highly trackable such that it can easily navigate the pathway to tortuous neurovascular vessels. In one embodiment the engagement surface comprises a substantially tubular structure for advancement through the vasculature in the collapsed state. Preferably in the collapsed state the tubular structure comprises a short tubular structure. The engagement surface in one embodiment comprises a cylindrical surface in the collapsed state.

In the expanded state the engagement surface is preferably configured for the transmission of force or pressure to the clot. The engagement surface may comprise an annular surface. With this embodiment the engagement surface has an outer diameter and an inner diameter. In one embodiment the outer diameter is sized to be similar to the diameter of the vessel or to the diameter of the clot and the inner diameter is similar in diameter to the dimensions of the guidewire 2020.

In one embodiment the engagement surface comprises a flared surface. In another embodiment the engagement surface comprises a plurality of struts said struts configured to apply pressure to the clot over a substantial portion of the cross-section of the vessel. In one embodiment the engagement surface of the clot debonding device is configured to apply an axial displacement to the entire body of the clot. Preferably the engagement surface of the clot debonding device is configured to displace the clot without fragmenting the clot.

In one embodiment the engagement surface comprises a plurality of elongate struts. In the delivery configuration the elongate struts are substantially aligned with the axis of the vessel while in the expanded configuration the struts project radially outward from the axis of the vessel. In one embodiment the struts are connected to each other. In one embodiment the struts of the engagement surface comprises an outer ring member and a plurality of radial struts connected to said outer ring member. In another embodiment the strut arrangement of the engagement surface comprises a plurality of cells. In another embodiment the engagement surface comprises an outer ring member and an inner ring member.

The inner ring member may be connected to or separate of the outer ring member. In one embodiment the outer ring member is connected to the collar 2095 by a plurality of radial struts. In one embodiment the outer ring member comprises a plurality of zig zag strut elements. In one embodiment the struts are cut from a tube and the tube comprises an 'as cut' configuration and an expanded configuration.

In another embodiment the engagement surface comprises a plurality of wires. The wires comprise a collapsed state and an expanded state and in the collapsed delivery state the wires are substantially aligned with the axis of the vessel. In the expanded state the wires project radially outwardly of the axis of the clot debonding device. In this or in any of the other embodiments the engagement surface may expand concentrically about its axis, or may take up an eccentric configuration.

FIG. 59*d* shows the clot capture basket 2090 in its deployed state distal of the occlusive clot. The deployment is effected by advancing the clot debonding device 2091. The expandable engagement element 2093 abuts the collar 2023 of the basket 2090 and deploys the basket 2090. The expandable engagement element 2093 remains in the collapsed state at the distal end of the microcatheter 2041. The microcatheter 2041 is withdrawn until its distal end is proximal of the occlusive clot.

With reference to FIG. 59*e*, the system further comprises a tether 2092 which limits the movement of the clot retrieval basket relative to either the microcatheter 2041 or the clot debonding device 2091. In the embodiment shown the tether 2092 is attached to the clot debonding device 2091. As the microcatheter 2041 is withdrawn the distance between the clot engagement device and the microcatheter 2041 increases until all the slack in the tether 2092 is removed.

With reference to FIG. 59*f*, the tip of the microcatheter is proximal of the occlusive clot, the basket 2090 is deployed distal of the clot and the expandable engagement element 2093 is deployed. This is achieved by advancing the proximal shaft 2096 relative to the microcatheter 2041. Upon deployment the struts or wires 2094 of the expandable engagement element 2093 expanded to their remembered expanded state. The guidewire is now moved proximally until the step engages with the clot capture basket 2090 and then both the basket 2090 and guidewire 2020 move proximally until the basket frame 2012 engages with the distal side of the occlusive clot. At this point the clot debonding device is advanced until the expanded struts 2094 engage with the proximal side of the occlusive clot. With the occlusive clot engaged at both ends the clot debonding device is advanced while holding the capture basket 2090 steadfast. This breaks the bonds between the clot and the vessel without applying any force to the distal vessels. This arrangement ensures that most of the forces of clot debonding are contained in the segment of the vessel where the clot is adherent. This is usually a segment of a few millimetres and the forces applied are shear forces rather than tensile forces. It may be necessary to adjust the position of the basket 2090 during the debonding step to continue to keep vessel tensile forces very low.

It will be appreciated that in order to remove an occlusive clot from a vessel that two sets of forces need to be dealt with. Firstly there is a blood pressure drop that lodges the clot in the vessel. More importantly, the presence of an initial clot results in platelet activation and inflammation at the site. During the inflammatory response a complex series of reactions are occurring including the cross linking of blood soluble fibrinogen into fibrin (a blood insoluble macromolecule that is the main component of clot) and the formation of platelet bridges. These reactions result in the progressive formation of chemical bonds between the clot and the vessel wall. Over time the clot becomes more rigidly fixed or bonded at the site of occlusion. In order to break these bonds a force needs to be applied and as the inflammation process progresses these bonds become more difficult to break. Furthermore, where a mechanical force is applied to the clot there is automatically a reaction force which is equal in size but acting in the opposite direction. With conventional devices this force is absorbed by the vessel. It is an object of this invention to prevent significant force being applied to the vessel during clot debonding.

In another embodiment the clot debonding device 2091 is deployed in the clot and a first portion of the clot is debonded from the vessel wall. It will be appreciated that this step could be repeated until all the clot has been debonded and captured in the clot capture basket 2090.

In an alternative method both the clot capture basket 2090 and the clot debonding device 2091 are both engaged with the occlusive clot as described above. Then the clot capture basket 2090 is pulled proximally while the clot debonding device is held steadfast. Which ever method is employed one element (either the clot debonding device, or the clot capture basket) is held steadfast and this element absorbs the reaction forces of clot debonding and thus prevents force being transmitted to the vessel.

With reference to FIG. 59g, after the clot has been debonded and captured in the clot capture basket 2090 the clot debonding device 2091 can be collapsed. This is achieved by pulling the device proximally such that the microcatheter tip collapses the struts 2094 of the expandable engagement element 2093. As the clot debonding device 2091 is pulled proximally the tether 2092 becomes taut and the clot capture basket is also drawn proximally.

In FIG. 59h the clot debonding device is withdrawn to the point where at least a portion of the frame 2012 of the clot capture basket 2090 is inside the distal end of the microcatheter 2041. The clot debonding device 2091 and the clot capture basket 2090 can be withdrawn from the patient at this point. Because of the tether between the clot debonding device 2091 and the capture basket 2090 the clot capture basket 2090 can be removed without removing the Guidewire 2020. The guidewire 2020 is left behind (not shown) for a final angiogram before also being removed if no further intervention is required.

FIGS. 60a-b show end views of the clot debonding devices of this invention. The clot debonding element 2110 of FIG. 60a comprises a lumen 2113 sized to accommodate a guidewire, a plurality of struts or wires 2111 which have an expanded state and a collapsed state, and a tubular element 2095. In the expanded state the struts or wires 2095 project at least partially radially outward with respect to the tubular member. In the collapsed state the struts or wires 2095 assume a somewhat tubular configuration when collapsed inside a microcatheter. In the collapsed state the struts or wires are substantially aligned with the longitudinal axis of the microcatheter and comprise a channel or lumen that can accommodate a guidewire. The pattern of the expandable portion 2112 can be varied greatly. In the figures shown two patterns are shown. However it will be appreciated that a myriad of other patterns are possible. These patterns may comprise some of the following elements: Single struts, bifurcated struts, bifurcated wires, struts or wires with curved segments, curved struts or wires with points of inflection, struts or wires connected with tethers, struts or wires that are configured to create a closed cell, a combination of at least one open and one closed cell, closed cells with multiple curved segments, struts or wires configured to create a cell with multiple curved segments, struts or wires configured to create a planar cell, and/or struts or wires configured to create anon-planar cell.

The pattern of the clot debonding element 2110 of FIG. 60a has overlapping wires. The use of crossing wires provides for better engagement with the clot. In this case the wires over lap to achieve the cross. However where the struts are cut from hypotube, junctions can be created without the need to cross the wires, as shown in the pattern in FIGS. 62a-c.

FIG. 60b shows a pattern with no cross overs. This pattern may be manufactured from a hypotube. In the fully expanded state the clot debonder may comprise an outer rim 2116. With the embodiment shown in FIGS. 60a and 60b the outer rim 2116 comprises a plurality of curved segments. Each pair of radially projecting struts 2095 meet at their distal end and this region is characterised in that it comprises a curved atraumatic region. This curved region is preferably curved in the circumferential direction.

FIGS. 61 a-c show another clot debonder pattern 900 which features multiple longitudinal slots 902 which enable the distal end of tubular element 901 to expand radially outward to create an abutment surface as shown in side view in FIG. 61b and in end view in FIG. 61c. Tubular element 901 is preferentially cylindrical, and may be made from either a metallic or polymeric material, but preferentially metallic, and most preferentially nitinol.

In one embodiment the engagement surface comprises an axial strut segment 903, a curved strut segment 904 and a radial strut segment 905. With this embodiment the engagement surface 906 is connected to a tubular member 901 at its proximal end. The axial strut section 903 defines the expanded configuration the struts of the axial segment 903 are oriented substantially parallel to the axis of the clot debonding device. However the axial segment 903 is preferably extremely short. Immediately distal of the axial segment 903 comprises the curved segment 904. In the expanded state this segment is curved such that the struts assume a radial configuration. The radial section 905 preferably comprises most of the engagement surface 906 and provides a high area surface for the transmission of force to the clot.

It will be appreciated that the clot debonding element is designed to transmit force over the entire surface of the clot and this ensures that the clot is debonded in one piece. The clot debonder is further configured such that the clot does not snag on its surface and it is further configured to push the clot into the opening of the clot capture basket.

The clot debonder engagement surface is configured such that upon withdrawal it disengages from the clot without snagging, or fragmenting the clot and without removing the clot from the capture basket.

In another embodiment the engagement surface 906 of FIG. 61*a-c* comprises a plurality of wires. With this embodiment the engagement surface 906 comprises an axial wire segment 903 which is connected to the collar 2095. Preferably the connection between the wire and the collar is configured so as to orient the wire parallel to the axis of the clot debonding device. While the connection point with the collar is aligned with the axis of the vessel the segment of the wire immediately distal of the collar (curved wire segment) comprises a curve in the expanded configuration. The wire is curved no as to orient the wire radially and create an abutment surface. The intermediate segment of the wire is distal of the curved segment and is characterised in that the wire is substantially radial relative to the axis of the clot debonder. This plurality of radial wire segments is configured to deliver and distribute pressure to one face of the clot. The distal segment of the wires comprises a second curved segment 908. This second curved segment 908 defines an outer rim 2116 of the clot engagement surface 906. The curved segment 908 also presents an atraumatic surface to the vessel. This second curved segment 908 is curved in the circumferential direction.

In one variation the engagement surface 906 comprises a plurality of first wires and a plurality of second wires and said first and second wires are connected at the distal most point. In the embodiment described above said first and second wires may be integral and may comprise a single formed wire. With this embodiment the wire engagement surface comprises a plurality of petal like engagement elements. Each petal comprises a radial clot engagement element and a circumferential clot engagement element. Because the engagement surface 906 comprises radial and circumferential engagement elements force is transmitted to the surface in a manner similar to that of a piston.

In another embodiment the struts or wires of the engagement surface 906 comprise an articulation region. With this embodiment the engagement surface 906 assumes the expanded state by an articulation of the struts or wires about the articulation region.

FIG. 62*a-e* shows side views of a number of clot debonding devices. These devices could be employed with any of the clot retrieval devices described in FIG. 52-59 or FIG. 79-80. FIG. 62*a* shows a colt debonding device 2126 wherein the device comprises an expandable portion 2112, a collar 2095 connecting said expandable portion 2112 with the tubular member 2114. In use the tubular member 2114 extends from the site of occlusion proximally through the vasculature and extends outside the patient such that it can be manipulated by the user. The tubular member comprises a lumen 2113 extending over its entire length.

FIG. 62*b* shows an alternative configuration of the clot debonding device 2115. This device also comprises an expandable section 2112, struts or wires 2111, a connecting collar 2095 and a tubular member 2114. In this case the tubular member 2114 is shorter than in FIG. 62*a*. In use the tubular member extends from the site of occlusion only partially through the vasculature. In this case the user controls clot engagement using the connector element 2117. The connector element 2117 if fixed to the tubular member 2114 at an attachment point 2119. The lumen 2113 of the tubular member 2114 is sized to accommodate a guidewire. This embodiment has the advantage of providing single user wire exchange (a rapid exchange feature).

FIG. 62*c* shows an alternative configuration which is similar to that of FIG. 62*b* except that no collar is employed. The tubular member 2114 is connected directly with the expandable section 2112. The proximal end of tubular member 2114 comprises an exit port 2120 to facilitate rapid exchange delivery. FIG. 62*d* shows an alternative configuration which is similar to that of FIG. 62*b* except that no tubular member is employed. In this case the connector element 2117 is connected directly with the collar 2095.

FIG. 62*e* shows yet another configuration which is similar to that of FIG. 62*d* except that no collar is employed. The connector element 2117 is connected directly with the expandable section 2112.

FIGS. 63, 64 and 65 show three designs of clot debonders that can alter the shape of their distal ends to create an abutment surface to facilitate capture of clot into a clot retrieval device. FIG. 63*a* shows device 910 with an inflatable distal cuff 911, which is shown in the inflated state in FIG. 63*b*. Inflation may be with a liquid, such as saline or contrast media or a mix of the two, or may be with a gas such as carbon dioxide. The inflating media is injected from the proximal end of the device through a lumen (not shown) in the wall of tube 912.

FIG. 64*a* shows device 920 with an expandable section 924, which is shown in the expanded state in FIG. 64*b*. The expandable section 924 is formed from wound or braided elements, which form a structure which tends to increase in diameter when compressed, and reduce in diameter when elongated. Expansion of this cuff is effected by advancement of outer member 921 relative to inner member 922, which is connected to the distal end of the expandable section by means of distal cuff 923. Retraction of outer member 921 reverses the effect by elongating the expandable section and reducing it to its original diameter.

FIG. 65*a-b* show a clot debonder 915 with an expansile distal cuff 916 of a similar design to that of device 920, but in which no actuation is required to effect the expansion. The expansile distal cuff is configured to preferentially adopt the expansile state depicted in FIG. 65*b*, and is held in the unexpanded state by the constraint provided by the lumen of the catheter (not shown) through which it is advanced to the target site.

FIGS. 66 and 67 show two examples of self-expanding clot debonders that expand upon advancement past the end of an outer constraining surface such as that of the lumen of a microcatheter 926. Debonder 925 is shown in the constrained state in FIG. 66*a*, in the partially expanded state in FIG. 66*b*, and in the fully expanded state in end view in FIG. 66*c*. FIGS. 67*a* and *b* show a similar design to FIG. 66, wherein an additional element is employed to create a greater abutment surface area and perimeter.

FIGS. 68*a-c* show views of another clot debonding device, which could be employed with any of the clot retrieval devices described herein. FIG. 68*a* shows a side view of the debonder 950 in its unexpanded state. FIG. 68*b* shows a side view of the debonder in a partially expanded state. FIG. 68*c* shows an end view of the debonder in its fully expanded state. Device 950 contains multiple expandable portions 952, created by the addition of a plurality of longitudinal slots 953 to tubular member 954. An actuating element 951 is attached to the distal end of member 954, and runs within member 954 from the distal to the proximal end of the device. Retraction of the actuating element applies a compressive force to expandable portions 952 defined by slots 953.

Controlled buckling of areas 956 is facilitated by the presence of crease lines 956. Tubular member 954 may be configured in a similar manner to member 954 in FIG. 62*a* or FIG. 62*c*, such that the debonder is used as an "over the wire" or "rapid exchange" device. In one embodiment the clot debonder lumen 955 is sized so that it may be advanced through a pre-placed access microcatheter to the target site. In another embodiment the clot debonder lumen 955 is sized so that it may be backloaded onto a microcatheter prior to insertion of the microcatheter, and can then be advanced over the microcatheter to the target site.

FIGS. 69*a* and 69*b* show the clot debonder 950 depicted in FIG. 68 in use in conjunction with a clot retrieval device 961 and microcatheter 963. FIG. 69*b* shows the clot debonder advanced past the end of the microcatheter 963 and the actuator 951 retracted to expand the expandable distal area 952, which is shown in abutment with clot 962 just prior to retrieval of the clot into the clot retrieval device 961.

FIGS. 70-73 show the clot retrieval device of FIGS. 12 and 13 being used in conjunction with clot retrieval assist device 119. With this embodiment the clot retrieval device 91 is delivered across the obstructive clot and deployed as previously described. The clot retrieval assist device is delivered over the proximal section of the guidewire 92 until its distal tip is proximal of the obstructive clot. The clot retrieval assist device comprises a catheter 116 with a lumen, an expandable element(s) 117 wherein the expandable element 117 comprises a wire frame 118 that defines an inner space 132. The wire frame 118 has a remembered expanded configuration and a collapsed delivery configuration. In one embodiment the wire frame 118 defines an inner space 132 that has a paddle like expanded shape. In another the wire frame defines a circular inner space 132. In another embodiment the wire frame 118 defines a kidney shaped inner space 132. With the clot retrieval assist device 91 proximal of the occlusive clot 103 the expandable element 117 is deployed. The size of the expanded element 117 is controlled by the degree of deployment. When the expandable element 117 is at least partially deployed it is advanced against the occlusive clot 103 and forces the clot 103 into the clot retrieval device 91. In another embodiment the clot retrieval assist device 119 is held stationary with its expandable element 117 in the at least partially expanded state and clot retrieval device 91 is advanced proximally to capture the occlusive clot 103.

In another embodiment the clot retrieval device comprises a frame 94 a proximal collar 93 and a distal collar 90 and two connector elements 99. The proximal 93 and distal 90 collars are associated with the guidewire 92 and the connectors 99 connect the proximal and distal collars to the Guidewire 92. At least one of said proximal and distal collars is slidable relative to the guidewire 92.

FIG. 74 shows an alternative clot retrieval assist device 110. With this device 110 the expandable element 113 comprises a helical element and is attached to inner shaft 112. In the delivery configuration inner shaft 112 is retracted and both the inner shaft and expandable element 113 are housed inside the lumen of delivery catheter 111. With this embodiment advancement of the clot may be achieved by pushing as described with FIG. 19 or alternatively by rotation. With the rotation embodiment the expandable element 113 is either deployed in the body of the occlusive clot 103 or it is advanced in its expanded state until it is in the body of the occlusive clot. The inner shaft is rotated and the helical frame acts like an auger to move the occlusive clot into the clot retrieval device 91.

An alternative clot retrieval assist device 110 is shown in FIG. 75. With this device the expandable element 113 comprises multiple coil elements. An inner helical element 115 and outer element 114 are both connected to inner shaft 112 and rotation of inner shaft 112 rotates both coil elements.

Yet another clot retrieval assist device 120 is shown in FIG. 76*a* and FIG. 76*b*. The clot retrieval device is delivered over the proximal end 127 of guidewire 92. The clot retrieval assist device comprises an inner shaft 122, an expandable element 123 and a delivery catheter (not shown). The expandable element 113 comprises a wire formed into a spiral. The spiral has a gradually increasing diameter. An inner coil of the spiral 124 has a smaller diameter than outer coil 125. In the expanded configuration the clot retrieval assist device 120 is advanced distally over the guidewire 92 and the expandable element 113 engages the obstructive clot 100 and forces the clot 100 into the clot retrieval device 91. Alternatively the clot retrieval device 91 may be advanced proximally while the clot retrieval assist device 120 remains stationary and limits the proximal movement of the clot 100 and thus forces the clot into the clot retrieval device 91.

An alternative clot retrieval system is shown in FIG. 77*a-b*. The clot retrieval system 2160 comprises a clot capture basket 2154 mounted on a guidewire 2162. The clot retrieval system 2160 further comprises a clot debonding element 2161 mounted on the guidewire 2162. The clot capture basket 2163 comprises a frame 2164 a collar 2168 mounted on the guidewire 2162 and at least one connector 2167 connecting the collar 2168 with the frame 2164. The frame 2164 comprises one or more pairs of struts 2166. In one embodiment the struts comprise a series of net attachment points 2175. The attachment points 2175 comprise a change in the cross section of the strut 2166 and provide a location for the attachment of a fibre of the net 2163 to the frame 2164. In one embodiment the attachment point 2175 comprises an eyelet. In another the point of attachment comprises a recess or a nick, or a reduction in the strut dimension.

The collar 2168 may be fixedly mounted on the guidewire 2162. In the embodiment shown the collar 2168 is rotationally mounted on the guidewire 2162. This is achieved by the use of a proximal stop 2170 and distal stop 172 mounted on either side of the collar 2168. The capture net 2163 is connected to the guidewire distal of the collar 2168. In one embodiment a distal collar 2169 is employed to provide an attachment point between the net 2163 and the guidewire 2162.

The frame 2164 has a collapsed state and an expanded state and in the expanded state (shown) comprises a hoop 2165. The hoop 2165 allows the frame to effectively engage with the outer bonded surface of the clot. The hoop 2165 is created by constructing that portion of the frame with at least one pairs of struts 2166. The pairs of struts form segments of a hoop 2165 in the expanded state but lay adjacent each other and parallel to the guidewire in the collapsed state.

The clot debonding element comprises at least one strut 2173 and it also has an expanded configuration (shown) and a collapsed configuration. In the collapsed state the struts 2173 of the clot debonding element 2161 lie adjacent and substantially parallel to the guidewire 2162. The at least one strut 2173 comprises a strut distal end 2178 and a strut proximal end 2177. At least one of said distal 2178 and proximal 2177 strut ends is slidable relative to the guidewire 2162. Furthermore, at least one of said distal strut ends 2178 or proximal strut ends 2177 are restricted from rotational motion relative to the guidewire 2162. The ability of at least one strut end to slide relative to the guidewire provides a first means of allowing the clot debonding element to assume an expanded configuration when not constrained. On the other hand preventing at least one strut end from rotating relative to the guidewire 2162 allows torque transmitted from the proximal end of the guidewire to be applied to the occlusive clot 2001 and debond said clot from the vessel wall 2002.

In the collapsed state both the basket and the clot debonding element collapse inside a microcatheter 2041 (not shown) in a fashion similar to that described earlier.

It will be appreciated that the clot debonding element as described with reference to FIG. 77 could equally be employed with any of the baskets described in any of the other clot capture basket devices of the invention.

With reference to FIG. 78 there is shown a schematic representation of a vessel with an acute occlusion with a piece of thrombus (clot). The clot may be embolic in origin or it may be thrombotic. Embolic occlusions of cerebral vessels are responsible for between 20% and 35% of all strokes. Embolic strokes are most frequently of cardiogenic origin with carotid and aortic disease also being major contributors. Thrombotic occlusions occur when thrombus forms in the vessel usually in response to underlying vascular disease. Thrombotic occlusions are responsible for between 45% and 50% of all strokes. The acute occlusion 2001 of FIG. 78*a* is fixed in the vessel 2002 primarily by the forces of blood pressure acting on the proximal side and force fitting it in a tapered vessel 2002.

However, the presence of the clot causes an inflammatory response at the site and platelets 2003 in the area are activated (FIG. 78*b*). The inflammatory response results in the formation of more thrombus and bonds 2004 start to form between the occlusive thrombus 2001 and the vessel wall 2002. Over time the bonding forces between the clot and the vessel wall become more significant and make removal of the clot more difficult. FIG. 78*c* shows a schematic representation of the occlusive clot 2001 after a time has passed with further thrombus deposited at the site and bonds 2004 formed between the clot 2001 and the vessel wall 2002.

FIG. 79*a*-I shows a method of using the devices of this invention. FIG. 79*a* shows a vessel 2002 with an occlusive clot 2001. The vessel 2002 has a proximal end 2005 and a distal end. The procedure to treat the occlusion per this invention comprises firstly gaining access to the vasculature. This is carried out by conventional means (the Seldenger technique). A guide catheter is placed in a large vessel proximal of the occlusion (not shown). A procedural guidewire 2020 is advanced through the guide catheter or sheath and is advanced across the occlusive clot 2001 as in FIG. 79*b*. When the guidewire 2020 is in place a microcatheter is advanced over the guidewire until the tip of the microcatheter is across the occlusion (FIG. 79*c*). As can be seen with reference to FIG. 79*d* the guidewire 2020 is now removed thus leaving the microcatheter 2041 in place with its tip 2047 across the occlusion 2001 and an empty lumen prepared for device advancement. With reference to FIG. 79*e*, the clot retrieval device 2130 is advanced in its collapsed state through the lumen of the microcatheter 2041 until it is deployed out of the distal end of the microcatheter 2041. Upon deployment the frame 2012 of the clot retrieval device 2130 causes the basket to expands. In the embodiment described in FIG. 79*e*, the frame 2012 is attached to the wire. The frame may be fixedly attached to the guidewire or it may be rotationally attached to the guidewire or it may be attached such that it has at least some rotational and/or some translational freedom.

With reference to FIG. 79*f*, the microcatheter is withdrawn to the proximal side of the occlusion 2001 when the clot capture device 2130 is deployed. The clot capture device 2130 is manipulated to ensure that it is fully engaged with the vessel wall. The clot debonding device 2091 is now advanced through the lumen of the microcatheter and its distal end is advanced distal of the microcatheter tip 2047. When the distal portion of the clot debonding device exits the microcatheter 2041 the expandable segment 2112 expands to its remembered expanded state. In the expanded state the clot debonding device 2091 is advanced until it engages with the proximal portion of the clot 2001 (FIG. 79*h*). At this point the clot capture basket 2130 is advanced proximally while the clot debonding device 2091 is held steadfast. This action breaks the bonds between the clot and the vessel and the clot 2001 is forced into the capture basket 2130. The clot debonding device 2091 can now be removed. This is achieved by withdrawing it back into the lumen of the microcatheter 2041. In its expanded state the clot debonding device has a conical aspect and this facilitates the retrieval of the device 2091 into the microcatheter 2041 (FIG. 79*i*). The clot debonding device 2091 can be fully withdrawn through the lumen of the microcatheter or it can be advanced a sufficient distance proximally to allow recovery of the clot capture basket 2130.

The clot capture basket recovery steps are described with reference to FIGS. 79*j* and 79*k*. The microcatheter distal end 2047 is engaged with the frame 2012 of the capture basket 2130. The guidewire is pulled proximally to force the proximal section of the frame 2012 into the lumen of the microcatheter. As the proximal section of the frame enters the microcatheter the frame struts 2009 collapse and the mouth of the basket closes. This allows the basket to be withdrawn from the vessel without the frame engaging with the vessel wall. The capture basket 2130, the microcatheter 2041 and the guidewire 2020 are removed together. The capture net 2015 scaffolds the clot during removal and prevents fragments from embolizing. The capture basket 2130, the microcatheter 2041 and the guidewire 2020 are withdrawn through the lumen of the guide catheter or sheath and removed from the patient. The net allows the clot to deform and change shape as it is pulled into the guide catheter or sheath without allowing particles or fragments to embolize.

FIG. 80*a-m* shows another method of using the devices of this invention. FIG. 80*a* shows a vessel 2002 with an occlusive clot 2001. The vessel 2002 has a proximal end 2005 and a distal end. The procedure to treat the occlusion per this invention comprises firstly gaining access to the vasculature. This is carried out by conventional means (the Seldenger technique). A guide catheter is placed in a large vessel proximal of the occlusion (not shown). A procedural guidewire 2020 is advanced through the guide catheter or sheath and is advanced across the occlusive clot 2001 as in FIG. 80*b*. When the guidewire 2020 is in place a microcatheter is advanced over the guidewire until the tip of the microcatheter is across the occlusion (FIG. 80*c*). As can be seen with reference to FIG. 80*d* the guidewire 2020 is removed thus leaving the microcatheter 2041 in place with its tip 2047 across the occlusion 2001 and an empty lumen prepared for device advancement. With reference to FIG. 80*e*, a special clot retrieval guidewire 2142 is advanced through the microcatheter until its distal tip is distal of the microcatheter 2041. The clot retrieval guidewire 2142 has a stop 2144 at its distal end. The stop 2142 limits the movement of the clot capture basket 2140 on the wire and prevents the clot capture device 2140 from sliding off the distal end of the guidewire 2142.

The clot retrieval device 2140 is advanced over the guidewire 2142 in its collapsed state through the lumen of the microcatheter 2041 until it is deployed out of the distal end of the microcatheter 2041. Upon deployment the frame 2012 of the clot retrieval device 2140 causes the basket to expand. In the embodiment described in FIG. 80*f*, the capture basket 2140 is slidable on the clot capture guidewire 2142.

With reference to FIG. 80*g*, the microcatheter 2041 is withdrawn to the proximal side of the occlusion 2001 when the clot capture device 2140 is deployed. The clot capture device 2140 may be manipulated to ensure that it is fully engaged with the vessel wall 2002. The clot debonding device 2091 is now advanced through the lumen of the microcatheter 2041 and its distal end is advanced distal of the microcatheter tip 2047. When the distal portion of the clot debonding device 2091 exits the microcatheter 2041 the expandable segment 2112 expands to its remembered expanded state. In the expanded state the clot debonding device 2091 is advanced until it engages with the proximal portion of the clot 2001 (FIG. 80*i*). At this point the clot capture guidewire 2142 is advanced proximally until the stop 2144 engages with the capture basket 2140. In one embodiment the stop 2144 engages with either the collar 2023 of the capture basket 2140. In another the stop 2144 engages with a tube extending from the proximal end of the basket. Further withdrawal of the guidewire 2142 causes the clot capture basket 2140 to advance proximally. The guidewire 2142 is advanced proximally until the capture basket engages with the distal end of the occlusive clot 2001. With the clot debonding device 2091 held steadfast the basket is withdrawn proximally until the clot is debonded and enters the basket.

The clot debonding device 2091 can now be removed. This is achieved by withdrawing it back into the lumen of the microcatheter 2041. In its expanded state the clot debonding device has a conical aspect and this facilitates the retrieval of the device 2091 into the microcatheter 2041 (FIG. 80*j*). The clot debonding device 2091 can be fully withdrawn through the lumen of the microcatheter or it can be advanced a sufficient distance proximally to allow recovery of the clot capture basket 2130.

The clot capture basket recovery steps are described with reference to FIGS. 80*k* to 80*m*. The microcatheter distal end 2047 is engaged with the frame 2012 of the capture basket 2140. The guidewire is pulled proximally to force the proximal section of the frame 2012 into the lumen of the microcatheter 2041. As the proximal section of the frame enters the microcatheter the frame struts 2009 collapse and the mouth of the basket closes. This allows the basket 2140 to be withdrawn from the vessel without the frame 2012 engaging with the vessel wall 2002. In this embodiment the capture basket 2140 and the microcatheter 2041 are removed together. The guidewire is left in the vessel until the very end of the procedure. This has the advantage of allowing the physician carry out final imaging steps prior to loosing access to the vessel. The capture net 2015 scaffolds the clot during removal and prevents fragments from embolizing. The capture basket 2140, the microcatheter 2041 and the clot 2001 are withdrawn through the lumen of the guide catheter or sheath and removed from the patient. The net allows the clot 2001 to deform and change shape as it is pulled into the guide catheter or sheath without allowing particles or fragments to embolize.

It will be appreciated that the various features illustrated and/or described herein may be used as appropriate with any of the devices, methods or systems described.

The invention is not limited to the embodiments hereinbefore described which may be varied in detail.

The present invention is related to an apparatus and methods for the removal of obstructions in vessels. The present invention is directed towards the treatment of occlusions to blood vessels, especially arterial vessels and more particularly the removal of occlusive clots from cerebral arterial vessels.

Accessing cerebral vessels involves the use of a number of commercially available products and conventional procedural steps. Access products such as guidewires, guide catheters and microcatheters are described elsewhere and are regularly used in procedures carried out in cerebral vessels. It is assumed in the descriptions below that these products and methods are employed in conjunction with the device and methods of this invention and do not need to be described in detail.

With reference to FIG. 81 there is shown a schematic representation of a device 1 for the removal of an obstruction 40 to a vessel 41. The device 1 comprises a clot debonder device 2 and a clot engagement and capture basket 3. The capture basket 3 comprises a collapsed configuration for delivery and an expanded configuration for clot engagement and capture. The clot engagement and capture basket 3 is biased towards the expanded configuration. The clot debonder 2 comprises a collapsed state for delivery through the vasculature and an expanded state for engagement with the clot and for disengaging the clot from the vessel wall.

The capture basket 3 further comprises a frame 4 and a capture net 5. The frame 4 comprises rigid strut members 30 configured to from a hoop. The frame 4 comprises a capture opening 31. The capture opening 31 comprises a hoop shaped opening or an elliptical shaped opening or a circular shaped opening. In one embodiment the frame 4 comprises a metallic frame manufactured from either a wire or a tube. In one embodiment the frame is manufactured from nitinol. The frame 4 may be manufactured from a hypo tube. This allows the struts 30 of the frame 4 to be shaped and profiled, including drilling the eyelets 6 in the frame.

In one embodiment the frame comprises eyelets 6 for the attachment of a net 5. The eyelets are preferably machined in the frame. Eyelets may be laser drilled in the frame 4. The frame 4 may be a profiled frame. The frame 4 comprises cable guides 7. The cable guides 7 comprise holes or guiding features in the frame through which a small high tension cable 21 passes. The cable guides 7 are configured such that the cable 21 (not shown) can slide through the cable guide 7.

The cable guides 7 are configured so as to guide the cable 21 substantially parallel to the axis of the strut 30 over at least a portion of its length. The cable guide 7 is further configured so as to ensure that when the cable 21 is under tension that it is spaced apart from the neutral axis of the strut 30 of the frame 4 over at least a portion of its length. In spacing the cable 21 from the neutral axis the cable 21 imparts a bending moment to the strut 30 when tensioned. This bending moment has the effect of changing the shape of the frame 4. The bending moment may be used to change the angle of articulation of the frame 4 relative to the axis of the frame support tube 13. To do this the cable 21 is axially spaced apart from the neutral axis of the frame 4, with the cable 21 positioned axially proximal of the frame 4.

In another embodiment the bending moment associated with tensioning the cable 21 is used to change the shape of the capture opening 31 of the frame 4. To do this the cable is spaced apart radially relative to the neutral axis of the frame 4. It will be appreciated that the cable 21 may be guided so as to articulate the frame over one portion of its length and to change the shape of the frame over another portion of its length.

In another embodiment two cables are employed. The first cable is used to control the articulation of the frame 4 with respect to a support element and the second cable is employed to change the shape of the capture opening 31 of the frame 4. In one embodiment the support element comprises a tubular support 13 extending proximally of the basket 3.

The basket 3 further comprises a connector member 9 that connects the hoop shaped portion of the frame 4 to the support 13. The connector member 9 may comprise a strut element and in one embodiment the connector member is integral with the hoop shaped portion of the frame 4. The connector is mounted to the support tube 13 with frame collar 10. The frame collar 10 is configured to swivel or rotate around support tube 13. This is achieved by providing proximal and distal abutment surfaces for the collar 10 to engage with. In the embodiment shown the abutment surfaces comprise first fixed collar 11 and second fixed collar 12. It will be appreciated that other abutment surface configurations are possible including: a flared on the tubular support 13, a step on the support 13, a recess on the support 13, one or more projecting tabs on the support 13 or combinations of these.

The connector member 9 is configured to lie substantially parallel to the support tube 13 in the delivery configuration and to lie at an angle to the support tube in the expanded configuration (shown). Where the angle between the connector element 9 and the support tube 13 is shallow then the axis of the support tube 13 shall be spaced apart from the centre of the capture opening 31 and the support tube 13 will be biased towards the wall of the vessel adjacent the clot 40. In one embodiment the length and angle of the connector element 9 are configured such that the axis of the support tube 13 and the centre of the capture opening 31 are substantially coaxial. In another embodiment the length and angle of the connector element 9 are configured such that the axis of the support tube 13 and the centre of the capture opening 31 are spaced apart. In another embodiment the length and angle of the connector member 9 are configured such that the axis of the support tube 13 lies between the centre of the capture opening 31 and the rim of the capture opening 31. The rim of the capture opening 31 is defined as the inner most surface of the struts 30 of the capture opening 31.

The net 5 is configured to be highly soft and flexible and is made from a yarn that is exceptionally fine. The fineness of a yarn is defined by its linear density.

The linear density, (or linear mass) is a measure of mass per unit of length, and is used to characterise yarns, strings and other similar one-dimensional objects. The SI unit of linear density is the kilogram per metre (kg/m). The linear density, $\mu$ (sometimes denoted by $\lambda$), of an object is defined as:

$$\mu = \frac{\partial m}{\partial x}$$

where m is the mass, and x is a coordinate along the (one dimensional) object.

A common unit of measure of the linear density of a yarn is Dtex. Dtex is defined as the number of decigrams in one kilometer of the yarn. Thus 1Dtex=1 dg/km=0.1 mg/m.

The net is preferably made from a Ultra High Molecular Weight Polyethylene yarn, an aramid yarn, a liquid crystal polymer yarn, an aromatic yarn, a Zylon yarn, a nitinol yarn, a stainless steel yarn, a stainless steel alloy yarn, or a tungsten yarn. It will be appreciated that these yarns may be used in conjunction with any of the baskets and debonders of this invention. The net may also be constructed from a monofilament of any of the above materials.

Commercially available UHMWPE yarns include Dyneema by DSM and Spectra BY Honeywell. The aramid yarn is preferably a para-aramid yarn. Commercially available aramid yarns include Kevlar by DuPont, Twaron, and Technora both supplied by Teijin. Commercially available LCPs include Vectra by Ticona, Vectran by Kuraray, and Zydar by Solvay Advanced Polymers. Zylon is commercially available from Toyoba.

The Table below outlines the suitable linear densities, preferred linear densities and most preferred linear density for each of the polymer yarns described above.

| Yarn Material | Suitable linear density | Preferred Linear density | More preferred linear density | Most preferred linear density |
| --- | --- | --- | --- | --- |
| UHMWPE | Less than 19 Dtex | Less than 10 Dtex | Less than 7 Dtex and greater than 1 Dtex | Less than 3 Dtex and greater than 1 Dtex |
| Aramid | Less than 22 Dtex | Less than 12 Dtex | Less than 8 Dtex and greater than 1 Dtex | Less than 4 Dtex and greater than 1 Dtex |
| Zylon | Less than 28 Dtex | Less than 15 Dtex | Less than 12 Dtex and greater than 1 | Less than 5 Dtex and greater than 1 Dtex |
| LCP | Less than 25 Dtex | Less than 14 Dtex | Less than 9 Dtex and greater than 1 | Less than 5 Dtex and greater than 1 Dtex |

The device shaft is an elongate member that extends in use from a point exterior of the patient to a point adjacent the target clot to be retrieved. Various shaft constructions are disclosed and described herein, including means by which the shaft may be rendered flexible for ease of delivery through tortuous vasculature. It is however also desirable that the shaft is not made so flexible that it becomes difficult to deliver a sufficient push force to advance it to the target site. To deal with this apparent conflict it is desirable that the shaft have a stiffness gradient along its length, with the flexural stiffness of the proximal region of the shaft being greater than that of the distal region. Specifically it is desirable that the flexural stiffness of the proximal region of the shaft be more than four times greater than that of the region adjacent the clot engaging portions at the distal end of the device. For the purposes of this specification flexural stiffness is defined as the stiffness measured by a 5% deflection in a three point bend test such as described by ASTM D790.

In one embodiment as shown in FIG. 81a the shaft comprises an assembly of tubular members and an inner cable. The support tube 13 extends in use from the region of the occlusion through the vasculature to the user. The support tube 13 allows the user to advance or retract the basket 3. The support tube comprises an inner lumen 33 and an exit port 14. The inner lumen 33 guides the cable 21 from the user interface 70 (not shown) which is exterior of the patient to a region adjacent the frame 4 where the cable 21 exits the lumen 33 via exit port 14. The exit port 14 is shown at the end of the tube 13. It will be appreciated that the exit port 14 may also be placed proximal of the distal end of the support tube 13. In this case the exit port 14 comprises a hole or a slot or a skive in the wall of the support tube 13. The support tube 13 is required to track through tortuous anatomy and deliver excellent mechanical force transmission to the treatment region. It is also required to facilitate relative motion between its inner lumen 33 and the pull cable 21.

It is generally recognized that providing good surface finish to metal tubes whose inner diameter is less than 0.010" is very difficult. Normally metal tubes are formed in a cold drawing process. In order to provide for a smooth and dimensionally accurate inner lumen an inner plug is used during the drawing step. However, with very small inner diameter tubes it is not possible to support a floating plug inside the ID during drawing which results in a less accurate tolerance on the ID and a rougher surface.

In one embodiment of the invention the inner surface of the support tube 13 comprises a polished surface. The surface may be polished by injecting polishing slurry through the lumen of the support tube 13 at high pressure. In another embodiment the inner surface of the support tube 13 comprises a low friction liner. In one embodiment the liner is at least partially composed of a fluoropolymer or a polyolefin (PTFE or HDPE or UHMWPE).

FIG. 81b shows another embodiment of the support tube 13 where the tube comprises a plurality of helical wires 34. With this embodiment a plurality of small diameter wires 34 are twisted to form a tube 13. The wires 34 are preferably sized greater than 30 microns and less than 80 microns. More preferably the wires 34 are between 30 microns and 60 microns. Even more preferably the wires 34 are sized between 30 and 60 micrometers. The number of wires 34 and the twist angle can be varied but which ever configuration is used the wires 34 are arranged such that a line of force contact exists between each pair of adjacent wires. This contact force keeps the wires in a tubular configuration and prevents collapse of the structure. It also ensures that the interface between the wires 34 is substantially sealed.

In another embodiment, support tube 13 comprises an inner layer of wires and an outer layer of wires 34. In one embodiment the inner layer and the outer layer have different wire diameters.

In another embodiment, support tube 13 comprises a plurality of helical wires 34 comprising non-circular cross-sections. In one embodiment the wires 34 comprise at least one substantially flat surface. In another embodiment the wires 34 comprise an elliptical cross-section.

Support tubes comprised of helical wires provide a number of important advantages that are not possible with other technologies. Firstly the inside surface of the tube is as smooth as the outer surface even at diameters of 0.010" or less. This in combination with the undulating inner surface provides an excellent interface for relative motion between the tube and an inner member such as a core wire or a pull cable or a tether. The mechanical properties of the construction are also excellent since the twisted wire tubes have excellent push properties and good trackability features.

The construction of the elongate tube 19 may comprise a plurality of helical wires as described for the support tube 13 above. Although the inner diameter and outer diameter of the elongate tube 19 are larger than the support tube 13 the descriptions, construction details and embodiments of the elongate tube 19 are the same as for the support tube and will not be repeated.

The clot debonder 2 comprises an abutment surface 36 and an elongate tube 19. The abutment surface 36 comprises an engagement frame 16 and engagement yarn 17. The abutment surface 36 comprises a collapsed state for delivery and an expanded state for abutment with the occlusion. The distal end of the elongate tube 19 comprises a mounting section 18. The frame 16 and the elongate tube 19 are connected in the mounting section 18. In one embodiment the mounting section and the frame 16 are integral. This may be achieved by cutting the frame 16 from a metallic tube, such as nitinol, and heat treating it such that the frame is biased towards the expanded configuration. In another embodiment the mounting section 18 comprises a frame attachment 28. In one embodiment the frame attachment comprises a slot or a recess in the mounting section. The frame 16 comprises at least one projecting strut and said strut is engaged with said slot or recess. The at least one projecting strut may further be welded, glued, laminated or bonded to the mounting section 18.

The clot engagement yarn 17 of the abutment surface 36 comprises very fine yarn that is attached to the frame 16 at fixing points 15 along the frame 16. The fixing points 15 facilitate the yarn 17 being laced over and back across the opening of the frame 16 so as to create a clot engagement surface (like a tennis racquet). Preferably the yarn 17 has a slight tension in the laced configuration when expanded. This ensures that all segments of the yarn 17 engage with the proximal end of the clot 40 at the same time. It will be appreciated that the yarns will not be tensioned in the collapsed configuration. In one embodiment the fixing points 15 comprise eyelets. The frame 16 is sized such that it is the same size or smaller than the proximal lumen of the vessel. Since the primary function of the debonding element 2 is to provide an abutment surface 36 it is not necessary that the debonding frame 16 be precisely sized to the vessel. The abutment surface 36 needs to be configured to engage with at least a portion of the proximal surface of the clot 40 and provide a reaction force to the forces associated with retracting the basket 3 over the clot 40.

In another embodiment the basket 3 comprises a collapsed state for delivery, a deployed partially expanded state and an activated fully expanded state. In the collapsed state the two struts 30 of the frame 4 lie parallel to each other and substantially parallel to the axis of the micro-catheter 20 through which they are delivered. In the deployed partially expanded state the two struts move apart to form a hoop shaped frame. However the engagement force of the frame 4 is low and the hoop frame 4 makes a shallow angle with the axis of the support tube 13. When the cable 21 is activated by the user the hoop frame is articulated to a steeper angle relative to the axis of the support tube and the hoop comes into contact with the wall of the vessel. In this configuration with the cable 21 tensioned the frame 4 can engage strongly with the clot 40. The fact that the device is configured to have three configurations as opposed to two brings significant advantages. Firstly it is desired that the device strongly engage the clot such that the vessel van be recannalised rapidly without the basket pulling through the clot, a common problem with current technology. However, where the physician judges that the clot is too firmly bonded to the wall and the risks of debonding the clot are too high it is desirable that the device can be disengaged from the clot and removed. In this situation a low engagement force deployed configuration is a big advantage as otherwise removal without debonding would be problematic.

The basket of FIG. 81a can be used with the following procedural steps:

A guide catheter or sheath of between 6 F to 9 F is advanced through the vasculature until the tip of the catheter or sheath is in the carotid artery.

A guidewire and microcatheter 20 are advanced through the lumen of the guide catheter and further advanced through the internal carotid and cerebral vasculature until the tip of the microcatheter 20 is adjacent the occlusion 40.

The distal tip of the guidewire is advanced across the occlusion 40.

The microcatheter 20 is advanced over the guidewire until the tip of the microcatheter 20 is across the occlusion 40.

The guidewire is removed from the patient.

The device 1 is advanced through the lumen of the microcatheter 20 until the basket 3 emerges from the distal end of the microcatheter 20.

The basket 3 self expands to the partially expanded state.

The user activates the cable 21 at the user interface 70 and the basket 3 assumes the fully expanded state.

The microcatheter 20 is withdrawn until the tip of the microcatheter 20 is proximal of the occlusion 40.

The Debonding element 2 is advanced until the debonding frame 16 is distal of the tip of the microcatheter 20.

The debonding frame 16 self expands.

The support tube 13 is retracted by the user until the frame 4 of the basket 3 engages with the clot 40.

The debonder 2 is advanced over the support tube 13 until the debonder abutment surface 36 engages with the clot 40.

The basket 3 is retracted while holding the debonder 2 steadfast and the clot 40 is disengaged from the vessel wall.

The basket is retracted further and captures the clot.

The tether is deactivated and the frame partially collapses

The microcatheter 20, the device 1 and the clot 40 are removed from the vasculature through the lumen of the guide catheter.

In one embodiment the method involves the steps of; disengaging the basket from the occlusion, deactivating the cable, at least partially collapsing the basket, and retracting the basket across the occlusion in the partially collapsed state.

It will be noted that the use of an expansion cable allows the frame to be made with finer struts. These finer struts in general provide reduced radial force. However since the basket is relaxed in the partially expanded state there is a reduction in the strain required to collapse it fully and this feature further reduces the radial force of the frame when fully collapsed. Both of these features make it possible to deliver a high clot engagement force frame through a small microcatheter. It also makes it easier to retract the partially collapsed frame through an occlusion without causing a vessel dissection.

FIG. 82a shows another embodiment of the invention. The device 60 is similar to the device of FIG. 81a and FIG. 81b and similar elements carry the same numbers. The device 60 comprises a basket 61 and a clot debonder 2. The basket 61 comprises a frame 4, which is metallic and comprises a pair of struts 30 which in the expanded configuration comprise a clot capture opening 63. Unlike the frame of FIG. 81a and FIG. 81b which was a planar hoop the frame 4 of basket 61 is a curved hoop. When viewed in end-view the frame 4 of basket 61 comprises a hoop and said hoop is sized to appose the wall of the vessel in the region of the occlusion. In a side elevation view the frame comprises a C shaped element with the connector member 9 extending between the frame 4 and the support tube.

FIG. 82a shows a portion of the net 5 attached to the frame 4. The net may be a knitted net, a braided net or a weaved net. A pair of cables 21 extend from the user interface 70 through the lumen of the support tube 13 and are attached to the frame at cable attachment points 8. It will be noted that the cable attachment points 8 are fashioned in the frame 4 between the centre of the clot capture opening and the point where the connector member 9 is connected to the frame 4. With this embodiment the cables 21 pull the frame 4 towards the exit port 14 of the support tube 13. In so doing the cables 21 pull the frame 4 into a fully expanded configuration. The cables 21, when tensioned add significantly to the force with which the frame 4 engages with the occlusion. However this increase in engagement force (or engagement resistance) is directional. The frame 4 provides strong engagement when being retracted towards the clot 40 but has reduced resistance when being advanced away from the clot 40.

As with the previous design the frame 4 may be partially collapsed by deactivating the cable 21. The frame 4 of basket 61 may be cut from a flat sheet. With this embodiment the frame and connector element may be easily cut in a single pattern. With this method of manufacture no expansion steps are required and the connector is subsequently attached to the collar 10.

In another embodiment of the processing method the collar 10 is also cut from a flat sheet. With this embodiment the collar 10 is cut as a flat rectangle where the width of the rectangle is equal to the circumference of the collar. The rectangle is then rolled or formed into a collar 10. The formed or rolled collar 10 may then be welded to itself or heat set to permanently assume the shape of a collar 10.

The flat sheet frame 4 of basket 61 has a collapsed configuration, a partially expanded configuration and a fully expanded configuration. The collapsed configuration of the frame 4 is as described for FIG. 81a and FIG. 81b. The frame 4 comprises a Nitinol frame and can be heat set to a remembered shape or a biased shape. The partially expanded configuration is the biased shape of the frame 4 of basket 61. The partially expanded state requires some compressive deformation in order to fully collapse the frame and some expansive deformation in order to fully expand the frame.

FIG. 82b to FIG. 82e shows a schematic side view of the frame 4 of basket 61 in the partially expanded state and in the fully expanded state. The frame comprises a distal segment 62 and a proximal segment 64. The cable attachment point 8 separates the distal and proximal segments. When the cable 21 is activated the proximal frame segment 64 and the connector 9 change shape. The distal segment 62 of the frame 4 does not undergo significant shape change when the cable is activated. However this segment is displaced by the movement of the proximal segment 64.

FIG. 82*d* shows the frame 4 in the partially expanded state. The frame has a gentle C shaped curve when viewed in side elevation. If viewed in plan view the capture opening 31 would be generally elliptical or oval in shape. In FIG. 82*e* the frame 4 of FIG. 82*b* is shown in the fully expanded state (with the cable activated). The distal segment 62 of the frame 4 still comprises a gentle C shaped curve in side elevation while the proximal segment 64 and the connector 9 have a smaller radius of curvature. FIG. 82*c* shows another partially expanded frame 4 where the distal segment has a smaller radius of curvature than the proximal segment. In the fully expanded configuration as shown in FIG. 82*e* the radius of curvature of the proximal segment is now similar to that of the distal segment due to the activation of the cable 21.

In another embodiment the proximal segment 64 of the frame 4 and/or the connector 9 comprise areas of articulation. These areas are configured to bend more readily than neighboring segments and these articulation areas facilitate the shape change in the proximal segment 64 and connector 9 when the cable 21 is tensioned.

In one embodiment the cable attachment point is adjacent the neutral axis of the strut 30 of the frame 4. In another embodiment the cable attachment point is spaced apart from the neutral axis of the strut. With this embodiment the tension in the pull cable 21 sets up a torque in the strut 30 to which the attachment point 8 is fixed and this assists in changing the shape of the frame 4.

The frame 4 of FIGS. 82*a* to 82*e* is attached to the support tube 13 as described in FIG. 81*a* to FIG. 81*b* and the features of the debonder are also the same as described in FIG. 81*a* to FIG. 81*b*.

The user interface 70 is shown in FIG. 82*f* The user interface comprises a handle 24 for control of the basket and a control element 23 to control the position and orientation of the debonder 2. The user interface 70 of device 60 could be applied to any of the devices of this invention which employ a cable activated basket and a debonder. The handle 24 comprises a thumb wheel 25 and a hand grip 26. The handle further comprises graduations 65 to guide the user in expanding the basket. The handle 24 is fixed to the proximal end of the support tube 13. The cable 21 extends from the proximal end of the support tube 13 into the handle 24 where it is mounted to a tension mechanism 66. The tension mechanism 66 comprises a cable wheel 67 or drum onto which the cable can be wound when being tensioned. The cable wheel 67 is rotated by activating the thumb wheel 25. The cable 21 can thus be tensioned or relaxed by rotation of the thumb wheel 25 in either a clockwise direction or an anticlockwise direction. It will be appreciated that the cable wheel 67 could also be activated with a sliding mechanism.

The control element 23 is fixed to the proximal end 27 of the elongate tube 19 and is configured to allow the user to advance or retract the debonder 2 relative to the basket 61. The control element is also configured to allow rotation of the elongate element 19. It will be appreciated that the elongate tube 19 is moveable and rotatable relative to the support tube 13.

The control element 23 is comprises a locking element such that the control element 23 and the elongate member 19 can be to the support tube 13. This allows the basket 61 and the clot debonder 2 to be fixed together and can thus advanced together or retracted together or rotated together. In one embodiment the locking element comprises a touhyborst arrangement. In another embodiment the control element comprises a clamp. In either case the control element can be locked to the support tube 13 by the user and can subsequently be unlocked from the support tube 13 by the user.

In another embodiment the control element comprises a luer fitting such that the annular space between the support tube 13 and the elongate tube 19 can be flushed by a physiological fluid like saline. The construction of the support tube 13 and the elongate tube 19 are as described in FIGS. 82*f-h*.

The proximal end of the microcatheter 20 is shown in FIG. 82*f* with the elongate tube extending through the lumen of the microcatheter. A guide catheter is not shown but it will be appreciated that the microcatheter is inserted through the lumen of the guide catheter and the proximal end of the microcatheter 20 extends out of the proximal hub of the guide catheter (or sheath). The microcatheter hub 22 is shown and allows flushing with standard syringes and luer connectors.

FIG. 82*g* shows a close-up view of the support tube 13, and FIG. 82*h* shows a longitudinal cross-section of the same tube 13 in which the undulating inner surface 35 can be observed. The combination of the helix angle and the curved cross-section of the wire 13 ensures that the inside surface of the lumen is a smooth undulating surface 35. The undulating surface 35 provides for an excellent frictional interface with pull cables 21. In a curved vessel the pull cable 21 slides over the high points of the undulating surface 35. The cable therefore has a reduced amount of contact with the surface over its length. Furthermore, because the wires 34 are drawn before being fashioned into a tube they have a smooth outer surface which also improves the frictional interface. A portion of the outer surface of the wires 34 makes up the inner surface of the tube 13. The undulating surface reduces the frictional drag and this allows for better control of the articulation of the frame 4 with the cable 21.

FIG. 83*a* shows another device 50 of the invention. The device 50 is similar to devices of FIG. 81*a-b* and FIG. 82*a-h* in that the Debonder and user interface 70 are the same. In this embodiment the basket 51 comprises a double hoop frame 52. The double hoop frame comprises a distal hoop 53, a proximal hoop 54, an articulating bridge 55 and a connector member 9. The distal hoop 53 and the proximal hoop 54 are constructed from struts 30 wherein each hoop comprises at least one pair of struts 30. The distal hoop and the proximal hoop 54 are connected to each other by articulating bridge 55. The connector member 9 is connected to the support tube 13 as described in FIG. 81*a-b* and FIG. 82*a-h*. The cable 21 is attached to an attachment point on the distal hoop 53. The attachment point 8 is radially opposite the point where the articulating bridge 55 is connected to the distal hoop 53. The cable 21 extends from the attachment point through the opening of the proximal hoop 54 and through the lumen 33 of the support tube 13 to the cable wheel 57 of the handle 24. The construction of the attachment point is shown more clearly in FIG. 83*e*. The cable 21 is attached at attachment point 8. The attachment point 8 may comprise an eyelet as shown in FIG. 83*e*. The area adjacent the attachment point 8 is an area that undergoes significant strain in moving to the collapsed configuration. FIG. 83*e* shows a strain relieving feature adjacent attachment point 8 which is designed to allow the struts 30 of the hoop frame to collapse to a configuration whereby they are substantially parallel while distributing the strains associated with said collapse.

In another embodiment the proximal hoop 54 comprises a cable guide 7 (as described previously) and said cable guide directs the path of the cable 21 between the attachment point 8 and the exit port 14 of the support tube 13. In one embodiment the cable guide 7 is positioned at the base of the proximal hoop 54 diametrically opposite the bridge 55. In yet another embodiment the cable guide 7 is associated with the connector.

The double hoop frame 52 comprises a collapsed delivery configuration, a deployed partially expanded configuration and a fully expanded configuration. In the collapsed state the single strut of the connector member 9 the pair of struts of the proximal hoop 54 and the pair of struts of the distal hoop 53 are connected in series and all lie substantially parallel to the axis of the microcatheter within which they are housed. When deployed from the microcatheter 20 the pair of struts 30 of the proximal hoop 54 move apart in the centre to form an elliptical or hoop shape. Likewise the struts of the distal hoop move apart to form an ellipse of hoop shaped frame. The connector member 9 expands such that it forms an angle with the axis of the support tube.

In the fully expanded configuration the cable 21 is tensioned and this draws the cable attachment point 8 proximally which causes the articulating bridge 55 to articulate and the frame 52 moves to the expanded configuration (as shown in FIG. 83a).

The bridge 55 connects the proximal hoop 54 and the distal hoop 53 and allows them to articulate with respect to one another. A number of bridge configurations are possible and some variants are shown in FIG. 83b to FIG. 83d. In FIG. 3b the bridge 55 comprises a connector strut 56. The connector strut is sized so as to be a point of flexure as the proximal and distal hoops are articulated relative to each other. The wall thickness of the connector strut may be thinner than that of the struts 30 over at least a portion of its length. The cross sectional area of the connector may be less than the cross-sectional area of a strut 30 of the fame 52. FIG. 83c shows another variant where by the bridge 55 comprises a pair of strut connectors. With this embodiment the proximal frame hoop and the distal frame hoop are not fully closed as a slight gap exists in the region of the bridge. The two open hoops are connected by two connector struts 56. The two connector struts are free to move relative to each other. FIG. 83d shows another variant which is almost identical to that described in FIG. 83c except that the two connector struts are tethered together. The tether 57 reduces the movement between the two connectors 56 and this ensures that the hoop shape is always preserved irrespective of the forces of clot engagement and capture.

FIGS. 83f and 83g show two alternative net attachment configurations. In FIG. 83f the net is attached to distal hoop 53, while in FIG. 83g the net is attached to proximal hoop 54.

FIG. 84a through to FIG. 84e show another device 100 of the invention. The device 100 comprises a basket 101 and a clot debonder 102. The basket 101 comprises a frame 103 with a large unobstructed capture opening 113 and a support member 104 connected directly to the rim of the capture opening 113. The debonder 102 is slidable over the support member 104 and comprises a clot engagement surface 106. The clot engagement surface 106 comprises radially projecting elements 107 and circumferential filaments 108. The circumferential filaments 108 are configured to distribute the clot engagement forces between the radially projecting elements. In one embodiment the radially projecting elements 107 comprise struts. In one embodiment the radially projecting struts 107 comprise metal struts. Preferably the metal struts 107 are made from spring steel, a shape memory metal or a super elastic metal such as nitinol. The circumferential filaments 108 may comprise a thin strut, a wire, a fiber, a yarn or a multi-filament yarn. In the embodiment shown in FIG. 84c the filament 108 interconnects the radially projection struts at the outer diameter. It will be appreciated that the circumferential filaments 108 may interconnect the radially projecting struts 107 at multiple diameters. In so doing an engagement surface 106 that is comprised of a plurality of spaced apart radial elements and a plurality of spaced apart circumferential filaments. The net result is an engagement surface 106 with a spiders web pattern.

With reference to FIG. 84a the basket 101 of the clot removal device 100 is shown. The basket 101 is shown with the net 105 removed. The basket 101 comprises a double hoop frame 103 which is similar to the frame 52 of FIG. 83. However in this case the frame 103 does not employ a cable to effect deployment. The frame 103 has an enlarged deployment configuration for engagement with and removal of occlusions and a collapsed configuration for delivery through the vasculature and the frame is biased towards the deployed configuration.

The frame 103 is shown in the collapsed configuration in FIG. 84b. In this case the frame 103 is collapsed inside the lumen of a micro catheter 112. The two struts 117 of the proximal hoop 116 lie substantially parallel to one another in the collapsed state. Likewise the two struts 117 of the distal hoop 115 lie substantially parallel to one another in the collapsed state.

The frame 103 further comprises a bridge section 114 which interconnects the two hoops of the frame 103. The bridge section 114 is configured to articulate as the frame 103 moves between the collapsed configuration and the expanded configuration. In this case the bridge 114 needs to be sufficiently strong to expand the frame 103 and thus the bridge is preferably a strut or a plurality of struts.

FIG. 84c shows the debonder 102 separated from the basket 101. The debonder 102 comprises a collapsed configuration for delivery through a microcatheter 112 and an expanded configuration for engagement with an occlusion 40. The debonder is shown in the expanded configuration with the struts 107 projecting radially outward over a portion of their length. The proximal portion of the struts 107 lie substantially parallel to the axis of the debonder tube 110. In the collapsed configuration the radially projecting section of the struts 107 are collapsed such that they lie substantially parallel to the axis of the debonder tube 110. In this collapsed state the debonder 102 may be advanced through the lumen of a low profile microcatheter.

FIG. 84d shows the debonder mounted on the support member with both the basket 101 and the engagement surface 106 of the debonder 102 in the expanded configuration. The device 100 is shown projecting from the lumen of a microcatheter 112. This configuration corresponds to the device configuration just prior to the step of debonding the clot from the vessel wall. FIG. 84e shows the device 100 in the same configuration but this time in a vessel with the basket 101 and debonder 102 deployed either side of clot 40.

A number of different frame designs are shown in FIGS. 85a to 94g. It will be appreciated that these frames could be employed with any of the baskets in this invention.

FIG. 85a shows an isometric view and FIG. 85b shows an end view of frame 150. Frame 150 comprises a clot engagement ring 156, a pair of connector elements and a collar 151. The clot engagement ring 156 is shown in the expanded state and comprises four struts 153. The four struts 153 are arranged to form a hoop 156 in the expanded state. The hoop is configured to engage with an occlusive clot and to disengage the clot from the wall of the vessel. The clot engagement ring 156 further comprises articulation points 154 at the intersections of the four struts 153. These articulation points 154 allow the frame 150 to move between the collapsed and expanded states. The connector elements 152 ensure the frame is stable in the expanded state.

FIG. 86a shows an isometric view and FIG. 86b shows an end view of frame 160. Frame 160 comprises a hoop section 165 an articulating support 162 and a collar 151. The hoop section 165 of the frame 160 comprises struts 164 and the hoop section 165 is sized such that it is in contact with substantially the entire circumference of the vessel when deployed. The hoop section 165 of the frame 160 is sized so it will engage the clot at or adjacent to the interface between the clot and the vessel wall. In so doing the hoop section 165 of the frame 160 will be effective in peeling or delaminating the clot from the vessel wall. The hoop section 165 of the frame 160 comprises a large unobstructed capture opening 161 which allows disengaged obstruction to enter the basket without resistance. The articulating support 162 is integral with the hoop section 165 of frame 160 and provides support to the hoop section 165 of frame 160. In the expanded state the articulating support 162 engages with the wall of the vessel and prevents the collapse of the hoop section 165 as it engages with the obstruction. The frame 160 further comprises a collar 151. The collar 151 facilitates the mounting of the frame 160 on an elongate member such as a support member 104 or a support tube 13 of a basket assembly.

FIG. 87a shows an isometric view and FIG. 87b shows an end view of frame 210. This frame 210 is similar to the frame 160 in FIG. 86, except that it does not have an articulating support. The frame comprises a hoop section 165 and a collar 151.

FIGS. 88a and 88b shows another frame 170 which is similar to the frame 160 of FIG. 86. In this case the frame comprises a hoop section 165 an articulating support 162 and a support wire 171. The hoop section 165 and the articulating support are as described in FIG. 86. The support wire 171 may be integral with the hoop section 165 of the frame 170. In this case the support wire 171 is configured in the same way as support members or support tubes described with other baskets of the invention. In another embodiment the support wire 171 is fixed to a support member at its proximal end. FIG. 88c shows the frame 170 in the collapsed configuration with the struts of both the hoop section 165 and the articulating support 162 being substantially parallel.

FIG. 89a shows an isometric view and FIG. 89b an end view of frame assembly 180 which is composed of a frame 181, an expansion cable 184 and a bumper tube 183. The frame 181 comprises a proximal hoop 190 and a distal hoop 191 and a bridge element 187 connecting the two hoops. The frame further comprises a cable attachment 188 on the distal hoop 191 and a cable guide 189 on the proximal hoop. The cable guide 189 comprises an abutment surface 192 on its proximal side. In one embodiment the frame 181 has a collapsed state for delivery and an expanded state for clot engagement and the frame 181 is biased towards the expanded configuration. With this embodiment the cable 184 serves to purpose of reinforcing the frame 181 in the expanded configuration such that it provides strong resistance to collapse and thus good clot engagement. With this embodiment the bridge 187 comprises an articulating element. While the bridge 187 is configured to allow the proximal hoop 190 and distal hoop 191 to articulate through a large angle of displacement it is a relatively stiff element so as to provide good radial strength to the frame 181 in the expanded state.

In another embodiment the bridge 187 comprises a flexible hinge. With this embodiment the frame has three configurations. In the collapsed delivery configuration the frame sits within the microcatheter. The two struts 185 of the proximal hoop 190 lie substantially parallel to one another in the collapsed state. Likewise the two struts 185 of the distal hoop 191 lie substantially parallel to one another in the collapsed state. In the deployed configuration the proximal hoop 190 and the distal hoop 191 expand into a hoop shape but do not articulate. The deployed frame assumes a planar configuration along the axis of the vessel. When the cable 184 is activated the abutment surface 192 of the cable guide 189 engages with the distal abutment 182 of the bumper tube 183. Further activation of the tether causes the cable attachment point 188 to move towards the cable guide 189 and this is facilitated by the hinge 187 connecting the proximal hoop 190 to the distal hoop 191. By controlling the displacement of the cable the size of the expanded frame can be adjusted by the user. The frame can be expanded such that it is in interference with the walls of the vessel, or it can be expanded such that it is closely sized to the lumen of the vessel or it can be undersized relative to the vessel. This one size fits all feature is a significant advantage of this embodiment.

In the final device configuration the frame assembly has a net attached to the frame and a debonder mounted over the bumper tube 183. The net may be attached to either the proximal hoop 190 or the distal hoop 191. Where the net is attached to the proximal hoop 190 the net must pass the struts of the distal hoop 191. In one embodiment the net passes over the distal hoop 191 and is attached to the proximal hoop 190. With this embodiment the collapsing and expanding of the frame requires the distal hoop to slide inside the net.

In another embodiment the net passes through the opening of the distal hoop 191 and is attached to the proximal hoop 190. With this embodiment the net slides through the mouth of the distal frame 191 during deployment or collapse of the frame 181.

It will be appreciated that any of the clot debonders disclosed in this invention could be employed in conjunction with the frames or frame assemblies described in FIG. 85 to FIG. 94.

FIG. 90a shows an isometric view and FIG. 90b an end view of another frame assembly 200 which is similar to the frame assembly 180 in FIGS. 89a and 89b. In this case the frame assembly 200 is composed of a frame 201, an expansion cable 203 and a support member 202. The frame 201 comprises a proximal hoop 208 and a distal hoop 209 and a bridge element 207 connecting the two hoops. The frame 201 further comprises a cable attachment 206 on the distal hoop 209. The cable 203 extends from the cable attachment 206 parallel to the support member 202 back to the user interface (not shown). The support member 202 comprises an elongate member and is fixed to the frame 201 at its distal end. In one embodiment the frame 201 has a collapsed state for delivery and an expanded state for clot engagement and the frame 201 is biased towards the expanded configuration. With this embodiment the cable 203 serves to purpose of reinforcing the frame 201 in the expanded configuration such that it provides strong resistance to collapse and thus good clot engagement. With this embodiment the bridge 207 comprises an articulating element. While the bridge 207 is configured to allow the proximal hoop 208 and distal hoop 209 to articulate through a large angle of displacement it is a relatively stiff element so as to provide good radial strength to the frame 201 in the expanded state.

In another embodiment the bridge 207 comprises a flexible hinge. In one embodiment the flexible hinge comprise a tether. With the flexible hinge embodiment the frame has three configurations as were described in FIG. 89 above.

FIG. 91a shows an isometric view and FIG. 91b an end view of another frame assembly 220. In this case the frame assembly comprises a hoop frame 221, an expansion strut 222, a cable 223 and a support member 224. The hoop frame 221 comprises a pair of struts 225 and a capture opening 226. The expansion strut is connected to the frame 221 at one end 228 and comprises a vessel wall engagement section 227 at the other end. The vessel wall engagement 227 engages the vessel wall and provides support to the frame 221 in the expanded state. In order to avoid trauma to the vessel the vessel wall engagement 227 comprises an engagement surface. Preferably the engagement surface is soft. Preferably the engagement surface engages the vessel wall over a segment of the vessel wall. The expansion strut 222 further comprises a cable attachment 229 where expansion cable 223 is attached. Expansion cable 223 and support member 224 extend proximally to the user interface (which is described elsewhere in this specification).

Another frame assembly 240 is shown in FIG. 92 which could be incorporated into any of the baskets of the devices of the invention. The frame assembly 240 is similar to the frame assembly described in FIG. 81 and FIG. 82 and it will be appreciated that the frame assembly 240 could be incorporated with the clot debonder 2 and user interface 70 of FIG. 81 and FIG. 82. The frame assembly 240 comprises an elastic, a shape memory or a super elastic frame and has a remembered at least partially expanded state and a deformed state. In the deformed state the frame assembly is strained by an external restraining element. In one embodiment the deformed state comprises a collapsed delivery state. In one embodiment the restraining element comprises a microcatheter. In another embodiment the restraining element comprises a tether which ties the frame assembly 240 in the restrained delivery configuration. The frame assembly 240 comprises a frame 241, a vessel engagement strut 242, a support member 246 and a pull tether 245. The frame 241 comprises a capture ring 247. The capture ring 247 comprises a vessel opposing ring in its expanded state. Said ring 247 comprises a first ring segment 248 and a second ring segment 249. Said first ring segment 248 and said second ring 249 are connected by two articulation regions 243. Said first ring segment 248 is articulated relative to said second ring segment 249 by activation of the pull tether 245.

In one embodiment the frame assembly 240 comprises cable guides 7 as described in FIG. 81. In one embodiment the pull tether 245 runs substantially parallel to capture ring 247 over at least a portion of its length. The pull tether 245 is spaced apart from the neutral axis of the capture ring 247 of the frame 241 over at least a portion of its length. The spacing of the pull tether from the neutral axis the capture ring 247 imparts a bending moment to the capture ring 247 when the pull tether 245 is tensioned. This bending moment causes the first ring segment 248 to articulate relative to the second ring segment 249 about articulation region 243. In another embodiment the pull tether 245 causes the capture ring 247 to articulate relative to the support member 246. The vessel engagement strut 242 comprises a curved segment and the ends of said segment are connected to the capture ring 247. Preferably the vessel engagement strut 242 is integral with the capture ring 247. The vessel engagement strut 242 engages with the vessel wall and prevents the capture ring 247 from collapsing under the forces of clot engagement. The support member 246 is connected to the frame 241 and extends proximally to the user interface 70. The pull tether 245 extends proximally from the frame to the user interface 70 from where it is activated or deactivated as previously described. In one embodiment the pull tether 245 extends parallel to the support member 246 over a substantial portion of its length. In another embodiment the support member comprises a tubular member over at least a portion of its length. In one embodiment the tubular segment of the support member comprises exit port and the tether extends through the lumen of the tubular segment and exits the tubular segment via said exit port.

FIG. 93 shows another frame assembly 260 which is similar to the frame assembly of FIG. 81. However in this case the frame assembly comprises a frame 261 and a support member 262. The frame 261 comprises a one piece frame which comprises a capture ring 263, a support strut 264, a connector strut 265 and a collar 266. The frame 261 is preferably cut from a tube. In one embodiment the frame 261 is laser cut from a hypo tube. The engagement of the support strut 264 with the wall of the vessel prevents the collapse of the frame when the clot engagement ring 263 engages with the occlusion 40. The support strut 264 is connected to the engagement ring 263 at connection points 267. The connection points 267 comprise regions of bending when the frame 261 is collapsed for delivery. The engagement ring must collapse in concert with the support strut 264 and the strains of collapse are absorbed in the bending regions 268. The frame 261 further comprises net attachment points 269 on both the ring 263 and the support strut 264. In one embodiment the attachments 269 comprise eyelets in the struts of the frame 261. The connector strut 265 is configured to connect the engagement ring 263 to the support member 262. The connector strut 265 may flex such that the axis of the support member 262 may move apart from or towards the axis of the vessel while the ring 263 is engaged with the wall of the vessel. The collar 266 is fixed to the support member 262 and holds the frame 261 steadfast relative to the support member 262.

With reference to FIG. 94a to FIG. 94f there is shown basket assembly 300 including frame assembly 280. The basket assembly 300 has a collapsed state for delivery as shown in FIG. 94g, a partially expanded unconstrained configuration as shown in FIG. 94a and FIG. 94b and a fully expanded state as shown in FIG. 94c and FIG. 94f The basket assembly 300 comprises a frame assembly 280 and a net 287. The basket assembly may be integrated with any of the clot debonder assemblies and user interfaces of the invention to create a device for the recannalization of vascular occlusions especially acute stroke occlusions.

The frame assembly comprises a frame 281, a control tube 282, and a pull cable 288. The frame 281 comprises an engagement ring 283, and a hinged support 284. The hinged support 284 is connected to the engagement ring 283 with hinges 285. The pull cable is attached to the hinged support 284 at an attachment junction 289. The attachment junction lies substantially midway between the hinges 285. The pull cable 288 extends from the attachment junction through cable guide 290 and further extends through the lumen of control tube 282. Preferably the cable 288 is activated with the assistance of a control mechanism at the user interface 70.

With reference to FIG. 94a and FIG. 94b, the frame assembly 280 is shown in the partially expanded state. The frame assembly 280 assumes the partially expanded state when the frame assembly is deployed from the microcatheter 293 with the pull cable 288 is deactivated. The pull cable 288 is deactivated when the distal abutment surface 292 of the control tube 282 is not engaged with the cable guide abutment 291. In this configuration the engagement ring 283 is expanded as is the hinged support 284 with the hinged support 284 being substantially parallel to engagement ring 283. In one embodiment the engagement ring 283 and the support 284 lie substantially parallel to the axis of the vessel in the partially expanded state. In another embodiment the engagement ring 283 and the support 284 lie substantially parallel to the axis of the control tube 282 in the partially expanded state. FIG. 94c shows the frame assembly 280 in the expanded configuration. In this configuration the pull cable 288 is activated and this causes the abutment 292 of the control tube 282 to engage with the cable guide abutment 292 of the cable guide 290. Activation of the pull cable 288 further causes the hinged support 284 to articulate relative to the engagement ring 283. The articulation of the support 284 causes the ring to articulate relative to the control tube 282 and the user may control the degree of articulation by the displacement of the pull cable 288. In this way the user may size the mouth of the engagement ring to the size of the occlusion that is to be disengaged and captured.

In one embodiment the hinge 285 comprises a pin and eyelet arrangement. In another embodiment the hinge 285 comprises a tether. In another embodiment the hinge 285 comprises an integral hinge. One embodiment of an integral hinge is shown in FIG. 94d and FIG. 94e where the hinge 285 comprises a relief section 286. The relief section 286 comprises a thinned section of the wall of the support 284. The relief section 286 allows the support 284 to articulate relative to the engagement ring 283. FIG. 94d shows a close up view of the hinge 285 when the frame 281 is in the expanded configuration. FIG. 94e shows a close up of the hinge 285 when the frame 281 is in the collapsed or the partially deployed state.

In one embodiment the integral hinge 285 is made from an elastic, a super elastic or a shape memory material and said hinge comprises a biased configuration. In one embodiment the biased configuration comprises the collapsed state. In another embodiment the biased configuration comprises the expanded state.

FIG. 94f shows a basket assembly incorporating the frame assembly 280 as described above. The basket assembly 300 is shown with the frame 281 in the fully expanded configuration. In the expanded configuration the hinged support 284 is subtended at an angle relative to the engagement ring 283.

FIG. 94g shows the frame assembly 280 in the fully collapsed configuration inside microcatheter 293. In this configuration the struts 294 of the engagement ring 283 and the hinged support 284 all lie substantially parallel to the axis of the microcatheter 293.

FIG. 95 shows another basket assembly 320 according to the invention. The basket assembly comprises a frame 321, a net 322, an expansion cable 323, a support member 325 and a expansion member 328. The frame comprises an engagement hoop 324 a collar 327 connecting said hoop 324 with elongate support member 325. The frame 321 further comprises cable attachment 326 which facilitates fixing of the cable 323 to the frame 321. The net 322 comprises a closed end net with openings of 500 micrometers or less configured to prevent captured clot from fragment during removal. The net 322 is attached to the frame 324 at a plurality of connection points around the circumference of the frame 321. The frame comprises a collapsed configuration for delivery, a first expanded state and a second expanded state. In the first expanded state the frame 321 self expands such that the hoop frame 324 comprises a substantially elliptical opening and said hoop frame 324 is at least partially engaged with the vessel wall. In the second expanded state the expansion member 328 is moved proximally relative to the support member 325 and this brings the cable 323 into a state of tension. The cable 323 provides additional support to the frame 321. In one embodiment the resistance of the frame to collapse is greater in the second expanded state than the first expanded state. In another embodiment the radial force of the frame is greater in the second expanded state when compared to the first expanded state.

The expansion member 328 is slidable relative to the support member 325. In one embodiment the expansion member is configured such that a debondong assembly can be mounted on its outside diameter.

FIG. 96 shows another basket assembly 340 according to the invention. The basket assembly comprises a frame 341, a net 342, an expansion cable 343, and a support member 345. The frame 341 comprises an engagement hoop 344 a collar 347 connecting said hoop 324 with elongate support member 345. The support member 345 comprises an elongate tube and the pull cable 343 extends from the attachment point 346 through the lumen of said tube to the user interface 70. The collar 347 is fixed to the support member 345. In one embodiment the support member 345 comprises a tube and the collar 347 is integral with said tube. The frame 341 further comprises cable attachment 346 which facilitates fixing of the cable 343 to the frame 341. The net 342 comprises a closed end net with openings of 500 micrometers or less configured to prevent captured clot from fragment during removal. The net 342 is attached to the frame 344 at a plurality of connection points around the circumference of the frame 341. The frame comprises a collapsed configuration for delivery, a first expanded state and a second expanded state. In the first expanded state the frame 341 self expands such that the hoop frame 344 comprises a substantially elliptical opening and said hoop frame 344 is at least partially engaged with the vessel wall. In the second expanded state the cable 343 is pulled proximally relative to the support member 345 and this brings the cable 343 into a state of tension. The cable 343 provides additional support to the frame 341. In one embodiment the resistance of the frame to collapse is greater in the second expanded state than the first expanded state. In another embodiment the radial force of the frame 341 is greater in the second expanded state when compared to the first expanded state.

FIG. 97 shows another basket assembly 360 according to the invention. The basket assembly 360 comprises a frame 361, a net 362, an expansion cable 363, and a support member 365. The frame 361 comprises an engagement hoop 364 a collar 367 connecting said hoop 364 with elongate support member 365. The support member 365 comprises an elongate tube and the pull cable 363 extends from the attachment point 346 through the lumen of said tube to the user interface 70. The collar 367 is fixed to the support member 365. In one embodiment the support member 365 comprises a tube and the collar 367 is integral with said tube. The frame 361 further comprises cable attachment 366 which facilitates fixing of the cable 363 to the frame 361. The frame 361 further comprises a plurality of cable guides 368. The cable guides 368 comprise guide elements through which the cables 363 can slide. The cable guides are configured such that the path of the cable is parallel to the neutral axis of the hoop frame 364 over at least a portion of the length of the hoop frame 364. The support member 365 comprises a lumen and the expansion cable 363 extends through the lumen of the support member 365 to the user interface 70 (not shown).

The net 362 comprises a closed end net with openings of 500 micrometers or less configured to prevent captured clot from fragment during removal. The net 362 is attached to the frame 364 at a plurality of connection points around the circumference of the frame 361. The frame 361 comprises a collapsed configuration for delivery, a first expanded state and a second expanded state. In the first expanded state the frame 361 self expands such that the hoop frame 364 comprises a substantially elliptical opening and said hoop frame 364 is at least partially engaged with the vessel wall. In the second expanded state the cable 363 is pulled proximally relative to the support member 365 and this brings the cable 363 into a state of tension. The cable 363 provides additional support to the frame 361. In one embodiment the resistance of the frame to collapse is greater in the second expanded state than the first expanded state. In another embodiment the radial force of the frame 361 is greater in the second expanded state when compared to the first expanded state.

FIGS. 98a and 98b show a device 400 comprised of a basket assembly 380 and a debonder assembly 401. The basket assembly 380 is very similar to the basket assembly 360 of FIG. 97 with the exception that the support member is directly connected to the hoop frame. This eliminates the collar element 367 shown in the previous drawing. The basket assembly 380 functions in exactly the same way as that of basket assembly 360 of FIG. 97. The debonder 401 comprises a ring member 402 and an outer member 404. The ring member comprises a collapsed delivery configuration as shown in FIG. 98b and an expanded engagement configuration as shown in FIG. 98a. The outer member 404 comprises an elongate tube and is sized to facilitate relative movement with the support member 365 of the basket assembly 380. In the deployed configuration the ring member 402 engages with the proximal end of the clot and the ring member 402 comprises an abutment against which the basket is retracted so as to disengage the clot from the wall of the vessel without applying significant tensile forces to the wall of the vessel.

Figure 99A:
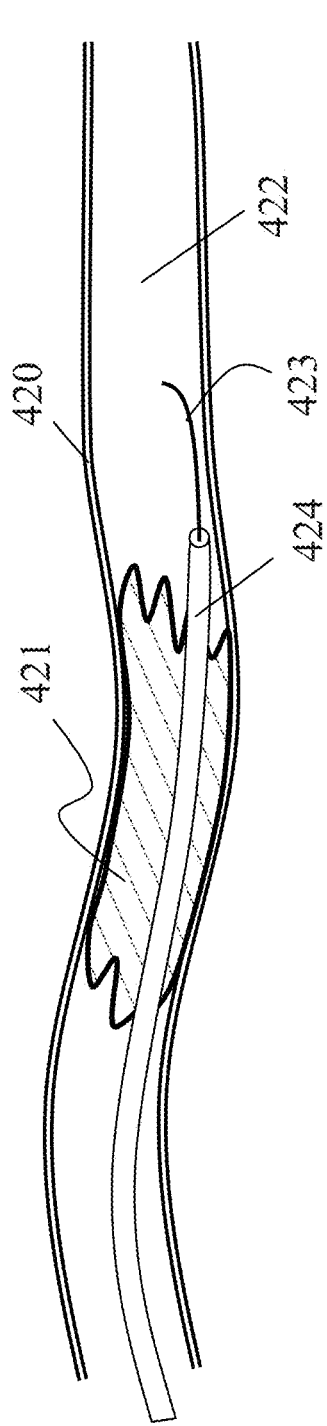

The method use of the devices described in FIG. 95 through to FIG. 98b will be described below with reference to FIG. 99a-i. FIG. 99a shows an occlusive clot 421 in a vessel 420. The occlusive clot 421 is fixed strongly to the vessel wall 422 of the vessel 420. A guide catheter is advanced into an upstream vessel of larger diameter. In the case of an occlusion of an anterior vessel of the cerebral circulation the guide catheter 425 is placed in a carotid artery. The guide catheter 425 is preferably 8 F in diameter or less. More preferably the guide catheter 425 is 7 F in diameter or less. Even more preferably the guide catheter 425 is 6 F in diameter or less. In one embodiment the procedure comprises the step of advancing a transition catheter 426 through the lumen of the guide catheter 425 such that the tip of the transition catheter 426 extends from the distal tip of the guide catheter 425 and the transition catheter 426 is advanced to into a smaller bore vessel than is possible with the guide catheter. In the example above the transition catheter 426 may be advanced into the internal carotid vessel. The tip of the transition catheter 426 may be placed in the cervical section of the internal carotid artery. For the purposes of the remaining descriptions associated with FIG. 99a-i reference to the guide catheter 425 may be interpreted to include the transition catheter 426 or not since the procedure may be conducted with or without the transition catheter 426.

With the guide catheter 425 in place (not shown) a microcatheter 424 is advanced through the lumen of the guide catheter 425 until its distal end is advanced distal of the tip of the microcatheter. The microcatheter is advanced further with the assistance of a guidewire 423 within the lumen of the microcatheter 424 and both instruments are manipulated until the tip of the microcatheter is across the occlusive clot. At this point the guidewire 423 is withdrawn.

Figure 99B:
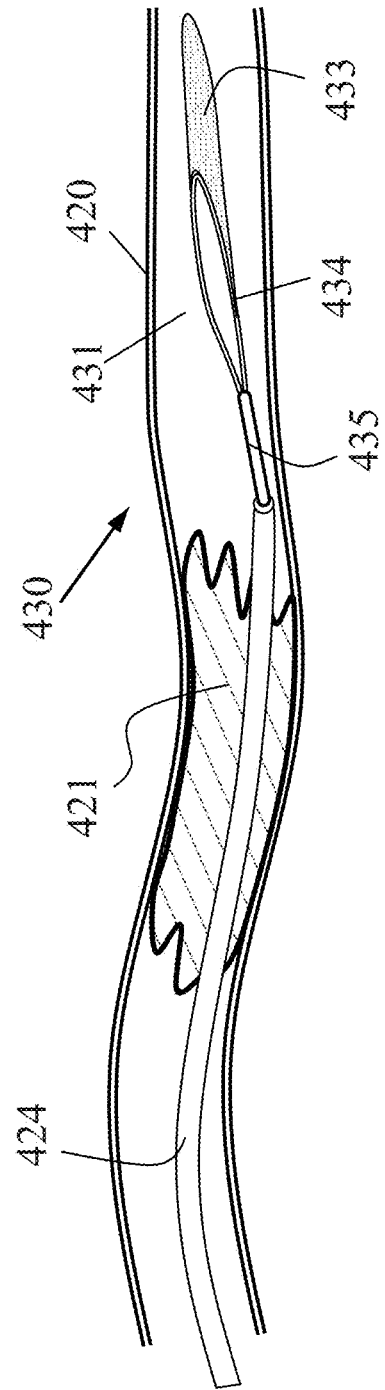

Referring now to FIG. 99b the device 430 is advance through the lumen of the microcatheter 424 with the basket 431 and the debonder 432 in the collapsed configuration until the basket 431 is advanced distal of the tip of the microcatheter 424 with the debonder still restrained in the collapsed configuration. The basket 431 is partially expanded.

Figure 99C:
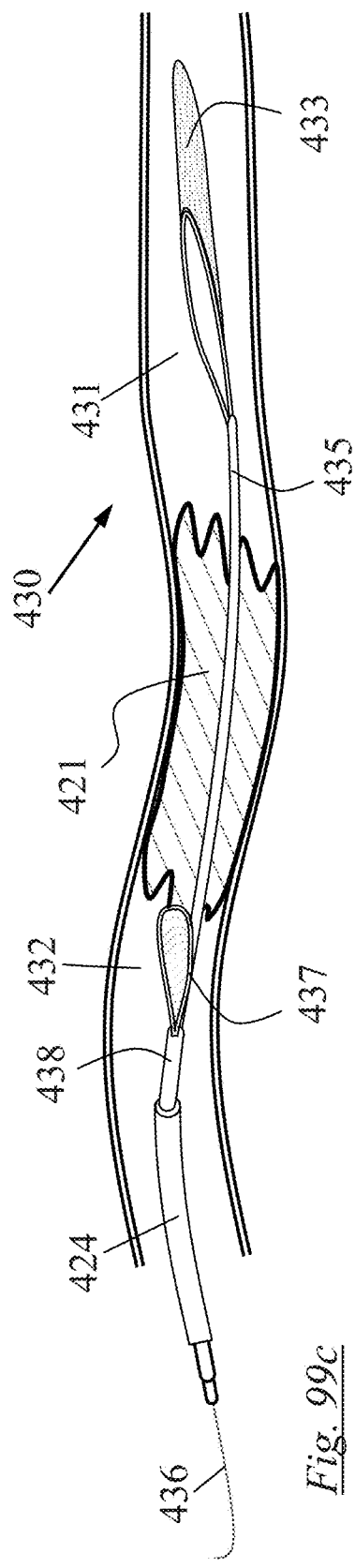

Referring to FIG. 99c, the microcatheter 424 is withdrawn while holding the basket 431 stationary until the tip of the microcatheter 424 is proximal of the occlusion 421. The debonder 432 is deployed proximal of the occlusion 421. In one embodiment the debonder 432 is deployed by withdrawing the microcatheter proximally while holding the debonder hub 442 stationary. In another embodiment the debonder 432 is deployed by holding the microcatheter 424 stationary while advancing the debonder assembly 432.

Referring to FIG. 99d, the basket 431 is fully expanded by activating the pull cable 436 with the activator 441 of the handle 440. In one embodiment the activator 441 comprises a thumbscrew. In another the cable activator 441 comprises a slider. In yet another embodiment the activator comprises a lever. The cable 436 is tensioned by the user activating the activator 441. The tension may be transmitted to the cable via a number of mechanisms. In one embodiment the mechanism comprises a rack and pinion mechanism. In another embodiment the mechanism comprises a circular drum onto which the cable 436 is wound. The fully expanded basket is withdrawn proximally until the frame 434 engages with the distal end of the clot. In one embodiment the frame comprises radiopaque elements to facilitate visualisation under fluoroscopy. The step of engaging the basket with the distal end of the clot involves sizing the vessel 420 in the region distal of the clot 421, moving the activator 441 so as to expand the frame 434, and monitoring the expansion of the frame 434 on fluoroscopy. The debonder 432 is advanced distally until the ring member contacts the proximal end of the clot 421. The debonder is advanced further to ensure the ring member 437 is fully engaged with the clot. In one embodiment the ring member 437 is deployed in a partially expanded state with the ring member deployed at an angle relative to the support member 435. With this embodiment when the ring member 437 is further advanced, engagement with the clot causes it to expand to a fully deployed configuration. Preferably the relative angle is greater than 40°.

FIG. 99e shows the basket 431 and debonder 432 fully engaged with the clot. The basket is withdrawn proximally while holding the debonder steadfast and this action breaks the bonds between the vessel wall and the clot. The debonder forces the clot into the open mouth of the basket as the basket is withdrawn. In another embodiment, as shown in FIG. 99f, the step of debonding the clot 421 from the vessel wall 420 and the step of forcing the clot 421 into the open mouth of the basket 431 comprise advancing the debonder 432 while holding the basket 431 steadfast. FIG. 99f shows the clot 421 almost completely enveloped by the net 433.

The debonder 432 is advanced until the clot 421 is completely enveloped by the basket 431. In one embodiment the debonder 432 is advanced until the outer member 438 of the debonder 432 abuts the frame 434. In another embodiment the debonder 432 is configured such that at least a portion of the debonder 432 may enter the mouth of the basket 431.

In one embodiment the basket 431 and clot 421 are removed with the ring member 437 of the debonder 432 occluding the mouth of the basket 431. With this embodiment the removal steps comprise:
- Slightly disengaging the debonder 432 from the proximal end of the clot 421 so as to reduce applied pressure.
- Deactivating the frame 434 and partially collapsing the basket 431 by deactivating the pull cable 436.
- Locking the debonder 432 to the support member 435 (thus, locking the debonder 432 to the basket 431).
- Retracting the device 430 and withdrawing the basket 431 and clot 421 through the lumen of the guide catheter 425.

Referring to FIG. 99g to FIG. 99i another embodiment of the steps of removing the basket and clot comprises:
- Disengaging the ring member 437 from the proximal end of the clot 421.
- Retracting the debonder from the vessel segment.
- Deactivating the activator 441 so as to remove the tension in the cable 436 and at least partially collapsing the basket 431.
- Retracting the basket 431 proximally and removing the basket from the vessel segment.
- Removing the basket 431 through the lumen of the guide catheter 425.

In one embodiment the microcatheter 424, debonder 432 and basket 431 are removed through the lumen of the guide catheter 425 together.

Referring now to FIG. 100a to FIG. 100c there is shown yet another embodiment of the invention. In this case a basket assembly 450 comprises a support member 451, an engagement ring 452, a pull cable 454 and a net 454. The support ring 452 comprises two struts 458 and the net is attached to said struts 458. The support member comprises a lumen and the pull cable extends through the lumen of the support member 451. The basket assembly 450 comprises a collapsed delivery configuration as shown in FIG. 100a, an expanded configuration and an expanded articulated configuration as shown in FIG. 100c. The ring member is comprised of Nitinol and has a remembered expanded configuration. The remembered expanded configuration of the engagement ring 452 comprises a substantially planar hoop and the plane of the hoop is aligned with the axis of the elongate support member 451. The basket assembly 450 further comprises a junction 456 where the support member 451 and the engagement ring 452 are interconnected.

With reference to FIG. 100c, the basket assembly further comprises an articulation region 457 adjacent to the junction 456. Pulling the pull cable 454 relative to the support member 451 causes the ring member to articulate relative to the support member and the ring member 452 makes an angle with the support member 451. In one embodiment the angle is less than 90°. In another embodiment the angle is equal to or greater than 90°. In one embodiment the articulation region 457 is adjacent the junction 456. In one embodiment the articulation region forms part of the engagement ring 452 adjacent the junction 456. In another embodiment the junction 456 comprises the articulation region 457.

Yet another embodiment is shown in FIG. 100d to FIG. 100f where the articulation region 457 forms part of the distal end 459 of the support member 451 adjacent the junction 456. With this embodiment activation of the pull cable 454 causes the distal end 459 of the support member 451 to change shape and this results in the engagement ring 452 articulating relative to the proximal end 460 of the support member 451. The shape change of the distal end 459 of the support member 451 comprises a change from a straight configuration to a curved configuration. The curved segment at the distal end 459 of the support member 451 has the effect of displaces and angulates the ring member 452 relative to the proximal end of the support member 451 and this allows the basket to reach around curved segments. This feature is especially useful at bifurcations where the occlusion needs to be removed from two branches simultaneously.

FIG. 100e and FIG. 100f show close up views of one embodiment of articulating basket assembly described in FIG. 100d. With this embodiment the support member 451 comprises a tube and the distal end 459 of said tube comprises a slotted section. The slots 461 in the slotted section are partial slots that extend around a portion of the diameter. In the embodiment shown the slots are all on one side of the tubular member 451. The side of the tubular member 451 with the slots 461 is more compressible than the side of the tube that possesses no slots. The pull cable is connected to the tubular member distal of the slotted section. In one embodiment the cable 454 is fixed to the support member 451. In another embodiment the cable is fixed to the junction 456. In another embodiment the cable 454 is fixed to the ring member 452. In yet another embodiment the slotted section 459 of the support member 451 comprises an exit port and the cable 454 extends through the exit port and is fixed to the engagement ring 452.

When the pull cable 454 is activated (tensioned) it applies a compressive force on the support member 451. Since the distal end 459 of the support member 451 has a compressible section this section compresses under the force. The compression of the distal section 459 comprises the closing of the slots in the tubing and this is shown in FIG. 100f. The compression of the slots 461 causes the distal section of the support member to change shape. In the embodiment shown in FIG. 100f the deformed shape comprises a curved segment at the distal end 459 of the support member 451. It will be appreciated that curves of tighter radius can be achieved by increasing the number of slots in the support member.

With reference to FIG. 101a and FIG. 101b another device 480 of the invention is described. The device 480 comprises a basket assembly 481, and a debonder assembly 482. The basket assembly 481 comprises a frame 483 a support member 484 and a handle 485. The support member comprises an elongate tube and the frame 483 is fixed to the distal end of the support tube 484. The frame comprises a collapsed configuration for delivery through the vasculature and an expanded configuration. The frame further comprises a clot engagement opening 505 and in the expanded configuration the clot engagement opening is sized such that the frame can engage the outer circumference of the clot and such that the clot can be forced through the opening and into the capture net 499. In the collapsed state the engagement opening 505 is substantially closed as is shown in FIG. 101a. The frame expanded state further comprises an angulation of the frame 483 with respect to the support member 484. In the collapsed state the axis of the frame lies substantially parallel to the axis of the support member 484. For the purposes of FIG. 101a-b the axis of the frame 483 shall mean a line drawn between the exit port 496 at the distal end of the support member 484 and the attachment point 494 on the frame 483. In the expanded state the axis of the frame is subtended at an angle to the axis of the support member. In one embodiment the axis of the frame 483 makes an angle of 30° or greater with the axis of the support member 484. In another embodiment the axis of the frame 483 makes an angle of 45° or greater with the axis of the support member 484. In yet another embodiment the axis of the frame 483 makes an angle of 60° or greater with the axis of the support member 484. In yet another embodiment the axis of the frame 483 makes an angle of 90° or greater with the axis of the support member 484.

The basket assembly 481 further comprises a first cable 492 extending from the handle 485 through the lumen of the support member 484, exiting the support member 484 at first exit port 496 and attaching to the frame 483 at first cable attachment 494. The first cable 492 when tensioned is responsible for expanding the ring member 490. It will be appreciated that the strut 491 width and thickness dimensions can be adjusted along the length of the strut 491 so as to assist in opening the ring member 490. The proximal end of the first cable 492 is fixed to an activation mechanism in the handle 485. In one embodiment the activation mechanism comprises a thumb wheel 486, and a first spool 487 fixed to the thumbwheel 486. A portion of the thumbwheel 486 extends through the wall of the handle 485 and allows the user to rotate the thumbwheel 486. The spool 487 is configured such that rotation of the thumbwheel 486 causes the first cable 492 to be wound onto the spool 487. The diameter of the first spool 487 controls the rate at which the first cable 492 is wound and thus the rate at which the engagement opening 505 of the ring member 490 is expanded.

The basket assembly 481 further comprises a second cable 493 extending from the handle 485 through the lumen of the support member 484, exiting the support member 484 at the second exit port 497 and attaching to the frame 483 at second cable attachment points 495. In one embodiment the second cable comprises two cables and the second attachment point comprises two attachment points. The second cable 493 when tensioned is responsible for angulating the ring member 490 with respect to the distal end of the support member 484. The basket assembly 481 comprises an articulation region adjacent the end of the support member. In one embodiment the frame 483 comprises an articulation region adjacent the junction 498 between the frame 483 and the support member 484. In another embodiment the distal end of the support member 484 comprises an articulation region. The proximal end of the second cable 493 is also fixed to an activation mechanism in the handle 485. In one embodiment the activation mechanism comprises the thumb wheel 486, and a second spool 488 fixed to the thumbwheel 486. The second spool 488 is configured such that rotation of the thumbwheel 486 causes the second cable 493 to be wound onto the spool 488. The diameter of the second spool 488 controls the rate at which the second cable 493 is wound and thus the rate at which the angulation of the engagement ring 490 is changed with respect to the support member 484. FIG. 101*b* shows a representation of the thumbwheel 486 wherein the first spool 487 and the second spool 488 are integral with the thumbwheel. The diameter of the first spool 487 and the second spool 488 can be independently adjusted so as to balance the rate of ring member 490 opening with the rate of angulation of the frame 483. It will also be appreciated that the first spool 487 and the second spool 488 may be mounted on separate thumbwheels. In this case the handle 485 would comprise two thumbwheels.

The device further comprises a net 499 mounted to the ring member as previously described. In one embodiment the device comprises a clot debonder 482. The clot debonder is as shown in FIG. 101*c* and comprises a debonding ring 500, a connector strut 501, an elongate tube 503 and a hub 504. The debonding ring 500 further comprises a lased surface 502 and said lased surface 502 comprises filaments lased across the opening defined by the debonder ring 500. The debonding ring 500 is connected to the tubular member 503 and the tubular member 503 extends proximally to control hub 504. The elongate tube 503 is configured to slide over the support member 484 such that the lased surface 502 can be advanced to engage with the occlusion.

A significant advantage of the device 480 of this invention is that the frame 483 assumes the collapsed configuration when not activated. This means that it can be advanced through the lumen of a microcatheter without any restraint and that it applies no radial force to the wall of the microcatheter. This allows the device to be constructed with a very low profile and allows the frame 483 to be advanced through the lumen of a microcatheter with ease. Neurovascular vessels are highly tortuous and ease of advancement is key to delivering the device to the target vessel segment.

Another aspect of the invention is shown in FIG. 102 through to FIG. 110 where a variety of debonder assemblies are disclosed. These debonder assemblies generally comprise a distal section wherein said distal section comprises an elongate member in the delivery configuration and the elongate member undergoes a shape change to form a ring member under the influence of a pull cable and said ring member is employed in conjunction with baskets to break the bonds that exist between occlusive clot and the wall of a vessel.

FIG. 102 shows a debonder assembly comprising an elongate tube 521 and a pull cable 524. The elongate tube further comprises a distal section 522 an exit port 523 a distal cable attachment 525 and an articulation region 527. The pull cable 524 and the elongate tube extend proximally to a handle 528. The pull cable 524 is connected to an activator 529 in the handle 528 and said activator 529 is configured to allow the user to tension the pull cable 524. In one embodiment the activator 529 comprises a slider. In another embodiment the activator 529 comprises a thumbscrew. In one embodiment the proximal end of the elongate tube 521 is fixed to the distal end of the handle 528 and the pull cable exits the elongate tube via its proximal lumen. In another embodiment the elongate tubing extends through the handle and provides a continuous lumen through the handle such that the assembly can be interfaced with other devices. With this embodiment the proximal end of the elongate tube 521 comprises a proximal exit port 531 and the cable 524 exits the lumen of the elongate tube 521 through the proximal exit port. The proximal exit port 531 is preferably distal of the activator 529. The distal end of the cable 524 is fixed at attachment point 525 at the distal end of the distal section 522. The assembly is delivered to the treatment site in the collapsed configuration as shown in FIG. 22 with the pull cable relaxed. In a preferred embodiment the pull cable 524 encircles the distal section 522 once between the exit port 523 and the attachment point 525. At the treatment site the distal section is transformed into a ring member 600 as shown in FIG. 25. The ring member comprises a generally circular or elliptical hoop and is configured to abut a vessel occlusion. The ring member 600 preferably engages the occlusion adjacent the interface between the occlusion and the vessel wall. In this way the ring member 600 delivers an abutment force to the interface between the clot and the vessel wall and this is the region where clot separation is most desired. The device further comprises an articulation region 527 adjacent the exit port 523. In one embodiment the articulation region comprises a local weakening of the tube in that region. In another embodiment the articulation region comprises at least one cut or slot in the wall of the tube in the articulation region. In another embodiment the cut comprises a spiral cut. In another embodiment the cut comprises a circular cut. In another embodiment the cut comprises at least one helical cut. In another embodiment the cut comprises a cut thickness. In another the cut thickness comprises at least two cut thicknesses. In yet another embodiment the articulation region comprises a plurality of patterned slots.

FIG. 103 shows a debonder assembly 540 which is similar to the assembly shown in FIG. 102 and comprises an elongate tube 541 and a pull cable 544. The elongate tube 541 further comprises a distal section 542 a lumen 546, a lumen distal end 543 a distal cable attachment 545 and an articulation region 547. The pull cable 544 and the elongate tube extend proximally to a handle 528. The construction and functions of the handle 528 are the same as was described in FIG. 102.

The lumen 546 extends from its distal end 543 to the proximal end of the handle 528 and is sized so as to accommodate the pull cable 544 and another elongate assembly such as a basket assembly. The debonder assembly 540 is delivered to the treatment site in the collapsed configuration as shown in FIG. 103 with the pull cable 544 relaxed. At the treatment site the distal section 542 is transformed into a ring member 600 as shown in FIG. 105. The distal section 542 comprises a strut 548. The strut 548 preferably comprises a spiral member. In one embodiment the strut 548 is cut from a hypotube and the spiral extends the entire length of the strut. In one embodiment the spiral comprises a 360° spiral. The pull cable extends from the lumen distal end 543 and is attached at attachment point 545. In a preferred embodiment the pull cable encircles the distal section 542 once between the lumen distal end 543 and the attachment point 545. When the pull cable is activated the distal attachment moves towards the lumen distal end 543. The strut progressively forms into a hoop and articulates about the articulation region 547.

The ring member 600 when formed comprises a generally circular or elliptical hoop and is configured to abut a vessel occlusion. The ring member 600 preferably engages the occlusion adjacent the interface between the occlusion and the vessel wall. The assembly 540 further comprises an articulation region 547 adjacent the distal end 543 of lumen 546. In one embodiment the articulation region 547 comprises a local weakening of the strut 548 in that region. In another embodiment the articulation region 547 comprises at least one cut or slot in the wall of the strut in the distal section 542.

FIG. 104 shows a debonder assembly 560 which is similar to the assembly shown in FIG. 22 and comprises an elongate tube 561 and a pull cable 564. The only difference between the device 520 of FIG. 102 and the debonder assembly 560 of FIG. 104 lies in the construction of the distal section 562. The distal section 562 comprises a plurality of slots 568 arranged along the substantially the entire length of the distal section. The plurality of slots 568 are arranged in a helical pattern. Each slot has a significant circumferential component and each slot comprises a width. In one embodiment the circumferential component of the slot comprises at least one quadrant. The width of the slot 568 is configured so as to facilitate compression of the slot 568 by the pull cable 564. Preferably the sum of the widths of all the slots 568 in the distal section 562 should add up to a dimension that is less than the difference between the inner and outer circumference of the ring member 600 when the ring member 600 sized to the diameter of the target vessel. In a preferred embodiment the pull cable 564 encircles the distal section 562 once between the exit port 563 and the attachment point 565.

FIG. 105 shows a debonder assembly 580 with the distal section formed into a hoop shaped ring member 600. The debonder assembly 580 represents the expanded configuration of the debonder assemblies 520, 540 and 560 of FIG. 102-104. The assembly comprises a ring member 600, a support member 601, a support member lumen 606, a distal section 602, a cable exit (port/lumen) 603, a pull cable 604, a handle assembly 528 (not shown), and a distal attachment 605.

FIG. 106*a* to FIG. 106*c* shows the arrangement of a device 620 wherein a debonder assembly 580 as described in FIG. 102-105 is being used in conjunction with a basket assembly 621. The basket assembly 621 comprises a hoop frame 622, a net 623 and a support member 624. The frame 622 is similar to the frame construction employed in FIG. 86. The support member 624 of the basket assembly 621 extends parallel to the elongate tube 601 of the debonder assembly 580. The support member 624 extends between the pull cable 604 and the distal section 602 of the debonder assembly 580. In one embodiment both the support member and the elongate tube extend through the lumen of a microcatheter. In another embodiment the support member extnds through the lumen of the elongate tube and the elongate tube is configured to be advanced or retracted relative to the support member. In FIG. 106*a* the basket assembly 621 is shown in the expanded configuration with the debonder assembly in the collapsed configuration. In FIG. 106*b* the pull cable 604 is activated and the distal section 602 is being reshaped into an engagement ring 600. In FIG. 106*c* the pull cable 604 is activated further through the handle 528 (not shown) and the reshaping of the distal section 602 is almost complete. It will be appreciated that the engagement ring 600 engages the occlusion in an area adjacent the wall of the vessel and that some clot may project through the opening in the engagement ring 600. However the primary purpose of the engagement ring 600 is to provide a reaction force to the action of the basket assembly 621. This reaction force allows the basket assembly to be retracted strongly without fear of vessel rupture or dissection.

Using the device 620 of the invention comprises at least some of the following steps:

Advancing a guide catheter into a large diameter vessel proximal of the cerebral vasculature (the CCA or the ICA).

Advancing a microcatheter through the lumen of the guide catheter until its distal end is advanced distal of the tip of the guide catheter.

Further advancing the microcatheter with the assistance of a guidewire within the lumen of the microcatheter.

Manipulating both the microcatheter and the guidewire until the tip of the microcatheter is across the occlusive clot.

Withdrawing the guidewire 423 from the lumen of the microcatheter.

Advancing the device 620 through the lumen of the microcatheter with both the basket and the clot debonder in the collapsed configuration.

Deploying the basket from the microcatheter distal of the occlusion.

Expanding the fame of the basket distal of the occlusion.

Retracting the microcatheter and exposing the distal section 602 of the debonder assembly 580.

Activating the cable such that the distal section 602 of the debonder assembly changes shape and forms an engagement ring.

Engaging the engagement ring with the proximal end of the clot.

Engaging the hoop frame 622 of the basket assembly 621 with the distal face of the clot.

Retracting the basket assembly while holding the debonder assembly 580 stationary.

Disengaging the clot from the vessel wall.

Applying a capture force to the clot.

Forcing the clot into the capture opening of the basket.

Disengaging the engagement ring 600 from the proximal face of the occlusion.

The step of disengaging the engagement ring 600 comprises at least removing some of the tension in the cable such that the engagement ring 600 at least partially reverts to its original configuration.

FIG. 107 shows a device 640 which comprises a basket assembly 621 and a debonder assembly 650. The basket assembly 621 is as described in FIG. 106a-c. The debonder assembly 650 comprises an elongate tube 651, a distal section 652, a cable 654, a cable exit port 653 and a cable attachment 655. The distal section 652 comprises a tube and the tube comprises a spiral cut. The spiral cut allows the distal section 652 to deform into a ring member for clot abutment when the cable 654 is tensioned. The distal section 652 further comprises a cable loop 656. The cable loop 656 comprises a loop of yarn wherein both ends of the yarn are fixed to the distal section 652. The loop 656 is sized to accommodate the support member 624 of the basket assembly 621 and the loop 656 holds at least a portion of the support member 624 adjacent the distal section 652. When the distal section 652 is expanded and assumes its expanded configuration as a ring member the loop guides the ring member along the support member 624 as it is advanced and retracted.

FIG. 108 shows a device 660 which comprises a basket assembly 621 and a debonder assembly 670. The debonder assembly 670 is very similar to the debonder assembly 650 of FIG. 107. The debonder assembly 670 comprises an elongate tube 671, a distal section 672, a cable 674, a cable exit port 673 and a cable attachment 675. The distal section 672 comprises a tube and the tube comprises a plurality of slots. The plurality of slots 677 controls the bending of the distal section 652 when the cable 654 is tensioned. The slots 677 are arranged such that the distal section deforms into a hoop and said hoop is articulated so as to create a distal abutment ring for clot engagement. The distal section 672 further comprises a cable loop 676 and the cable loop 676 functions in the same manner as cable loop 656 of FIG. 107.

The device 680 of FIG. 109a and FIG. 109b comprises a basket assembly 621 and a debonder assembly 690. The debonder assembly 690 comprises an elongate tube 671, a distal section 672, a cable 674, a cable exit port 673 and a cable attachment 675. The distal section 672 comprises a tube and the tube comprises a plurality of slots 677. The plurality of slots 677 controls the bending of the distal section 652 when the cable 654 is tensioned. The slots 677 are arranged such that the distal section deforms into a hoop and said hoop is articulated so as to create a distal abutment ring for clot engagement. The distal section 672 further comprises a cable loop 676 and the cable loop 676 functions in the same manner as cable loop 656 of FIG. 107. The elongate tube 671 comprises an inner lumen 691 and said inner lumen is sized to accommodate the support member 624 over at least a portion of the length of the elongate tube 671. The elongate tube 671 further comprises an inlet 691 and said inlet 691 is sized to allow the support member 624 access the lumen of the catheter. In one embodiment the inlet 691 is located proximal of the cable exit port 673. In another embodiment the inlet 691 is distal of the exit port 653. In another embodiment the inlet 691 is adjacent the exit port 653. In yet another embodiment the exit port 653 comprises the inlet 691.

In yet another embodiment the shape change of the distal section 672 is achieved using two cables. The first cable is attached to the distal section at the distal end of the distal section. This cable when activated pulls the attachment 676 towards the exit port 673 and thus forms an engagement ring 678. The second cable is attached to the distal section 672 proximal of the distal end and causes the ring to articulate such that the ring 678 comprises a distally facing abutment ring. In one embodiment the first and second cables are activated with a single activator 529. In another embodiment the first and second thumbwheels are activated by two separate thumbwheels.

The device 700 of FIG. 110 comprises the basket assembly 621 and the debonder assembly 540 both of which have been described previously. The figure shows the two assemblies configured as a device for use in treating acute occlusions. The strut 548 of the distal section 542 is wrapped around the support member 651 of the basket assembly 621 in the delivery configuration.

FIG. 111a-111c show another device 720 of the invention. The device comprises a debonder assembly 722 and a basket assembly 721. The basket assembly comprises support struts 723 and a net 724. The support struts 723 are connected to the user end at the basket proximal hub 727 via a plurality of pull cables 726. The pull cables 726 are spaced apart from the support member 725. The pull cables are assembled through cable guides 732 of the struts 731 in the debonder assembly 722. In this embodiment the debonder assembly 722 and basket assembly 721 move relative to each other in order to retrieve a vessel obstruction while the pull cables 726 remain adjacent the vessel wall.

FIG. 111b is an elevation view of the device of FIG. 111a in the collapsed configuration and FIG. 111b shows the device of FIG. 111a in an expanded configuration. The support member 225 is assembled inside elongate tube 728. The support struts 731 are connected to elongate tybe 728. The elongate tube contains a plurality of exit ports 730. In this embodiment the pull cables are fixed to the support struts 723 at the distal end and the basket proximal hub 727, and are moveable through the cable guides 732 and exit ports 730.

FIG. 111c shows the device in a partially activated state with the support struts 723 and struts 731 expanded. The device may be partially actuated by mobbing the proximal basket hum 727 relative to the debonder hub 735.

FIG. 111d-FIG. 111f shows the device of FIG. 111a inside a vessel removing an occlusive clot 421. FIG. 111d shows the device with the basket assembly 721 distal of a clot and the debonder assembly 722 proximal of the clot. FIG. 111e shows the device 720 in a partially actuated state with the struts 731 and support struts 723 in an expanded configuration. In FIG. 111f the basked assembly is located adjacent the occlusive clot and the pull cables 726 are in tension. This draws the basket assembly 721 and the debonder assembly 722 together. The engagement segment 729 of the debonder assembly provides a support surface for the clot as the basket assembly 721 engulfs the occlusive clot.

FIG. 112a-FIG. 112c show another device 750 of the invention. In FIG. 112a the debonder assembly 722 is fixed to an elongate tube 728 similar to the device of FIG. 111a but in this device the basket assembly 751 is slidable relative to a guidewire 753. FIG. 112b shows the device 750 in a vessel with an occlusive clot 421 with the basket assembly deployed distal of the occlusive clot. In FIG. 112c the control hub 734 is moved relative to the debonder hub 735 to draw the basket assembly 751 over the clot. The guidewire 753 is movable relative to the debonder assembly 722 and the basket assembly 751. With this device the user may leave the guidewire 753 in place after removing the basket assembly 751 containing the occlusive clot 421.

FIG. 113a and FIG. 113b show another device 800 of the invention. In this case the device 800 comprises an eccentric basket 801 and an eccentric debonder 802. The eccentric basket 801 comprises a frame 803, a net 804 and a support member 805. The frame comprises a proximal hoop 806, a distal hoop 807 and an expansion member 809. The frame expansion comprises of two components. Firstly the proximal and distal hoops form. The proximal and distal hoops comprise pairs of struts in the collapsed configuration. The struts move apart to form a hoop when the external restraint is removed. Secondly the first and second hoops undergo an angular displacement with respect to each other. This angular displacement is driven by elastic energy stored in the expansion member 809. The expansion member 809 also interconnects the proximal hoop 806 to the distal hoop 807. When the frame 803 is in the expanded configuration the expansion member 809 provides the frame 803 with a significant portion of its resistance to collapse.

Thus the expansion member 809 is configured to withstand significant strain and provide good resistance to collapse. Preferably the expansion member 809 comprises a metal. More preferably the metal comprises a nitinol. Preferably the expansion member 809 and the frame 803 comprise the same material and preferably the expansion member 809 and the frame 803 are integral. In one embodiment the expansion member 809 comprises a strut connecting the proximal hoop 806 to the distal hoop 807. In one embodiment the strut comprises a width and a thickness and the ratio of the width and the thickness comprises the aspect ratio of the strut. Preferably the aspect ratio of the strut is greater than 1. More preferably the aspect ratio is 1.5 or greater.

The frame 803 is mounted to the support member 805 at attachment 808. Preferably the attachment 808 comprises an attachment between the proximal hoop 806 and the support member 805. In one embodiment the net 804 is attached to the distal hoop 807. In another embodiment the net 804 is attached to the proximal hoop 806.

The debonder 802 comprises an elongate tube 812, a control handle 816 and a debonding element 815. The debonding element 815 comprises a plurality of engagement struts 814 and the engagement struts are configured so as to create the clot engagement face 813 when expanded.

In one embodiment the debonding element or clot engager 815 comprises a plurality of struts forming a first section and a second section, with the first section tapering outward and distally from elongate member 812 and connected to the second section, and the second section comprising a plurality of cells defined by a plurality of struts and arranged around at least a portion of the circumference of an axis substantially parallel to that of the elongate member. In another embodiment these cells are arranged around the entire circumference of said axis.

The debonding element 815 comprises a plurality of cells 817 wherein each cell is defined by a plurality of boundary struts 814. It will be appreciated that a number of cell 817 and strut 814 arrangements are possible in creating a clot engagement surface 813.

The debonding element is connected to the elongate tube 812 and the debonding element 815 is advanced or retracted using the control handle 816 at the user interface 817. The user interface comprises the proximal hub 818 of the guide catheter 811, the proximal hub 819 of the microcatheter 810, the control handle 816 of the debonder 802 and the proximal end of the support member 805. The guide catheter hub 818 and the microcatheter hub 819 both comprise luer connectors and both facilitate the addition of accessories such as Y-connectors, Touhy Borsts and syringes. These accessories facilitate flushing as well as locking the guide catheter to the microcatheter 810 or locking the microcatheter 810 to the elongate tube 812. In one embodiment the control handle 816 comprises a luer fitting. In another embodiment the control handle 816 comprises a locking element for locking the control handle to the support member 805.

FIG. 114 shows a blown up view of one embodiment of the clot debonding element 815 of FIG. 113. In the embodiment shown the struts 814 are integral with the distal end of the elongate tube 812. In another embodiment the clot debonding or clot engaging element 815 may be a separate component to elongate member 812.

FIG. 115 shows an end view of another eccentric debonding element 830. The debonding element 830 comprises a plurality of cells 833 defined by a plurality of struts 831. The plurality of cells 833 are configured such that in the expanded state the debonding element 830 will engage with a substantial portion of a vessel with a substantially circular cross-section. The struts 831 are connected to an elongate tube 832.

Now with reference to FIG. 116a to FIG. 116i there is shown another device 850 which is very similar to the device describe in FIG. 113 to FIG. 115 and similar numerals will be employed to describe similar elements. FIG. 116a to FIG. 116i show the procedural steps associated with using the device 850. The device 850 comprises a basket 801 and a debonder 851. The debonder 851 is an eccentric debonder and is similar to the debonder 802 described with reference to FIG. 33. The debonder 851 comprises a debonding element 852 and an elongate tube 812. The elongate tube 812 comprises a lumen sized to accommodate the support member 805 of the basket 801. The debonding element 852 is fixed to the distal end of the elongate tube 812 and comprises a collapsed state for delivery, a deployed partially expanded state and a fully deployed state. The debonder element 852 comprises a plurality of struts 814 and said struts 814 are configured to expand on deployment. The engagement struts 814 are configured so as to create a clot engagement surface 853 when expanded. The debonding element 852 comprises a plurality of cells 817 wherein each cell is defined by a plurality of boundary struts 814. It will be appreciated that a number of arrangements of cells 817 and struts 814 are possible in creating a clot engagement surface 853.

The debonding element 852 deployed state comprises an intermediate diameter when expanded in an unconstrained fashion. Preferably the debonding element 852 comprises a nitinol, a shape memory or a super elastic material. The debonding element 852 comprises an engagement surface 853 in the deployed state. The engagement surface 853 is a distally facing surface and is configured to engage with the occlusion 840. The engagement surface 813 comprises a tapered surface and when the tapered surface engages with the clot 840 the reaction force of the clot 840 causes the debonding element 852 to expand further. In one embodiment the further expansion of the debonding element 852 comprises an articulation of at least a portion of the engagement surface 853. In another embodiment the further expansion comprises a change in shape of the cells 817 of the debonding element 852. Conversely, when the debonding element 852 is disengaged from the occlusion 840 the debonding element 852 partially collapses, returning to its biased partially expanded configuration. Furthermore, when the debonding element is withdrawn through an occlusion 840 or a partial occlusion the outer side of the tapered surface engages with the clot and the debonding element 852 is further collapsed by the reaction force of the occlusion 840 on its outer surface. Thus the debonding element 852 spontaneously engages when advanced against an occlusion 840 and collapses when retracted through a restriction or occlusion 840.

Figure 116A:
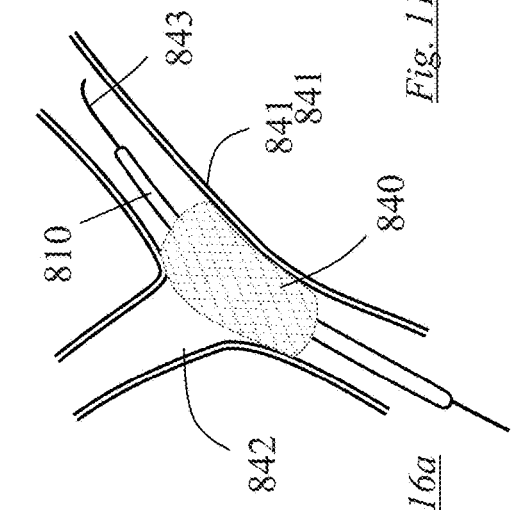

FIG. 116*a* shows the start of the procedure and the steps for gaining access to the distal side of the occlusion. The steps comprise:

Advancing a guide catheter 811 into a large supra aortic vessel.

Advancing a guidewire 843 and a microcatheter 810 through the lumen of the guide catheter 811.

Manipulating the guidewire 843 and the microcatheter in concert so as to access the target vessel.

Passing the guidewire 843 and the tip of the microcatheter 810 across the occlusion 840.

Removing the guidewire 843 from the lumen of the microcatheter.

Figure 116B:
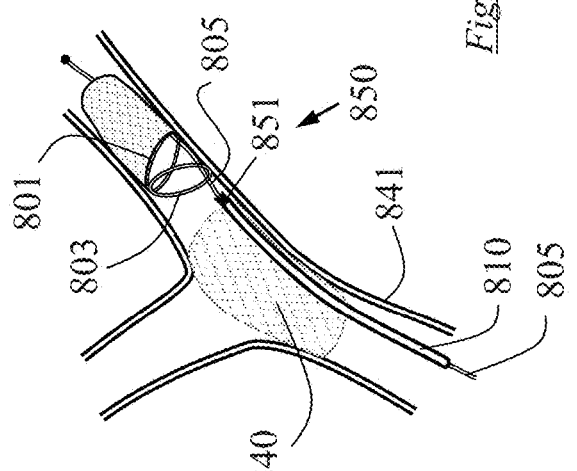

With reference to FIG. 116*b*, the device 850 is advanced through the lumen of the microcatheter 810. The procedural steps involved in delivering and deploying the basket 801 comprise:

Providing the device with the basket 801 and the debonder 851 in the collapsed configuration.

Inserting the distal end of the device 850 into the lumen of the microcatheter 810.

Advancing the device 850 through the lumen of the microcatheter 810 until the basket frame 803 exits the microcatheter 810.

Expanding the frame to the deployed clot engagement configuration.

Figure 116C:
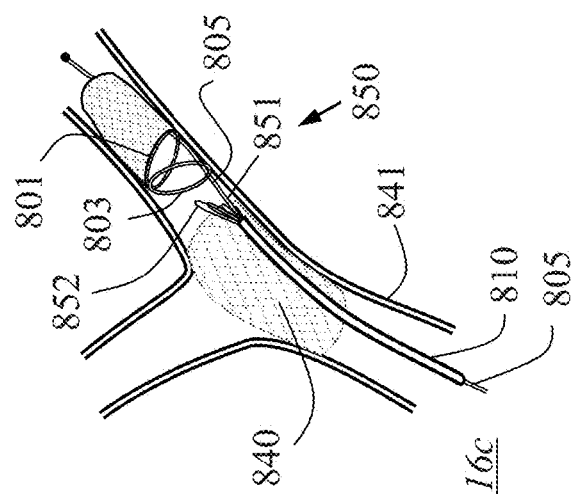
Figure 116D:
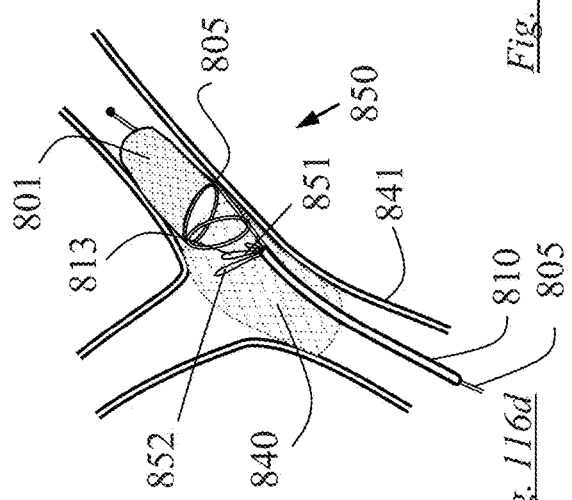

With reference to FIG. 116*c* and FIG. 116*d* the microcatheter 810 is withdrawn and unsheathes the debonding element 852 which expands towards its intermediate diameter. The expansion of the debonding element occurs adjacent the distal end of the occlusion 840. The orientation of the debonding element 852 is checked and if necessary the orientation of the debonding element adjusted. The debonder 851 is withdrawn into the distal body of the occlusion 840. The basket 801 is retracted and engaged with the clot 840. The debonder 851 is advanced slightly and the debonding element 852 engages with the clot, expands under the reaction force of the clot and in so doing sets up a shearing force on the body of the clot. The procedural steps comprise:

Deploying the debonding element 852 within the target vessel.

Orienting the debonding element 852.

Retracting the debonding element 852 into the body of the occlusion 840, wherein the retraction step comprises an incremental collapse of the debonding element 852.

Engaging the basket 801 with the distal end of the clot 840.

Engaging the debonding element 852 with the clot 840, said engagement comprising a spontaneous incremental expansion of the debonding element 852.

Figure 116E:
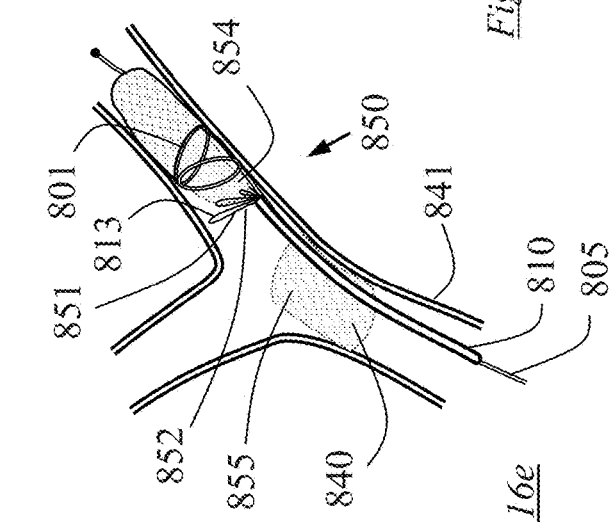

With reference to FIG. 116*e* the device 850 is shown with a distal portion 854 of the clot 840 sheared from the main body of the clot 840 and being forced into the mouth of the basket 801.

The spontaneous expansion of the debonding element 852 when engaged with the clot helps the debonder 851 to shear away a portion 854 of the clot 840. This approach is particularly advantageous where the occlusion is an especially long occlusion. Occlusions of 30 mm are not unusual in cerebral vessels. Breaking the occlusion into chunks reduced the stress applied to the vessel wall and this reduces complications. It will be appreciated that the device 850 can be used to debond and capture short length occlusions without breaking up the clot. The steps associated with the shearing off and capture of the first chunk 854 of the occlusion 840 comprise:

Shearing off a segment 854 of the clot 840

Advancing the debonder with the sheared segment 854 distal while holding the basket 801 steadfast and forcing the sheared segment 854 into the basket 801.

Disengaging the debonding element 852 from the clot segment 854.

Figure 116F:
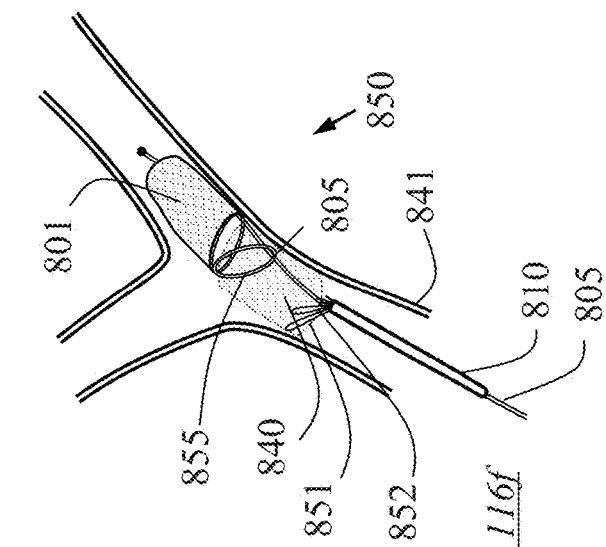
Figure 116I:
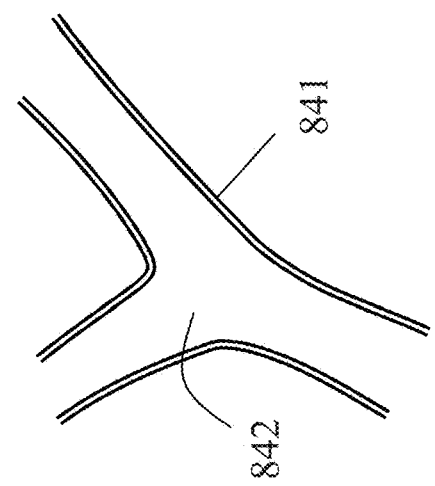
Figure 116H:
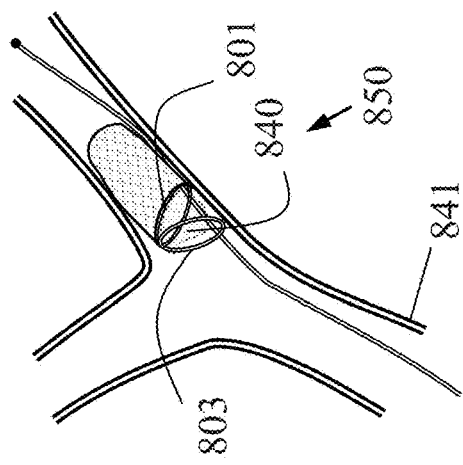
Figure 116G:
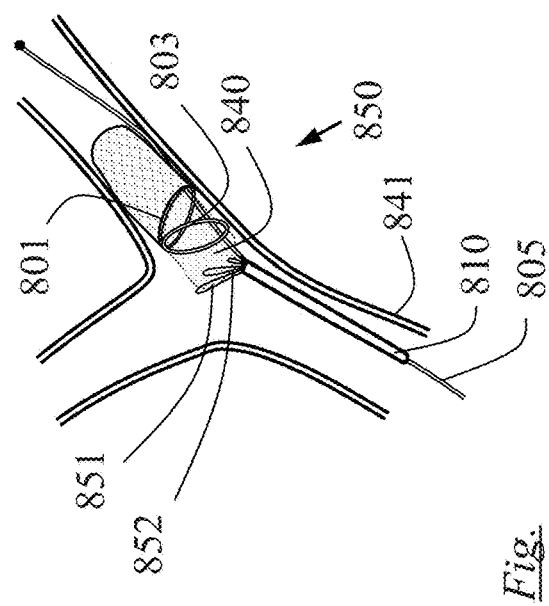

With reference to FIG. 116*f* and FIG. 116*g* the device is shown engaging with and capturing a second segment 855 of the clot 840. The debonder 851 is withdrawn proximally and the debonding element 852 is withdrawn into the remaining clot. When the user is satisfied with the size of the second clot segment 855 the debonder 851 is advanced slightly such that the debonding element 852 engages with the clot. The basket 801 is withdrawn proximally while holding the debonder 851 stationary and the basket 801 is engaged with the distal end of the clot segment 855. The debonder 851 is advanced while holding the basket 801 steadfast and the second clot segment 855 is sheared off and captured in the basket 801. The steps associated with capturing the second clot segment comprise:

Retracting the debonding element 852 into the body of the remaining occlusion 840, wherein the retraction step comprises an incremental collapse of the debonding element 852 as it engages with the occlusive material.

Engaging the basket 801 with the distal end of the second clot segment 855.

Engaging the debonding element 852 with the clot 840, in the body of the remaining clot, said engagement comprising a spontaneous incremental expansion of the debonding element 852.

Shearing off a second segment 855 of the clot 840.

Advancing the debonder with the sheared segment 855 distal while holding the basket 801 steadfast and forcing the sheared segment 855 into the basket 801.

In one embodiment the second segment comprises all of the remaining clot. In this case the method comprises the steps of:

Retracting the debonding element 852 through the remaining occlusion 840, wherein the retraction step comprises an incremental collapse of the debonding element 852 as it engages with the occlusive material, the debonding element 852 spontaneously expanding when the debonding element 852 emerges on the proximal side of the occlusion.

Engaging the basket 801 with the distal end of the remaining clot segment.

Engaging the debonding element 852 with the proximal face of the clot 840, said engagement comprising a spontaneous incremental expansion of the debonding element 852.

Shearing the remaining clot segment 855 from the wall of the vessel 841.

Advancing the debonder with the remaining clot segment 855 distal while holding the basket 801 steadfast and forcing the sheared segment 855 into the basket 801.

The remaining steps in the procedure are described in FIG. 116h and FIG. 116i. The debonder is withdrawn from the vessel segment. The basket is then withdrawn from the vessel segment and a final angiogram is completed. In one embodiment the steps comprise:

Retracting the debonding element 852 from the vessel segment.

Retracting the basket 801 with the captured clot from the vessel segment.

Removing the device 850 and the clot from the vasculature through the lumen of the guide catheter 811.

In another embodiment the device 850 and the microcatheter 810 are removed in concert. This approach allows the lumen of the microcatheter 810 to protect the vessel wall from the some of the frictional forces of the elongate tube 812 and the support member 805 during removal. The method comprises the steps of:
1. Retracting the debonder 851 until the expanded section of the debonding element 852 engages with the distal end of the microcatheter 810.
2. Locking the debonder 851 and the microcatheter 810 together.
3. Retracting the basket 801 until the frame 803 is adjacent the debonding element 852.
4. Retracting the microcatheter 810 and debonder 851 through another segment of vessel.
5. Repeat steps 3 and 4 until the debonder element is adjacent the tip of the guide catheter 811.
6. Retract the microcatheter 810, the debonder 851 and the basket through the lumen of the Guide catheter 811 and remove from the patient.
7. Conduct a final angiogram by flushing contrast media through the lumen of the guide catheter 811.

The debonder and the microcatheter can be easily locked together where a Touhy Borst fitting is connected to the proximal luer of the microcatheter.

Another device 870 of the invention is described with reference to FIGS. 117a-e. FIG. 117a shows device 870 which comprises a basket assembly 871 and a debonding assembly 872. The basket assembly 871 comprises a frame 875, a net 876, a support member 877, pull cable 878, and a handle assembly 883. The support member 877 comprises a tubular member and the support member is connected to the frame at junction 881. The support member 877 comprises an inner lumen and an exit port 879. The pull cable extends from attachment point(s) 880 through the exit port 879 through the lumen of the support member 877 to the handle 883. In one embodiment the cable is interfaced with a slider 884 such that activation of the slider 884 causes the cable 878 to undergo tension and deactivation of the slider 884 reduces or removes tension from the cable 878. Tensioning the pull cables 878 causes the frame 875 to articulate about a region adjacent the junction 881. FIG. 117b and FIG. 117c show a top and side view respectively of the basket 871 with pull cable 878 in the untensioned state. FIG. 117d shows a top view of the basket 871 constrained in a vessel with pull cable 878 in the untensioned state. FIG. 117e shows a close-up of the debonding assembly 872 in the collapsed state for delivery.

In one embodiment the region of articulation is distal of the junction 881. In another embodiment the region of articulation is proximal of the junction 881. In another embodiment the region of articulation includes the junction. In one embodiment at least a portion of the region of articulation comprises a reduced section. In one embodiment the reduced section comprises a reduction in the width of the section. In another embodiment the reduced section comprises a reduction in the thickness of the section. In another embodiment the reduced section comprises a reduction in the cross sectional area of the section. In another embodiment the reduced section comprises a reduction in the stiffness of the material of the section.

FIG. 118a shows another debonder 900 which may be used in conjunction with previous devices disclosed in the invention. The debonder is connected to an elongate tube 901 and has an engagement surface 902 for abutment with an occlusive clot. The engagement struts 903 in FIG. 118b have a radial section 904, a curved segment 905, and a termination section 906. This debonder configuration provides a large abutment surface area for an occlusive clot. It will be appreciated that tethers may be attached to the termination sections 906 of the engagement struts to provide additional engagement for the struts. FIG. 118b shows an end view of the same debonder 900 with tethers.

FIGS. 119a and 119b shows another basket frame 911 according to the invention. The basket frame has a tether connection 912 at the distal end. The frame may be constructed from a cut sheet of material. The frame may be constructed from cut tubular material. The frame may be constructed of wire material. The frame may be constructed of ribbon material. The material may be Nitinol. In the frame of FIGS. 119a and 119b the pull tether 21 in integrally attached to the frame. It will be appreciated that the pull tether may be attached by other means such as welding, laser welding, bonding, or tied to the basket frame. The frame in FIG. 119 has eyelets 6 as net attachment points.

FIG. 120 shows another basket assembly 921 according to the invention. This basket frame has a proximal hoop 922 and a distal hoop 923. The frame may be constructed from a cut sheet of material. The frame may be constructed from cut tubular material. The frame may be constructed of wire material. The frame may be constructed of ribbon material. The material may be Nitinol. The struts of the proximal hoop and distal hoop are adjacent at a frame cross over 924. The struts of the proximal hoop and distal hoop may remain unconnected. FIG. 120a shows eyelets 6 of the proximal hoop struts and distal hoop struts may aligned at the frame cross over 924. FIG. 120b shows the frame cross over 924 wherein a pin 925 is inserted through eyelets 6. FIG. 120c shows the frame cross over 924 attached with a connecting wire 926. It will be appreciated that the means of connecting the struts shown in FIGS. 120b and 120c maintain the struts adjacent in the expanded configuration and in the collapsed configuration. The struts may move relative to each other in a scissors-like manner to move from an expanded configuration to a collapsed configuration.

FIGS. 121a and 121b illustrate another basket assembly 931 of the invention in an expanded configuration. This basket assembly has a proximal loop 932, a middle loop 933, and a distal loop 934. In FIG. 121a a cable or pull tether 21 is connected at tether connection point 935 adjacent the middle loop 933 and distal loop 934 cross over point. In FIG. 122b the tether connection 936 is on the distal loop 934. The frame comprises three loops substantially the same circumference in FIG. 121. It will be appreciated that the plurality of loops are be incorporated in order to provide additional support to the basket assembly, and further loops can be incorporated.

FIGS. 122a and 121b illustrate another basket assembly 941 of the invention with a proximal loop 942, a middle loop 943, and a distal loop 944. In basket assembly 941 the distal loop 944 has a circumference smaller than that of the proximal or middle loops. FIG. 122a shows the frame without a tether and FIG. 122b shows a basket assembly 941 with a cable or pull tether 21. The bending stiffness of the smaller distal loop 944 gives the basket assembly rigidity in the axial direction to facilitate encapsulation of an occlusive clot.

FIGS. 123a and 123b show another basket assembly 951 of the invention with a proximal loop 952 and a distal loop 953. FIG. 123b has a cable or pull tether 21 connected to the distal loop for actuation. The distal loop 953 has a larger circumference than proximal loop 952, but in end view each loop will have substantially circular shapes to appose a vessel wall.

In FIGS. 121-123 it will be appreciated that basket assemblies may comprise cut sheet material, cut tube material, ribbon material or wire material.

Modifications and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

The invention is not limited to the embodiments hereinbefore described, with reference to the accompanying drawings, which may be varied in construction and detail.

What is claimed is:

1. A system, including:
a tubular member defining a lumen extending therethrough;
a microcatheter slidably disposed in the lumen;
an expandable framework positioned at a distal end of the tubular member, the expandable framework defining a lumen in communication with the lumen of the tubular member and expandable between a collapsed state and an expanded state,
wherein in the expanded state, the expandable framework is advanced distal of a distal end of the microcatheter and then caused to expand from the collapsed state to the expanded state projecting radially outwardly of the tubular member with an open distalmost end defining a maximum radial size of the expandable framework,
wherein in the collapsed state, a proximalmost end of the expandable framework and the tubular member have a common radial dimension less than the maximum radial size of the expandable framework;
an expandable porous body configured to capture a clot, the expandable porous body being longitudinally moveable distally of the tubular member and the expandable framework; and
a gap disposed between the expandable framework and the expandable porous body, the gap sized to receive the clot.

2. The system of claim 1, wherein the expandable framework is monolithically formed with the tubular member.

3. The system of claim 1, wherein, in the collapsed state, a length of the expandable framework between the proximalmost end and the distalmost end and the tubular member have a common radial dimension.

4. The system of claim 1, wherein the expandable framework is a porous strut framework and includes a plurality of closed cells.

5. The system of claim 1, wherein the tubular member includes a non-porous circumferential wall.

6. The system of claim 1, further comprising an actuating element connected to the expandable framework for actuating the expandable framework between collapsed and expanded states, the actuating element running within the tubular member to the expandable framework, and wherein retraction of the actuating element applies a compressive force to the distalmost end of the expandable framework.

7. The system of claim 1, wherein the expandable porous body is tapered such that a proximal end of the expandable porous body has a first radial size and the distal end of the expandable porous body has a second radial size smaller than the first radial size.

8. The system of claim 1, wherein the expandable porous body includes an open proximal mouth facing the expandable framework.

9. A system, comprising:
a tubular member defining a lumen extending therethrough;
a microcatheter slidably disposed in the lumen;
an expandable framework positioned distally of a distal end of the tubular member, the expandable framework defining a lumen in communication with the lumen of the tubular member and having an open distal end, and self-expandable between a collapsed state and a expanded state,
wherein in the collapsed state, the expandable framework and the tubular member have a common radial dimension less than a maximum radial size of the expandable framework, and
wherein in the expanded state, the expandable framework is advanced distal of a distal end of the microcatheter and then caused to expand from the collapsed state to the expanded state projecting radially outwardly of the tubular member with a distalmost end having the maximum radial size of the expandable framework;
an expandable capture structure configured to capture a clot, the expandable capture structure being longitudinally moveable with respect to the tubular member from a collapsed delivery state to a deployed expanded state distally beyond the expandable framework, wherein the capture structure is porous and includes an open proximal mouth coupled to a longitudinally extending member moveably received within the lumen of the tubular member; and
a gap disposed between the expandable framework and the expandable capture structure, the gap sized to receive the clot.

10. The system of claim 9, wherein the tubular member includes a non-porous circumferential wall.

11. The system of claim 9, wherein the expandable capture structure is tapered such that a proximal end of the expandable capture structure has a first radial size and a distal end of the expandable capture structure has a second radial size smaller than the first radial size.

12. The system of claim 11, further comprising an actuating element connected to the expandable framework for causing the expandable framework to expand between collapsed and expanded states, the actuating element comprising an elongate member running within the tubular member to the expandable framework, and wherein retraction of the actuating element applies a compressive force to the distalmost end of the expandable framework.

13. The system of claim 9, wherein a proximal end of the expandable framework is longitudinally fixed relative to a distal end of the tubular member.

14. The system of claim 9, wherein the open proximal mouth faces the expandable framework.

15. A method, including:
   slidably positioning a tubular member over a microcatheter;
   expanding the tubular member from a collapsed state to an expanded state by:
      distally advancing an expandable framework located at a distal end of the tubular member distal of a distal end of a microcatheter; and
      subsequently projecting radially the tubular member with an open distalmost end defining a maximum radial size of the expandable framework,
   wherein the expandable framework defines a lumen in communication with a lumen of the tubular member, and wherein, in the collapsed state, a proximalmost end of the expandable framework and the tubular member have a common radial dimension less than the maximum radial size of the expandable framework;
   extending an expandable porous body distally of the tubular member to expand the expandable porous body from a collapsed delivery state to a deployed expanded state, the expandable porous body having a closed distal end and an open proximal mouth;
   positioning a gap between the expandable framework and the expandable porous body, the gap sized for capturing an obstruction; and
   receiving the obstruction in the gap via the expandable framework and the expandable porous body.

16. The method of claim 15, further including actuating the expandable framework by proximally retracting an actuating element coupled to the expandable framework; and
   applying a compressive force to the distalmost end of the expandable framework.

17. The method of claim 16, further including moving a longitudinally extending member coupled to the expandable porous body with respect to the lumen of the tubular member;
   wherein the open proximal mouth faces the expandable framework and the longitudinally extending member is coupled to the open proximal mouth.

18. The method of claim 16, wherein, in the collapsed state, a length of the expandable framework between the proximalmost end and the distalmost end and the tubular member have a common radial dimension.

19. The method of claim 16, further including dislodging the obstruction via the expandable framework.

* * * * *